US012173073B2

(12) United States Patent
Frenette et al.

(10) Patent No.: US 12,173,073 B2
(45) Date of Patent: Dec. 24, 2024

(54) METHODS OF TREATMENT BY TARGETING VCAM1 AND MAEA

(71) Applicant: Albert Einstein College of Medicine, Bronx, NY (US)

(72) Inventors: Paul S. Frenette, Bronx, NY (US); Sandra Pinho, Bronx, NY (US); Qiaozhi Wei, Bronx, NY (US); Sung Kyun Lee, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 26 days.

(21) Appl. No.: 18/146,951

(22) Filed: Dec. 27, 2022

(65) Prior Publication Data

US 2023/0212295 A1    Jul. 6, 2023

Related U.S. Application Data

(60) Division of application No. 16/773,907, filed on Jan. 27, 2020, now Pat. No. 11,560,433, which is a continuation-in-part of application No. 16/199,555, filed on Nov. 26, 2018, now abandoned, which is a continuation-in-part of application No. PCT/US2017/034365, filed on May 25, 2017.

(60) Provisional application No. 62/342,360, filed on May 27, 2016.

(51) Int. Cl.
| | |
|---|---|
| C07K 16/00 | (2006.01) |
| A61K 39/395 | (2006.01) |
| A61P 7/00 | (2006.01) |
| A61P 35/02 | (2006.01) |
| C07K 16/18 | (2006.01) |
| C07K 16/28 | (2006.01) |
| C07K 16/30 | (2006.01) |
| C07K 16/46 | (2006.01) |
| A61K 39/00 | (2006.01) |
| A61K 45/06 | (2006.01) |

(52) U.S. Cl.
CPC ...... *C07K 16/2836* (2013.01); *A61K 39/3955* (2013.01); *A61P 7/00* (2018.01); *A61P 35/02* (2018.01); *C07K 16/18* (2013.01); *C07K 16/2821* (2013.01); *C07K 16/2878* (2013.01); *C07K 16/2896* (2013.01); *C07K 16/3061* (2013.01); *A61K 2039/505* (2013.01); *A61K 45/06* (2013.01); *C07K 2317/51* (2013.01); *C07K 2317/515* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 8,623,368 B2 | 1/2014 | Lee et al. |
| 2002/0022028 A1 | 2/2002 | Mundy et al. |
| 2010/0172902 A1 | 7/2010 | Chung et al. |
| 2010/0266587 A1 | 10/2010 | Mclachlan |
| 2013/0309230 A1 | 11/2013 | Stagliano et al. |
| 2014/0255303 A1 | 9/2014 | Ghezzi et al. |
| 2015/0071905 A1 | 3/2015 | Ring et al. |
| 2015/0329616 A1 | 11/2015 | Uger et al. |
| 2016/0137733 A1 | 5/2016 | Frazier et al. |
| 2016/0137734 A1 | 5/2016 | Frazier et al. |
| 2016/0177276 A1 | 6/2016 | Lo et al. |
| 2016/0186150 A1 | 6/2016 | Deming et al. |
| 2017/0081407 A1 | 3/2017 | Grosveld et al. |
| 2017/0107270 A1 | 4/2017 | Pons et al. |
| 2019/0077878 A1 | 3/2019 | Frenette et al. |
| 2021/0095045 A1 | 4/2021 | Frenette et al. |

FOREIGN PATENT DOCUMENTS

| | | | |
|---|---|---|---|
| WO | 9314220 A1 | 7/1993 | |
| WO | WO-9507717 A1 * | 3/1995 | ....... C07K 14/70542 |
| WO | 2007139359 A1 | 12/2007 | |
| WO | 2010121141 A1 | 10/2010 | |
| WO | 2011049412 A2 | 4/2011 | |

OTHER PUBLICATIONS

Smolinski PA, Offermann MK, Eckman JR, Wick TM. Double-stranded RNA induces sickle erythrocyte adherence to endothelium: a potential role for viral infection in vaso-occlusive pain episodes in sickle cell anemia. Blood. May 15, 1995;85(10):2945-50. (Year: 1996).*
Gee BE, Platt OS. Sickle reticulocytes adhere to VCAM-1. Blood. Jan. 1, 1995;85(1):268-74. (Year: 1995).*
Bessis, M. "Erythroblastic island, functional unity of bone marrow" Rev Hematol, 1958, vol. 13, pp. 8-11.
Bradstock et al. Analysis of the Mechanism of Adhesion of Precursor-B Acute Lymphoblastic Leukemia Cells to Bone Marrow Fibroblasts. Blood 82(11):3437-3444, 1993). (Year: 1993).
Burns et al. Antibody Blockade of ICAM-1 an VCAM-1 Ameliorates inflammation in the SAMP-1/Yit Adoptive Transfer Model of Crohn's Disease in Mice. Gastroenterology. Dec. 2001; 121 (6): 1428-36. (Year: 2001).
Chen, Q., et al. Macrophage binding to receptor VCAM-1 transmits survival signals in breast cancer cells that invade the lungs. Cancer Cell 20, 538-549, doi:10.1016/j.ccr.2011.08.025 (2011).
Chow, A. et al. CD169(+) macrophages provide a niche promoting erythropoiesis under homeostasis and stress. Nat Med 19, 429-436, doi:10.1038/nm.3057 (2013).

(Continued)

*Primary Examiner* — Maher M Haddad
(74) *Attorney, Agent, or Firm* — Perkins Coie LLP

(57) ABSTRACT

Antibodies and antibody fragments that inhibit the activity of vascular cell adhesion molecule 1 (VCAM1) and/or macrophage erythroblast attacher (MAEA) are provided, along with formulations and kits comprising these antibodies and antibody fragments and the use of the disclosed compositions, formulations, and kits to treat cancers, sickle cell disease, and Polycythemia Vera.

10 Claims, 114 Drawing Sheets

Specification includes a Sequence Listing.

(56) References Cited

OTHER PUBLICATIONS

De Back et al. "Of macrophages and red blood cells; a complex love story" Front. Physiol., 2014, vol. 5, p. 9.

Ding, Y. B. et al. Association of VCAM-1 overexpression with oncogenesis, tumor angiogenesis and metastasis of gastric carcinoma. World J Gastroenterol 9, 1409-1414 (2003).

Dutta, P. et al. Macrophages retain hematopoietic stem cells in the spleen via VCAM-1. J Exp Med 212, 497-512, doi:10.1084/jem.20141642 (2015).

Filshie et al. VLA-4 is involved in the engraftment of the human pre-B acute lymphoblastic leukemia cell line NALM-6 in SCIO mice. British Journal of Hematology, 1998, 102, 1292-1300. (Year: 1998).

Frenette, P. S., Subbarao, S., Mazo, I. B., von Andrian, U. H. & Wagner, D. D. Endothelial selectins and vascular cell adhesion molecule-1 promote hematopoietic progenitor homing to bone marrow. Proc Natl Acad Sci U S A 95, 14423-14428 (1998).

Grooby et al., "Combined anti-vascular cell adhesion molecule-1 and anti-leukocyte function-associated molecule-1 monoclonal antibody therapy does not prolong allograft survival in an ovine model of renal transplantation." Transplantation. Oct. 1, 19985;66(7): 920-4. (Year: 1998) 12 pages.

Gurtner, G.C. et al. Targeted disruption of the murine VCAM1 gene: essential role of VCAM-1 in chorioallantoic fusion and placentation. Genes & development 9, 1-14 (1995).

Hamamura, K. et al. A critical role of VLA-4 in erythropoiesis in vivo. Blood 87, 2513-2517 (1996).

Hanspal, et al. The association of erythroblasts with macrophages promotes erythroid proliferation and maturation: a 30-kD heparin-binding protein is involved in this contact. Blood 84, 3494-3504 (1994).

Hom et al. "The erythroblastic island as an emerging paradigm in the anemia of inflammation" Immunol. Res., 2015, vol. 63, pp. 75-89.

Jacamo et al. "Reciprocal Leukemia-stroma VCAM-1VLA-4-dependent activation of NF-KB Mediates chemoresistance" Blood, 2014, vol. 123, No. 17, pp. 2691-2702.

Jacobsen, et al. "Macrophages and regulation of erythropoiesis" Curr. Opin. Hematol., 2015, vol. 22, pp. 212-219.

Justicia et al. "Anti-Vcam-1 antibodies did not protect against ischemic damage either in rats or in mice." J. Cerebral Blood Flow and Metabolism 26(3):421-32. (Year: 2006), 12 pages.

Klei et al. "From the Cradle to the Grave: The Role of Macrophages in Erythropoiesis and Erythrophagocytosis" Front. Immunol, 2017, vol. 8, pp. 73.

Koni, P. A. et al. Conditional vascular cell adhesion molecule 1 deletion in mice: impaired lymphocyte migration to bone marrow. J Exp Med 193, 741-754 (2001).

Lee et al. VCAM-1-, ELAM-1-, and ICAM-1-independent Adhesion of Melanoma Cells to Cultured Human Dermal Microvascular Endothelial Cells. J Invest Dermatol. Jan. 1992 98(1):79-85. (Year: 1992), 11 pages.

Lin, K. Y. et al. Ectopic expression of vascular cell adhesion molecule-1 as a new mechanism for tumor immune evasion. Cancer Res 67, 1832-1841, doi:10.1158/0008-5472.CAN-06-3014 (2007).

Lu et al. VCAM-1 promotes osteolytic expansion of indolent bone micrometastasis of breast cancer by engaging $\pi4\beta1$-positive osteoclast progenitors. Cancer Cell, 2011, vol. 20, No. 6, pp. 701-714.

Miyake, K. et al. A VCAM-like adhesion molecule on murine bone marrow stromal cells mediates binding of lymphocyte precursors in culture. J Cell Biol 114, 557-565 (1991).

Papayannopoulou, T., Priestley, G. V. & Nakamoto, B. Anti-VLA4/VCAM-1-induced mobilization requires cooperative signaling through the kit/mkit ligand pathway. Blood 91, 2231-2239 (1998).

Papayannopoulou, T., et al. The VLA4/VCAM-1 adhesion pathway defines contrasting mechanisms of lodgement of transplanted murine hemopoietic progenitors between bone marrow and spleen. Proceedings of the National Academy of Sciences of the United States of America 92, 9647-9651 (1995).

PCT International Search Report and Written Opinion dated Aug. 14, 2017 for PCT International Application No. PCT/US2017/034365, 9 pages.

Ramos, P. et al. Macrophages support pathological erythropoiesis in polycythemia vera and beta-thalassemia. Nat Med 19, 437-445, doi:10.1038/nm.3126 (2013).

Ren et al. "Inflammatory Cytokine-Induced Intercellular Adhesion Molecule-1 and Vascular Cell Adhesion Molecule-1 in Mesenchymal Stem Cells Are Critical for Immunosuppression". J Immunol. Mar. 1, 2010; 184(5): 2321-2328 (Year: 2010), 20 pages.

Rhodes et al. "Adherence to macrophages in erythroblastic islands enhances erythroblast proliferation and increases erythrocyte production by a different mechanism than erythropoietin" Blood, 2008, vol. 111, pp. 1700-1708.

Sadahira, et al. Very late activation antigen 4-vascular cell adhesion molecule 1 interaction is involved in the formation of erythroblastic islands. J Exp Med 181, 411-415 (1995).

Simmons, P. J. et al. Vascular cell adhesion molecule-1 expressed by bone marrow stromal cells mediates the binding of hematopoietic progenitor cells. Blood 80, 388-395 (1992).

Slack-Davis et al. Vascular Cell Adhesion Molecule-1 Is a Regulator of Ovarian Cancer Peritoneal Metastasis. Cancer Research, 2009, vol. 69, No. 4, pp. 1469-1476.

Tashiro et al. "Acute Myelogenous Leukemia Blasts Contribute to a Bone Marrow-Stroma in In Vivo NOD/SCID Mouse System" Blood, 2009, vol. 114, No. 22, pp. 1621.

Ulyanova, T. et al. VCAM-1 expression in adult hematopoietic and nonhematopoietic cells is controlled by tissue-inductive signals and reflects their developmental origin. Blood 106, 86-94 (2005).

Wei et al. Maea expressed by macrophages, but not erythroblasts, maintains postnatal murine bone marrow erythroblastic islands. Blood. 2019;133(11):1222-1232) (Year: 2019).

Yamashita, T. et al. The microenvironment for erythropoiesis is regulated by HIF-2alpha through VCAM-1 in endothelial cells. Blood 112, 1482-1492, doi:10.1182/blood-2007-11-122648 (2008).

* cited by examiner

☐ IgG
■ Anti-Vcam1
■ Cytarabine
☐ Anti-Vcam1+ Cytarabine

FIG. 5E

Table 1. Summary of blood analyses of wild-type mice treated with IgG and anti-Vcam1

|  | WBC $\times 10^3/\mu l$ | RBC $\times 10^6/\mu l$ | HGB g/dl | HCT % | PLT $\times 10^3/\mu l$ | % Neut. | % Lymph. | % Retic. |
|---|---|---|---|---|---|---|---|---|
| IgG treatment, n=5 | 4.3 ± 0.6 | 9.8 ± 0.2 | 14.0 ± 0.4 | 47.0 ± 1.0 | 1362 ± 26.8 | 16.6 ± 4.5 | 75.9 ± 5.0 | 2.6 ± 0.1 |
| Anti-Vcam1 treatment, n=5 | 5.5 ± 0.5 | 9.3 ± 0.3 | 13.0 ± 0.4 | 44.4 ± 1.9 | 1318 ± 166.1 | 17.1 ± 6.0 | 71.4 ± 8.5 | 3.3 ± 0.2 |
| P value | 0.130 | 0.165 | 0.153 | 0.263 | 0.808 | 0.942 | 0.662 | 0.011 |

□ Control (old)   ■ Maea$^{Csf1r\text{-}Cre}$ (old)

| Treatment | Mice, n | Venule, n | Venular Diameter, μm | Centerline Velocity, mm/s | Shear Rate, S-1 | Blood Flow, nL/sec |
|---|---|---|---|---|---|---|
| IgG | 5 | 51 | 17 ± 0.4 | 1.3 ± 0.1 | 848 ± 48.95 | 212 ± 12.26 |
| VCAM1 | 5 | 46 | 16 ± 0.4 | 1.5 ± 0.1 * | 1079 ± 45.61 *** | 197 ± 10.63 ns |

Data are presented as mean SEM.
*p<0.05, p<0.01, *p<0.001 versus Rat IgG1

METHODS OF TREATMENT BY TARGETING VCAM1 AND MAEA

CROSS-REFERENCE TO RELATED APPLICATIONS

This application is a divisional of U.S. patent application Ser. No. 16/773,907, filed Jan. 27, 2020, which is a continuation-in-part of U.S. patent application Ser. No. 16/199,555, filed Nov. 26, 2018, now abandoned, which is a continuation-in-part of and claims priority of PCT International Patent Application No. PCT/US2017/034365, filed May 25, 2017, which designates the United States of America and which claims the benefit of U.S. Provisional Patent Application No. 62/342,360, filed on May 27, 2016, the contents of which are incorporated herein by reference.

STATEMENT OF GOVERNMENT SUPPORT

This invention was made with government support under grant numbers HL116340, HL069438 and DK056638 awarded by the National Institutes of Health. The government has certain rights in the invention.

STATEMENT OF SEQUENCE LISTING

This application contains an ST.26 compliant Sequence Listing, which was submitted in xml format via Patent Center and is hereby incorporated by reference in its entirety. The .xml copy, created on Dec. 27, 2022 is named Sequence_Listing.xml and is 131 KB in size.

BACKGROUND

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

Hematopoietic stem cells (HSCs) possess the ability to maintain the entire population of blood cells throughout life and to replenish the hematopoietic system after transplantation into marrow-ablated recipients. During fetal and adult life, HSCs are able to migrate to ectopic niches via the blood stream. Once in the blood, HSCs home to perivascular stromal and endothelial cells expressing adhesion molecules, then navigate the vascular networks of the marrow, spleen, and liver before returning to potential bone marrow niches.

Under homeostasis, HSCs reside in the specialized bone marrow (BM) niche composed of various cellular and molecular constituents. Whereas mesenchymal stem and progenitor cells provide most niche factor activity contributing to HSC maintenance, differentiated hematopoietic cells such as macrophages can regulate indirectly HSC retention in BM via the niche. In addition, macrophages tightly interact with red blood cell precursors to form a structure known as the erythroblastic island (EI) in which interactions via vascular cell adhesion molecule 1 (VCAM1) and/or macrophage-erythroblast attacher (MAEA, also called EMP) are thought to play important roles in the terminal maturation of erythroblasts. The attachment of the developing erythroblasts (EBs) to the central macrophages within the islands is critical for survival, proliferation, and proper differentiation of developing erythrocytes both in vitro and in vivo.

VCAM1 is an adhesion molecule expressed by BM stromal and endothelial cells and certain classes of hematopoietic cells. VCAM1's major ligand is integrin α4β1 (also known as Very Late Antigen-4, "VLA-4"). The interaction between VCAM1 and VLA-4 mediates cell-cell interaction in multiple cell types, and both VCAM1 and VLA-4 have been implicated in HSC homing and retention into the bone marrow and mobilization into the peripheral blood.

VCAM1 protein mediates the adhesion of lymphocytes, monocytes, eosinophils, and basophils to the vascular endothelium. VCAM1 also functions in leukocyte-endothelial cell signal transduction, and it may play a role in the development of atherosclerosis and rheumatoid arthritis (RA).

MAEA is an adhesion molecule originally identified on macrophages and erythroblasts, and it is suggested to play a role in the formation of EIs. However, its function in the adult hematopoietic system is unknown due to the perinatal death of MAEA-deficient mice. Other candidate molecules, e.g., VCAM1, have also been suggested to participate in EI formation, but cell type-specific requirement of these molecules for EI formation and function in vivo has not been examined.

SCD is a blood disorder that causes red blood cells (RBCs) to have an abnormal "sickled" shape that is rigid.[121,124,125] Whereas RBCs in healthy individuals are elastic, sickled RBCs are rigid, and studies suggest that this loss of elasticity of RBCs is central to SCD. SCD is associated with a number of chronic and acute symptoms.[126]

The present disclosure provides anti-VCAM1 and anti-MAEA antibodies, formulations and kits comprising anti-VCAM1 and anti-MAEA antibodies, and therapies for treatment of hematological malignancies and other cancers as well as anti-VCAM1 therapies for treatment of sickle cell disease (SCD).

SUMMARY

The present disclosure provides methods of treating condition in a subject comprising administering to the subject an antibody or antibody fragment in an amount effective to inhibit the activity of vascular cell adhesion molecule 1 (VCAM1) and/or an antibody or antibody fragment in an amount effective to inhibit the activity of macrophage erythroblast attacher (MAEA) to treat a condition in a subject, wherein the antibody or antibody fragment is specific for VCAM1 or MAEA. For example, provided herein are methods of treating a condition in a subject, wherein the condition is a cancer (e.g., a hematologic malignancy or myeloproliferative disease). Also provided herein are methods for treating a condition, wherein the condition is sickle cell disease (SCD).

Also provided are methods of inhibiting engraftment of leukemia cells (e.g., acute myeloid leukemia (AML), chronic myeloid leukemia (CML), acute lymphoblastic leukemia (ALL), or chronic lymphocytic leukemia (CLL) cells) in a subject, the methods comprising administering to the subject an antibody or antibody fragment in an amount effective to inhibit the activity of VCAM1 and/or an antibody or antibody fragment in an amount effective to inhibit the activity of MAEA to inhibit leukemia (e.g., AML, CML, ALL or CLL) cell engraftment in a subject, wherein the antibody or antibody fragment is specific for VCAM1 or MAEA.

Still further provided are methods of enhancing the efficacy of cytarabine for treating a cancer in a subject, comprising administering to the subject an antibody or antibody fragment in an amount effective to inhibit the activity of VCAM1 and/or an antibody or antibody fragment in an amount effective to inhibit the activity of MAEA in combination with cytarabine to enhance the efficacy of cytarabine for treating a cancer in a subject. wherein the antibody or antibody fragment is specific for VCAM1 or MAEA.

Sickle cell disease (SCD), caused by a single missense mutation in the β-globin gene, affects around 100,000 patients in the United States and millions worldwide.[46-47] Mutated β-globin polymerizes under deoxygenation, leading to sickle-shaped RBCs, which exhibit increased adherence to other blood cells or to the endothelium, and are prone to undergo premature clearance and hemolysis.[48] The RBC alterations lead to a chronic inflammatory state resulting in ischemic tissue damage manifested by severe pain and organ failures. The pathophysiology of VOE and chronic organ damage is complex and involves the interplay of altered blood rheology, endothelial activation, and the secretion of inflammatory cytokines enabling leukocyte adhesion and activation.[49] Intravital microscopy analysis of the SCD mouse microcirculation has revealed that RBCs interact with adherent leukocytes in the inflamed vasculature.[50] The accumulation of activated neutrophils interacting with RBCs progressively reduces blood flow and produces venular occlusions.[51,52]

Polycythemia Vera (PV) is a myeloproliferative neoplasm (MPN) characterized by elevated erythropoiesis associated with a constitutively active mutant form of JAK2 tyrosine kinase, JAK2$^{V617F}$ PV patients show splenomegaly, expansion of erythroid progenitors and increase in reticulocytosis, of which only some can be managed by phlebotomy, hydroxyurea or JAK2 inhibitors.[53,54,55,56]

BRIEF DESCRIPTION OF THE DRAWINGS

FIGS. 1A-1C depict experimental results demonstrating that VCAM1 is expressed at higher levels on acute myelogenous leukaemia (AML) stem cells than on healthy hematopoietic stem cells. FIG. 1A is a chart depicting the percentage of VCAM1$^+$ cells within hematopoietic stem cells (HSC) and multipotent progenitors (MPP) from the bone marrow (BM), spleen, and blood (n=6-18). FIG. 1B depicts a schematic overview of experimental strategy to generate mouse leukemic MLL-AF9 cells. FIG. 1C is a chart depicting the median fluorescence intensity (MFI) of VCAM1 on bulk control healthy and leukemic MLL-AF9 BM cells (left panel), and healthy HSCs and leukaemia stem cells (LSCs, right panel). LSCs were phenotypically defined as Lineage$^-$ IL7Rα$^-$ Sca1$^-$ MLL-AF9 GFP$^+$ c-Kit$^{high}$ CD34$^{low}$ FcγRII/III$^{high}$ cells. (n=6-9); MPP (LSK CD150$^-$ CD48$^-$); HSC (LSK CD150$^+$ CD48$^-$).

FIGS. 2A-2G depict experimental results demonstrating that VCAM1 endogenous deletion does not cause significant hematopoietic defects. FIG. 2A is a chart depicting fluorescent-activated cell sorting (FACS) analysis of the BM of Csf1r-iCre;loxp-TdTomato transgenic mice showing the recombination efficiency of Csf1r-iCre in phagocytes, HSC and MPP (n=3-6). FIG. 2B depicts experimental results demonstrating that VCAM1 is efficiently depleted in VCAM1$^{Δ/Δ}$ BM HSCs, as seen by FACS (n=4-13) and mRNA (n=4-6) analyses (absolute number of BMNCs, HSCs and MPPs per femur in control and VCAM1$^{Δ/Δ}$ mice (n=5-6)). FIG. 2D is a chart depicting experimental results demonstrating that colony output on day 7 of BM colony-forming unit in culture from control and VCAM1$^{Δ/Δ}$ mice (n=3), (GEMM: granulocyte, macrophage, erythroid and megakaryocyte; GM: granulocyte and macrophage; M: macrophage; G: granulocyte; BFU-E: erythroid). FIG. 2E is a chart depicting experimental results comparing concentration of white blood cells (WBC), erythrocytes (RBC) and platelets (PLTs) in the blood of VCAM1$^{Δ/Δ}$ mice as compared to littermate controls (n=12). FIG. 2F Concentration of HSCs and MPPs in the blood of VCAM1$^{Δ/Δ}$ mice as compared to littermate VCAM1 floxed controls (n=3). FIG. 2G depicts a pair of charts quantifying spleen cellularity (left) and absolute number of HSC and MPP (right) per spleen in control and VCAM1$^{Δ/Δ}$ mice (n=5). Error bars, mean±s.e.m. *p<0.05, p<0.01, **p<0.0001; unpaired Student's t test.

FIGS. 3A-3E depict experimental results showing that VCAM1-deficient HSCs exhibit normal viability, cell cycle, and proliferation. FIG. 3A depicts a chart showing the percentage of viable (Annexin V$^-$ DAPI$^-$) HSC and MPP in the BM of control and VCAM1$^{Δ/Δ}$ mice (n=3). FIG. 3B is a chart showing cell cycle analysis, using anti-Ki67 and Hoechst 33342 staining of HSCs from control and VCAM1$^{Δ/Δ}$ mice (n=3-4). FIG. 3C is a chart showing the percentage of proliferating HSC in the BM of control and VCAM1$^{Δ/Δ}$ mice, as determined by BrdU incorporation (n=4). FIG. 3D Quantitative PCR (qPCR) analysis of cell cycle regulator genes within sorted HSCs from control and VCAM1$^{Δ/Δ}$ mice. FIG. 3E depicts a series of charts showing the number of BMNCs, MPP and HSC per femur in control and VCAM1$^{Δ/Δ}$ mice after 5-FU injection (n=3-5). Error bars, mean±s.e.m. Non-significant (ns); *p<0.05. Unpaired Student's t test (FIGS. 3A-3E).

FIGS. 4A-4E depict experimental results illustrating that blocking anti-VCAM1 antibody treatment decreases the number of leukaemia stem cells and synergizes with cytarabine in vivo. FIG. 4A is a graphical depiction of an outline of experiment strategy. Moribund sick secondary recipient leukemic mice were daily injected with IgG control (100 μg), anti-VCAM1 antibody (100 μg), cytarabine (100 mg/kg) or a combination of anti-VCAM1/cytarabine for 5 days. Mice were analysed by FACS 1 day after the last injection. FIG. 4B is a series of charts showing BM cellularity, absolute number, and percentage of bulk MLL-AF9-GFP$^+$ cells and LSCs in the BM of control and treatment groups (n=5-6). FIG. 4C is a chart showing the percentage of MLL-AF9-GFP$^+$ cells in the blood of recipient hosts comparing pre- and post-treatment (n=5). FIG. 4D depicts survival curves of leukemic treatment groups. Arrow points to the beginning of treatment. IgG and anti-VCAM1 were administered during 10 consecutive days every and cytarabine groups during 5 consecutive days. All treatments were repeated after 4 weeks. FIG. 4E depicts a series of charts quantifying BM cellularity (left) and absolute number of HSC, MPP, and LSK per femur (middle) and per mL of blood (right) in healthy C57BL/6 mice treated for 5 days with daily injections of either anti-VCAM1 or IgG control antibody (100 μg) (n=5). Error bars, mean±s.e.m. *p<0.05, p<0.01, *p<0.001, ****p<0.0001; unpaired Student's t test (FIG. 4E) and paired Student's t test (FIG. 4C). One-way ANOVA analyses followed by Tukey's multiple comparison tests were in (FIG. 4B). Log-rank analysis was used for the Kaplan-Meier survival curves in (FIG. 4D).

FIGS. 5A-5E. FIGS. 5A-5E are a series of figures showing that treatment of healthy wild-type mice with a blocking anti-VCAM1 monoclonal antibody. FIG. 5A depicts an outline of experiment strategy. FIG. 5B depicts experimental results from BM cells from treated groups that were incubated with an anti-rat antibody and after washing stained for phenotypic HSCs and probed for VCAM1 expression. FIG. 5C depicts a chart quantifying cells per mL of blood in healthy C57BL/6 mice treated for 5 days with daily injections of either anti-VCAM1 or IgG control antibody (n=5). FIG. 5D is a chart depicting body, liver, and spleen weight of IgG and anti-VCAM1-treated mice from FIG. 5A. FIG. 5E is a table depicting hematology lab analysis results of peripheral blood drawn post-treatment. White blood cell (WBC), red blood cell (RBC), hemoglobin (HGB), hematocrit (HCT), platelets (PLT), neutrophils (Neut.), lymphocytes (Lymph.), reticulocytes (Retic.). P-values of IgG compared to anti-VCAM1 treated mice are shown for each parameter (n=5). Error bars, mean±s.e.m. Non-significant (ns); unpaired Student's t test.

FIGS. 6A-6D are a series of figures showing that high VCAM1 expression is associated with poor prognosis in human AML patients. FIGS. 6A and 6B are charts depicting experimental results of Kaplan-Meier (FIG. 6A) overall and (FIG. 6-B) disease free survival of AML patients (TCGA, Ley et al., 2013) with high and low VCAM1 expression (mRNA expression z-Score threshold±2). FIGS. 6C and 6D depict survival curves of NSG mice transplanted with primary human AML samples and treated with (FIG. 6C) control IgG or anti-VCAM1 antibody or (FIG. 6D) with cytarabine or the combination cytarabine/anti-VCAM1. Log-rank analysis was used for the Kaplan-Meier survival curves to calculate p value.

FIGS. 7A and 7B depict VCAM1 expression in human cancer cell lines. FIG. 7A depicts a pie chart showing VCAM1 expression status across 675 human cancer cell lines. FIG. 7B is a chart showing mean distribution of VCAM1 expression (reads per kilobase of transcript per million mapped reads—RPKM) per human cancer cell line, grouped by metastatic tissue of origin.[45]

FIG. 8 depicts a chart showing VCAM1 genetic alterations in primary human cancer tissues. The chart displays a cross-cancer alteration summary for VCAM1 from 126 human cancer genomics studies generated by cBioPortal for Cancer Genomics from MSKCC.

FIGS. 9A-9G depict experimental result showing that VCAM1 provides "don't-eat-me" recognition. FIG. 9A depicts charts showing the concentration of HSCs, MPPs and colony-forming unit cell (CFU-C) in the blood of $VCAM1^{Csf1r-iCre}$ mice as compared to littermate $VCAM1^{fl/fl}$ (n=3-4). FIG. 9B depicts a chart showing the time course of blood chimerism post-transplant of $VCAM1^{fl/fl}$ and $VCAM1^{Csf1r-iCre}$ donor cells. FIG. 9C depicts a series of charts showing in vivo phagocytosis assay comparing $VCAM1^{fl/fl}$ and $VCAM1^{Csf1r-iCre}$ Lineage$^-$ cells labelled with CFDA-SE and transplanted. Recipient mice were sacrificed 4 days after and the percentage of recipient CD45.1 CFDA-SE$^+$ phagocytic cells determined by FACS in the BM and spleen (n=4-5). FIG. 9D depicts a representative immunofluorescence image of splenic F4/80$^+$ macrophages with $VCAM1^{Csf1r-iCre}$ phagocytosed CFDA-SE$^+$ cells (arrowheads). FIG. 9E depicts a chart showing experimental results where blood circulation was connected between CD45.2 $VCAM1^{fl/fl}$ and $VCAM1^{Csf1r-iCre}$ mice and CD45.1 mice by parabiotic surgery and mobilization induced by G-CSF injection. Frequency of donor CD45.2 HSC and MPP from $VCAM1^{fl/fl}$ and $VCAM1^{Csf1r-iCre}$ that homed and engrafted in the BM of CD45.1 paired mice, one week after the last G-CSF injection (n=3). FIG. 9F depicts a chart showing examples of BM HSC chimerism plots for $VCAM1^{fl/fl}$ and $VCAM1^{Csf1r-iCre}$ donors. MPP (LSK CD150$^-$ CD48$^-$); HSC (LSK CD150$^+$ CD48$^-$). Error bars, mean s.e.m. Unpaired Student's t test (FIGS. 9A-9C, 9E).

FIGS. 10A-10H depict experimental results showing that VCAM1 is essential for HSC engraftment in haplotype-mismatched transplantation. FIG. 10A depicts a schematic diagram and survival curve showing $VCAM1^{fl/fl}$ and $VCAM1^{Csf1r-iCre}$ syngeneic (H-2$^{b/b}$) and haplotype-mismatched (H-2$^{b/q}$) lines used. H-2$^b$ (C57BL/6 strain) and H-2$^q$ (FVB/N strain). Survival curve of recipient mice given lethal radiation and transplanted with 2 million BMNCs, non-competitive transplantation (n=6-11). FIGS. 10B and 10C depict charts showing quantification of long-term haematopoietic reconstitution from syngeneic and haplotype-mismatched $VCAM1^{fl/fl}$ and $VCAM1^{Csf1r-iCre}$ cells by competitive reconstitution assays in the blood (FIG. 10B) and in the BM (FIG. 10C), 16 weeks post-transplantation (n=6-14). FIG. 10D depicts a chart showing quantification of tri-lineage (My, myeloid; B cell and T cell) engraftment in the mice analyzed in FIGS. 10B and 10C. FIG. 10E depicts a chart showing percentage of BM immune cells double positive for VLA4 and PIR-B, as determined by FACS (n=3). FIG. 10F depicts a series of charts showing phospho-flow analysis of tyrosine phosphorylation (P-TYR) levels in host CD45.1$^+$ PIR-B$^+$ phagocytic cells transplanted with haplotype-mismatched CD45.2 $VCAM1^{fl/fl}$ and $VCAM1^{Csf1r-iCre}$ cells. P-TYR levels are represented as median fluorescent intensity (MFI) normalized to the basal P-TYR levels of phagocytic cells in Pirb$^{-/-}$ mice (n=5). FIG. 10G depicts a representative FACS histogram for P-TYR levels in host CD45.1$^+$ Gr1high PIR-B$^+$ monocytes from the mice in FIG. 10F. FIG. 10H depicts a chart showing quantification of hematopoietic reconstitution from syngeneic and haplotype-mismatched $VCAM1^{fl/fl}$ and $VCAM1^{Csf1r-iCre}$ cells by competitive reconstitution assays into Pirb$^{-/-}$ mice, 1 week post-transplantation (n=6). Donor cell engraftment was evaluated by detecting the levels of donor male DNA in the female recipient blood, by real-time PCR. Error bars, mean±s.e.m. unpaired Student's t test (FIGS. 10B, 10F). One-way ANOVA analyses followed by Tukey's multiple comparison tests (FIGS. 10C, 10D, 10H). Log-rank analysis was used for the Kaplan-Meier survival curves in (FIG. 10A).

FIGS. 11A-11F depict experimental results showing that loss of VCAM1 inhibits the establishment and progression of MLL-AF9-induced AML and markedly improved survival in mouse model. FIG. 11A depicts charts showing analysis of AML primary recipients transplanted with haplotype-mismatched $VCAM1^{fl/fl}$ and $VCAM1^{Csf1r-iCre}$ transduced MLL-AF9-GFP LSKs, after 55 days. BM cellularity and percentage of AML-GFP$^+$ cells and LSCs (n=5). FIG. 11B depicts representative images of a sternal BM segment from the mice analyzed in FIG. 11A. FIG. 11C depicts experimental results from pre-leukemic haplotype-mismatched $VCAM1^{fl/fl}$ and $VCAM1^{Csf1r-iCre}$ luciferase expressing AML cells that were transplanted into sub-lethally irradiated mice and leukemia progression was quantified by bioluminescence (n=5). Luciferase imaging of representative mice from each group is shown at week 10 post-transplant. FIG. 11D depicts a chart showing Kaplan-Meier survival analysis of secondary recipient mice receiving 20,000 GFP$^+$ leukemia cells from haplotype-mismatched $VCAM1^{fl/fl}$ and $VCAM1^{Csf1r-iCre}$ primary recipients. FIG. 11E depicts charts showing the BM cellularity and absolute number of macrophages per femur in C57BL/6 mice treated with PBS or clodronate liposomes and transplanted with $VCAM1^{fl/fl}$ and $VCAM1^{Csf1r-iCre}$ pre-leukemic cells, at week 4 (n=5). FIG. 11F depicts a chart showing the percentage of haplotype-mismatched AML-VCAM1$^{fl/fl}$ or AML-VCAM1$^{Csf1r-iCre}$ GFP$^+$ cells in the blood of recipient hosts treated with weekly injections of PBS or clodronate liposomes (n=5-10). Error bars, mean±s.e.m. unpaired Student's t test (FIGS. 11A, 11C, 11F). Log-rank analysis was used for the Kaplan-Meier survival curves in FIG. 11D. One-way ANOVA analyses followed by Tukey's multiple comparison tests were used in FIG. 11E.

FIGS. 12A-12C depict experimental results showing that anti-VCAM1 antibody treatment blocks human primary AML progression and extends the survival of NSG-transplanted mice. FIG. 12A depicts a schematic outline of experimental strategy. NSG mice were transplanted with primary human AML and upon disease establishment were daily injected with IgG1 control (100 μg) or anti-human VCAM1 antibody (100 μg) for 10 days. FIG. 12B depicts a chart showing survival of leukemic mice treated in FIG. 12A. FIG. 12C depicts a schematic diagram showing immune cells and receptors mediating the cooperative anti-phagocytic activity of VCAM1 and MHC-I enabling "don't-eat-me" or "kill-me" activity. Log-rank analysis was used for the Kaplan-Meier survival curves (FIG. 12B).

FIGS. 13A-13D depict experimental results showing VCAM1 is expressed on HSCs and progenitor cells. FIGS. 13A and 13B depict gating strategies for the analyses of HSC and progenitor populations. FIG. 13C depicts representative histograms of VCAM1 expression levels in the populations represented. FIG. 13D depicts a chart showing the percentage of VCAM1 positive cells within progenitor cell populations from the bone marrow (BM) and spleen (n=3).

FIGS. 14A-14D depict experimental results demonstrating that VCAM1-deficient HSCs exhibit normal viability, cell cycle, and proliferation. FIG. 14A depicts a schematic overview of experimental strategy. FIG. 14B depicts a survival curve of recipient mice given lethal radiation and transplanted with 2 million BM nuclear cells (BMNCs) from VCAM1$^{fl/fl}$ (control) and VCAM1$^{Csf1r-iCre}$ mice, non-competitive transplantation (n=7-8). FIG. 14C depicts a schematic overview of experimental strategy. FIG. 14D depicts a chart showing quantification of long-term reconstituting HSCs from VCAM1$^{fl/fl}$ and VCAM1$^{Csf1r-iCre}$ mice by competitive reconstitution assay in the blood (n=9-15).

FIGS. 15A-15C depict experimental results demonstrating that the distribution of HSCs in the mouse BM is not altered after VCAM1 deletion in Csf1r-iCre$^+$ cells. FIG. 15A depicts representative whole-mount images of the sternal BM of control and VCAM1$^{Csf1r-iCre}$ mice and magnified high power view. The dashed outline denotes bone-BM border. Arterioles (Art) are identified by CD31$^+$ CD144$^+$ Sca1$^+$ expression. Phenotypic HSC are identified by Lineage-CD41$^-$ CD48$^-$ CD150$^+$ expression, and megakaryocytes (Mk) are distinguished by their size, morphology, and CD41$^+$ CD150$^+$ expression. FIGS. 15B and 15C depict charts quantifying the localization of HSCs relative to arterioles (FIG. 15B) and Mks (FIG. 15C) in VCAM1$^{fl/fl}$ and VCAM1$^{Csf1r-iCre}$ mice. Error bars, mean±s.e.m. Two-sample Kolmogorov-Smirnov tests were used for comparisons of distribution patterns in FIGS. 15B and 15C.

FIGS. 16A-16C depict experimental results showing that VCAM1 acts as a "don't-eat-me" signal. FIG. 16A depicts a chart quantifying the absolute number of donor (CD45.2) VCAM1$^{fl/fl}$ and VCAM1$^{Csf1r-iCre}$ cells that homed to the BM of lethally irradiated CD45.1 recipients, 3 hours after injection (n=5). FIG. 16B depicts representative FACS plots of the in vivo phagocytosis assay in FIG. 9C. FIG. 16C depicts a schematic outline of experiment strategy. Lethally irradiated CD45.1 recipients were transplanted competitively with 2 million of VCAM1$^{Csf1r-iCre}$ or VCAM1$^{fl/fl}$ BMNCs. At day 6, the BM of recipient mice were analyzed by FACS and the number of host phagocytic Gr1$^{high}$ monocytes, Gr1$^{low}$ monocytes, macrophages and neutrophils quantified. Error bars, mean±s.e.m. Unpaired Student's t test (FIGS. 16A, 16C).

FIGS. 17A-17C depict experimental results showing that the Csf1r-iCre transgene is genetically linked to the MHC locus. FIG. 17A depicts representative FACS plots of DAPI$^-$ BMNCs cells from the same H-2$^{b/q}$ MHC-haplotype heterozygous mouse. Cells were stained with antibodies against MHC-I and II subclasses corresponding to the H-2$^b$ (C57BL/6 strain) and H-2$^q$ (FVB/N strain) haplotypes. FIG. 17B depicts a table showing calculation of the frequency of recombination between the Csf1r-iCre transgene and the MHC locus. FIG. 17C depicts a series of charts showing quantification of tri-lineage (myeloid, B cell, and T cell) engraftment in the blood of mice analyzed in FIG. 9C (n=6-14). Error bars, mean±s.e.m. Unpaired Student's t test (FIG. 17C).

FIGS. 18A-18C depict experimental results showing the survival defect of mice transplanted with VCAM1$^{Csf1r-iCre}$; H-2$^{b/q}$ BMNCs could not be rescued by CD8$^+$ T cells depletion. Recipient mice were treated with a monoclonal anti-CD8 antibody or IgG control, lethally irradiated and transplanted with 1 million BMNCs from haplotype-mismatched control VCAM1$^-$ or VCAM1$^{Csf1r-iCre}$ mice (FIGS. 18A, 18B). FIG. 18A depicts representative FACS plots and percentage of T cell populations in the peripheral blood of mice treated with anti-CD8 antibody or IgG control before transplantation. FIG. 18B depicts survival curves of recipient mice depleted of CD8$^+$ T cells and BM transplanted (n=5). FIG. 18C depicts a chart showing quantification of reconstituting HSPCs from syngeneic and haplotype mismatch VCAM1$^{fl/fl}$ and VCAM1$^{Csf1r-iCre}$ cells by competitive reconstitution assays into Pirb$^{-/-}$ mice (n=6). Donor cell engraftment was evaluated by detecting the levels of donor male DNA in the female recipient blood, by real-time PCR. Error bars, mean±s.e.m. Log-rank analysis was used for the Kaplan-Meier survival curves in FIG. 28B. One-way ANOVA analyses followed by Tukey's multiple comparison tests was used in FIG. 18C.

FIGS. 19A-19E depict experimental results showing that loss of VCAM1 inhibits the establishment and progression of MLL-AF9-induced AML. FIG. 19A depicts a schematic overview of experimental strategy. FIG. 19B shows representative FACS plots of BM leukemic stem cells (LSCs) from control AML-VCAM1$^{fl/fl}$ (top) and AML-VCAM1$^{Csf1r-iCre}$ (bottom) primary recipients, 55 days after transplantation. FIG. 19C depicts a histogram showing the presence of leukemic VCAM1$^+$ LSCs derived from VCAM1$^{Csf1r-iCre}$ mice in the BM of moribund secondary recipient mice, 103 days post-transplant. FIG. 19D depicts charts quantifying the number of phagocytic cells per femur in C57BL/6 mice treated with PBS or clodronate liposomes and transplanted with control VCAM1$^{fl/fl}$ or VCAM1$^{Csf1r-iCre}$ pre-leukemic cells, at week 4 (n=5). FIG. 19E depicts charts showing experimental results wherein MLL-AF9-GFP$^+$ cells were incubated in the presence of anti-VCAM1 blocking antibody, isotype control or camptothecin-positive control. After 4.5 hours incubation, apoptotic cells were identified by Annexin V staining, as determined by FACS (n=4). Error bars, mean±s.e.m. One-way ANOVA analyses followed by Tukey's multiple comparison tests (FIGS. 19D, 19E).

FIGS. 20A-20J depict experimental results showing that high VCAM1 expression correlates with poor prognosis in human AML. FIG. 20A depicts a schematic overview of experiment strategy. MOLM-13 cells were transduced with a human VCAM1-ZsGreen expressing (hVCAM1) or ZsGreen control (Mock) lentivirus and transplanted into immunocompromised NODscid Il2rg$^{-/-}$ (NSG) mice. FIG. 20B depicts a histogram showing human VCAM1 expression on Mock$^-$ and hVCAM1-MOLM-13 cells. FIG. 20C depicts a chart showing percentage of human CD45$^+$ AML cells in the blood of MOLM-13 transplanted mice. FIG. 20D depicts Kaplan-Meier survival analysis of mice receiving Mock– and hVCAM1-MOLM-13 cells. FIGS. 20E and 20F depict charts showing BM cellularity (FIG. 20E) and number of MOLM-13 cells that homed to the BM of recipient mice (FIG. 20F), 3 hours after injection. FIGS. 20G and 20H depict a chart showing the percentage of Annexin V$^+$ apoptotic (FIG. 20G) and proliferating BrdU$^+$ MOLM-13 cells (FIG. 20H) in the BM of recipient mice. FIG. 20I depicts the Kaplan-Meier survival analysis of mice with established hVCAM1-MOLM-13 AML (>1% human CD45$^+$ cells in the blood) and treated with daily injections of IgG1 (100 µg) and anti-human VCAM1 monoclonal antibody (100 µg) for 10 days. FIG. 20J depicts a chart quantifying VCAM1 gene expression data from sorted human AML BM samples and healthy controls. Lineage$^-$ CD34$^+$ CD38$^-$ CD90$^+$ cells (referred to as LT-HSCs), Lineage$^-$ CD34$^+$ CD38$^-$ CD90$^-$ cells (referred to as ST-HSCs), and Lineage$^-$ CD34$^+$ CD38$^+$ CD123$^+$ CD45RA$^+$ cells (referred to as GMPs). Cytogenetic abnormalities are depicted as: NK, normal karyotype; CK, complex karyotype; 7q, deletion of chromosome 7 (n=4-6). Error bars, mean±s.e.m. Unpaired student's t test (FIGS. 20C, 20E-20H). Log-rank analysis was used for the Kaplan-Meier survival curves in FIGS. 20D, and 20I. One-way ANOVA analyses followed by Tukey's multiple comparison tests (FIG. 20J). ns, non-significant.

FIGS. 21A-21G depict a series of experimental results showing that deletion of MAEA impairs bone marrow macrophage development and the erythroblastic island. FIG. 21A depicts a representative histogram showing MAEA expression on BM leukocytes from MAEA$^{fl/fl}$ control and MAEA$^{Csf1r-Cre}$ mice. FIG. 21B depicts a chart showing deletion efficiency by Csf1r-Cre of MAEA on bone marrow macrophages as determined by FACS (n=8). FIG. 21C depicts a chart showing quantification of total BM cellularity in MAEA$^{fl/fl}$ and MAEA$^{Csf1r-Cre}$ mice (n=8). FIGS. 21D and 21E depict representative FACS plots and quantification showing significant reduction of macrophage (FIG. 21D) and erythroblast (FIG. 21E) numbers in the bone marrow of MAEA$^{Csf1r-Cre}$ mice compared to littermate control (n=8). FIG. 21F is a chart depicting quantification of erythroblasts at various stages of maturation (subpopulation I-V represents: I: proerythroblasts, II: basophilic erythroblasts, III: polychromatic erythroblasts, IV: orthochromatic erythroblasts and reticulocytes, V: mature RBCs) (n=8). FIG. 21G is a chart depicting RBC counts of MAEA$^{fl/fl}$ and MAEA$^{Csf1r-Cre}$ mice (n=10). Data are shown as mean±s.e.m. *p<0.05, p<0.01, *p<0.001, ****p<0.0001 by unpaired Student's t test.

FIGS. 22A-22H depict a series of experimental results showing that deletion of MAEA impairs bone marrow macrophage development and erythroblastic niche. FIG. 22A depicts a schematic representation of the MAEA$^{targeted}$ allele, MAEA$^{floxed}$ allele and MAEA$^{delta}$ allele generated using EuMMCR targeting vector PG00141_Z_1_G10. Exons are depicted by boxes with coding regions indicated by shading. FRT sites are marked as white triangles and LoxP sites as black triangles. The IRES-LacZ reporter (LacZ) and the neomycin resistance cassette (Neo) were deleted by crossing with a Flpe-expressing deleter strain. Upon tissue-specific or temporal Cre recombinase induction, the MAEA exon 5 will be deleted which will result in a null MAEA$^{delta}$ allele caused by non-sense mediated decay. FIG. 22B is an image of PCR analysis identifying the wild-type (WT), MAEA$^{floxed}$, and MAEA$^{targeted}$ alleles. FIG. 22C depicts representative FACS plots and quantification showing impaired in vivo formation of BM erythroblastic islands (F4/80$^+$ Ter 19$^+$ live multiplets) in MAEA$^{Csf1r-Cre}$ mice (n=5). FIG. 22D depicts Wright-Giemsa stained smears from control and MAEA$^{Csf1r-Cre}$ peripheral blood. Scale bar=50 µm. FIG. 22E depicts a chart showing quantification of spleen erythroblasts in MAEA$^{Csf1r-Cre}$ mice (n=8). FIG. 22F depicts a chart showing burst-forming unit-erythroid (BFU-E) in MAEA$^{Csf1r-Cre}$ spleen (n=5). FIG. 22G depicts representative histograms and quantification shown prolonged half-life of in vivo biotinylated RBCs in MAEA$^{Csf1r-Cre}$ mice (n=5). FIG. 22H depicts charts showing RBC counts and HCT in splenectomized control and MAEA$^{Csf1r-Cre}$ mice (n=5). Data are shown as mean±s.e.m. *p<0.05, p<0.01, *p<0.001, ****p<0.0001 by unpaired Student's t test.

FIGS. 23A-23H depict experimental results showing that MAEA is required for HSC engraftment. FIG. 23A depicts a series of charts showing the reconstitution capability of MAEA$^{fl/fl}$ and MAEA$^{Csf1r-Cre}$ HSCs as determined by competitive BM transplantation (n=5). 1×10$^6$ of donor (CD45.2) BM cells were competitively transplanted with equal number of competitor (CD45.1) BM cells into lethally irradiated recipient mice (CD45.1). Percentage of donor derived B220$^+$ B, CD3$^+$ T, and CD11b$^+$Gr1$^+$ myeloid cells were quantified at indicated time points. FIG. 23B is a schematic diagram of the experimental design of the reciprocal BMT performed. FIG. 23C depicts a chart showing the percentage of donor derived cells were quantified in the BM, peripheral blood, and spleen of the control and MAEA$^{Csf1r-Cre}$ recipients 16 weeks after the transplant. FIGS. 23D and 23E depict charts quantifying WBC counts (FIG. 23D) and BM cellularity (FIG. 23E) in control and MAEA$^{Csf1r-Cre}$ recipient mice 16 weeks after the transplant (n=5). FIG. 23F depicts a chart quantifying the frequency of B, T, and myeloid cells in total WBCs of control and MAEA$^{Csf1r-Cre}$ reciprocal recipients (n=5). FIGS. 23G and 23H depict charts showing the quantification of BM macrophages (FIG. 23G) and erythroblasts (FIG. 23H) control and MAEA$^{Csf1r-Cre}$ reciprocal recipients (n=5). Data are shown as mean±s.e.m.

FIGS. 24A-24F depict experimental results demonstrating that MAEA is required for HSC engraftment but dispensable for their maintenance. FIG. 24A depicts plots of cell cycle analysis of BM HSCs by Ki-67 and H33342 dye staining (n=3). FIG. 24B depicts charts quantifying cleaved caspase3 expression in BM LSKs from the control and MAEA$^{Csf1r-Cre}$ mice (n=3). FIG. 24C depicts charts showing an assessment of peripheral blood recovery of the control and MAEA$^{Csf1r-Cre}$ mice after 250 mg/kg of 5-FU challenge (n=6). FIG. 24D depicts charts showing BM total cellularity, LSK, and HSC numbers of the control and MAEA$^{Csf1r-Cre}$ mice 4 weeks after 5-FU injection. FIG. 24E depicts charts showing the quantification of homed BMNCs and LK cells from control and MAEA$^{Csf1r-Cre}$ mice in lethally irradiated WT CD45.1 recipients (n=5). FIG. 24F depicts a chart showing comparable differentiation potential of control and MAEA$^{Csf1r-Cre}$ LSK cells measured by colony-forming assays (n=4).

FIGS. 25A-25D depict experimental results demonstrating that MAEA over-expression is associated with poor prognosis of human cancers. FIG. 25A depicts a chart showing cross-cancer alteration summary for MAEA from 126 human cancer genomics studies generated by cBioPortal for Cancer Genomics from MSKCC. FIG. 25B depicts charts showing Kaplan-Meier overall and disease-free survival of AML patients (TCGA, NEJM 2013) with high and low MAEA expression (mRNA expression z-Score threshold±2). FIGS. 25C and 25D depict charts showing Kaplan-Meier overall survival of ovarian cancer and lung adenocarcinoma patients (TCGA) with high and low MAEA expression (mRNA expression z-Score threshold±2). The significance is based on log rank test estimate of p values.

FIGS. 26A-26K depict experimental results demonstrating that MAEA is required for mouse AML engraftment and progression. FIG. 26A depicts a schematic showing development of an MLL-AF9 acute myeloid leukemia (AML) model. FIG. 26B depicts a chart showing expression level of MAEA, measured by mean fluorescent intensity (MFI), in total bone marrow cells (BM), LSK, lineage$^-$ ckit$^+$ (LK) and granulocyte-macrophage progenitors (GMP) of healthy and AML mice. In leukemic mice, both GFP$^+$ AML cells (AML) and their residual GFP$^-$ healthy counterparts (non-AML) were assessed. FIG. 26C depicts a chart quantifying of GFP$^+$ AML cells in primary sub-lethally irradiated recipients that received Ctrl and MAEA$^{Csf1r-Cre-}$ pre-leukemic cells. FIG. 26D depicts charts showing an assessment of the peripheral blood of mice transplanted with control and MAEA$^{Csf1r-Cre}$ pre-leukemic cells at 10-12 weeks after transplant (PLT=platelet). FIG. 26E depicts a survival curve of mice transplanted with control and MAEA$^{Csf1r-Cre}$ pre-leukemic cells (n=5). p value is determined by Log-rank test. FIG. 26F depicts representative FACS analysis of BM cells from control and MAEA$^{Csf1r-Cre}$ pre-leukemic mice at 10-12 weeks after transplant. FIGS. 26G and 26H depict charts showing quantification of total leukaemia load (GFP$^+$) (FIG. 26G) and leukemic GMP (L-GMP) (FIG. 26H) in recipients of control (black) and MAEA$^{Csf1r-Cre}$ (grey) pre-leukemic cells at 10-12 weeks after transplant (n=5). FIG. 26I depicts a chart showing the progression of circulating control and MAEA$^{Mx1-Cre}$ AML cells after a single injection of pIpC (arrow). FIG. 26J depicts a chart showing the progression of circulating wild type AML cells after injections of 60 µg anti-MAEA polyclonal antibody (arrows). FIG. 26K depicts a schematic of experimental design and a Kaplan-Meyer survival curve of wildtype mice transplanted with MLL-AF9 leukemic BM cells treated with IgG or anti-MAEA monoclonal antibody (92.25) after establishment of the leukaemia (n=5). Data are shown as mean±s.e.m. *p<0.05, p<0.01, *p<0.001, ****p<0.0001 by unpaired Student's t test.

FIGS. 27A-27E depict experimental results of wild type mice treated with IgG and anti-MAEA antibody. Wild type mice were given three doses of 60 µg IgG and anti-MAEA antibody i.v. every other day and analysed 2 days after the last injection. FIGS. 27A-27D depict a series of charts showing total body, spleen, and liver weight (FIG. 27A), BM and spleen cellularity (FIG. 27B), erythroblasts percentage in the BM (FIG. 27C), and LSK and HSC percentages in the BM and spleen (FIG. 27D) of IgG and anti-MAEA antibody treated mice. FIG. 27E depicts a table summary of peripheral blood parameters from mice treated with IgG and anti-MAEA antibody. (WBC=white blood cells; RBC=red blood cells; HGB=haemoglobin; HCT=haematocrit; MCV=mean corpuscular volume; PLT=platelets; Retic=reticulocyte; Lymph=lymphocyte). Data are shown as mean±s.e.m. *p<0.05, **p<0.01 by unpaired Student's t test.

FIGS. 28A-28D depict experimental results showing MAEA expression in human cancer cell lines. RNA-seq data of 675 human cancer cell lines across tissue types were previously published[45] and made available on the web at research-pub.gene.com/KlijnEtAl2014. FIG. 28A depicts a chart showing the distribution of MAEA mRNA expression (RPKM) across all 675 lines. FIG. 28B depicts a chart showing MAEA expression in cancer cell lines across their tissue origin. FIGS. 28C and 28D depict charts showing MAEA expression in lung (FIG. 28C) and ovarian (FIG. 28D) cancer cell lines.

FIGS. 29A-29F depict experimental results showing that MAEA maintains an adult BM erythroblastic island niche. FIG. 29A depicts a chart showing validation of the specificity of mAb produced by hybridoma clone 92.25 by FACS staining of BM macrophages from wild type control and MAEA$^{Csf1r-Cre}$ mice. FIGS. 29B-29E depict charts showing quantification of total BM cellularity (FIG. 29B), BM EB numbers (FIG. 29C), EB maturation profile (FIG. 29D), and BM macrophage numbers (FIG. 29E) in isotype or anti-MAEA mAb-treated mice (n=5). FIG. 29F depicts a chart showing quantification of erythroid cells per erythroblastic island reconstituted in the presence of 10 µg/mL isotype or anti-MAEA mAb. Data are shown as mean±s.e.m. *p<0.05, p<0.01, **p<0.0001 by unpaired Student's t test.

FIGS. 30A-30J depict experimental results demonstrating that MAEA expression is enriched and required in HSCs for hematopoiesis. FIG. 30A depicts representative histograms showing MAEA expression on LSK and HSCs in control and MAEA$^{Csf1r-Cre}$ BM. FIG. 30B depicts a chart showing FACS quantification of MAEA expression on control and MAEA$^{Csf1r-Cre}$ BM HSPCs (LMPP=lymphoid-primed multipotent progenitors; CMP=common myeloid progenitors; CLP=common lymphoid progenitors; GMP=granulocyte-macrophage progenitors; MEP=megakaryocyte-erythrocyte progenitors; neutrophils=Neu; B cells=B; and monocytes=MN) (n=3 each group). FIG. 30C depicts a chart showing the Kaplan-Meyer survival curve of control and MAEA$^{Csf1r-Cre}$ mice. p value was calculated by log-rank test (n=5-8). FIG. 30D depicts charts showing WBC counts in peripheral blood and frequency of B, T and myeloid cells in total WBCs of young adult control and MAEA$^{Csf1r-Cre}$ mice. FIG. 30E depicts charts showing quantifications of HSC and LSK numbers in BM of control and MAEA$^{Csf1r-Cre}$ mice. FIG. 30F depicts charts showing quantification of myeloid progenitors in BM of control and MAEA$^{Csf1r-Cre}$ mice. FIG. 30G depicts charts showing quantification of lymphoid progenitors in BM of control and MAEA$^{Csf1r-Cre}$ mice. FIG. 30H depicts a schematic of an experimental scheme and charts depicting results for evaluating lymphoid differentiation potential of HSC and LMPP at single cell level. Data are shown as mean±s.e.m. *p<0.05 by unpaired Student's t test.

FIGS. 31A-31K depict experimental results demonstrating that an MAEA-deletion impairs HSC quiescence and function in a mTOR-dependent manner. FIG. 31A depicts a schematic diagram of an experimental scheme for deleting MAEA in adult mice using Mx1-Cre.

FIG. 31B depicts a chart showing quantification of BM HSC numbers at indicated time points after poly I:C injection. FIG. 31C depicts representative FACS plots and cell cycle profiles of control and MAEA$^{Mx1-Cre}$ HSCs at 21 days after a first poly I:C injection. FIG. 31D depicts a schematic of an experimental scheme for deleting MAEA in 1:1 wild type and MAEA$^{Mx1-Cre}$ BM chimeras after stable (8 weeks) reconstitution. FIG. 31E depicts a series of charts showing donor chimerism in BM LSK and HSCs and peripheral blood total leukocytes from control and MAEA$^{Mx1-Cre}$ mixed chimeric mice at indicated time points after poly I:C injection. FIG. 31F depicts RNA-seq and Gene Set Enrichment Analysis (GSEA) of control and MAEA$^{Csf1r-Cre}$ HSCs. Three replicates with 2000 HSCs were pooled from 2 mice each replicate were processed and analyzed for each group. Top KEGG (Kyoto Encyclopedia of Genes and Genomes) pathways that are up-regulated and downregulated in MAEA$^{Csf1r-Cre}$ HSCs are shown. FIG. 31G depicts three examples of GSEA enrichment plots showing enrichment of Proteasome, Oxidative phosphorylation, and mTOR signaling pathways in MAEA$^{Csf1r-Cre}$ HSCs. FIG. 31H depicts a GSEA enrichment plot showing significant down-regulation of lymphoid potential related gene set in MAEA$^{Csf1r-Cre}$ HSCs. FIG. 31I depicts a heat map showing mean expression of HSC related genes in control and MAEA$^{Csf1r-Cre}$ HSCs. FIG. 31J depicts a schematic representation of an experimental scheme and a chart quantifying LSKs and HSCs in control and MAEA$^{Mx1-Cre}$ mice treated with vehicle, carfilzomib, rapamycin, or NAC 3 weeks after poly I:C induction. FIG. 31K depicts a chart showing donor chimerism in peripheral blood of CD45.1 lethally irradiated wild-type recipients at indicated time points after competitive BM transplantation of equal number of CD45.1 wild type competitor BM cells and CD45.2 donor BM cells from indicated groups (n=5 each group). Data are mean±s.e.m. *p<0.05, p<0.01, *p<0.001, ****p<0.0001 by unpaired Student's t test. n.s., not significant.

FIGS. 32A-32I depict experimental results demonstrating that MAEA regulates cytokine receptor stability and autophagy in HSCs. FIG. 32A depicts representative immunofluorescence images showing MAEA and CD150 expression in HSCs (scale bar=10 m). FIG. 32B depicts representative ubiquitin array images and quantified mean spot pixel intensity of selected targets from freshly isolated control and MAEA$^{Csf1r-Cre}$ lineage negative BM cells (n=5). *p<0.05, p<0.01, *p<0.001, ****p<0.0001 by unpaired Student's t test. FIG. 32C depicts representative histograms and FACS evaluation of Flt3 half-life in control and MAEA$^{Csf1r-Cre}$ LSK cells incubated in the presence of 50 μM cycloheximide (n=4). *p<0.05, p<0.01, *p<0.001 by two-way ANOVA multiple comparisons. FIG. 32D depicts a schematic overview of an experimental scheme and evaluation of autophagy flux in control and MAEA$^{Csf1r-Cre}$ HSCs. Percent autophagy flux is calculated as 100×(1−(−L/N))/(+L/N). N: NH4Cl. L: leupeptin. FIG. 32E depicts representative EM micrographs of control and MAEA$^{Csf1r-Cre}$ HSCs for ultrastructural analysis of the autophagic compartments (arrows point to an autolysosome in control and an autophagosome in MAEA$^{Csf1r-Cre}$). FIG. 32F depicts charts showing morphometric analysis of control and MAEA$^{Csf1r-Cre}$ HSCs: quantification of the numbers of autophagic vacuoles (AV) and their break down into number (left) and percentage (right) of autophagosomes (APG) and autolysosomes (AUT), per cell area. At least 20 cells were analyzed in each group. FIG. 32G depicts a chart showing frequencies of HSCs in control and MAEA$^{Csf1r-Cre}$ BM cells before and after 3 hours of starvation in culture. FIG. 32H depicts charts showing quantification of LSKs and HSCs in control and MAEA$^{Mx1-Cre}$ BM treated with vehicle, lithium chloride, or verapamil 3 weeks after poly I:C induction. FIG. 32I depicts a chart showing overall peripheral blood donor chimerism in CD45.1 lethally irradiated wild type recipients at indicated time points after competitive BM transplantation of equal number of CD45.1 wild type competitor BM cells and CD45.2 donor BM cells from indicated groups (n=5 each group). Data are shown as mean±s.e.m. n.s., not significant. *p<0.05, p<0.01, *p<0.001, ****p<0.0001 by unpaired Student's t test unless otherwise indicated.

FIGS. 33A-33D depict experimental results demonstrating that MAEA$^{Csf1r-Cre}$ mice develop myeloproliferation and lymphopenia. FIG. 33A is a series of charts showing peripheral blood indices of 7 months old control and MAEA$^{Csf1r-Cre}$ mice. FIG. 33B depicts representative H&E stained paraffin sections from the livers and lungs of 7 months old control and MAEA$^{Csf1r-Cre}$ mice. Scale bar=50 μm. FIGS. 33C and 33D depict representative FACS plots (FIG. 33C) and quantification (FIG. 33D) of BM cellularity, Gr-1$^+$ and B220$^+$ cells in total BM nucleated cells in 7 months old control and MAEA$^{Csf1r-Cre}$ mice. Data are shown as mean±s.e.m. *p<0.05, p<0.01, *p<0.001, ****p<0.0001 by unpaired Student's t test.

FIGS. 34A-34E depict experimental results showing altered hematopoiesis in MAEA$^{Csf1r-Cre}$ mice. FIG. 34A depicts representative FACS plots and quantifications showing increased LSK, LK, and HSCs in the MAEA$^{Csf1r-Cre}$ mice. Events are pre-gated on the lineage$^-$ populations. FIG. 34B depicts a representative gating strategy for GMP, CMP, MEP, and MkP from the LK population in FIG. 34A. FIG. 34C depicts representative FACS plots showing decreased frequencies of LMPPs in the LSK population from the MAEA$^{Csf1r-Cre}$ mice. FIG. 34D depicts representative FACS plots showing decreased frequencies of CLPs in the Lin-Sca1$^{lo}$ckit$^{lo}$ population from the MAEA$^{Csf1r-Cre}$ mice. FIG. 34E depicts charts showing homed control and MAEA$^{Csf1r-Cre}$ total BM cells and ckit$^+$ cells in recipient BM 3 hours after transplantation (n=5 each group). Data are shown as mean±s.e.m. p<0.01, *p<0.001, ****p<0.0001 by unpaired Student's t test.

FIGS. 35A-35E depict experimental results demonstrating that MAEA-deletion impairs HSC quiescence and function. FIG. 35A depicts a chart quantifying LSK numbers per femur in control and MAEA$^{Mx1-Cre}$ BM at indicated time points after 1st poly I:C injection. FIG. 35B depicts a chart quantifying BM cellularity of control and MAEA$^{Mx1-Cre}$ mice at indicated time points after 1st poly I:C injection. FIG. 35C depicts quantifying cell cycle profiles of control and MAEA$^{Mx1-Cre}$ total lineage$^+$ and lineage$^-$ cells at 21 days after 1st poly I:C injection. FIG. 35D depicts a chart quantifying cell cycle analysis of BM HSCs from control and MAEA$^{Csf1r-Cre}$ mice by Ki-67 and H33342 dye staining (n=4). FIG. 35E depicts a chart quantifying HSC numbers in 7-month-old control and MAEA$^{Csf1r-Cre}$ BM. Data are shown as mean±s.e.m. *p<0.05, p<0.01, *p<0.001, ****p<0.0001 by unpaired Student's t test.

FIGS. 36A-36G show experimental results demonstrating that deletion of MAEA results in aberrant HSC activation and depletion in a mTOR-dependent manner. FIG. 36A depicts a GSEA enrichment plot showing significant upregulation of DNA replication pathway (left) and down-regulation of insulin signalling pathway (right) in MAEA$^{Csf1r-Cre}$ HSCs. FIG. 36B depicts representative histograms showing total S6 and pS6 levels and pS6/S6 ratio in control and MAEA$^{Csf1r-Cre}$ HSCs. FIG. 36C depicts a pair of charts showing pAKT (S473) and pERK1/2 (p44/42 MAPK, T202/Y204) levels in control and MAEA$^{Csf1r-Cre}$ HSCs. FIGS. 36D and 36E depict charts showing quantification of BM cellularity (FIG. 36D) and BM LSK numbers (FIG. 36E) in control and MAEA$^{Mx1-Cre}$ mice treated with vehicle, carfilzomib, rapamycin, or NAC 3 weeks after poly I:C induction. FIG. 36F depicts a series of charts showing donor chimerism in peripheral blood of CD45.1 lethally irradiated wild type recipients at the indicated time points after competitive BM transplantation of equal number of CD45.1 wild type competitor BM cells and CD45.2 donor BM cells from indicated groups (n=5 each group). FIG. 36G depicts a chart showing quantification of BM macrophage numbers in control and MAEA$^{Mx1-Cre}$ mice treated with vehicle, carfilzomib, rapamycin, or NAC 3 weeks after poly I:C induction. Data are shown as mean±s.e.m. n.s., not significant. *p<0.05, p<0.01, *p<0.001, ****p<0.0001 by unpaired Student's t test.

FIGS. 37A and 37B depict experimental results showing that MAEA regulates receptor stability and signaling. FIG. 37A is a pair of charts depicting a FACS evaluation of surface receptor Mpl and ckit half-lives in control and MAEA$^{Csf1r-Cre}$ HSPCs incubated in the presence of 50 µM cycloheximide (n=4). FIG. 37B is a series of charts depicting phospho-flow evaluation of signaling molecules pAkt, pErk and pS6/S6 ratio in control and MAEA$^{Csf1r-Cre}$ HSPCs after cytokine (TPO, FLT3, and SCF 20 ng/ml each) stimulation. Data in 37A and 37B are shown as mean±s.e.m. *p<0.05, ****p<0.0001 by two-way ANOVA multiple comparisons.

FIGS. 38A-38F depict experimental results demonstrating that MAEA regulates autophagy in HSCs. FIG. 38A is a chart showing expression of core autophagy machinery in control and MAEA$^{Csf1r-Cre}$ HSCs from RNA-seq analysis. FIG. 38B is a chart showing expression of pro-autophagy genes in control and MAEA$^{Csf1r-Cre}$ HSCs from RNA-seq analysis. FIG. 38C depicts representative histograms and FACS quantifications showing autophagy flux by LC3-II in control and MAEA$^{Csf1r-Cre}$ lineage$^+$ (upper) and lineage$^-$ (lower) BM cells, measured at the same time as in FIG. 33C. FIG. 38D depicts micrographs of whole cells (left) and examples of autophagosomes (APG, yellow arrows) and autolysosomes (AUT, red arrows) from control and MAEA$^{Csf1r-Cre}$ HSCs. Bars in inserts=0.1 mm. FIG. 38E depicts a chart showing quantification of BM macrophages in control and MAEA$^{Mx1-Cre}$ mice treated with vehicle, lithium chloride, or verapamil 3 weeks after poly I:C induction. FIG. 38F depicts a series of charts showing donor chimerism in peripheral blood of CD45.1 lethally irradiated wild type recipients at indicated time points after competitive BM transplantation of equal number of CD45.1 wild type competitor BM cells and CD45.2 donor BM cells from indicated groups (n=5 each group). Data are shown as mean±s.e.m. *p<0.05, p<0.01, *p<0.001, ****p<0.0001 by unpaired Student's t test.

FIGS. 39A-39OG depict experimental results showing the effect of a VCAM-1 antibody on sickle cell disease (SCD) mice suggesting that VCAM1 works via inhibition of leukocyte activation. FIG. 39A depicts a schematic overview of experimental design. Mice were injected by intravenous with 200 µg/mice rat IgG1 or VCAM1 antibody at 16 hours and 2 hours before TNF-α challenge (n=5, rat IgG1 antibody 200 µg/mice or VCAM1 antibody 200 µg/mice). FIG. 39B depicts a chart showing white blood cell (WBC) rolling in mice injected with rat IgG or VCAM1 antibody (p<0.0001). FIG. 39C depicts a chart quantifying number of adhesions per 100 µm in mice injected with rat IgG1 or VCAM1 antibody (p<0.0001). FIG. 39D depicts a chart quantifying red blood cell (RBC) interactions per WBCs in mice injected with rat IgG or VCAM1 antibody (p<0.05). FIG. 39E depicts extravasated WBCs in mice injected with rat IgG1 or VCAM1 antibody (n.s.). FIG. 39F depicts a chart showing a survival curve for mice injected with rat IgG or VCAM1 antibody. FIG. 39G depicts a table showing number of venules, venule diameter, centerline velocity, shear rate, and blood flow in mice injected with rat IgG1 or VCAM1 antibody.

FIGS. 40A-40D depict experimental results quantifying white blood cell numbers and types in mice injected with rat IgG1 or VCAM1 antibody. FIG. 40A depicts a chart quantifying WBCs in mice injected with rat IgG1 or VCAM1 antibody (p<0.05). FIG. 40B depicts a chart quantifying the blood differential count (by percent) in mice injected with rat IgG1 or VCAM1 antibody (eosinophils=white; lymphocytes=grey; neutrophils=black). FIG. 40C depicts a chart quantifying the blood cell count in mice injected with rat IgG1 or VCAM1 antibody (eosinophils=white; lymphocytes=grey; neutrophils=black). FIG. 40D is a chart depicting serum inflammatory cytokine levels (pg/ml) in mice injected with rat IgG1 or VCAM1 antibody.

FIG. 41 depicts a chart showing data indicating that the VCAM1 receptor CD49d is expressed on mouse neutrophils from SA and SS SCD mice.

FIGS. 42A-42C depict experimental results demonstrating that anti-MAEA monoclonal antibody treatment benefits Jak2$^{V617F}$-induced (R/R) Polycythemia Vera (PV). FIG. 42A depicts a series of charts quantifying complete blood count (CBC) results showing that anti-MAEA monoclonal antibody (92.25) injections lowered the reticulocytes, red blood cell counts (RBC), and haemoglobin levels (HGB) in the peripheral blood of Jak2$^{R/R}$ mice without affecting the control mice. FIG. 42B depicts a series of charts quantifying erythroblast (EB) numbers in bone marrow (BM) following anti-MAEA monoclonal antibody (92.25) injections. EB numbers were reduced by 92.25 injections in both control and Jak2$^{R/R}$ mice relative to IgG control groups, while macrophage numbers were only reduced in the Jak2$^{R/R}$ mice. FIG. 42C depicts a pair of charts showing anti-MAEA monoclonal antibody (92.25) injections enhanced the maturation of EBs in the BM of Jak2$^{R/R}$ mice without altering the EB maturation profile in wild type (WT) control mice.

DETAILED DESCRIPTION

Figure 1A:
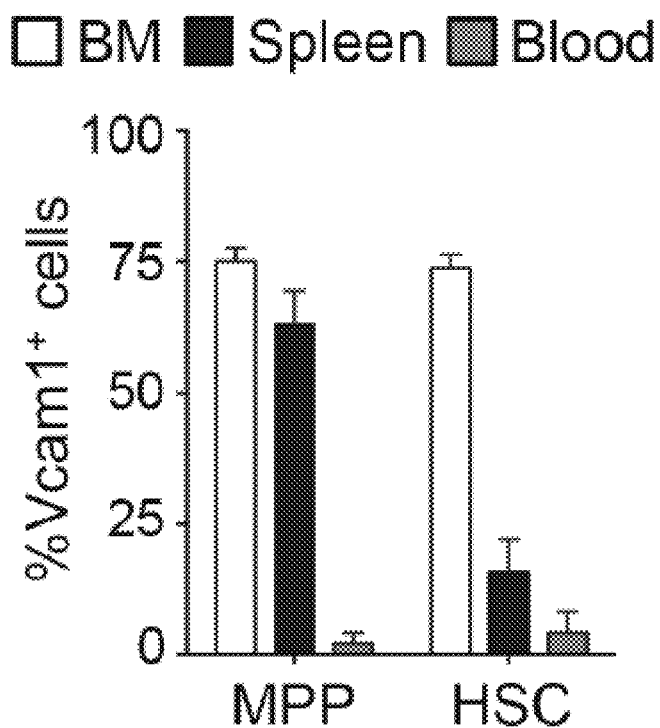
FIGS. 1A-1C.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Haematopoietic stem cells (HSCs) home to the bone marrow (BM) via, in part, the interactions with vascular cell adhesion molecule-1 (VCAM1).[57-59] Upon migrating into the BM, HSCs are vetted by perivascular phagocytes to ensure their self-integrity. As set forth in the experimental results provided herein, VCAM1 is also expressed on healthy HSCs and upregulated on leukemic stem cells (LSCs) where it serves as a quality-control checkpoint for entry into BM by providing 'don't-eat-me' stamping in the context of major histocompatibility complex (MHC) class-I presentation. The results provided herein suggest that VCAM1 engagement regulates a critical immune checkpoint gate in the BM and offers a novel strategy to eliminate cancer cells via modulation of the innate immune tolerance.

Sickle cell disease (SCD) is characterized by sickle-shaped RBCs, which exhibit increased adherence to other blood cells or to the endothelium, and are prone to undergo premature clearance and hemolysis.[48] The RBC alterations lead to a chronic inflammatory state resulting in ischemic tissue damage manifested by severe pain and organ failures. The pathophysiology of VOE and chronic organ damage is complex and involves the interplay of altered blood rheology, endothelial activation, and the secretion of inflammatory cytokines enabling leukocyte adhesion and activation.[49] Intravital microscopy analysis of the SCD mouse microcirculation has revealed that RBCs interact with adherent leukocytes in the inflamed vasculature.[50] The accumulation of activated neutrophils interacting with RBCs progressively reduces blood flow and produces venular occlusions.[51,52] Results provided herein indicate that blocking VCAM1 function may help treat SCD by reducing the number of WBC adhesions, reducing the strength for rolling interactions (increased the number of rolling WBCs), reducing RBC/WBC interactions, increasing centerline velocity, decreasing shear rate, and prolonging survival.

Macrophage-Erythroblast Attacher (MAEA, also known as EMP) was originally identified as an adhesion molecule required for erythroblastic island formation.[7] Germline deletion of MAEA led to severe anemia and perinatal mortality.[97] Sequence analysis indicates that MAEA is a highly conserved RING finger domain-containing E3 ubiquitin ligase.[98,99] MAEA's functions, however, remain obscure. As shown by results provided herein, MAEA is highly expressed in hematopoietic stem cells (HSCs) where it is required for their maintenance by restricting cytokine receptor signaling and promoting autophagy. Constitutive MAEA deletion produces severe defects in HSC repopulation capacity, B- and T-lymphoid differentiation, and premature death of animals from a myeloproliferative syndrome. Postnatal MAEA deletion leads to transient HSC expansion followed by their depletion. Mechanistically, Applicants found that the surface expression of several hematopoietic cytokine receptors (e.g., MPL, FLT3) is stabilized in absence of MAEA, thereby prolonging their intracellular signaling. Additionally, the autophagy flux in HSCs, but not in mature hematopoietic cells, is markedly impaired. Administration of autophagy-inducing compounds rescued the functional defects of MAEA-deficient HSCs. Further, MAEA is upregulated in various cancers and associated with poor survival of acute myelogenous leukemia (AML), and MLL-AF9-driven AML does not develop in the absence of MAEA. Moreover, treatment of AML-bearing mice with an anti-MAEA antibody significantly improved their survival.

Antibodies and antibody fragments that inhibit the activity of vascular cell adhesion molecule 1 (VCAM1) and/or macrophage erythroblast attacher (MAEA) are provided, along with formulations and kits comprising these antibodies and antibody fragments. Also provided are methods of treatment using the disclosed compositions, formulations, and kits to treat conditions such as cancers, sickle cell disease (SCD), and Polycythemia Vera. Methods of treating SCD by blocking VCAM1 are provided based on the surprising findings disclosed herein.

Provided herein are VCAM1 inhibitors and MAEA inhibitors, e.g., VCAM1 or MAEA antibodies, and formulations and kits comprising those inhibitors. Also provided herein are methods for treating Polycythemia Vera (PV) by blocking VCAM1 or MAEA using a VCAM1 inhibitor or MAEA inhibitor, e.g., by using one of the antibodies of the present disclosure. Further provided are methods for treating sickle cell disease (SCD) by blocking VCAM1 using a VCAM inhibitor, e.g., by using one of the antibodies of the present disclosure.

A "VCAM1 inhibitor" as used herein refers to any molecule that inhibits the activity of VCAM1, either partially or completely. An "MAEA inhibitor" as used herein refers to any molecule that inhibits the activity of MAEA, either partially or completely.

In certain embodiments of the methods, compositions, and kits provided herein, the VCAM1 and/or MAEA inhibitor inhibits VCAM1 and/or MAEA by binding to VCAM1 and/or MAEA. Examples of such VCAM1 and/or MAEA inhibitors include, e.g., antagonistic VCAM1 and/or MAEA antibodies or fusion proteins thereof, inactive forms of a VCAM1 and/or MAEA ligand (e.g., a truncated or otherwise mutated form of a VCAM1 and/or MAEA ligand) or fusion proteins thereof, small molecules, siRNAs, or aptamers.

In certain preferred embodiments of the methods, compositions, and kits provided herein, the antibody or antibody fragment is an antagonistic or blocking antibody or fragment. The antibody or antibody fragment that specifically inhibits the activity of VCAM1 is preferably a blocking antibody to VCAM1 or an antibody fragment that blocks the activity of VCAM1. The antibody or antibody fragment that specifically inhibits the activity of MAEA is preferably a blocking antibody to MAEA or an antibody fragment that blocks the activity of MAEA. As used herein, the term "antibody" refers to an intact antibody, i.e., with complete Fc and Fv regions. Antibody "fragment" refers to any portion of an antibody, or portions of an antibody linked together, such as, in non-limiting examples, a Fab, F(ab)$_2$, a single-chain Fv (scFv), which is less than the whole antibody but which is an antigen-binding portion and which competes with the intact antibody of which it is a fragment for specific binding to the target. As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (γ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3).

Also provided is an Anti-MAEA mAb 92.25 having the following sequences, where the Signal sequence/peptide is in italics, CDRs 1-3 are underlined, and the framework (FR) regions are not italicized or underlined.

```
Heavy chain: DNA sequence (417 bp)
Signal sequence-FR1-CDR1-FR2-CDR2-FR3-CDR3-FR4
                                                  (SEQ ID NO: 8)
ATGGAATGGAGCTGGATCTTTCTCTTTCTCCTGTCAGGAACTGCAGGTGTCCTCTCTGAGGTCCA
GCTGCAACAGTTTGGAGCTGAGCTGGTGAGGCCTGGGGCTTCAGTGAAGATATCCTGCAAG
GCTTCTGGCTACACATTCACTGACTACAACATGGACTGGGTGAAGCAGAGCCATGCAAAG
AGACTTGAGTGGATTGGAGATATTAATCCTAACTATGATAGTCCTACCTACAGCCAGAA
GTTCAAGGGAAGGGCCACATTGACTGTAGACAACTCCTCCAGCACCGCCTACATGGAGCT
CCGCAGCCTGACATCTGAGGACACTGCAGTCTATTACTGTGCAAGGGGACATTACTACGG
CTACGGATACTTCGATGTCTGGGGCGCGGGGACCACGGTCACCGTCTCCTCA;

Heavy chain FR1: DNA sequence
                                                  (SEQ ID NO: 20)
GTCCAGCTGCAACAGTTTGGAGCTGAGCTGGTGAGGCCTGGGGCTTCAGTGAAGATATCCT
GCAAGGCTTCTGGCTACACATTCACT;

Heavy chain CDR1: DNA sequence
                                                  (SEQ ID NO: 21)
GACTACAACATGGAC;

Heavy chain FR2: DNA sequence
                                                  (SEQ ID NO: 22)
TGGGTGAAGCAGAGCCATGCAAAGAGACTTGAGTGGATTGGA Heavy chain CDR2: DNA sequence
                                                  (SEQ ID NO: 23)
GATATTAATCCTAACTATGATAGTCCTACCTACAGCCAGAAGTTCAAGGGA;

Heavy chain FR3: DNA sequence
                                                  (SEQ ID NO: 24)
AGGGCCACATTGACTGTAGACAACTCCTCCAGCACCGCCTACATGGAGCTCCGCAGCCTGA
CATCTGAGGACACTGCAGTCTATTACTGTGCAAGG;

Heavy chain CDR3: DNA sequence
                                                  (SEQ ID NO: 25)
GGACATTACTACGGCTACGGATACTTCGATGTC;

Heavy chain FR4: DNA sequence
                                                  (SEQ ID NO: 26)
TGGGGCGCGGGGACCACGGTCACCGTCTCCTCA;

Heavy chain: Amino acid sequence (139 aa)
Signal peptide-FR1-CDR1-FR2-CDR2-FR3-CDR3-FR4
                                                  (SEQ ID NO: 9)
MEWSWIFLFLLSGTAGVLSEVQLQQFGAELVRPGASVKISCKASGYTFTDYNMDWVKQSHAKR
LEWIGDINPNYDSPTYSQKFKGRATLTVDNSSTAYMELRSLTSEDTAVYYCARGHYYGYGY
FDVWGAGTTVTVSS;

Heavy chain FR1: Amino acid sequence
                                                  (SEQ ID NO: 27)
EVQLQQFGAELVRPGASVKISCKASGYTFT;

Heavy chain CDR1: Amino acid sequence
                                                  (SEQ ID NO: 28)
DYNMD
```

```
Heavy chain FR2: Amino acid sequence
                                                    (SEQ ID NO: 29)
WVKQSHAKRLEWIG;

Heavy chain CDR2: Amino acid sequence
                                                    (SEQ ID NO: 30)
DINPNYDSPTYSQKFKG;

Heavy chain FR3: Amino acid sequence
                                                    (SEQ ID NO: 31)
RATLTVDNSSSTAYMELRSLTSEDTAVYYCAR Heavy chain CDR3: Amino acid sequence
                                                    (SEQ ID NO: 32)
GHYYGYGYFDV;

Heavy chain FR4: Amino acid sequence
                                                    (SEQ ID NO: 33)
WGAGTTVTVSS;

Light chain: DNA sequence (381 bp)
Signal sequence-FR1-CDR1-FR2-CDR2-FR3-CDR3-FR4
                                                    (SEQ ID NO: 10)
ATGGAGTCACAGACTCAGGTCTTTGTATACATGTTGCTGTGGTTGTCTGGTGTTGATGGAGACAA
TGAGATGACCCAGTCTCAAAAATTCATGTCCACAGCAGTAGGAGACAGGGTCAGCGTCACC
TGCAAGGCCAGTCAGAATGTGGGTACTAATGTAGCCTGGTATCAACAGAAACCAGGGA
AATCTCCTAAAGTACTGATTTACTCGGCATCCTACCGCTACAGTGGAGTCCCTGATCGCT
TCAGAGGCAGTAGATCTGGGACAGATTTCACTCTCACCATCAGCAATGTGCAGTCTGAAGA
CTTGGCAGAGTATTTCTGTCAGCAATATAACACCTATCCGTGGACGTTCGGTGGAGGCAC
CAAGCTGGAAATCAAA;

Light chain FR1: DNA sequence
                                                    (SEQ ID NO: 34)
GACATTGAGATGACCCAGTCTCAAAAATTCATGTCCACAGCAGTAGGAGACAGGGTCAGC
GTCACCTGC;

Light chain CDR1: DNA sequence
                                                    (SEQ ID NO: 35)
AAGGCCAGTCAGAATGTGGGTACTAATGTAGCC Light chain FR2: DNA sequence
                                                    (SEQ ID NO: 36)
TGGTATCAACAGAAACCAGGGAAATCTCCTAAAGTACTGATTTAC;

Light chain CDR2: DNA sequence
                                                    (SEQ ID NO: 37)
TCGGCATCCTACCGCTACAGT;

Light chain FR3: DNA sequence
                                                    (SEQ ID NO: 38)
GGAGTCCCTGATCGCTTCAGAGGCAGTAGATCTGGGACAGATTTCACTCTCACCATCAGCA
ATGTGCAGTCTGAAGACTTGGCAGAGTATTTCTGT;

Light chain CDR3: DNA sequence
                                                    (SEQ ID NO: 39)
CAGCAATATAACACCTATCCGTGGACG;

Light chain FR4: DNA sequence
                                                    (SEQ ID NO: 40)
TTCGGTGGAGGCACCAAGCTGGAAATCAAA;

Light chain: Amino acid sequence (127 aa)
Signal peptide-FR1-CDR1-FR2-CDR2-FR3-CDR3-FR4
                                                    (SEQ ID NO: 11)
MESQTQVFVYMLLWLSGVDGDIEMTQSQKFMSTAVGDRVSVTCKASQNVGTNVAWYQQKPG
KSPKVLIYSASYRYSGVPDRFRGSRSGTDFTLTISNVQSEDLAEYFCQQYNTYPWTFGGGTKLE
IK.

Light chain FR1: Amino acid sequence
                                                    (SEQ ID NO: 41)
DIEMTQSQKFMSTAVGDRVSVTC;

Light chain CDR1: Amino acid sequence
                                                    (SEQ ID NO: 42)
KASQNVGTNVA;

Light chain FR2: Amino acid sequence
                                                    (SEQ ID NO: 43)
WYQQKPGKSPKVLIY;
```

-continued

Light chain CDR2: Amino acid sequence
(SEQ ID NO: 102)
SASYRYS;

Light chain FR3: Amino acid sequence
(SEQ ID NO: 103)
GVPDRFRGSRSGTDFTLTISNVQSEDLAEYFC;

Light chain CDR3: Amino acid sequence
(SEQ ID NO: 44)
QQYNTYPWT;

Light chain FR4: Amino acid sequence
(SEQ ID NO: 45)
FGGGTKLEIK;

Also provided is an anti-VCAM1 mAb V64-8 having the following sequences, where the Signal sequence/peptide is in italics, CDRs 1-3 are underlined, and the framework (FR) regions are not italicized or underlined.

```
Heavy chain: DNA sequence (396 bp)
Signal sequence-FR1-CDR1-FR2-CDR2-FR3-CDR3-FR4
                                            (SEQ ID NO: 12)
ATGAACTTCGGGCTCAGCTTGATTTTCCTTGTCCCTATTTTAAAAGGTGTCCAGTGTGAAGTACA
GCTGGTGGAGTCTGGGGGAGGCTTAGTGAAGCCTGGAGGGTCCCTGAAACTCTCCTGTGCA
GCCTCTGGATTCACTTTCAGTAGTTATACCATGTCTTGGGTTCGCCAGTCTCCAGAGAAGA
GGCTGGAGTGGGTCGCAGAGATTAGTAGTGGTGGTAGTTACACCCACTATGCAGCCAC
TGTGACGGGCCGATTCACCATCTCCAGAGACAATGTCAAGAACACCCTGTACCTGGAAAT
GAGCAGTCTGAGGTCTGAGGACACGGCCATGTATTACTGTGCAAGGGGAGAACTTTACTG
GGGCCAAGGGACTCTGGTCACTGTCTCTGCA;

Heavy chain FR1: DNA sequence
                                            (SEQ ID NO: 46)
GAAGTACAGCTGGTGGAGTCTGGGGGAGGCTTAGTGAAGCCTGGAGGGTCCCTGAAACTC
TCCTGTGCAGCCTCTGGATTCACTTTCAGT;

Heavy chain CDR1: DNA sequence
                                            (SEQ ID NO: 47)
AGTTATACCATGTCT;

Heavy chain FR2: DNA sequence
                                            (SEQ ID NO: 48)
TGGGTTCGCCAGTCTCCAGAGAAGAGGCTGGAGTGGGTCGCA;

Heavy chain CDR2: DNA sequence
                                            (SEQ ID NO: 49)
GAGATTAGTAGTGGTGGTAGTTACACCCACTATGCAGCCACTGTGACGGGC;

Heavy chain FR3: DNA sequence
                                            (SEQ ID NO: 50)
CGATTCACCATCTCCAGAGACAATGTCAAGAACACCCTGTACCTGGAAATGAGCAGTCTGA
GGTCTGAGGACACGGCCATGTATTACTGTGCAAGG;

Heavy chain CDR3: DNA sequence
                                            (SEQ ID NO: 51)
GGAGAACTTTAC;

Heavy chain FR4: DNA sequence
                                            (SEQ ID NO: 52)
TGGGGCCAAGGGACTCTGGTCACTGTCTCTGCA;

Heavy chain: Amino acid sequence (132 aa)
Signal peptide-FR1-CDR1-FR2-CDR2-FR3-CDR3-FR4
                                            (SEQ ID NO: 13)
MNFGLSLIFLVPILKGVQCEVQLVESGGGLVKPGGSLKLSCAASGFTFSSYTMSWVRQSPEKRLE
WVAEISSGGSYTHYAATVTGRFTISRDNVKNTLYLEMSSLRSEDTAMYYCARGELYWGQGT
LVTVSA;

Heavy chain FR1: Amino acid sequence
                                            (SEQ ID NO: 53)
EVQLVESGGGLVKPGGSLKLSCAASGFTFS;

Heavy chain CDR1: Amino acid sequence
                                            (SEQ ID NO: 54)
SYTMS;

Heavy chain FR2: Amino acid sequence
                                            (SEQ ID NO: 55)
WVRQSPEKRLEWVA;
```

```
Heavy chain CDR2: Amino acid sequence
                                                          (SEQ ID NO: 56)
EISSGGSYTHYAATVTG Heavy chain FR3: Amino acid sequence
                                                          (SEQ ID NO: 57)
RQSPEKRLEWVAEISSGGSYTHYAATVTG;

Heavy chain CDR3: Amino acid sequence
                                                          (SEQ ID NO: 58)
GELY;

Heavy chain FR4: Amino acid sequence
                                                          (SEQ ID NO: 59)
WGQGTLVTVSA;

Light chain: DNA sequence (393 bp)
Signal sequence-FR1-CDR1-FR2-CDR2-FR3-CDR3-FR4
                                                          (SEQ ID NO: 14)
ATGAGTCCTGCCCAGTTCCTGTTTCTGTTAGTGCTCTGGATTCGGGAAACCAACGGTGATGTTGT
GTTGACCCAGATTCCATCCACTTTGTCGGTTACCTTTGGACAACCAGCCTCCATCTCTTGCA
AGGCAAGTCAGAGCCTCTTAGATAGAGGTGGAAAGACATTTTTTCAATTGGTTGTTACA
GAGGCCAGGCCAGTCTCCAAAGCGCCTAATCTATCTGGTGTCTAAACTGGACTCTGGAGT
CCCTGACAGGTTCACTGGCAGTGGATCAGGGACAGATTTCACACTGAAAATCAGCAGAGTG
GAGGCTGAGGATTTGGGAGTCTATTATTGCTGGCAAGGTACACATTTTCCGTGGACGTTC
GGTGGAGGCACCAGACTGGAAATCAAA;

Light chain FR1: DNA sequence
                                                          (SEQ ID NO: 60)
ATGTTGTGTTGACCCAGATTCCATCCACTTTGTCGGTTACCTTTGGACAACCAGCCTCCATC
TCTTGC;

Light chain CDR1: DNA sequence
                                                          (SEQ ID NO: 61)
AAGGCAAGTCAGAGCCTCTTAGATAGAGGTGGAAAGACATTTTTTCAAT;

Light chain FR2: DNA sequence
                                                          (SEQ ID NO: 62)
TGGTTGTTACAGAGGCCAGGCCAGTCTCCAAAGCGCCTAATCTAT;

Light chain CDR2: DNA sequence
                                                          (SEQ ID NO: 63)
CTGGTGTCTAAACTGGACTCT;

Light chain FR3: DNA sequence
                                                          (SEQ ID NO: 64)
GGAGTCCCTGACAGGTTCACTGGCAGTGGATCAGGGACAGATTTCACACTGAAAATCAGCA
GAGTGGAGGCTGAGGATTTGGGAGTCTATTATTGC;

Light chain CDR3: DNA sequence
                                                          (SEQ ID NO: 65)
TGGCAAGGTACACATTTTCCGTGGACG;

Light chain FR4: DNA sequence
                                                          (SEQ ID NO: 66)
TTCGGTGGAGGCACCAGACTGGAAATCAAA;

Light chain: Amino acid sequence (131 aa)
Signal peptide-FR1-CDR1-FR2-CDR2-FR3-CDR3-FR4
                                                          (SEQ ID NO: 15)
MSPAQFLFLLVLWIRETNGDVVLTQIPSTLSVTFGQPASISCKASQSLLDRGGKTFFNWLLQRPG
QSPKRLIYLVSKLDSGVPDRFTGSGSGTDFTLKISRVEAEDLGVYYCWQGTHFPWTFGGGTRL
EIK.

Light chain FR1: Amino acid sequence
                                                          (SEQ ID NO: 67)
DVVLTQIPSTLSVTFGQPASISC;

Light chain CDR1: Amino acid sequence
                                                          (SEQ ID NO: 68)
KASQSLLDRGGKTFFN;

Light chain FR2: Amino acid sequence
                                                          (SEQ ID NO: 69)
WLLQRPGQSPKRLIY;

Light chain CDR2: Amino acid sequence
                                                          (SEQ ID NO: 70)
LVSKLDS;
```

-continued

Light chain FR3: Amino acid sequence
(SEQ ID NO: 71)
GVPDRFTGSGSGTDFTLKISRVEAEDLGVYYC;

Light chain CDR3: Amino acid sequence
(SEQ ID NO: 72)
WQGTHFPWT;

Light chain FR4: Amino acid sequence
(SEQ ID NO: 73)
FGGGTRLEIK;

Also provided is an Anti-VCAM1 mAb V196-4 having the following sequences, where the Signal sequence/peptide is in italics, CDRs 1-3 are underlined, and the framework (FR) regions are not italicized or underlined.

```
Heavy chain: DNA sequence (396 bp)
Signal sequence-FR1-CDR1-FR2-CDR2-FR3-CDR3-FR4
                                                    (SEQ ID NO: 16)
ATGAACTTCGGGCTCAGCTTGATTTTCCTTGTCCTTATTTTAAAAGGTGTCCATTGTGAAGTGCAG
CTGGTGGAGTCTGGGGGAGCCTTAGTGAAGCCTGGAGGGTCCCTGAAACTCTCCTGTGTAG
CCTCTGGATTCACTTTCAGTAGCTATGCCATGTCTTGGGTTCGCCAGTCTCCAGAGAAGAA
GCTGGAGTGGGTCGCAGAAATTAGTAGTACTGGTAGTTACACCCACTATCCCGACACTG
TGACGGGCCGATTCACCATCTCCAGAGACAATGCCAAGAACACCCTGTACCTGGAAATGA
GCAGTCTGAGGTCTGAGGACACGGCCATGTATTACTGTGCAAGAGGGGAGGCGCTCTGGG
GTCAAGGAACCTCAGTCACCGTCTCCTCA;

Heavy chain FR1: DNA sequence
                                                    (SEQ ID NO: 74)
GAAGTGCAGCTGGTGGAGTCTGGGGGAGCCTTAGTGAAGCCTGGAGGGTCCCTGAAACTCT
CCTGTGTAGCCTCTGGATTCACTTTCAGT;

Heavy chain CDR1: DNA sequence
                                                    (SEQ ID NO: 75)
AGCTATGCCATGTCT;

Heavy chain FR2: DNA sequence
                                                    (SEQ ID NO: 76)
TGGGTTCGCCAGTCTCCAGAGAAGAAGCTGGAGTGGGTCGCA;

Heavy chain CDR2: DNA sequence
                                                    (SEQ ID NO: 77)
GAAATTAGTAGTACTGGTAGTTACACCCACTATCCCGACACTGTGACGGGC;

Heavy chain FR3: DNA sequence
                                                    (SEQ ID NO: 78)
CGATTCACCATCTCCAGAGACAATGCCAAGAACACCCTGTACCTGGAAATGAGCAGTCTGA
GGTCTGAGGACACGGCCATGTATTACTGTGCAAGA;

Heavy chain CDR3: DNA sequence
                                                    (SEQ ID NO: 79)
GGGGAGGCGCTC;

Heavy chain FR4: DNA sequence
                                                    (SEQ ID NO: 80)
TGGGGTCAAGGAACCTCAGTCACCGTCTCCTCA;

Heavy chain: Amino acid sequence (132 aa)
Signal peptide-FR1-CDR1-FR2-CDR2-FR3-CDR3-FR4
                                                    (SEQ ID NO: 17)
MNFGLSLIFLVLILKGVHCEVQLVESGGALVKPGGSLKLSCVASGFTFSSYAMSWVRQSPEKKLE
WVAEISSTGSYTHYPDTVTGRFTISRDNAKNTLYLEMSSLRSEDTAMYYCARGEALWGQGTS
VTVSS;

Heavy chain FR1: Amino acid sequence
                                                    (SEQ ID NO: 81)
EVQLVESGGALVKPGGSLKLSCVASGFTFS;

Heavy chain CDR1: Amino acid sequence
                                                    (SEQ ID NO: 82)
SYAMS;

Heavy chain FR2: Amino acid sequence
                                                    (SEQ ID NO: 83)
WVRQSPEKKLEWVA;

Heavy chain CDR2: Amino acid sequence
                                                    (SEQ ID NO: 84)
EISSTGSYTHYPDTVTG;
```

Heavy chain FR3: Amino acid sequence
(SEQ ID NO: 85)
RFTISRDNAKNTLYLEMSSLRSEDTAMYYCAR;

Heavy chain CDR3: Amino acid sequence
(SEQ ID NO: 86)
GEAL;

Heavy chain FR4: Amino acid sequence
(SEQ ID NO: 87)
WGQGTSVTVSS;

Light chain: DNA sequence (393 bp)
Signal sequence-FR1-CDR1-FR2-CDR2-FR3-CDR3-FR4
(SEQ ID NO: 18)
*ATGAGTCCTGCCCAGTTCCTGTTTCTGTTAGTGCTCTGGATTCGGGAAACCAACGGT*GATGTTGT
GATGACCCAGACTCCACTCACTTTGTCGGTTACCGTTGGACAACCAGCCTCCATCTCTTGC**A
AGTCAAGTCATAGCCTCTTAGATAGTTATGGAAAGACATATTTGAAT**TGGTTTTTACAG
AGGCCAGGCCAGTCTCCAAAGCGCCTAATCTATCTGGTGTCTAAACTGGACTCTGGAGTC
CCTGACAGGTTCACTGGCAGTGGATCAGGGACAGATTTCACACTGAAAATCAGCAGAGTG
GAGGCTGAGGATTTGGGACTTTATTATTGCTGGCAGGGTACACATTTTCCGTGGACGTTC
GGTGGAGGCACCAAGCTGGAAATCAAA;

Light chain FR1: DNA sequence
(SEQ ID NO: 88)
GATGTTGTGATGACCCAGACTCCACTCACTTTGTCGGTTACCGTTGGACAACCAGCCTCCAT
CTCTTGC;

Light chain CDR1: DNA sequence
(SEQ ID NO: 89)
AAGTCAAGTCATAGCCTCTTAGATAGTTATGGAAAGACATATTTGAAT;

Light chain FR2: DNA sequence
(SEQ ID NO: 90)
TGGTTTTTACAGAGGCCAGGCCAGTCTCCAAAGCGCCTAATCTAT;

Light chain CDR2: DNA sequence
(SEQ ID NO: 91)
CTGGTGTCTAAACTGGACTC;

Light chain FR3: DNA sequence
(SEQ ID NO: 92)
TGGAGTCCCTGACAGGTTCACTGGCAGTGGATCAGGGACAGATTTCACACTGAAAATCAGC
AGAGTGGAGGCTGAGGATTTGGGACTTTATTATTGC;

Light chain CDR3: DNA sequence
(SEQ ID NO: 93)
TGGCAGGGTACACATTTTCCGTGGACG;

Light chain FR4: DNA sequence
(SEQ ID NO: 94)
TTCGGTGGAGGCACCAAGCTGGAAATCAAA;

Light chain: Amino acid sequence (131 aa)
Signal peptide-FR1-CDR1-FR2-CDR2-FR3-CDR3-FR4
(SEQ ID NO: 19)
*MSPAQFLFLLVLWIRETNG*DVVMTQTPLTLSVTVGQPASISCKSSHSLLDSYGKTYLNWFLQRP
GQSPKRLIYLVSKLDSGVPDRFTGSGSGTDFTLKISRVEAEDLGLYYCWQGTHFPWTFGGGTK
LEIK;

Light chain FR1: Amino acid sequence
(SEQ ID NO: 95)
DVVMTQTPLTLSVTVGQPASISC;

Light chain CDR1: Amino acid sequence
(SEQ ID NO: 96)
KSSHSLLDSYGKTYLN;

Light chain FR2: Amino acid sequence
(SEQ ID NO: 97)
WFLQRPGQSPKRLIY;

Light chain CDR2: Amino acid sequence
(SEQ ID NO: 98)
LVSKLDS;

Light chain FR3: Amino acid sequence
(SEQ ID NO: 99)
GVPDRFTGSGSGTDFTLKISRVEAEDLGLYYC;

```
                                                          -continued
Light chain CDR3: Amino acid sequence
                                                                                                (SEQ ID NO: 100)
WQGTHFPWT;

Light chain FR4: Amino acid sequence
                                                                                                (SEQ ID NO: 101)
FGGGTKLEIK.
```

In other embodiments, a monoclonal antibody to MAEA for use in the present methods, compositions, and kits may be a monoclonal antibody to MAEA available from R&D Systems (MAB7288), and a recombinant mouse monoclonal antibody to human MAEA is available from Creative Biolabs. In other embodiments, a monoclonal antibody to VCAM1 for use in the present methods, compositions, and kits may be a monoclonal antibody available from, e.g., Thermo Fisher Scientific, Abcam, Sigma-Aldrich, and Abnova. VCAM1 monoclonal antibodies are also described in US2010/0172902, incorporated herein by reference.

The antibody can be a human antibody or a humanized antibody or a chimeric antibody. As used herein, a "human antibody" unless otherwise indicated is one whose sequences correspond to (i.e., are identical in sequence to) an antibody that could be produced by a human and/or has been made using any of the techniques used for making human antibodies, but not one which has been made in a human. "Chimeric antibodies" are forms of non-human (e.g., murine) antibodies that contain human sequences in the constant domain regions of the antibody in order to eliminate or reduce immunogenic effects. "Humanized" forms of non-human (e.g., murine) antibodies are chimeric antibodies that also contain human sequences in the variable domain regions of the antibody and thus contain minimal sequence derived from non-human immunoglobulin. In general, a humanized antibody can comprise substantially all of at least one, and typically two, variable domains, in which all or substantially all of the hypervariable loops correspond to those of a non-human immunoglobulin, and all or substantially all of the framework regions are those of a human immunoglobulin sequence. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. For example, the antibody to MAEA could be a human or humanized antibody having the CDRs of MAB7288 (which is a mouse IgG1 Ab). Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

Also provided is a monoclonal antibody to MAEA and a monoclonal antibody to VCAM1. The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified.

In certain embodiments, the antibody is a monoclonal antibody. Antibodies for use in the present methods, compositions, and kits may include natural antibodies, synthetic antibodies, monoclonal antibodies, polyclonal antibodies, chimeric antibodies, humanized antibodies, multispecific antibodies, bispecific antibodies, dual-specific antibodies, anti-idiotypic antibodies, or fragments thereof that retain the ability to bind a specific antigen, for example, VCAM1 or MAEA.

Compositions comprising the antibodies provided herein can additionally comprise stabilizers to prevent loss of activity or structural integrity of the protein due to the effects of denaturation, oxidation, or aggregation over a period of time during storage and transportation prior to use. The compositions can comprise one or more of any combination of salts, surfactants, pH and tonicity agents such as sugars can contribute to overcoming aggregation problems. Where a composition of the present disclosure is administered as an injection, it is desirable to have a pH value in an approximately neutral pH range, it is also advantageous to minimize surfactant levels to avoid bubbles in the formulation which are detrimental for injection into subjects. In an embodiment, the compositions can be in liquid form and stably supports high concentrations of bioactive antibody in solution and is suitable for inhalational or parenteral administration. In an embodiment, the composition is suitable for intravenous, intramuscular, intraperitoneal, intradermal and/or subcutaneous injection. In an embodiment, the composition is in liquid form and has minimized risk of bubble formation and anaphylactoid side effects. In an embodiment, the composition is isotonic. In an embodiment, the composition has a pH or 6.8 to 7.4.

Compositions comprising the antibodies or fragments thereof provided herein can also be lyophilized or provided in any suitable form including, but not limited to, injectable solutions, inhalable solutions, gel forms, or tablet forms.

Compositions comprising the antibodies or fragments thereof provided herein can be administered to the subject in a pharmaceutical composition comprising the antibody or fragment and a pharmaceutically acceptable carrier. The term "carrier" is used in accordance with its art-understood meaning, to refer to a material that is included in a pharmaceutical composition but does not abrogate the biological activity of the antibody or antibody fragment included within the composition. Pharmaceutically acceptable carriers include, for example, sterile isotonic saline, phosphate buffered saline solution, water, and emulsions, such as an oil/water or water/oil emulsions.

The antibody or antibody fragment can be conjugated with a cytotoxic agent.

The antibody or antibody fragment can be administered to subjects using routes of administration known in the art, including, but are not limited to, intravenous, intramuscular and intraperitoneal administration.

Also provided are a blocking antibody to VCAM1, an antibody fragment that blocks the activity of VCAM1, a blocking antibody to MAEA, and an antibody fragment that blocks the activity of MAEA for use as a medicament in treatment of cancer, in inhibiting engraftment of leukemia cells such as AML, CML, PV, ET, ALL, and CLL cells, and in enhancing the efficacy of cytarabine for treatment of cancer, wherein the antibody or antibody fragment is specific for VCAM1 or MAEA. The cancer can be, for example, one or more of bladder, breast, brain, colorectal, kidney, oesophagus, gastrointestinal tract, liver, lung, ovarian, pancreas, prostate, skin, stomach, and uterine cancer, melanoma, myelodysplastic syndrome (MDS) (a pre-leukemia), non-Hodgkin lymphoma, and a hematologic malignancy. Hematologic malignancies can derive from myeloid or lymphoid cell lines. Lymphomas, lymphocytic leukemias, and myeloma are from the lymphoid line, while acute and chronic myelogenous leukemia, myelodysplastic syndromes and myeloproliferative diseases are myeloid in origin. The hematologic malignancy can be a myeloproliferative disease. The hematologic malignancy can be, for example, AML, CML, PV, ET, ALL, or CLL.

The present disclosure provides a method of treating a condition (e.g., a cancer or sickle cell disease) in a subject comprising administering to the subject an antibody or antibody fragment in an amount effective to inhibit the activity of VCAM1 and/or an antibody or antibody fragment in an amount effective to inhibit the activity MAEA to treat the condition in a subject, wherein the antibody or antibody fragment is specific for VCAM1 or MAEA.

As used herein, the term "treat" a cancer means to eradicate the cancer in a subject, or to reduce the size of a cancer or cancer tumor in the subject, or to stabilize a cancer or cancer tumor in the subject so that it does not increase in size, or to prevent or reduce the spread of the cancer in the subject.

As used herein, the term "treat" sickle cell disease (SCD) means to reduce the acute (e.g., vaso-occlusion) or chronic (e.g., organ damage) manifestations of SCD.

A "therapeutically effective amount" of a composition as used herein is an amount of a composition that produces a desired therapeutic effect in a subject, such as treating cancer, treating SCD, or treating PV. In certain embodiments, the therapeutically effective amount is an amount of the composition that yields maximum therapeutic effect. In other embodiments, the therapeutically effective amount yields a therapeutic effect that is less than the maximum therapeutic effect. For example, a therapeutically effective amount may be an amount that produces a therapeutic effect but that also avoids one or more side effects that is associated with a dosage that yields the maximum therapeutic effect. A therapeutically effective amount for a particular composition will vary based on a variety of factors, including but not limited to the characteristics of the therapeutic composition (e.g., activity, pharmacokinetics, pharmacodynamics, and bioavailability), the physiological condition of the subject (e.g., age, body weight, sex, disease type and stage, medical history, general physical condition, responsiveness to a given dosage, and other present medications), the nature of any pharmaceutically acceptable carriers in the composition, and the route of administration. One skilled in the clinical and pharmacological arts will be able to determine a therapeutically effective amount through routine experimentation, namely by monitoring a subject's response to administration of a composition and adjusting the dosage accordingly. For additional guidance, see, e.g., Remington: The Science and Practice of Pharmacy, 22nd Edition, Pharmaceutical Press, London, 2012, and Goodman & Gilman's The Pharmacological Basis of Therapeutics, 12th Edition, McGraw-Hill, New York, N.Y., 2011, the entire disclosures of which are incorporated by reference herein.

The cancer can be, for example, one or more of bladder, breast, brain, colorectal, kidney, oesophagus, gastrointestinal tract, liver, lung, ovarian, pancreas, prostate, skin, stomach, and uterine cancer, melanoma, non-Hodgkin lymphoma, myelodysplastic syndrome (MDS) (a pre-leukemia), and a hematologic malignancy. Hematologic malignancies can derive from myeloid or lymphoid cell lines. Lymphomas, lymphocytic leukemias, and myeloma are from the lymphoid line, while acute and chronic myelogenous leukemia, myelodysplastic syndromes and myeloproliferative diseases are myeloid in origin. The hematologic malignancy can be a myeloproliferative disease. The hematologic malignancy can be, for example, acute myeloid leukemia (AML), chronic myeloid leukemia (CML), polycythemia vera (PV), essential thrombocytosis (ET), acute lymphoblastic leukemia (ALL), or chronic lymphocytic leukemia (CLL).

The treatment can comprise administering to a subject a combination of two or more of:
a) a blocking antibody to VCAM1 or an antibody fragment that blocks the activity of VCAM1, wherein the antibody or antibody fragment is specific for VCAM1;
b) a blocking antibody to MAEA or an antibody fragment that blocks the activity of MAEA, wherein the antibody or antibody fragment is specific for MAEA;
c) one or more chemotherapeutic agents; and
d) one or more immune system enhancing agents;
wherein the combination includes at least a) or b).

The different components of the combination can be administered at the same time, sequentially, or one spaced in time before the other. In certain embodiments of the methods, compositions, and kits provided herein, an VCAM1 inhibitor or MAEA inhibitor, e.g., a VCAM1 or MAEA antibody or antibody fragment, may be administered together as part of the same composition. In other embodiments of the methods provided herein, the MAEA inhibitor and the VCAM1 inhibitor may both be administered separately, i.e., as separate compositions. In these embodiments, the inhibitors may be administered sequentially or simultaneously, and may be administered via the same or different routes. In those embodiments where the inhibitors are administered sequentially, they may be administered at the same or different intervals. For example, one inhibitor may be administered more frequently than the other or may be administered over a longer time course. In certain of these embodiments, one inhibitor may be administered one or more times prior to the first administration of the second inhibitor. When administration of the second inhibitor is initiated, administration of the first inhibitor may either cease or continue for all or part of the course of administration of the second inhibitor. In certain embodiments wherein the MAEA inhibitor or the VCAM1 inhibitor is MAEA antagonist antibody or a VCAM1 antagonist antibody, the antibody may be administered two or more times per day, daily, two or more times per week, weekly, bi-weekly (i.e., every other week), every third week, or monthly. In certain embodiments, the antibody is administered weekly, bi-weekly, or every third week, or monthly. In certain embodiments, the MAEA inhibitor and/or the VCAM1 inhibitor may be administered for a specific time course determined in advance. For example, the MAEA and/or VCAM1 inhibitors may be administered for a time course of 1 day, 2 days, 3, days, 4 days, 5 days, 6 days, 1 week, 2 weeks, 3 weeks, 4 weeks, 5 weeks, 6 weeks, 7 weeks, 8 weeks, 9 weeks, or 10 weeks. In other embodiments, the MAEA and/or VCAM1 inhibitors may be administered indefinitely, or until a specific therapeutic benchmark is reached. For example, the MAEA and/or VCAM1 inhibitors may be administered until tumor growth is arrested or reversed, until one or more tumors are eliminated, or until the number of cancer cells are reduced to a specific level.

The one or more chemotherapeutic agents can be, for example, but not limited to, cytarabine (cytosine arabinoside or ara-C), an anthracycline drug (such as, e.g., daunorubicin (daunomycin), idarubicin, and/or mitoxantrone), cladribine (2-CdA), fludarabine (Fludara®), topotecan, etoposide (VP-16), 6-thioguanine (6-TG), hydroxyurea (Hydrea®), a corticosteroid drug (such as, e.g., prednisone or dexamethasone (Decadron®)), methotrexate (MTX), 6-mercaptopurine (6-MP), azacitidine (Vidaza®), and/or decitabine (Dacogen®).

The one or more immune system enhancing agents can be, for example, but not limited to, an inhibitor of CD47 (also called Cluster of Differentiation 47 and integrin associated protein (IAP)), PD-1 (also called Programmed cell death protein 1)/PD-L1 (also called Programmed death-ligand 1, Cluster of Differentiation 274 (CD274) and B7 homolog 1 (B7-H1)), CTLA-4 (also called cytotoxic T-lymphocyte-associated protein 4 and CD152 (Cluster of Differentiation 152)), CD200 (also called Cluster of Differentiation 200 or OX-2 membrane glycoprotein)/CD200R (CD200 receptor), LAG-3 (also called Lymphocyte-activation gene 3 protein), TIM-3 (also called T-cell immunoglobulin and mucin-domain containing-3), VISTA (also called V-domain Ig suppressor of T cell activation), or TIGIT (also called T cell immunoreceptor with Ig and ITIM domains). The agent that inhibits the activity of, for example, CD47 can be, for example, a blocking antibody to CD47 or an antibody fragment that blocks the activity of CD47, where the antibody or antibody fragment is specific to CD47. Examples of blocking antibodies to CD47 are described in US2016/0137733, US2016/0137734 and US2017/0081407, hereby incorporated by reference. The agent that inhibits the activity of CD47 can also be a construct having a SIRP alpha domain or variant thereof. Such constructs are described, for example, in US2015/0071905, US2015/0329616, US2016/0177276, US2016/0186150, and US20170107270, hereby incorporated by reference.

Also provided is a method of inhibiting engraftment of leukemia cells in a subject, the method comprising administering to the subject an antibody or antibody fragment in an amount effective to inhibit the activity of vascular cell adhesion molecule 1 (VCAM1) and/or an antibody or antibody fragment in an amount effective to inhibit the activity of macrophage erythroblast attacher (MAEA) to inhibit leukemia cell engraftment in a subject, wherein the antibody or antibody fragment is specific for VCAM1 or MAEA. The leukemia cells can be, for example, acute myeloid leukemia (AML), chronic myeloid leukemia (CML), polycythemia vera (PV), essential thrombocytosis (ET), acute lymphoblastic leukemia (ALL), or chronic lymphocytic leukemia (CLL) cells.

Still further provided is a method of enhancing the efficacy of cytarabine for treating a cancer in a subject, comprising administering to the subject an antibody or antibody fragment in an amount effective to inhibit the activity of VCAM1 and/or an antibody or antibody fragment in an amount effective to inhibit the activity of MAEA in combination with cytarabine to enhance the efficacy of cytarabine for treating a cancer in a subject, wherein the antibody or antibody fragment is specific for VCAM1 or MAEA. The cancer can be, for example, one or more of AML, CML, PV, ET, ALL, CLL or non-Hodgkin's lymphoma.

All combinations of the various elements described herein are within the scope of the invention unless otherwise indicated herein or otherwise clearly contradicted by context.

From the foregoing, it will be appreciated that specific embodiments of the invention have been described herein for purposes of illustration, but that various modifications may be made without deviating from the scope of the invention. Accordingly, the invention is not limited except as by the appended claims.

The following examples are provided in order to better illustrate the claimed invention and are not to be interpreted as limiting the scope of the invention. To the extent that specific materials are mentioned, they are only mentioned for purposes of illustration and are not intended to limit the invention. One skilled in the art may develop equivalent means or reactants without the exercise of inventive capacity and without departing from the scope of the present invention. It will be understood that many variations can be made in the procedures described herein while still remaining within the bounds of the present invention. The inventors intend such variations to be included within the scope of the invention. One skilled in the art will readily appreciate that the specific methods and results discussed are merely illustrative of the invention as described more fully in the claims that follow thereafter.

EXAMPLES

Example 1: Anti-VCAM1 Therapies

Figure 1B:
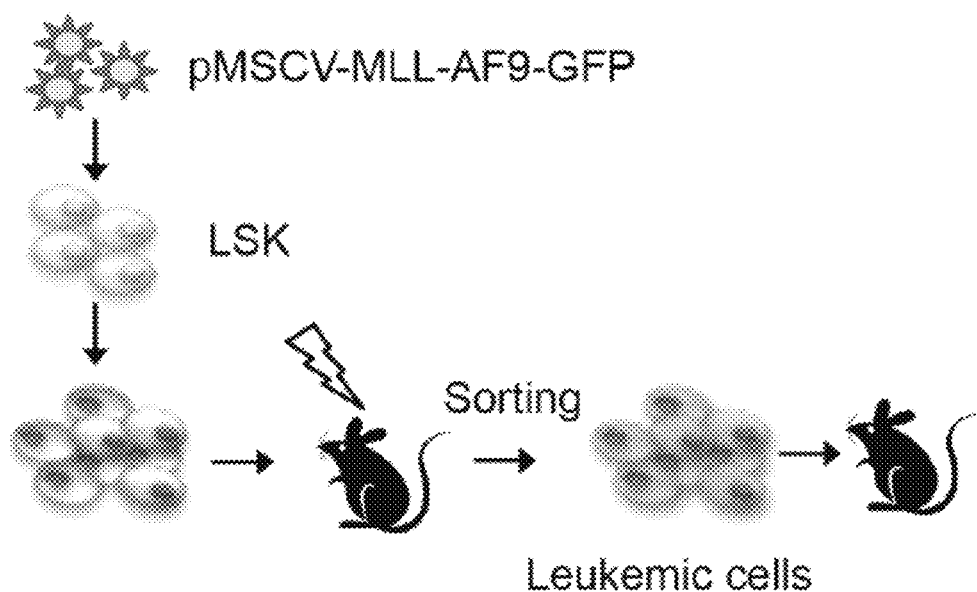
Figure 1C:
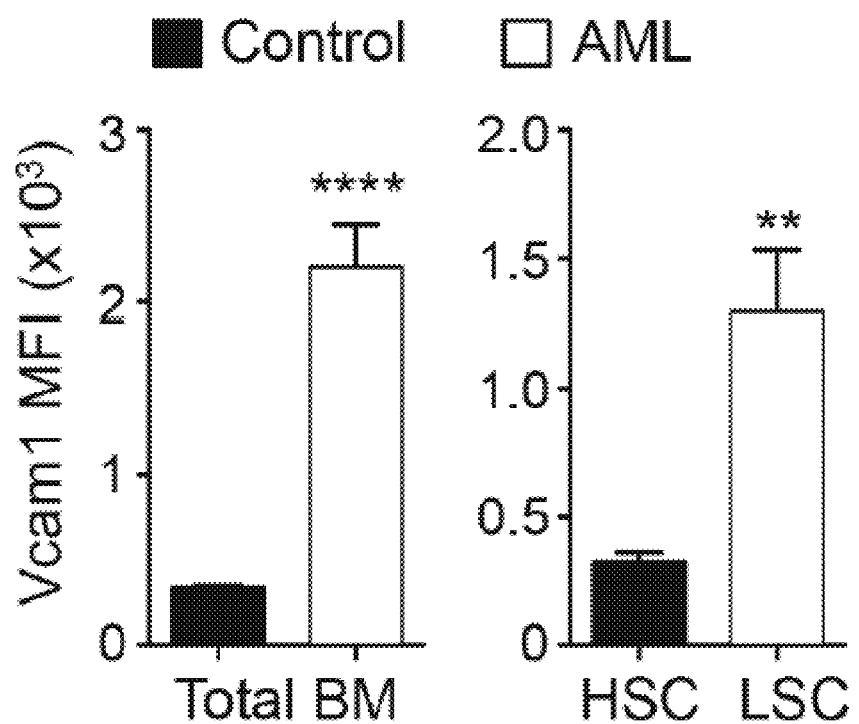
Figure 2A:
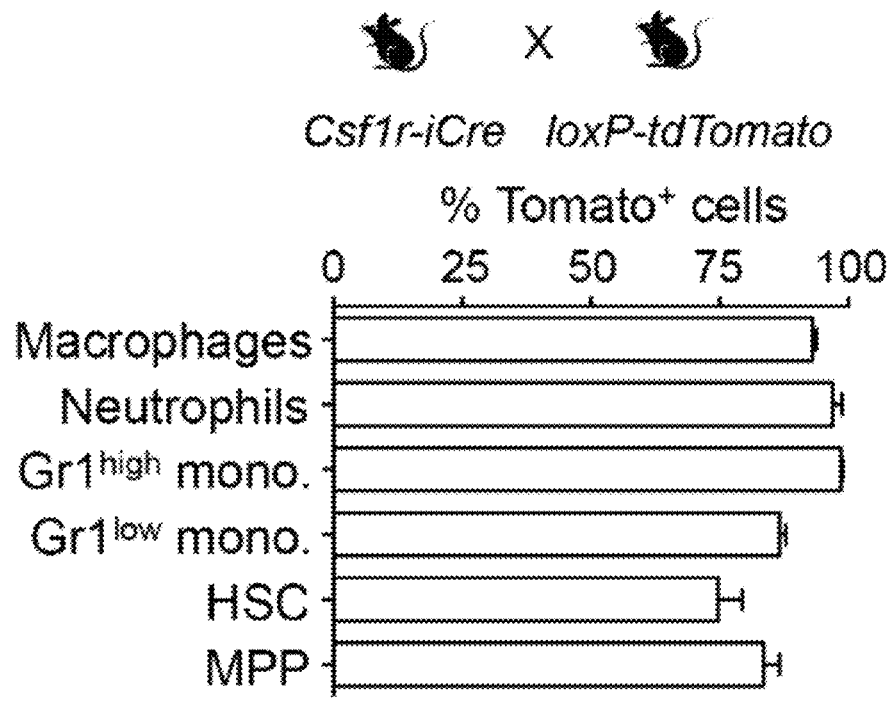
FIGS. 2A-2G.
Figure 2B:
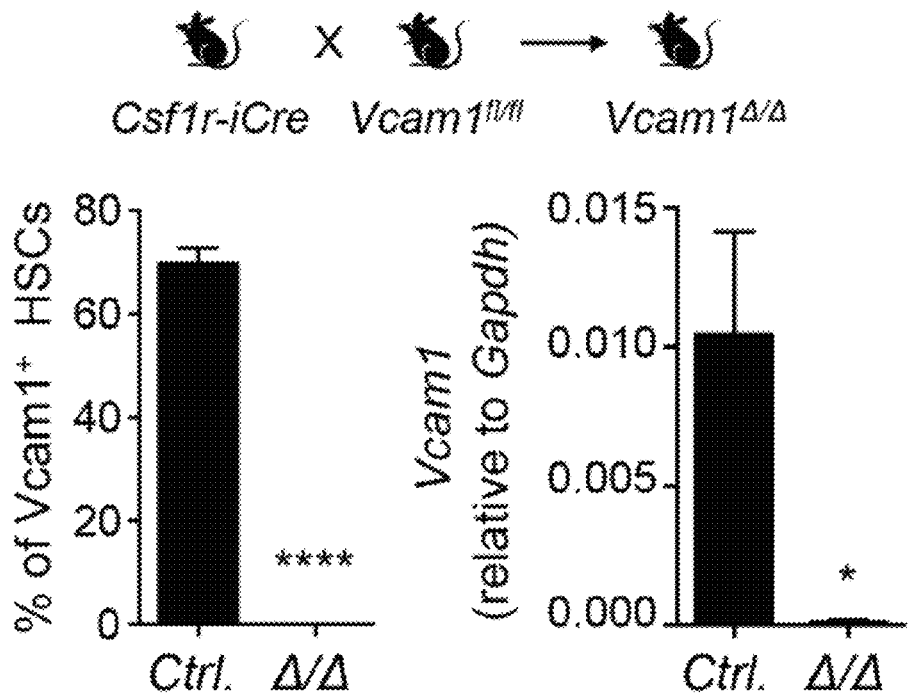
Figure 2C:
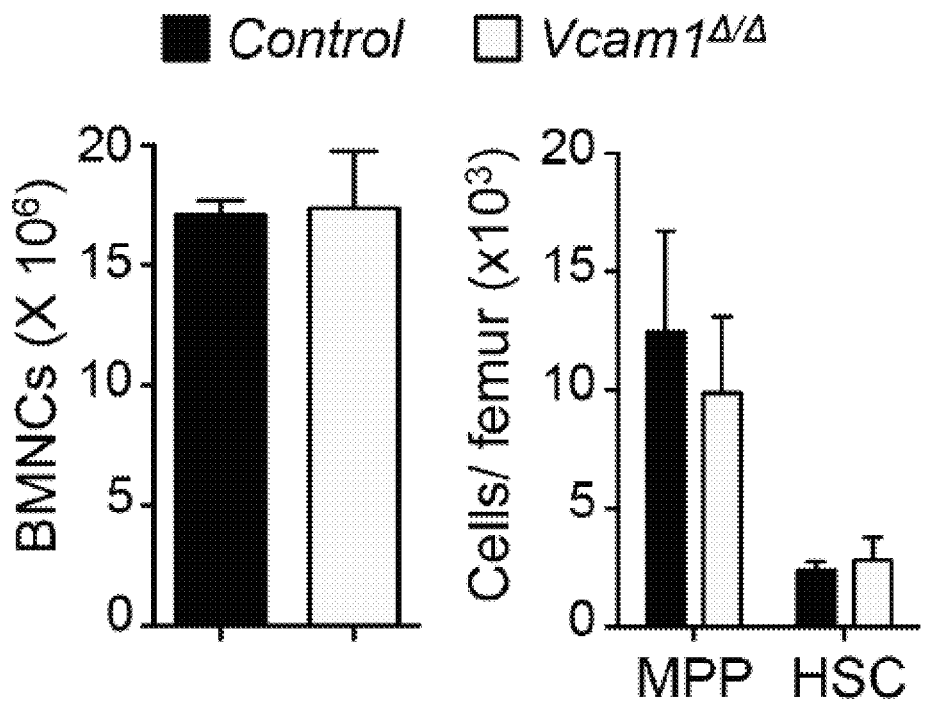
Figure 2D:
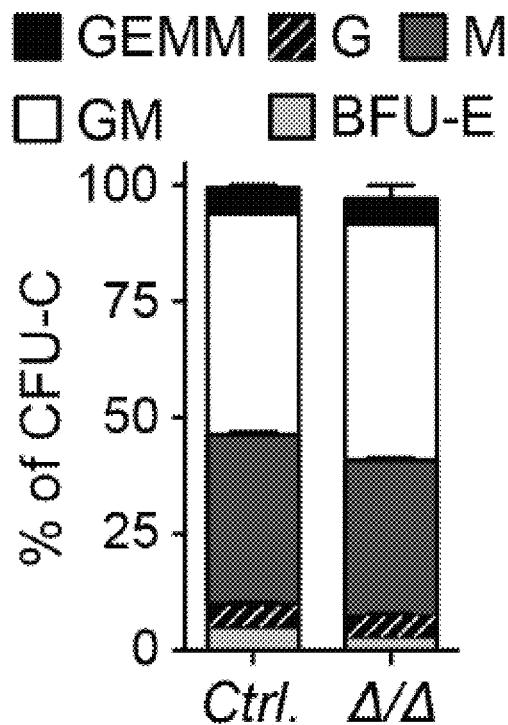
Figure 2E:
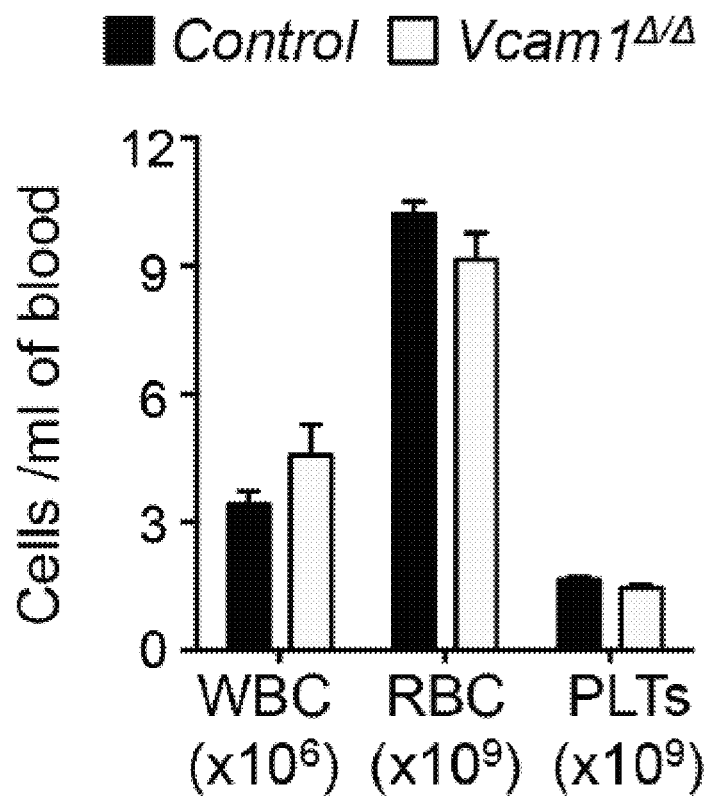
Figure 2F:
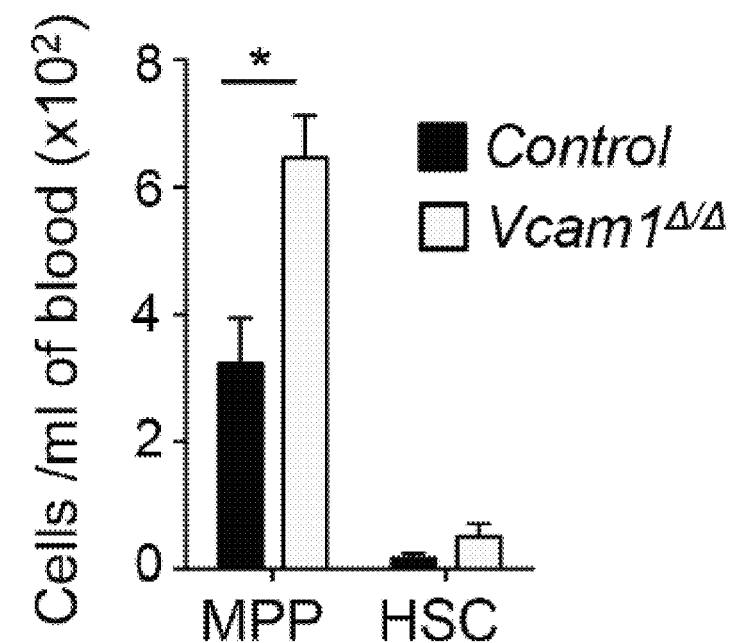
Figure 2G:
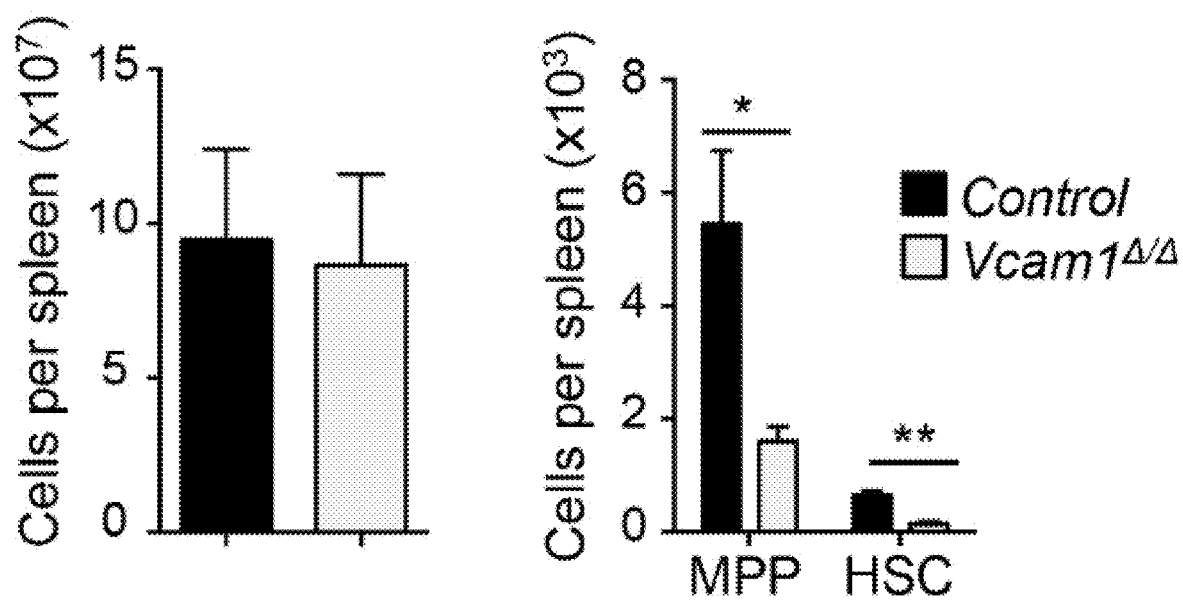
Figure 3A:
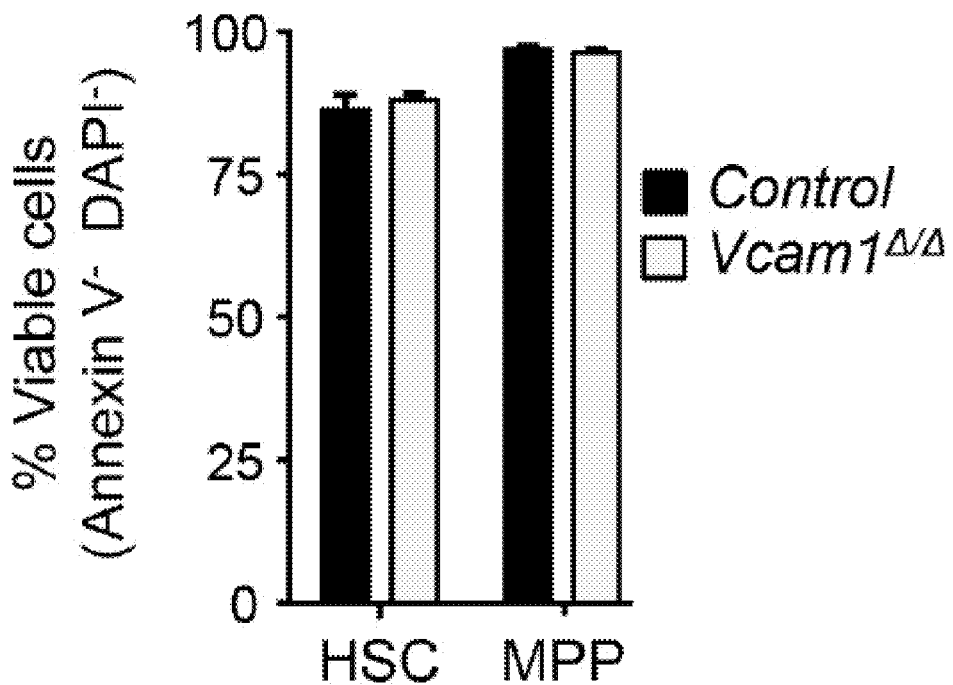
FIGS. 3A-3E.
Figure 3B:
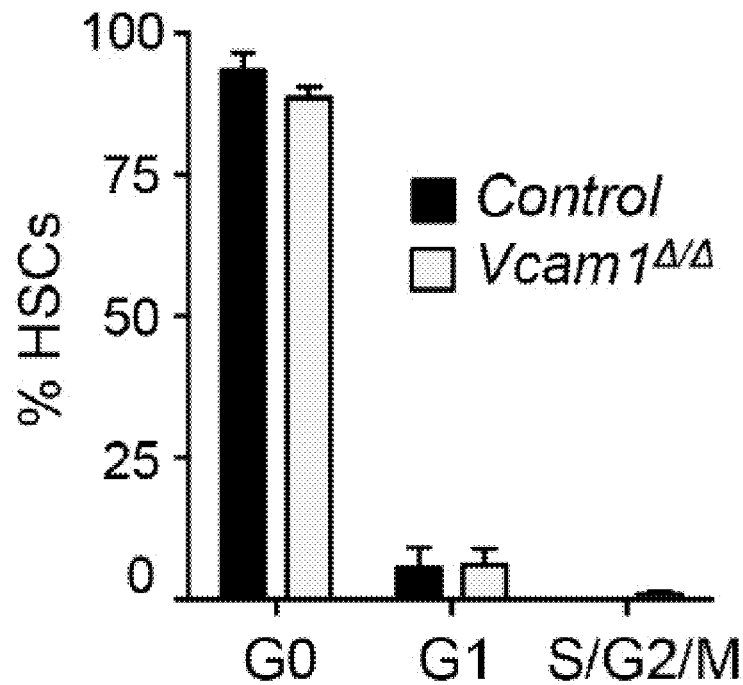
Figure 3C:
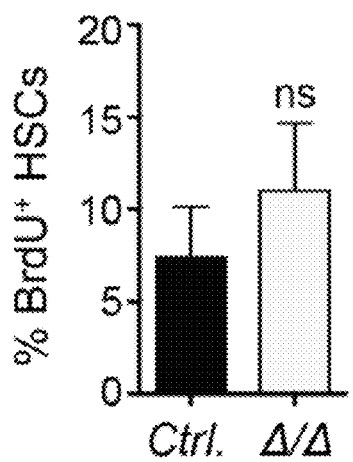
Figure 3D:
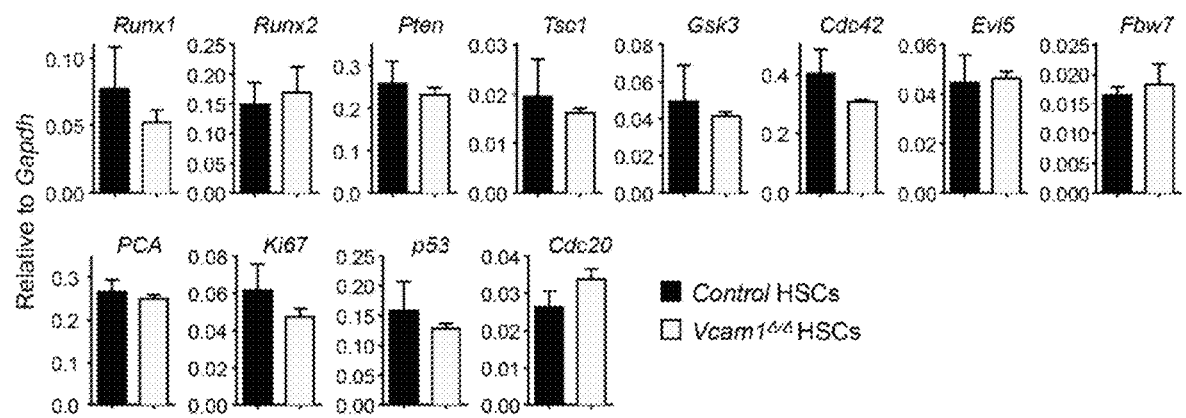
Figure 3E:
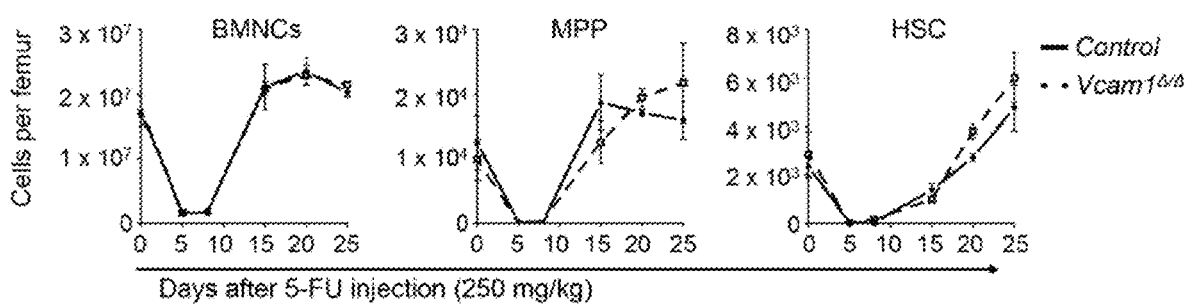

VCAM1 is expressed on hematopoietic stem and progenitor cells (HSPCs, FIG. 1A). Although VCAM1 expression in endothelial cells and its functional implications have been extensively described, the role of VCAM1 on HSCs has not been explored. Recent studies also suggest that VCAM1 expression on endothelial and bone marrow (BM) stromal cells may mediate in part leukemic cell resistance to conventional chemotherapy. VCAM1 is more highly expressed on acute myelogenous leukemia (AML) cells than their healthy counterparts (FIGS. 1B, 1C). Since Csf1r-iCre mice exhibit broad Cre expression in all hematopoietic cells, including most HSCs (FIG. 2A) and deletion of VCAM1 gene is embryonically lethal, VCAM1 floxed mice were bred with a Csf1r-iCre transgenic line (referred to as VCAM$^{\Delta/\Delta}$) to investigate VCAM1's function postnatally. In this model VCAM1 was efficiently depleted in phagocytic cells and also HSCs (FIG. 2B). VCAM1 deletion in Csf1r-icre+ cells induced HSPC mobilization into the peripheral blood; however, it did not significantly impair hematopoiesis (FIGS. 2C-2G). VCAM1 deletion did not increase the number of apoptotic HSCs as determined by Annexin V staining (FIG. 3A) and no significant changes were observed in the proportion of cycling HSCs or genes involved in HSC quiescence/proliferation (FIGS. 3B-3D). VCAM1$^{\Delta/\Delta}$ and control mice challenged with 5-FU did not reveal any deficit in hematopoietic stem and progenitor recovery (FIG. 3E).

Figure 4A:
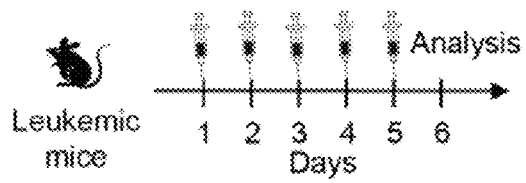
FIGS. 4A-4E.
Figure 4B:
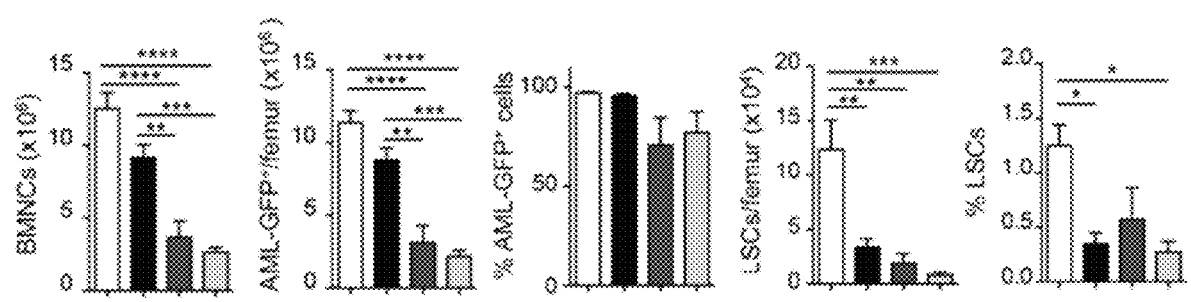
Figure 4C:
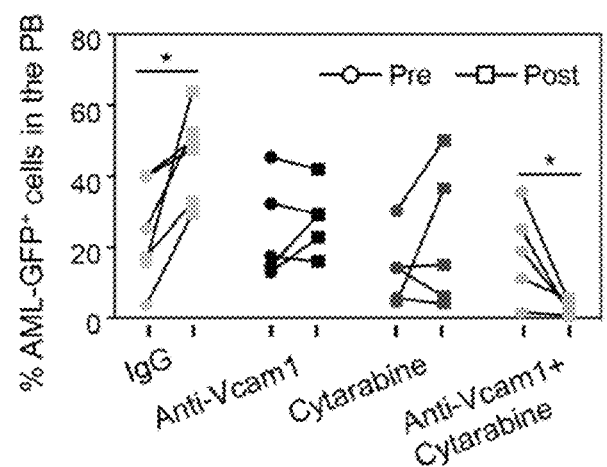
Figure 4D:
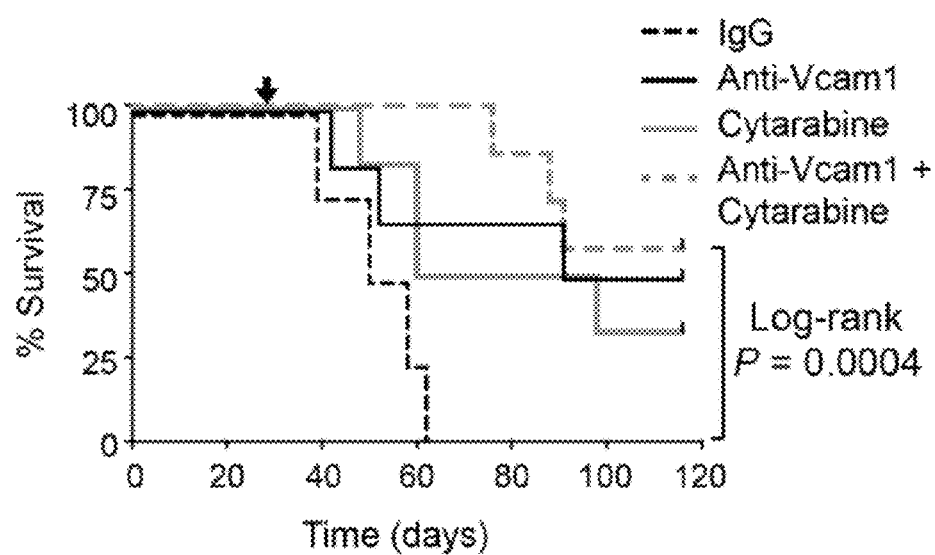
Figure 4E:
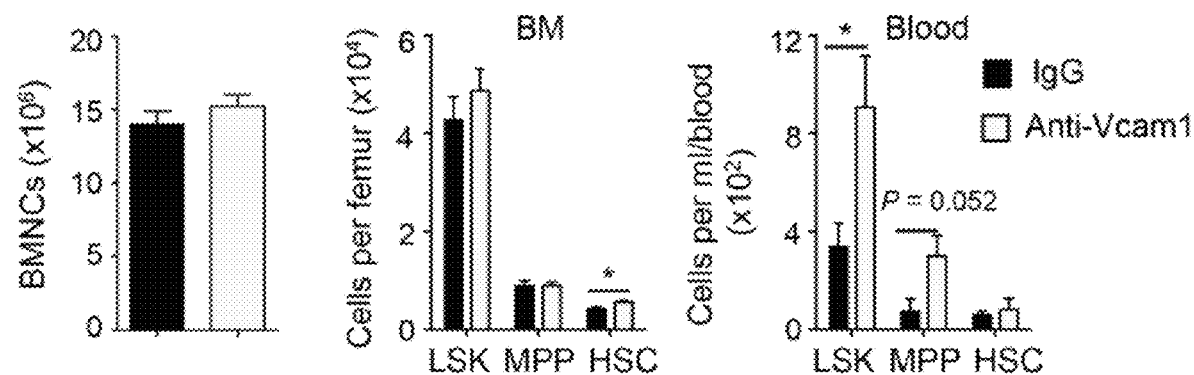
Figure 5A:
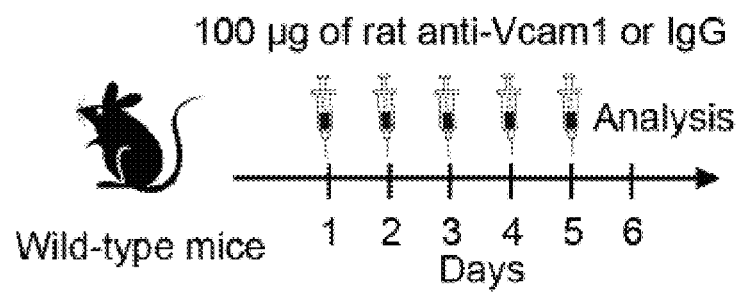
Figure 5B:
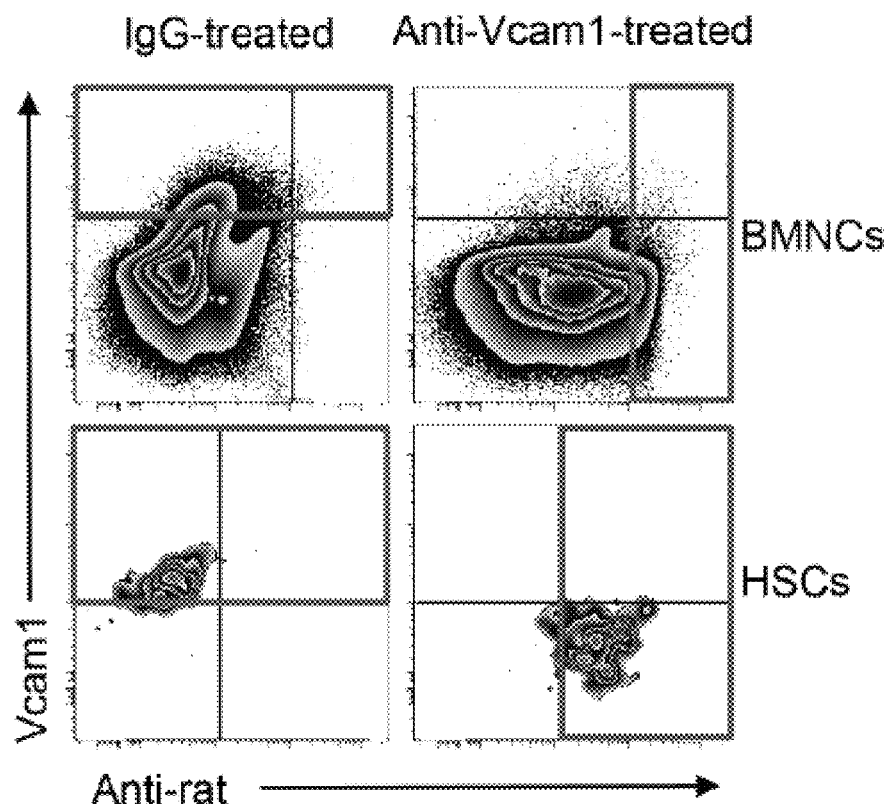
Figure 5C:
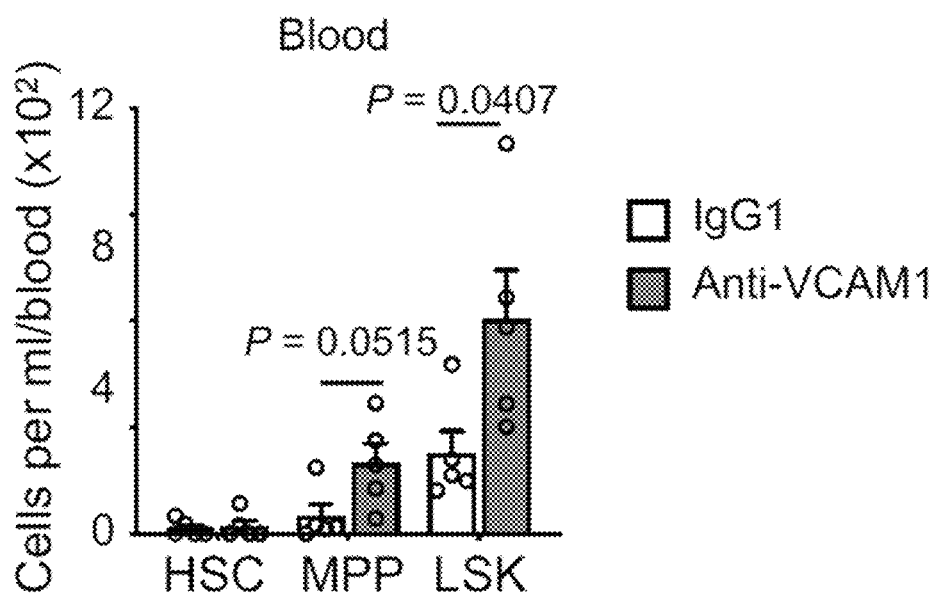
Figure 5D:
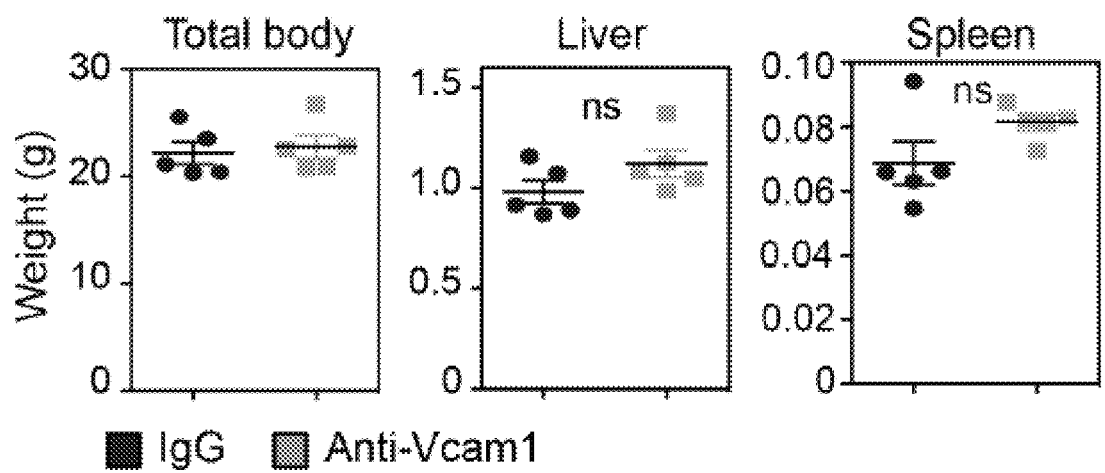
Figure 6A:
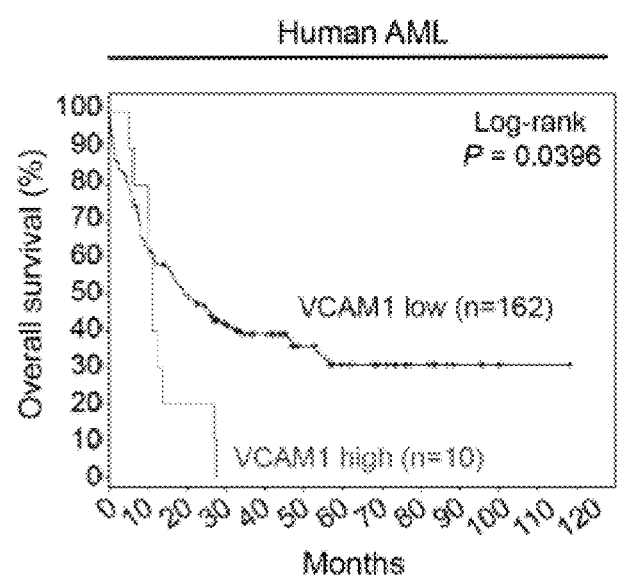
FIGS. 6A-6D.
Figure 6B:
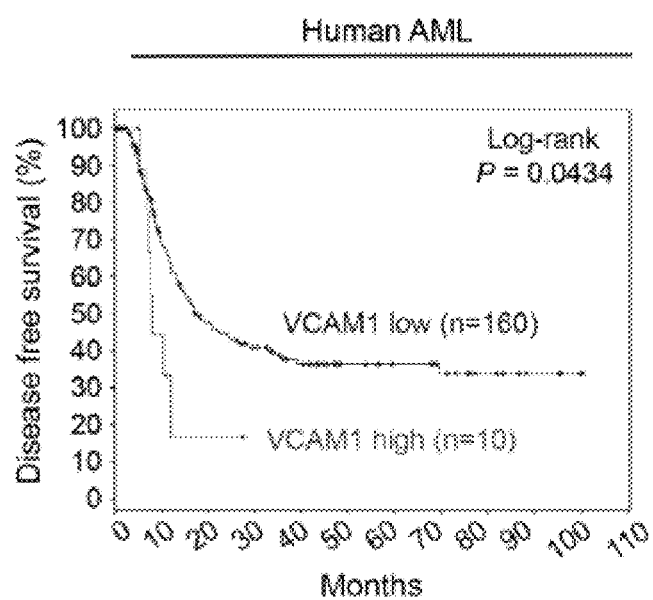
Figure 6C:
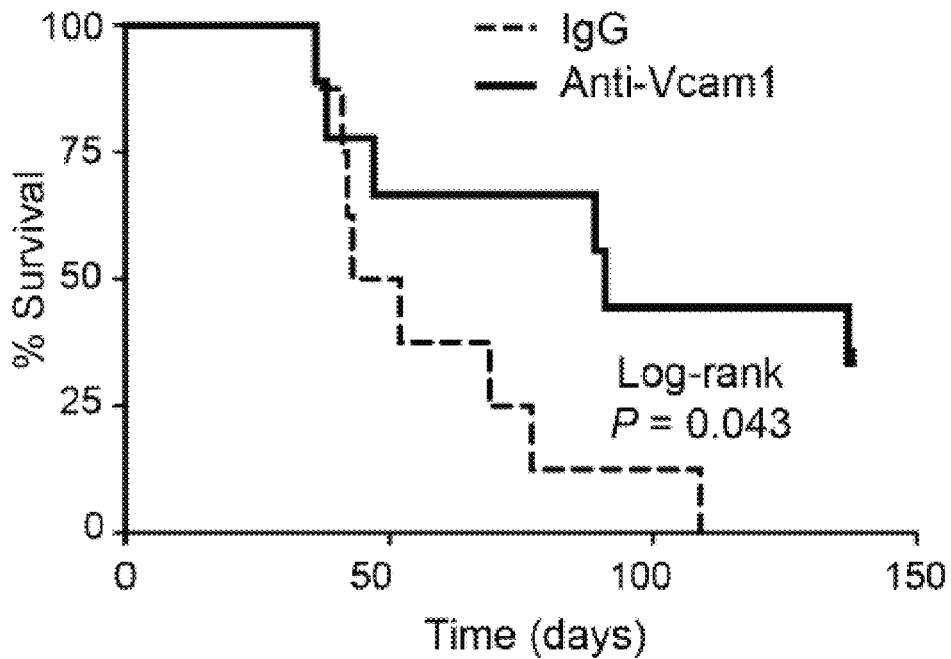
Figure 6D:
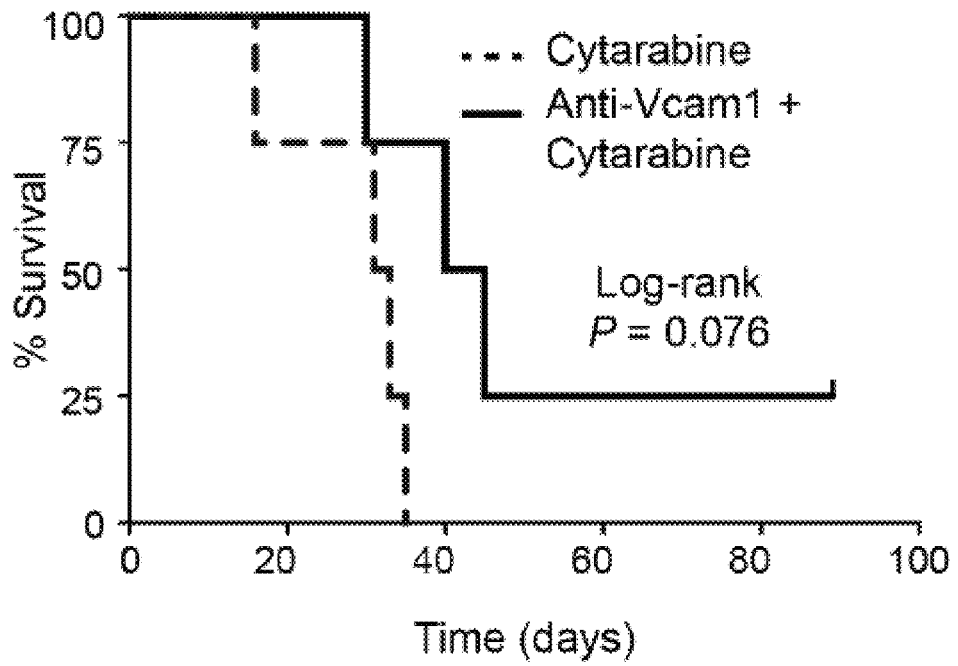

To test whether VCAM1 antibody blockade can improve conventional chemotherapy in animals with established disease, AML was established in immunocompetent C57BL/6 recipients and then therapy of moribund leukemic mice was initiated with a daily injection of IgG control, anti-VCAM1, cytarabine, or a combination of anti-VCAM1/cytarabine. Anti-VCAM1 antibody inhibition synergised with conventional chemotherapy to clear leukemic stem cells (LSCs) while sparing healthy HSCs, significantly prolonging mice survival (FIG. 4). The viability of targeting VCAM1 as a therapeutic strategy was investigated by injecting healthy wild-type mice with anti-VCAM1 antibody. After treatment, mice appeared healthy and body, liver and spleen weighs were unaltered (FIGS. 5A-5D). Complete blood counts showed no hematopoietic defects but did indicate a small increase in the percentage of reticulocytes (FIG. 5E). These results indicate that targeting VCAM1 function with a blocking monoclonal antibody should be well tolerated and a promising therapeutic strategy. Analysis of The Cancer Genome Atlas (TCGA) databases indicated that high VCAM1 expression was associated with poor prognosis in human AML patients (FIGS. 6A, 6B). Furthermore, anti-VCAM1 treatment was able to significantly extend the survival of immunocompromised mice transplanted with human primary AML samples (FIG. 6C).

Figure 7A:
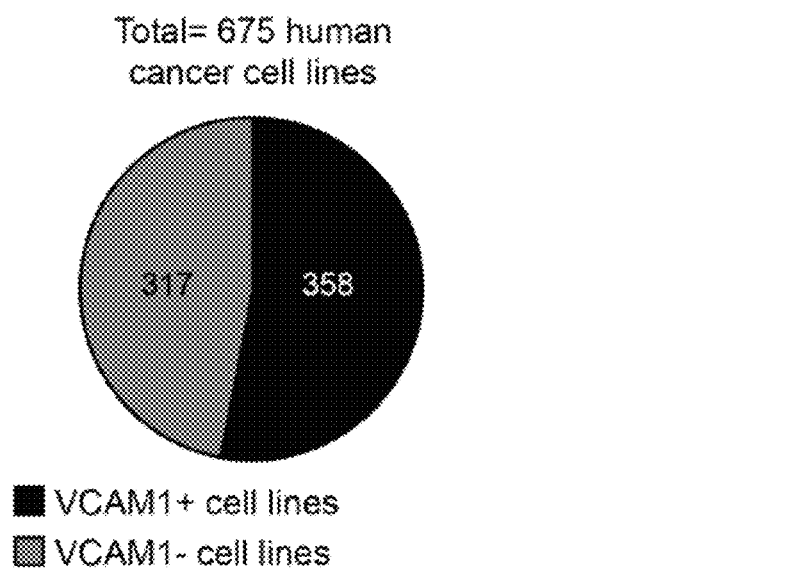
FIGS. 7A, 7B.
Figure 7B:
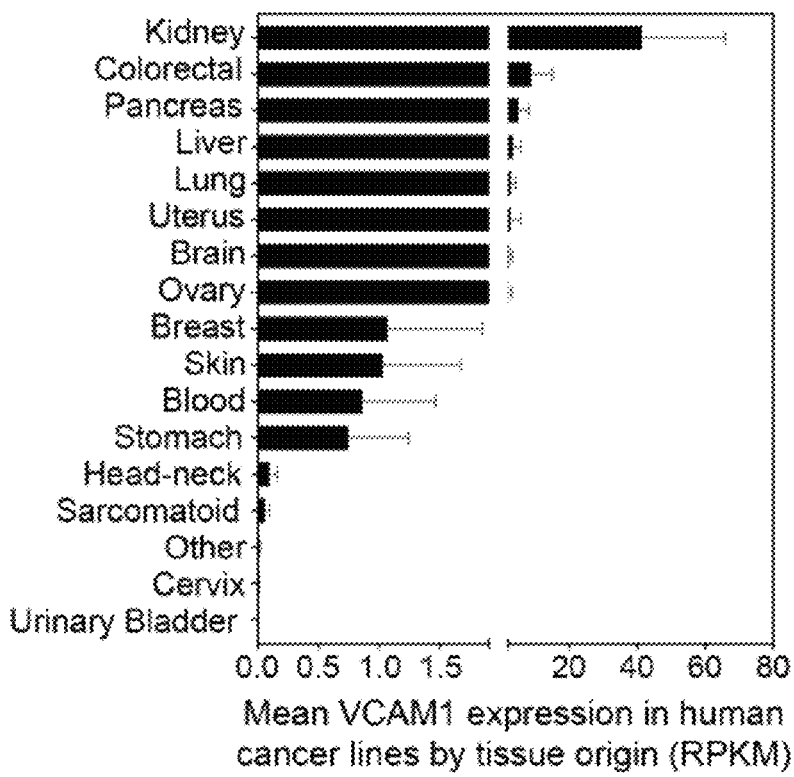
Figure 8:
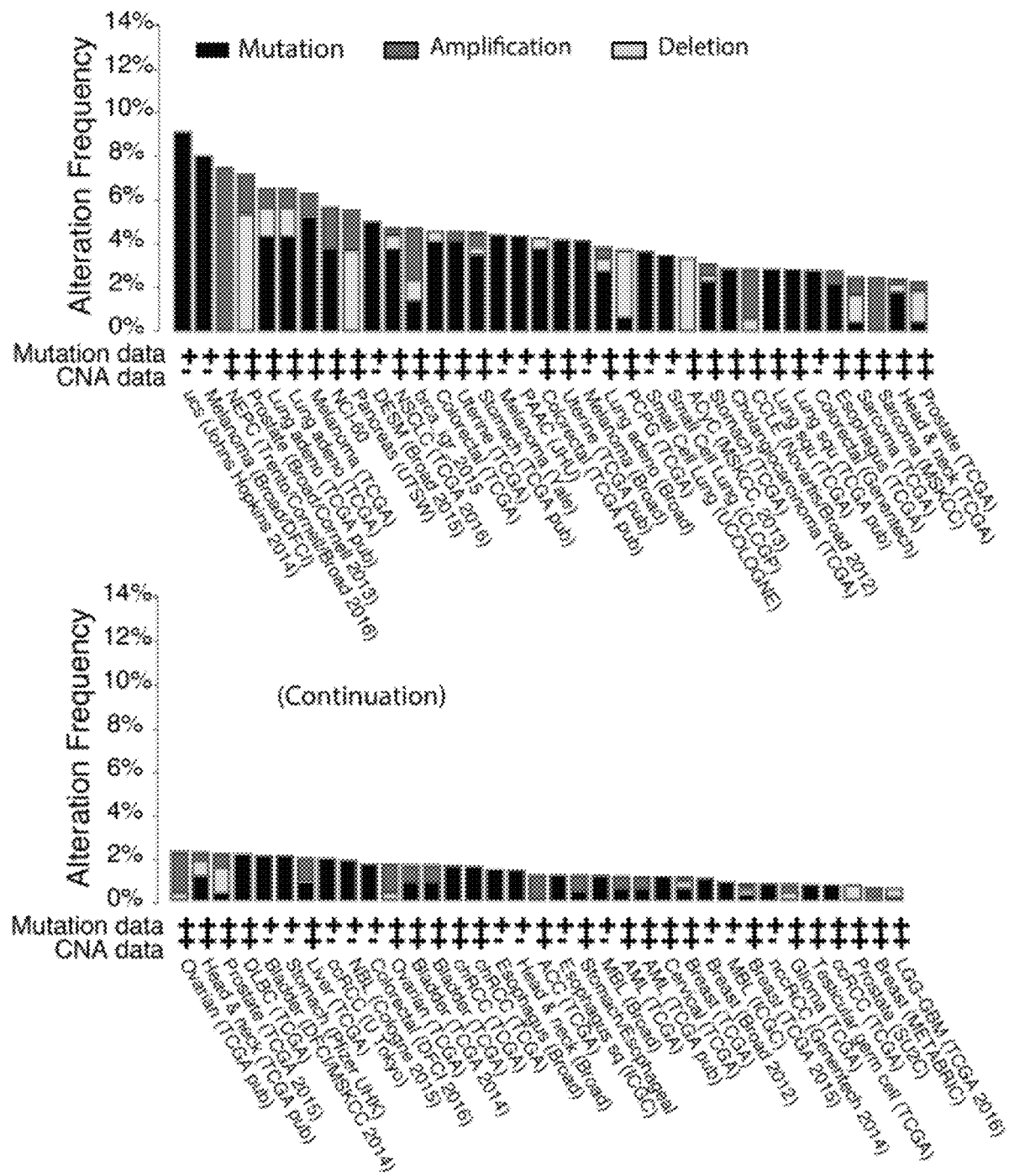
FIG. 8.

Analysis of a recently published RNA-sequencing dataset of 675 human cancer cell lines indicated that >50% of those lines express VCAM1 (FIG. 7A). In fact, different tissue types of human cancer cell lines express high levels of VCAM1, in particular kidney, colorectal and pancreas (FIG. 7B),[45] and significant association of VCAM1 gene alterations were found with many human cancer types (FIG. 8).

These studies demonstrate that VCAM1 is upregulated on malignant hematopoietic cells and that inhibition of binding of VCAM1 to its receptors will promote cancer cell clearance. These studies also indicate that this cell clearance mechanism is likely via a "don't-eat-me" signal since incubation of VCAM1$^{\Delta/\Delta}$ AML cells with macrophages led to enhanced phagocytosis of leukemic cells. This effect did not result from a reduced expression of CD47, since CD47 expression was not altered in VCAM1$^{\Delta/\Delta}$ mice. Monoclonal antibodies either alone or in combination with treatment such as cytarabine are an effective treatment for cancer.

Example 2: VCAM1 Confers Innate Immune Tolerance on Hematopoietic and Leukemic Stem Cells Haematopoietic stem cells (HSCs) home to the bone marrow (BM) via, in part, the interactions with vascular cell adhesion molecule-1 (VCAM1).[57-59] Upon migrating into the BM, HSCs are vetted by perivascular phagocytes to ensure their self-integrity. In this Example, results show that VCAM1 is also expressed on healthy HSCs and upregulated on leukemic stem cells (LSCs) where it serves as a quality-control checkpoint for entry into BM by providing 'don't-eat-me' stamping in the context of major histocompatibility complex (MHC) class-I presentation. While MHC haplotype-mismatched HSCs can engraft the BM of recipient mice, conditional VCAM1 deletion, in the setting of haplotype mismatch, leads to impaired hematopoietic recovery due to HSC recognition and clearance by phagocytes. Mechanistically, MHC mismatched HSCs are recognized at least in part by paired Ig-like receptor-B (PIR-B) expressed on murine phagocytic myeloid cells. VCAM1 is also used by cancer cells to escape immune detection as its expression is upregulated in multiple cancers, including acute myeloid leukemia (AML), where high expression is significantly associated with poor prognosis. In AML mouse models, VCAM1 promotes disease progression while VCAM1 inhibition or deletion significantly reduces the leukemia burden and extends the survival of mice. These results suggest that VCAM1 engagement regulates a critical immune checkpoint gate in the BM and offers a novel strategy to eliminate cancer cells via modulation of the innate immune tolerance.

Figure 13A:
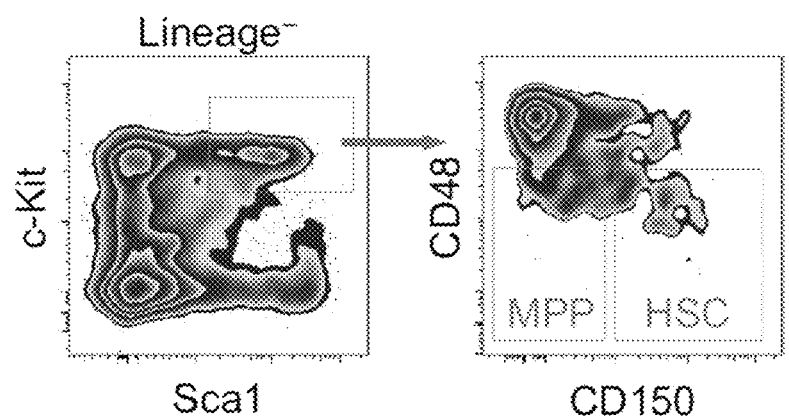
FIGS. 13A-13D.
Figure 13B:
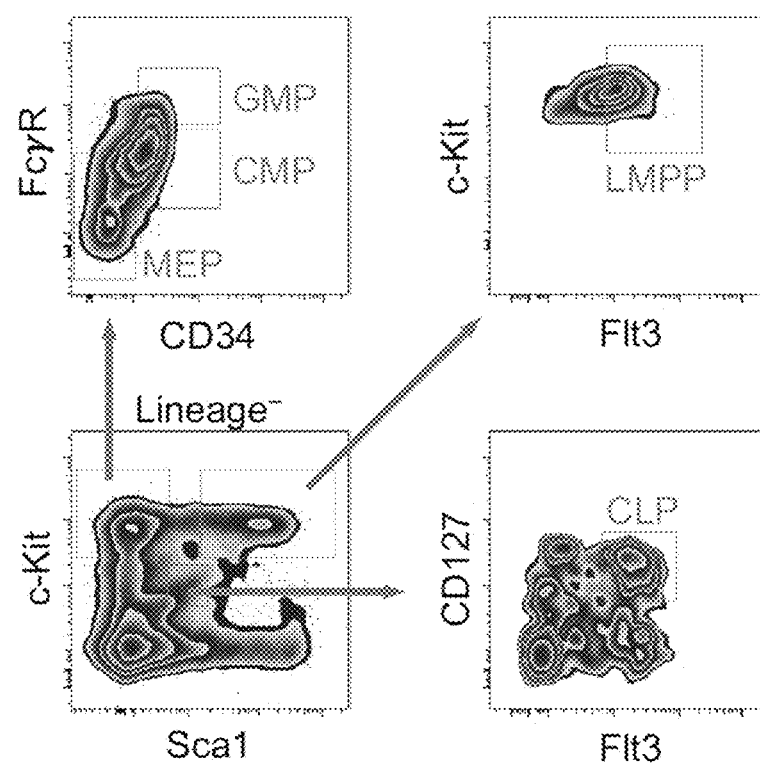
Figure 13C:
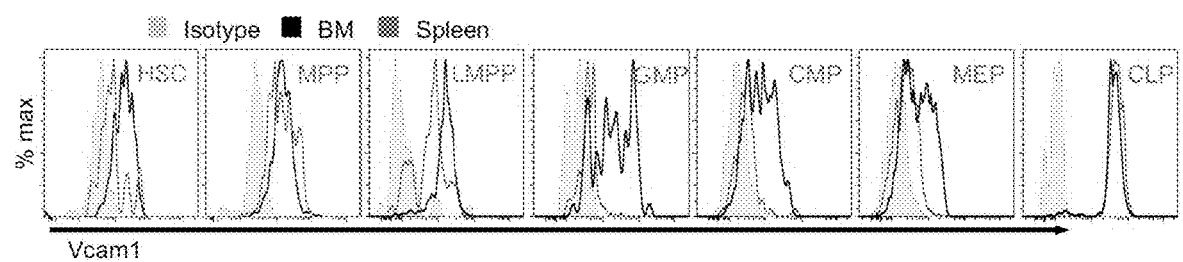
Figure 13D:
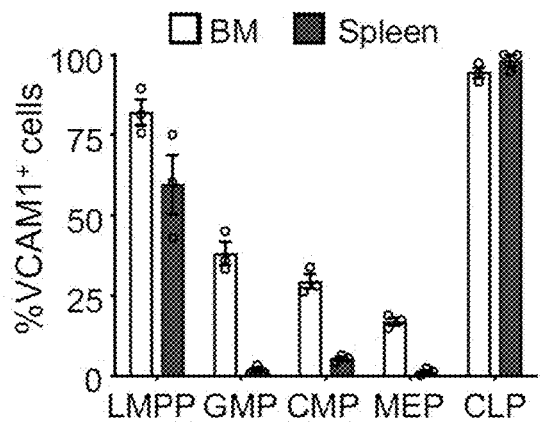
Figure 14A:
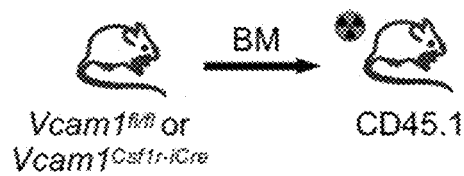
FIGS. 14A-14D.
Figure 14B:
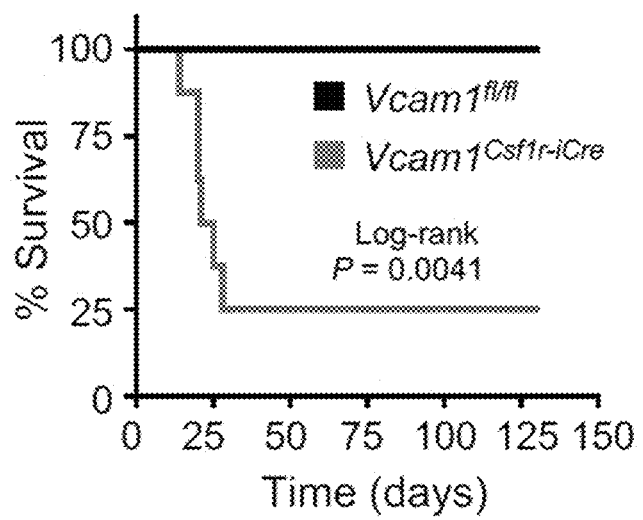
Figure 14C:
Figure 14D:
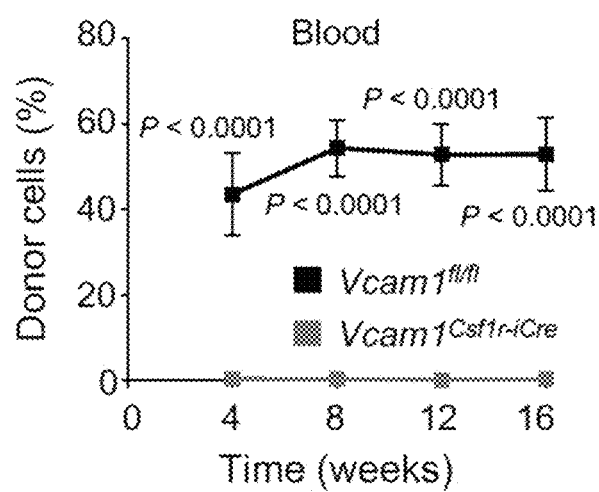
Figure 15A:
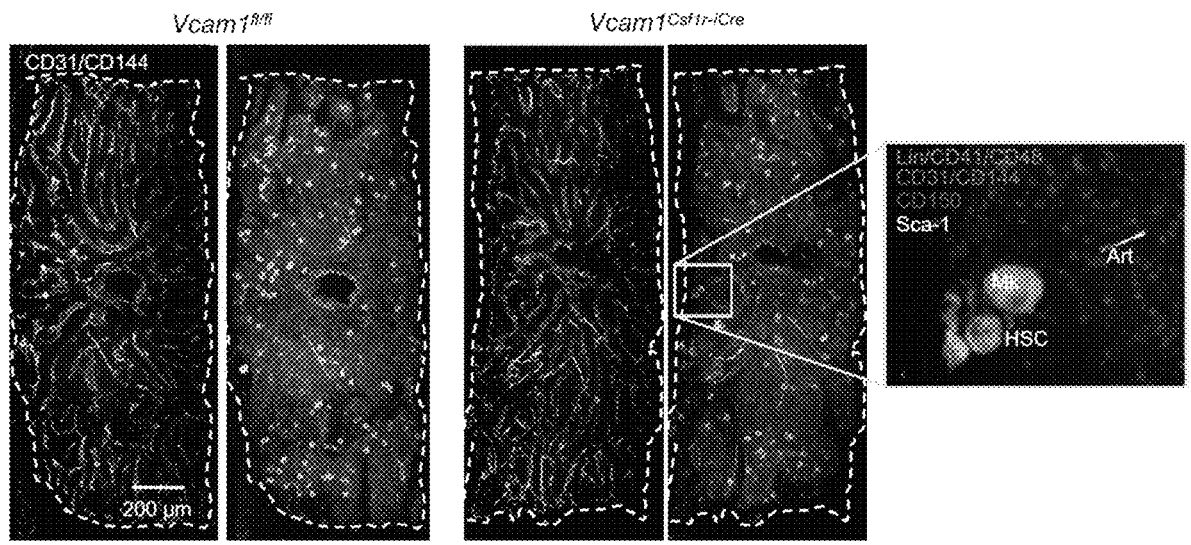
FIGS. 15A-15C.
Figure 15B:
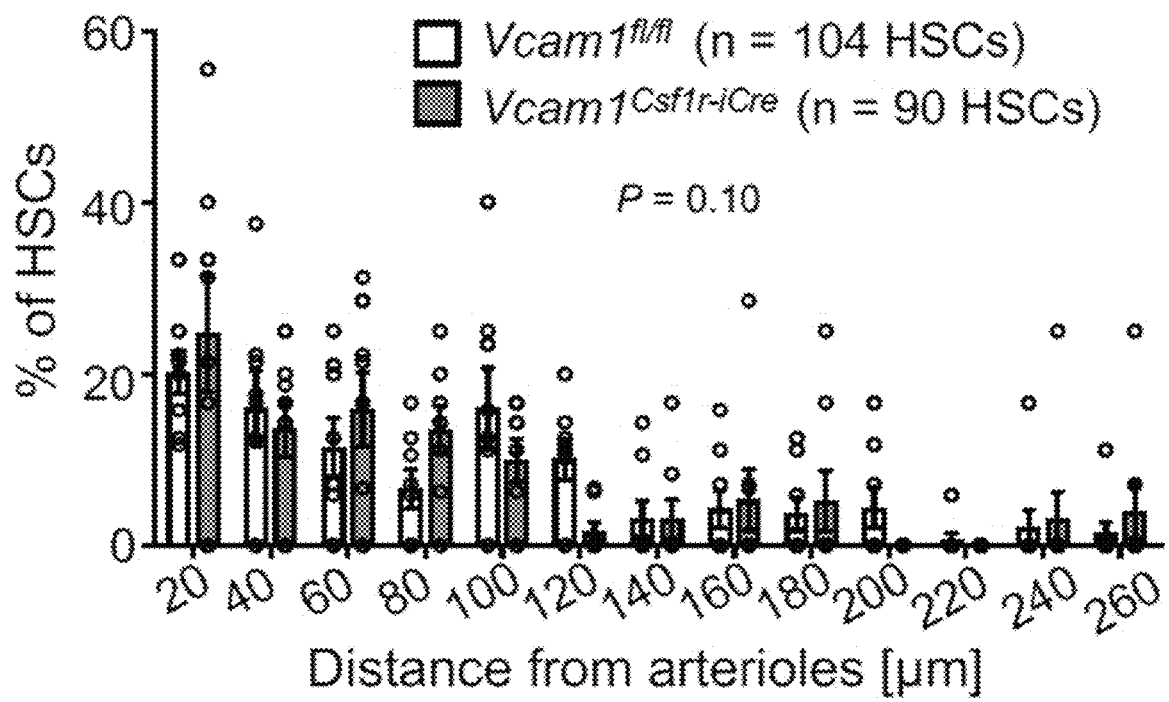
Figure 15C:
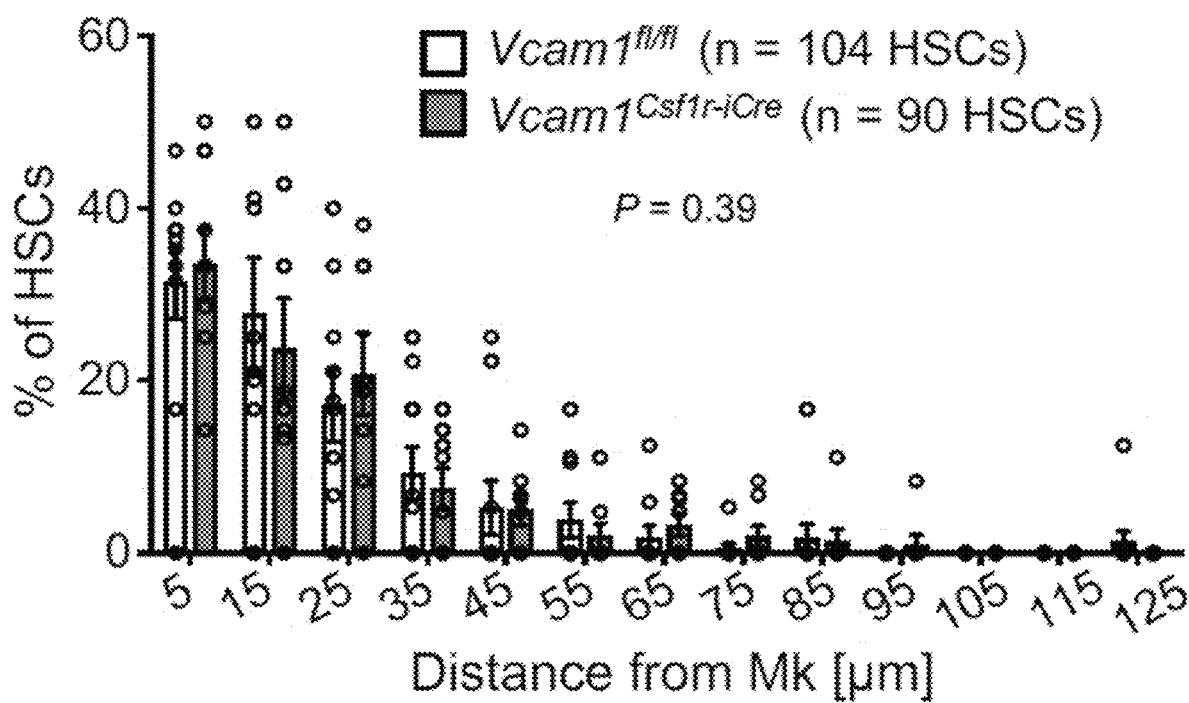

HSCs possess the ability to replenish the haematopoietic system following transplantation into marrow-ablated recipients.[60] VCAM1, a vascular endothelial and stromal adhesion molecule, is required for vascular development[61] and known to mediate the entry[62,63] and egress[63-65] of HSCs and progenitors between BM and the blood circulation. Using flow cytometry analysis, Applicants found that VCAM1 was also expressed at high levels on the majority of HSCs (~75%) and some progenitors in the BM, and its expression was downregulated in HSCs mobilized in the periphery (spleen and blood; FIGS. 1A, 13A-13D). Mice carrying floxed VCAM1 alleles (VCAM$^{fl/fl}$)[66] were bred with a Csf1r-iCre transgenic line[67] (hereafter referred to as VCAM1$^{Csf1r-iCre}$) to evaluate its role on macrophages of erythroblastic islands.[68] Applicants have also found, however, high Cre deletion efficiency in HSCs and their descendants consistent with the reported Csf1r expression in HSCs[69-70] (FIGS. 2B, 13E). To evaluate VCAM1's function on HSCs, VCAM1$^{Csf1r-iCre}$ BM cells were transplanted in lethally irradiated wild-type C57BL/6 recipients (FIG. 14A). Interestingly, the vast majority (~75%) of recipients transplanted with VCAM1$^{Csf1r-iCre}$ BM cells succumbed between days 14-28 (FIG. 14B). No repopulating contribution from VCAM1Csf1r-iCre was also obtained in competitive reconstitution experiments (FIGS. 14B, 14D). By contrast, the constitutive deletion of VCAM1 (without transplantation) did not alter HSC numbers, location, cycling status, or the numbers of multipotent progenitors (MPPs), colony-forming progenitors or blood cell counts (FIGS. 2C-2E, 2G, 3A, 3B, 3E). In addition, 5-FU treatment did not reveal any deficit in VCAM$^{Csf1r-iCre}$ HSPC recovery (FIG. 3E). However, VCAM1 deletion led to reduced numbers of splenic HSCs and progenitors (FIG. 2G) with slight augmentation of circulating progenitors in blood (FIG. 2F), in line with a previous report.[71] These results suggest that VCAM1 expressed on HSCs may regulate their engraftment in the BM, but may be dispensable for steady-state or stress hematopoiesis.

Figure 9A:
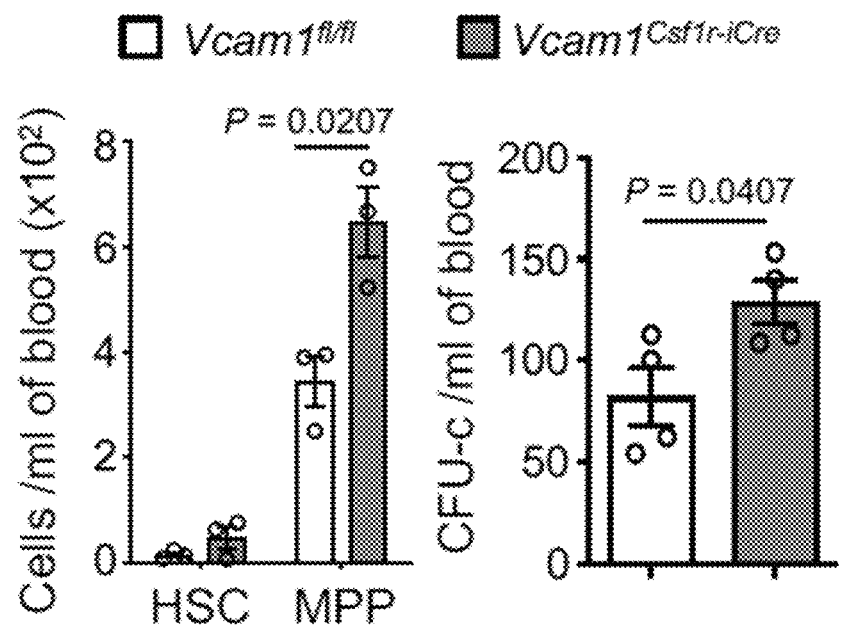
FIGS. 9A-9F.
Figure 9B:
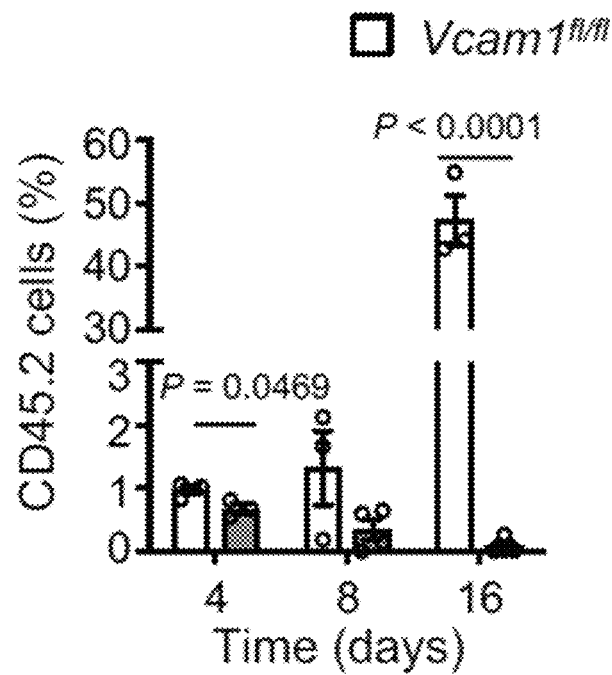
Figure 9C:
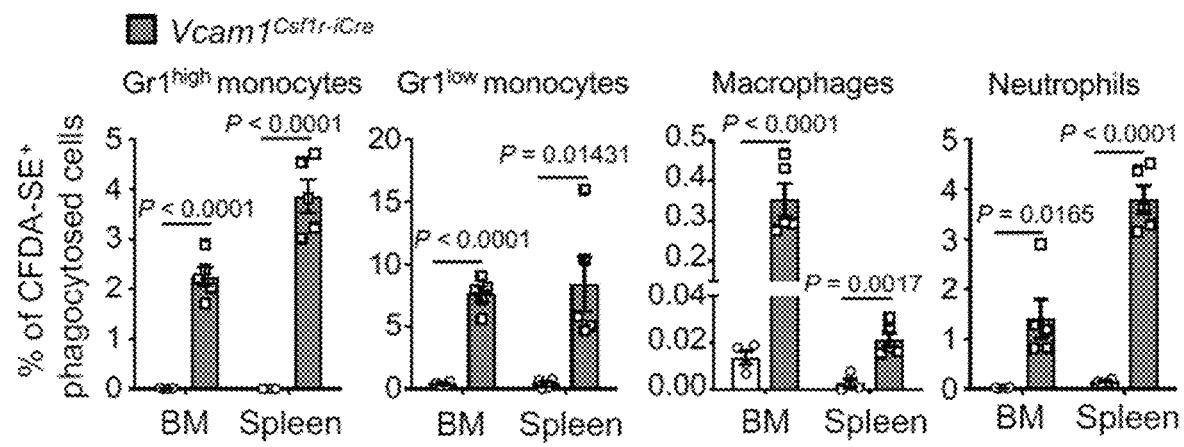
Figure 9D:
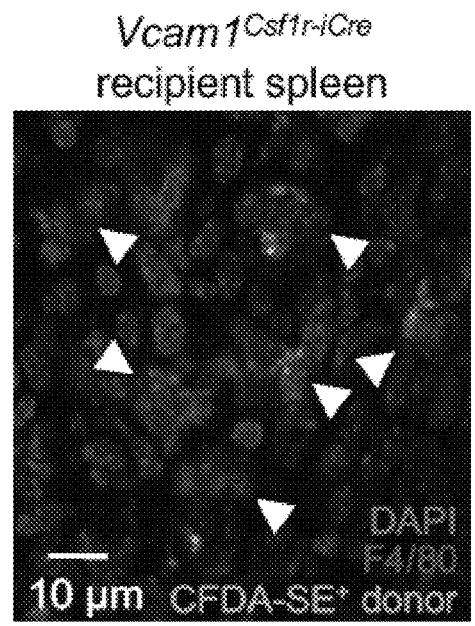
Figure 9E:
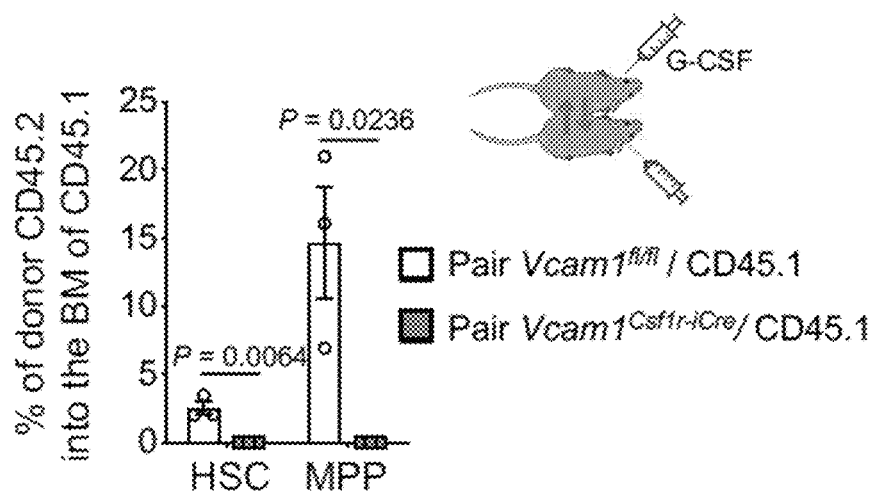
Figure 9F:
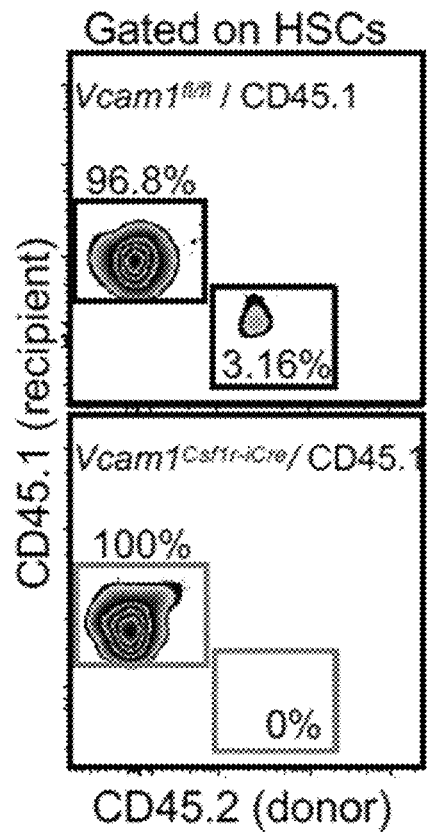
Figure 10A:
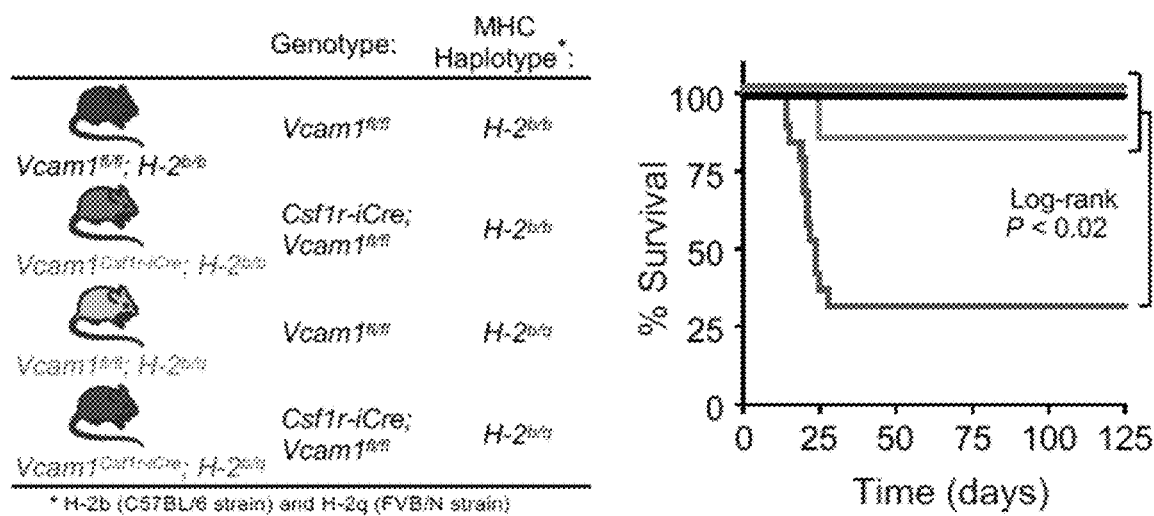
FIGS. 10A-10H.
Figure 10B:
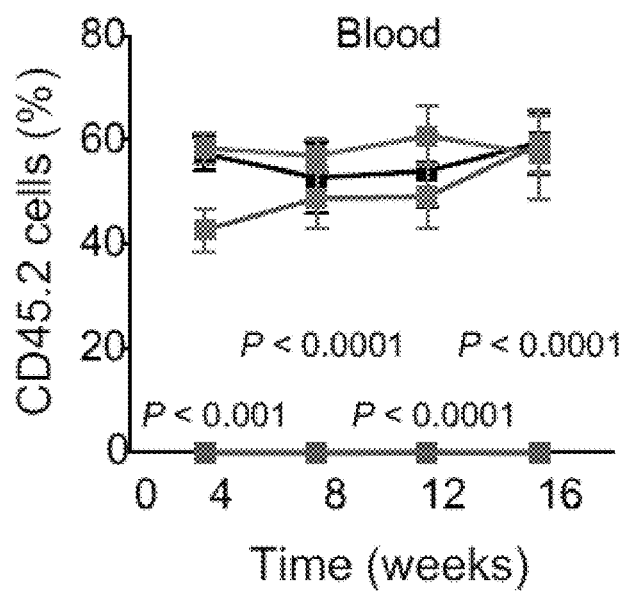
Figure 10C:
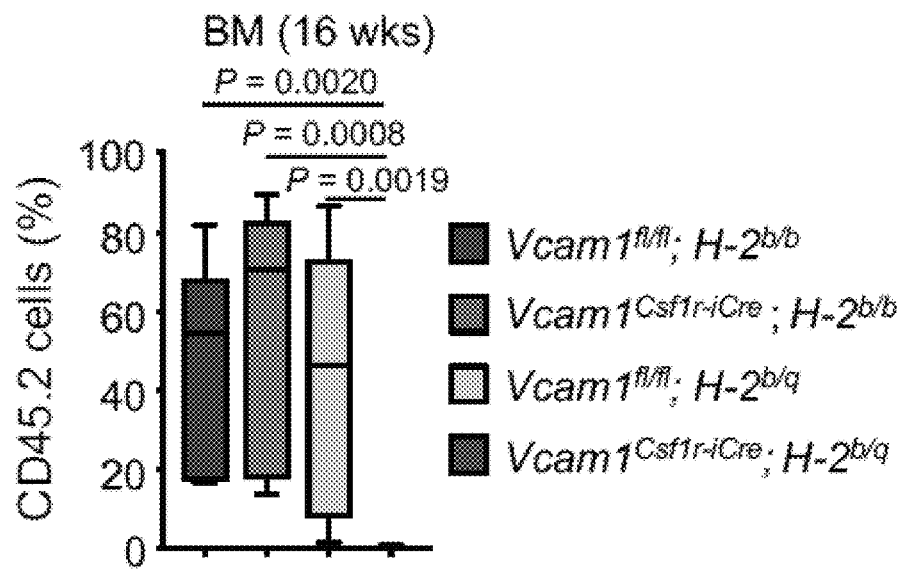
Figure 10D:
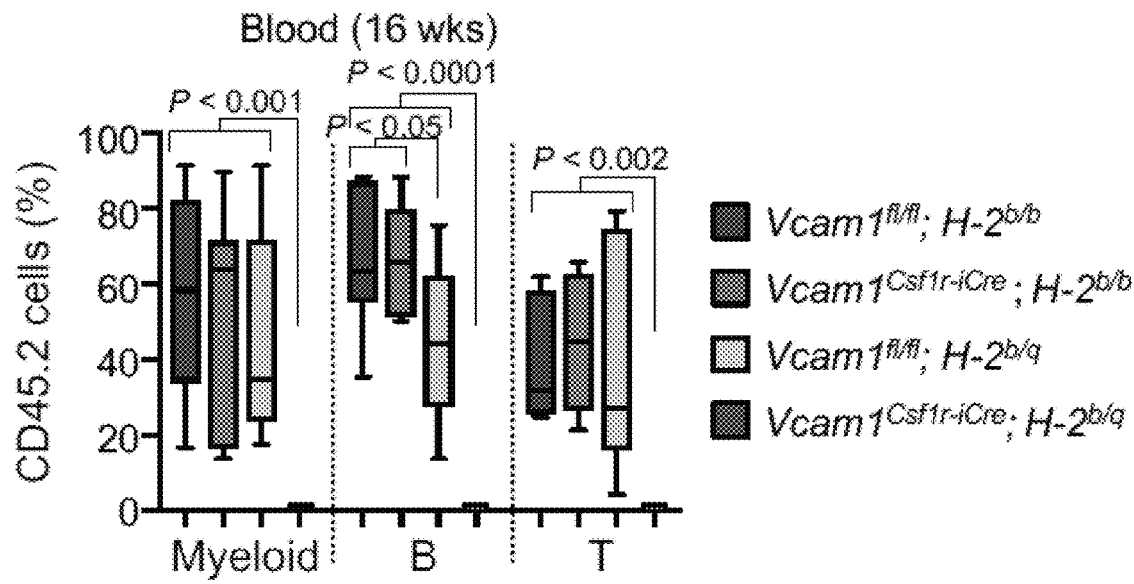
Figure 16A:
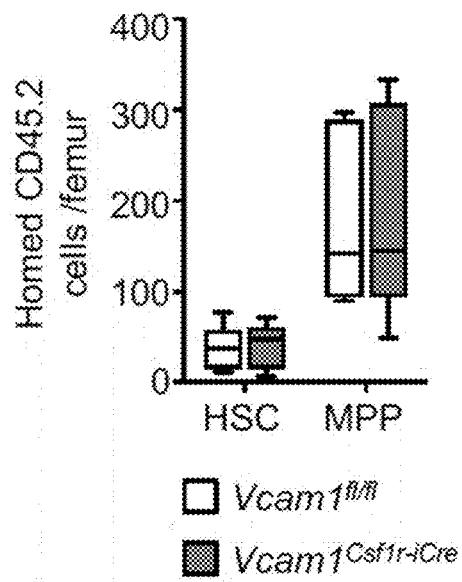
FIGS. 16A-16C.
Figure 16B:
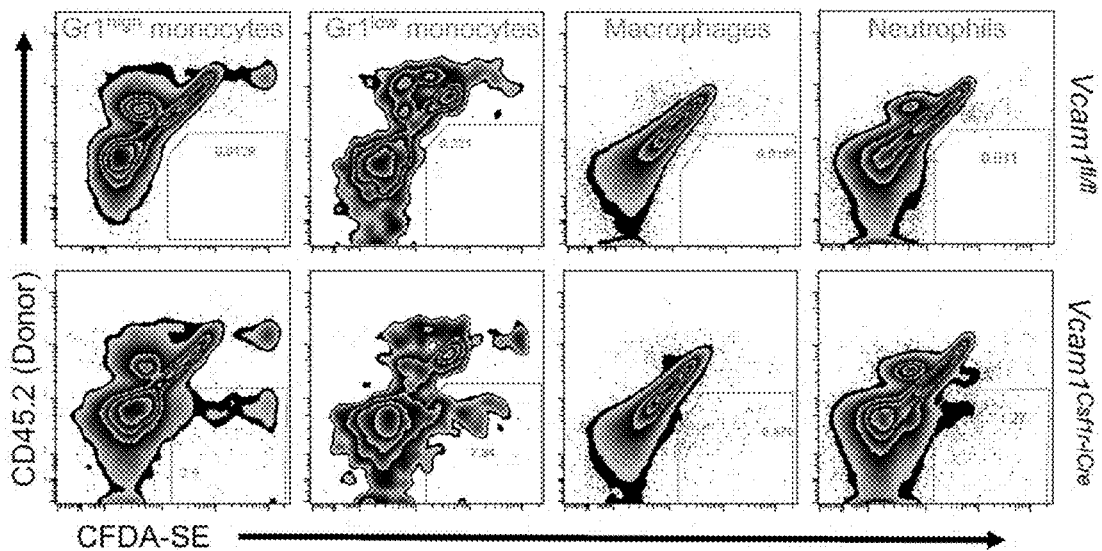
Figure 16C:
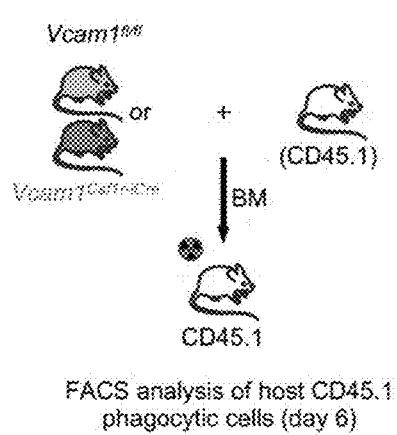
Figure 16C:
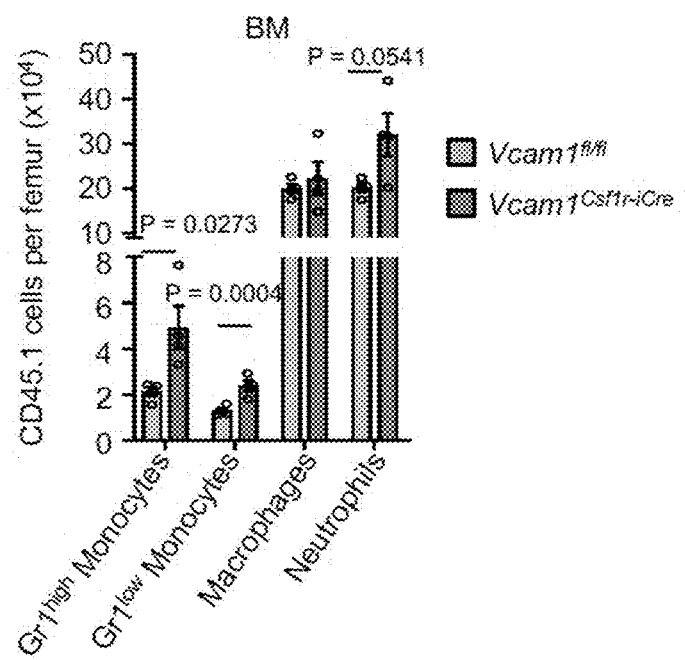

To resolve the discrepancy between the dramatic HSC transplantation phenotype and the absence of constitutive HSC phenotype, the fate of injected VCAM1$^{Csf1r-iCre}$ and VCAM1$^{fl/fl}$ BM cells was tracked after transplantation. While no difference in homing to BM 3 h after injection in lethally irradiated recipients was found (FIG. 16A), a time-course follow up revealed that the contribution of VCAM1$^{Csf1r-iCre}$ progenitors to the recipient blood was reduced by ~35% on day 4 and was barely detectable two weeks after transplantation (FIG. 9B). Post-transplantation failure was due to clearance by phagocytic cells as CFDA-SE fluorescently labelled VCAM1$^{Csf1r-iCre}$ Lineage$^-$ cells accumulated in host immune phagocytes (Gr-1high and Gr-1low monocytes, macrophages and neutrophils) after injection (FIGS. 9C, 9D, 16B). This was accompanied by increased numbers of host phagocytic monocytes and neutrophils in VCAM1$^{Csf1r-iCre}$-transplanted recipient mice compared to those transplanted with VCAM1$^{fl/fl}$ BM cells (FIG. 10C). To ascertain that the clearance was not dependent on the damaged inflicted by irradiation, applicant assessed the BM chimerism in G-CSF-mobilized parabiotic mice in which animals share the blood circulation. These results showed that while VCAM1$^{fl/fl}$ HSCs and MPPs significantly engrafted the partner mice, VCAM1$^{Csf1r-iCre}$ cells did not engraft the parabiont partner (FIGS. 9E, 9F).

These data indicate that VCAM1-deficient HSCs are susceptible to be recognized by host phagocytic cells in the BM.

Figure 17A:
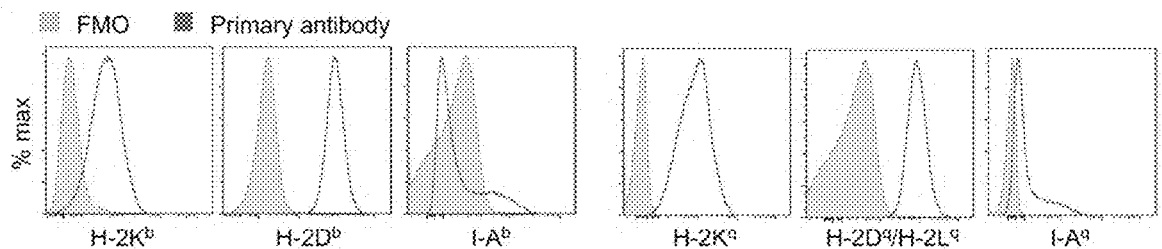
FIGS. 17A-17C.
Figure 17B:
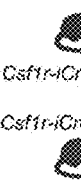
Figure 17C:
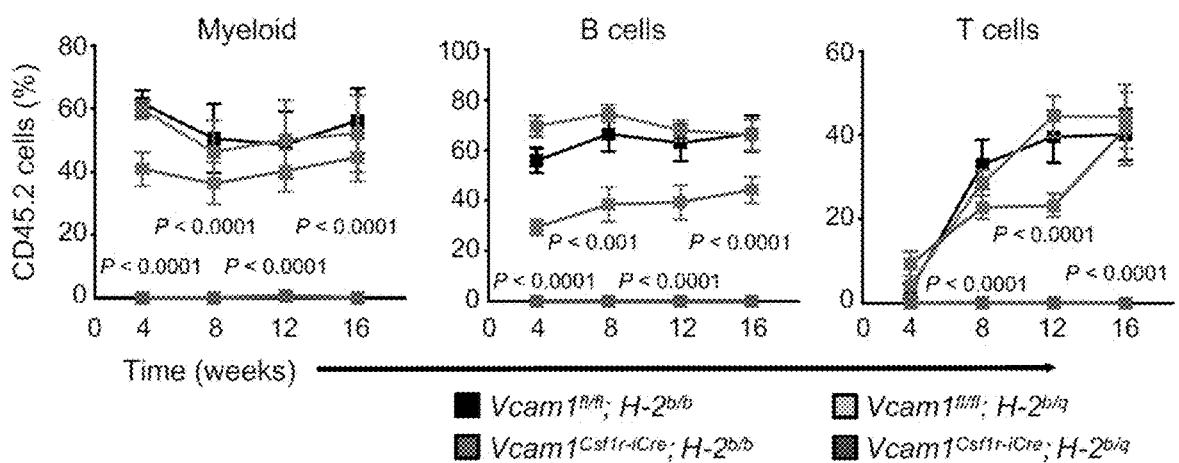
Figure 18A:
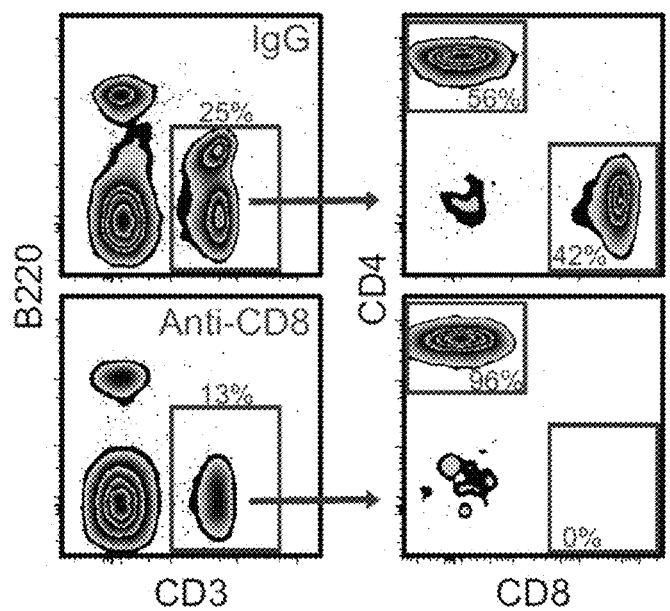
FIGS. 18A-18C.
Figure 18B:
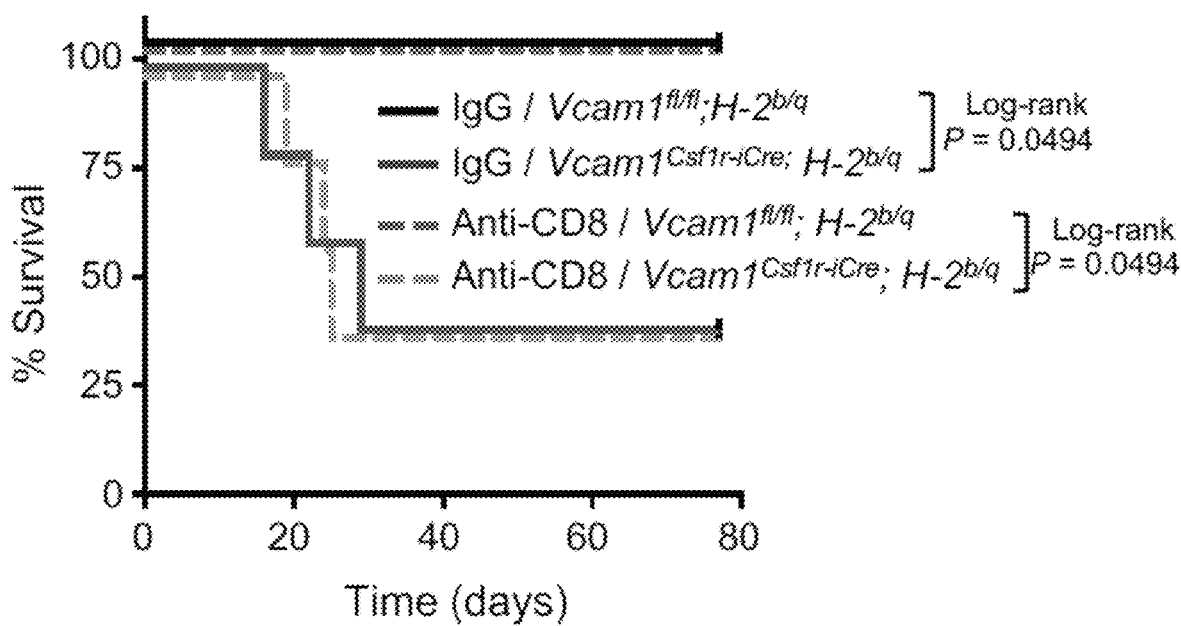

In the course of studies to identify the immunological mechanism underlying the engraftment failure of VCAM1-deficient HSCs, VCAM1$^{Csf1r\text{-}iCre}$ mice—where Csf1r-iCre transgenic mice generated in the FVB background were backcrossed over 10 generations into the C57BL/6 background—remained heterozygote for the MHC haplotypes H-2q (from FVB) and H-2b (from C57BL/6) (FIG. 17A). Indeed, the Csf1r-iCre transgene was genetically linked to the MHC locus with a frequency of meiotic recombination estimated at 7.87% (FIG. 17B). Accordingly, VCAM$^{Csf1r\text{-}iCre}$ and VCAM1$^{fl/fl}$ control mice were bred to generate either syngeneic (H-2$^{b/b}$) or haplotype mismatched (H-2$^{b/q}$) MHC status and to evaluate VCAM1's function on HSC engraftment in the context of syngeneic or haplotype-mismatched transplantation (FIG. 10A). These results show that VCAM1 deletion led to striking defects in hematopoietic engraftment only in the context of MHC haplotype-mismatched transplantation (donor H-2$^{b/q}$; recipient H-2$^{b/b}$; FIGS. 10A-10D, 17C). Whereas donor BM cells carrying the VCAM1$^{fl/fl}$ with haplotype-mismatched genotype exhibited engraftment and survival similar to syngeneic counterparts, those VCAM1-deficient with haplotype mismatch did not engraft and ~76% of the animals transplanted with these cells died (FIGS. 10A, 10B). Phagocytosis of donor HSCs in the BM was only triggered when HSCs were lacking VCAM1 combined with the haplotype-mismatched genotype (FIG. 9C), as syngeneic VCAM1$^{Csf1r\text{-}iCre}$;H-2$^{b/b}$ cells were not targeted (~0% phagocytosis, data not shown). As CD8$^+$ cells are classical responders to MHC-I mismatch,[72] Applicants evaluated their requirement for clearing the VCAM1$^{Csf1r\text{-}iCre}$;H-2$^{b/q}$ HSCs in vivo by antibody depletion of CD8$^+$ cells before transplantation. Results revealed that the survival defect of VCAM1$^{Csf1r\text{-}iCre}$;H-2$^{b/q}$ recipients could not be rescued by CD8$^+$ T cells depletion, suggesting that CD8$^+$ cells were dispensable (FIGS. 18A, 18B). Taken together, these results indicate that VCAM1 expression on HSCs is required for vetting by phagocytes to provide entry in the BM microenvironment.

Figure 10E:
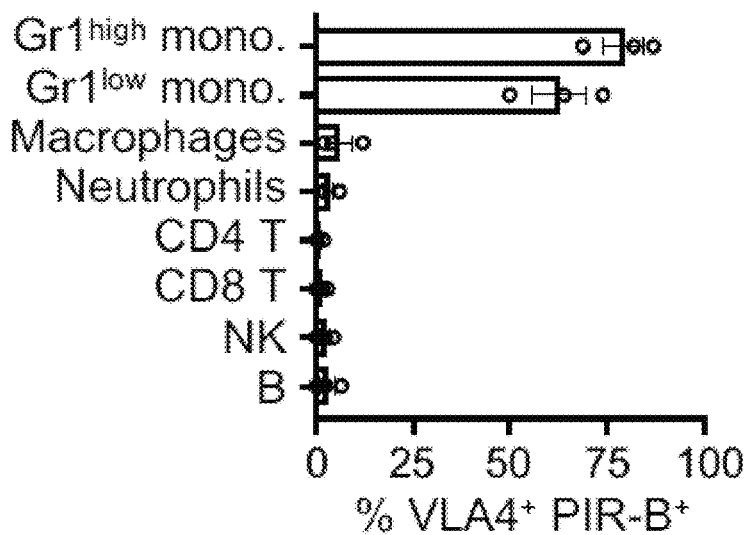
Figure 10F:
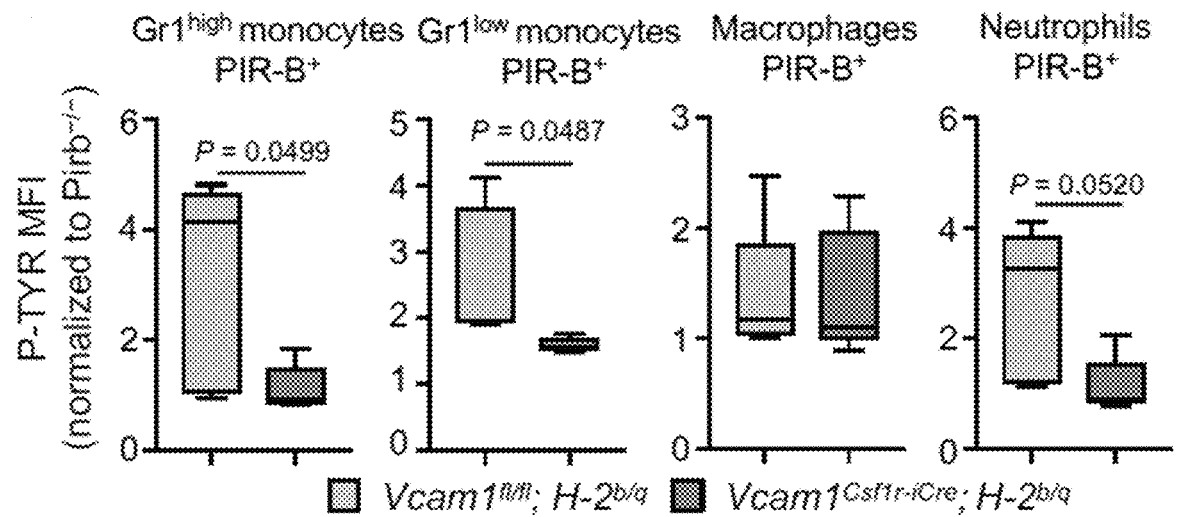
Figure 10G:
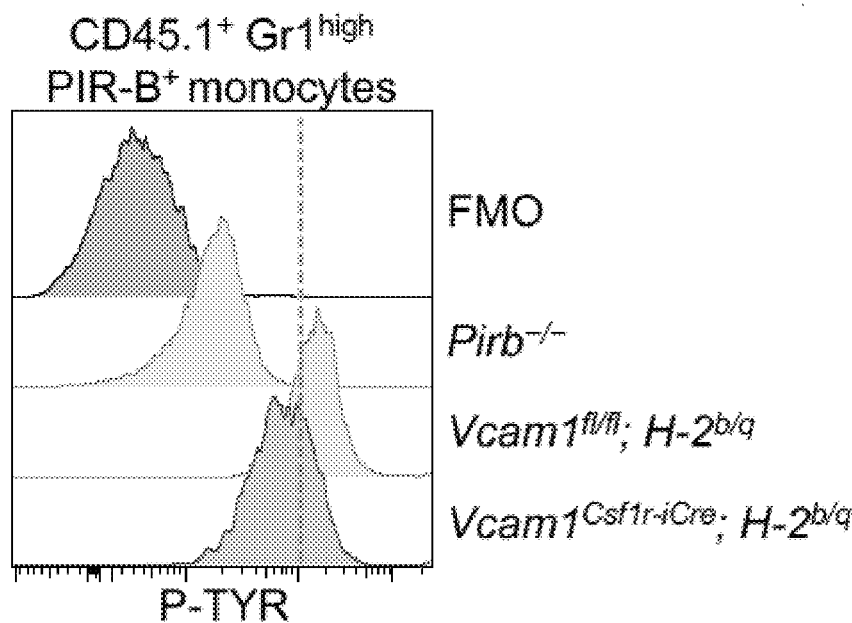
Figure 10H:
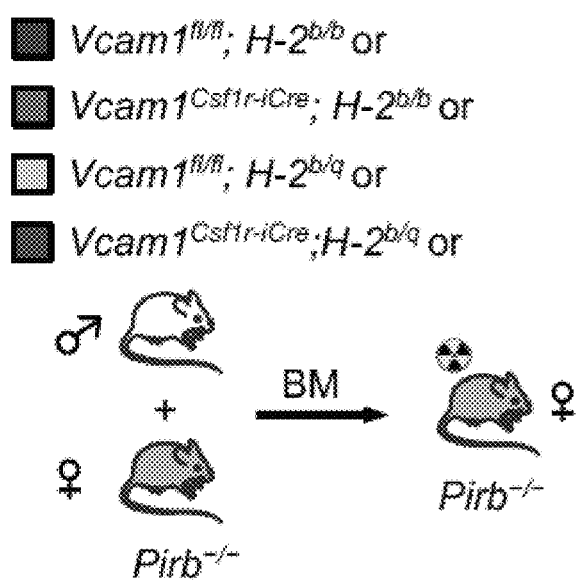
Figure 10H:
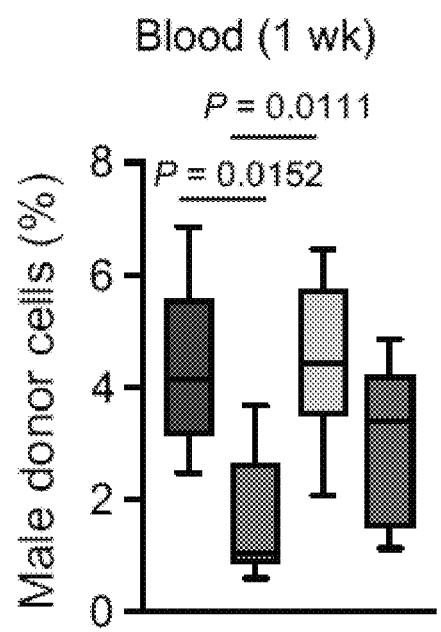
Figure 18C:
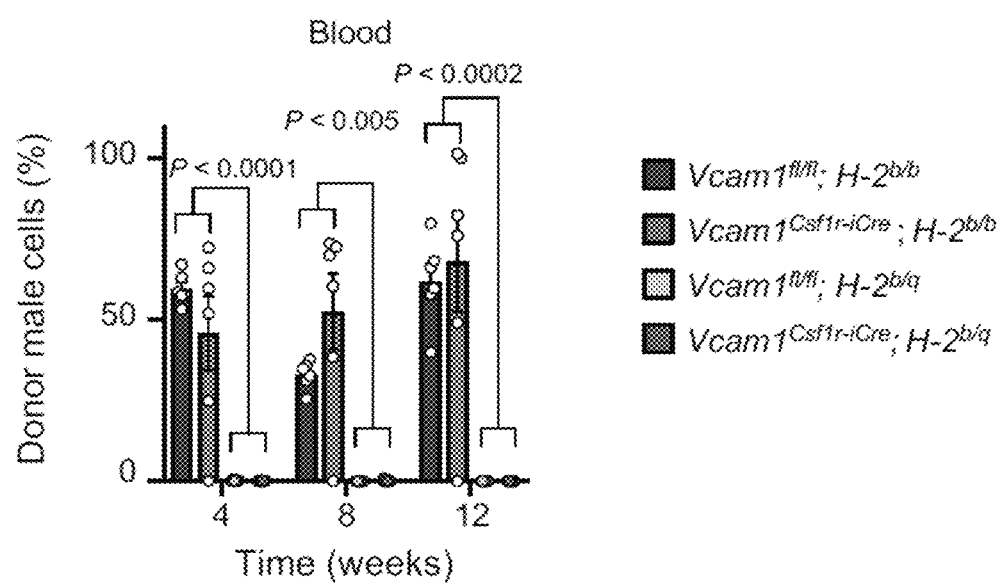
Figure 19A:
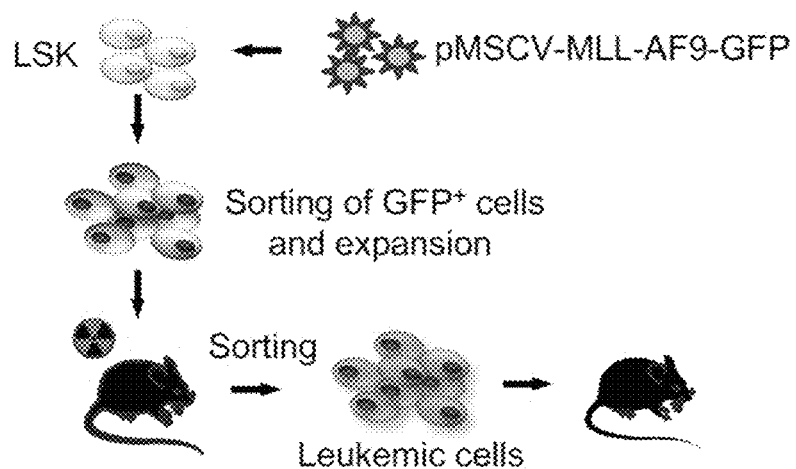
FIGS. 19A-19E.

VCAM1 interacts with α4β1 integrin (also known as VLA-4), which is expressed on most hematopoietic cells.[73] The mouse PIR-B receptor, expressed by myeloid phagocytes and B cells[74] provides negative regulation of immune cells upon recognition of MHC-I molecules.[75] Accordingly, PIR-B may cooperate in the anti-phagocytic activity of VCAM1 and MHC-I. Flow cytometry analysis of PIR-B expression in BM immune cells shows that the vast majority (>63%) of Gr1high and Gr1low monocytes express both PIR-B and the VCAM1 counterreceptor VLA4 whereas these are expressed in much lower fractions in other immune cells (FIG. 10E). The intracellular transduction of PIR-B inhibitory signaling correlates with the tyrosine phosphorylation (P-TYR) status of its immunoreceptor tyrosine-based inhibitory motifs.[74,75] Accordingly, on day 6 after transplantation of VCAM$^{Csf1ri\text{-}Cre}$;H-2$^{b/q}$ cells, the P-TYR levels in host CD45.1;H-2$^{b/b}$ PIR-B$^+$ Gr1$^{high}$ and Gr1$^{low}$ monocytes and neutrophils were significantly reduced compared to VCAM1$^{fl/fl}$;H-2$^{b/q}$ control (FIGS. 10F, 10G). To evaluate further the role of PIR-B, syngeneic and haplotype-mismatched VCAM$^{Csf1r\text{-}iCre}$ and VCAM1$^{fl/fl}$ BM cells were transplanted into Pirb$^{-/-}$ mice[76] and donor cell engraftment was evaluated by real-time PCR. In the absence of PIR-B inhibitory signal, VCAM1 deletion led to significant reductions (~60%) in the early (1 week) engraftment of syngeneic VCAM1$^{Csf1r\text{-}iCre}$;H-2$^{b/b}$ cells compared to VCAM$^{fl/fl}$;H-2$^{b/b}$ cells (FIG. 10H), suggesting that the absence of VCAM1 also promotes cell clearance by syngeneic Pirb$^{-/-}$ phagocytes. However, the engraftment levels in 5 out of 6 Pirb$^{-/-}$ recipients of syngeneic VCAM1-null cells recovered to the levels of syngeneic VCAM1-sufficient cells, 4 weeks post-transplantation (FIG. 18C). As expected, due to the hyper-responsiveness of Pirb$^{-/-}$ immune cells,[75] both haplotype-mismatched cohorts failed to engraft (FIG. 18C). These results suggest that PIR-B expression on phagocytes contributes to suppress the immune response triggered by VCAM1-deficient HSCs and progenitors, although the transient phenotype suggests that other molecules may also be at play. That VCAM1 expression would provide innate immune tolerance indicated that this pathway may be of use for cancer cells. Upregulation in VCAM1 expression has been reported in various cancer cell types, including gastric,[77] renal,[78] hepatocellular,[79] acute promyelocytic leukaemia,[80] and breast cancer, where VCAM1 promotes metastasis to the lungs and bones by providing survival signals[81] and recruiting osteolytic cells.[82] Recent studies suggest that VCAM1 expression on endothelial and BM stromal cells may mediate in part leukemia cell resistance to conventional chemotherapy.[83-86] Results provided herein suggest that cell autonomous expression of VCAM1 may confer immune evasion. In an immunocompetent mouse model of AML driven by MLLAF931 (FIG. 19A), results indicated that VCAM1 expression on AML cells was 7-fold higher than BM hematopoietic cells, and that expression on LSCs was 4-fold higher than healthy HSCs (FIG. 1C).

Figure 11A:
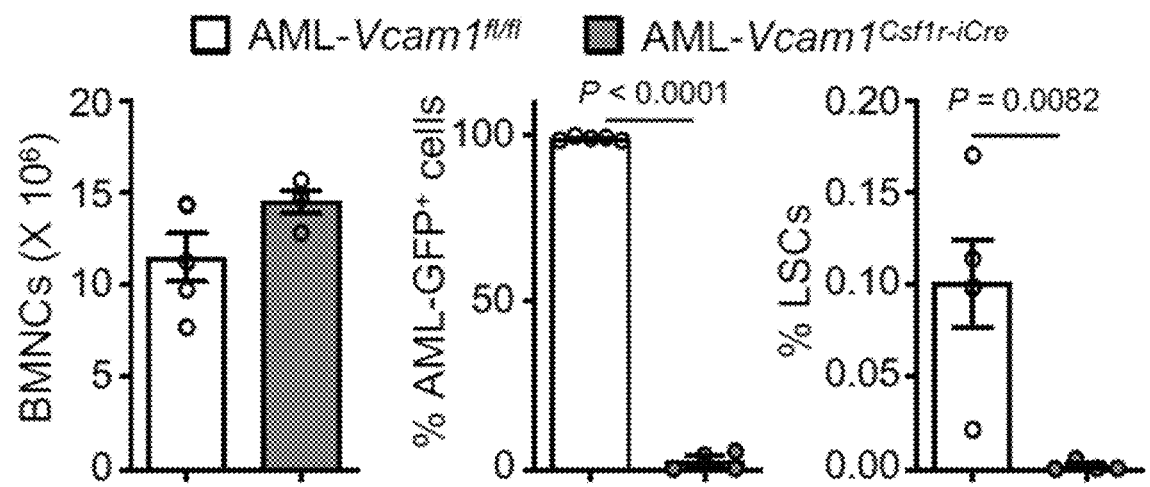
FIGS. 11A-11F.
Figure 11B:
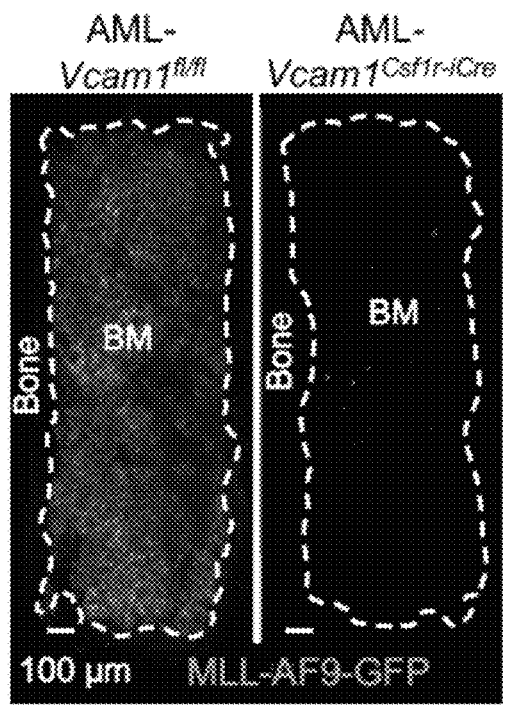
Figure 11C:
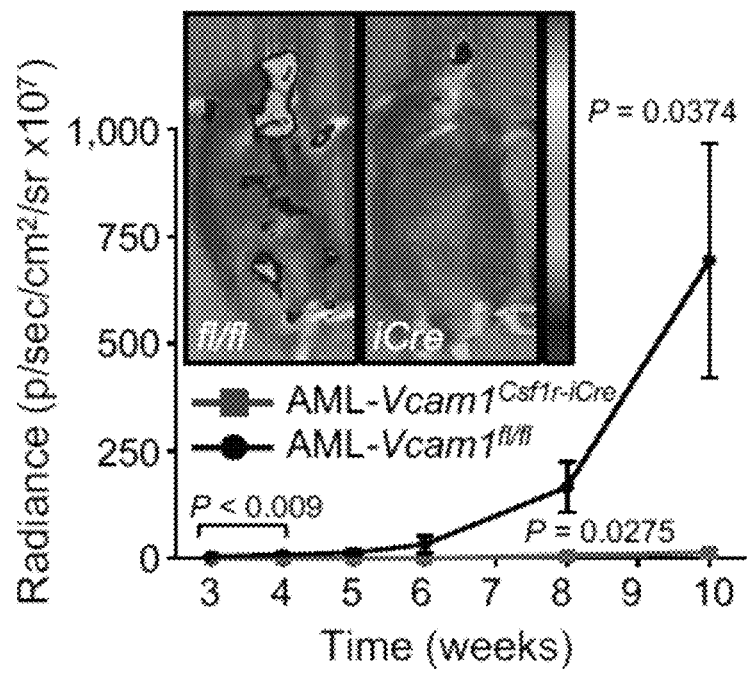
Figure 11D:
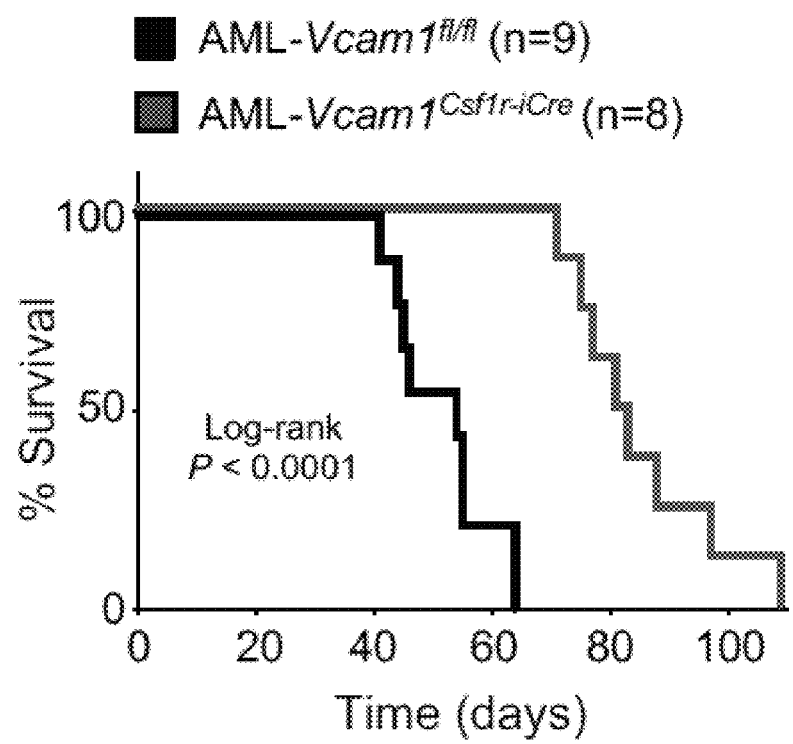
Figure 11E:
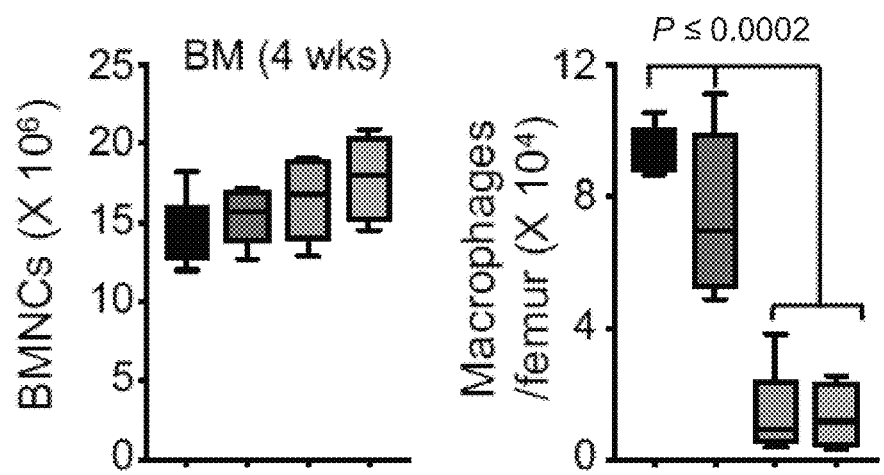
Figure 19B:
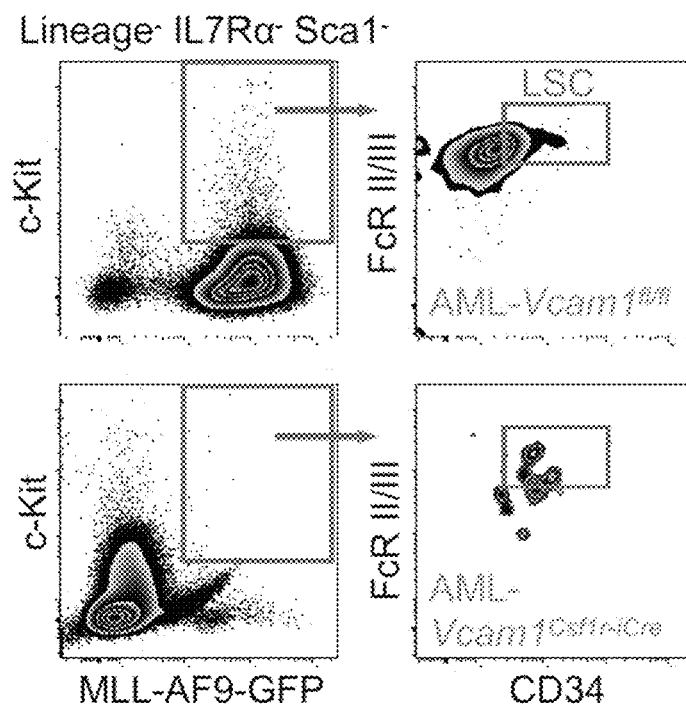
Figure 19C:
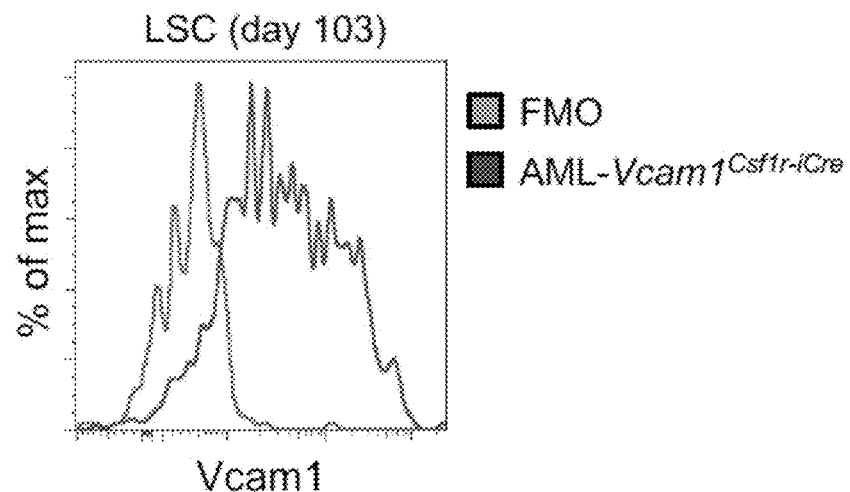

Leukemic cells can upregulate CD47[88,89] or MHC class-I[89] molecules to avoid phagocytosis or aberrantly express pro-phagocytic signals including AML-specific neo-antigens and AML-associated antigens that can elicit anti-leukemia immune responses if the balance between anti-phagocytic and phagocytic signals is perturbed.[72] To test the effect of genetic VCAM1 deletion and MHC-mismatch on AML progression, VCAM1$^{Csf1r\text{-}iCre}$;H-2$^b$/q and VCAM1$^{fl/fl}$;H-2$^{b/q}$ Lineage$^-$ Sca-1$^+$ c-Kit$^+$ (LSK) cells were transduced with the pMSCV-MLL-AF9-GFP oncogene. Strikingly, FACS analysis of primary AML recipient mouse BM revealed a marked reduction (>99%) of phenotypic VCAM1$^{Csf1r\text{-}iCre}$ LSCs compared to VCAM1$^{fl/fl}$ control (FIGS. 11B, 19B). Moreover, whole-mount confocal imaging of the sternal marrow showed little leukemia infiltration of VCAM1$^{Csf1r\text{-}iCre}$ AML compared to VCAM1$^{fl/fl}$ AML (FIG. 1C). These results were further confirmed in a luciferase-expressing MLL-AF9 reporter line that allowed monitor tumor progression using bioluminescence in live mice (FIG. 11D). Accordingly, the survival of secondary recipient mice receiving 20,000 sorted GFP$^+$ leukaemic cells from VCAM1$^{fl/fl}$ or VCAM1$^{Csf1r\text{-}iCre}$ primary recipients was significantly prolonged in mice harboring VCAM1$^{Csf1r\text{-}iCre}$ AML cells relative to VCAM1$^{fl/fl}$ AML (FIG. 11E). Of note, FACS analysis of the BM from moribund VCAM1$^{Csf1r\text{-}iCre}$ AML mice, revealed that >85% of LSCs in these mice expressed VCAM1 by day 103 post-transplantation (FIG. 19C), suggesting that incomplete Cre recombination in Csf1r-iCre model may have allowed rare VCAM1$^+$ LSCs to escape and colonize the marrow of secondary recipients, leading to their death. These results suggest that ablation of VCAM1 significantly impairs AML engraftment and disease progression in vivo.

Figure 11F:
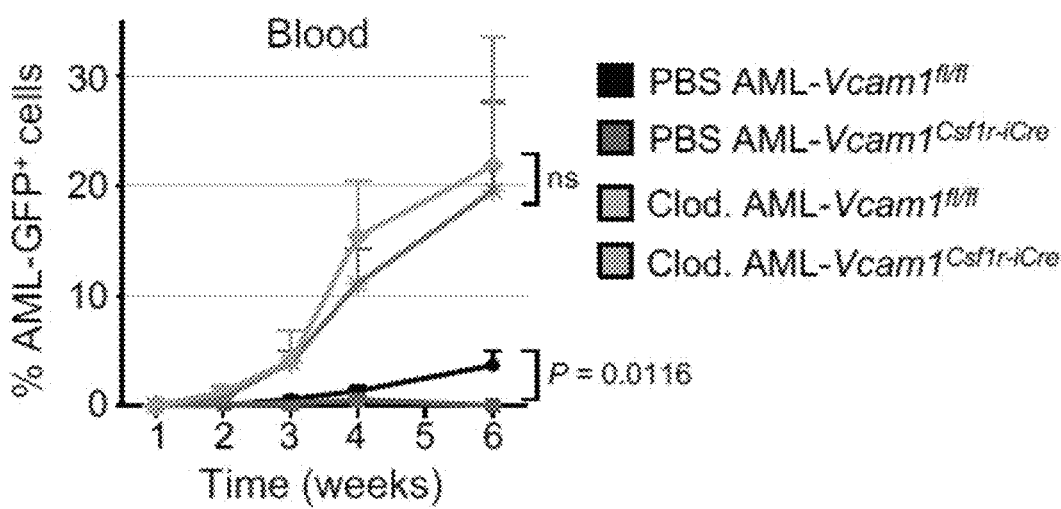
Figure 19D:
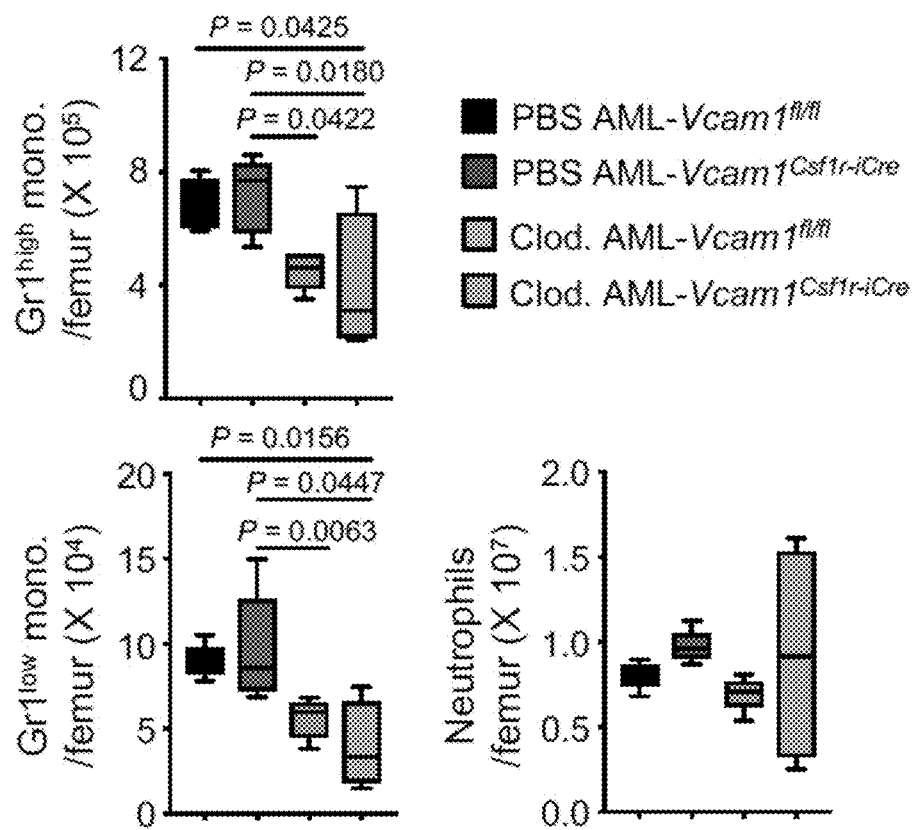
Figure 19E:
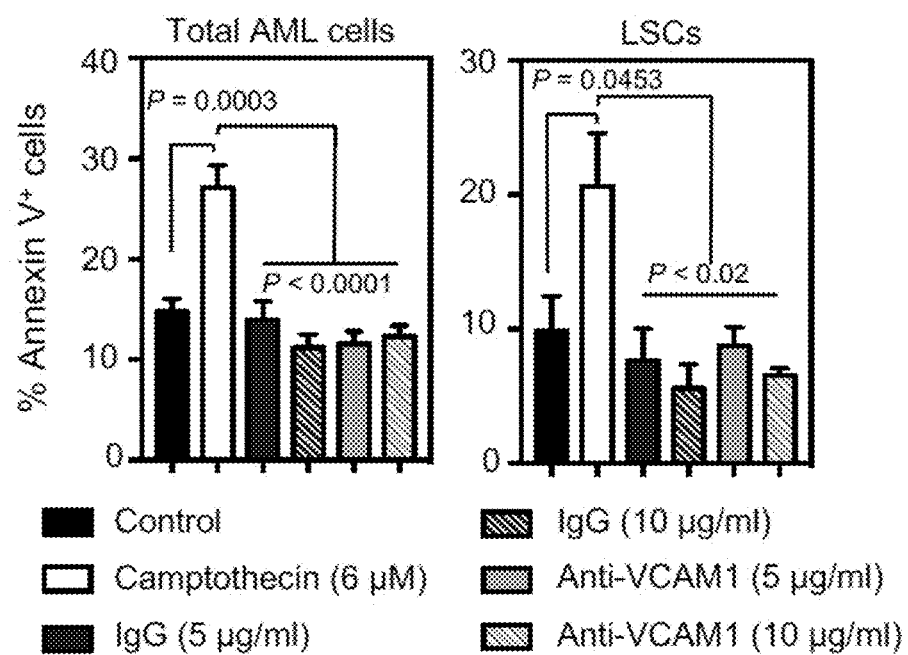

To investigate the requirements of phagocytic cells in the in vivo clearance of MHC mismatched VCAM1$^{Csf1r\text{-}iCre}$ AML, phagocytes were depleted by injection of clodronate liposomes (or control PBS liposomes) prior to and after transplant of VCAM1$^{fl/fl}$ and VCAM1$^{Csf1r\text{-}iCre}$ AML cells (FIGS. 11F, 19D). Engraftment was markedly enhanced by phagocyte depletion, and remarkably, the engraftment defect of VCAM1$^{Csf1r-iCre}$ AML cells was rescued (FIG. 11G), indicating an important role for phagocytes in the establishment of VCAM1-deficient AML. To evaluate whether phagocytosis was preceded by the induction of apoptosis, AML cells were incubated with IgG, anti-VCAM1 blocking antibody or camptothecin (a known inducer of AML apoptosis). Results showed no difference in the percentage of apoptotic LSCs cells between control and anti-VCAM1 treated groups 4.5 hours after treatment (FIG. 19E). Thus, these results suggest that clodronate-sensitive phagocytes play a key role in AML clearance and that the phagocyte recognition does not require AML cell apoptosis. To evaluate the safety and efficacy of VCAM1 inhibition in a clinical scenario in which the therapeutic intervention occurs after the disease is established, C57BL/6 syngeneic AML were allowed to develop (>50% circulating AML-GFP$^+$ cells) in immunocompetent C57BL/6 recipients, and then initiated therapy of these moribund leukemic mice with a daily injection of IgG1 control, anti-VCAM1, cytarabine (Ara-C), or a combination of anti-VCAM1/Ara-C for 5 days (FIG. 4A). Remarkably, this very short treatment with anti-VCAM1 antibody preferentially and significantly reduced the frequency and absolute number of phenotypic BM LSCs in vivo (FIG. 4B). Next, a similar treatment strategy was used in mice harboring ~20% circulating AML-GFP$^+$ cells. While the disease progressed in all IgG1-treated AML mice, it was stabilized by anti-VCAM1 treatment and dramatically reduced in mice treated with anti-VCAM1 in combination with Ara-C (FIG. 4C), significantly extending the survival of the animals (FIG. 4D). Anti-VCAM1 treatment regimen resulted in 100% antibody coating of VCAM1$^+$ HSCs and appeared to be safe for healthy HSCs since it did not deplete their numbers or altered blood counts (FIG. 4E).

Figure 20A:
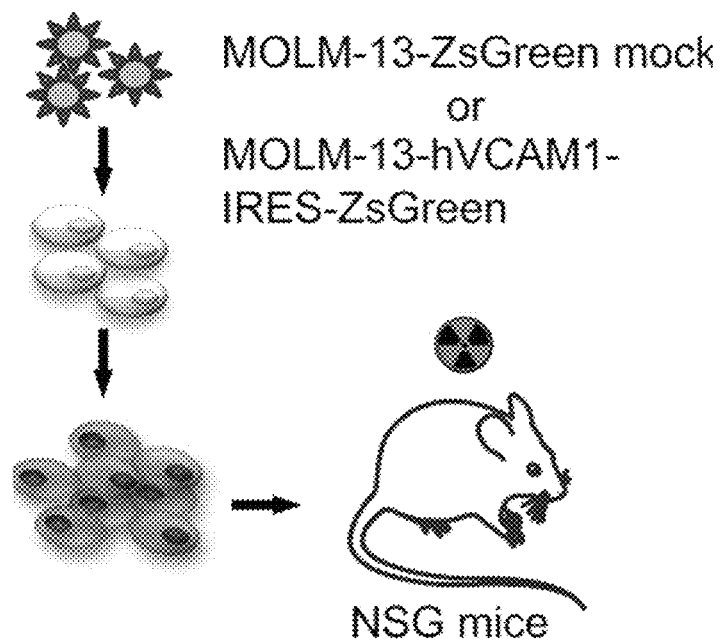
FIGS. 20A-20J.
Figure 20B:
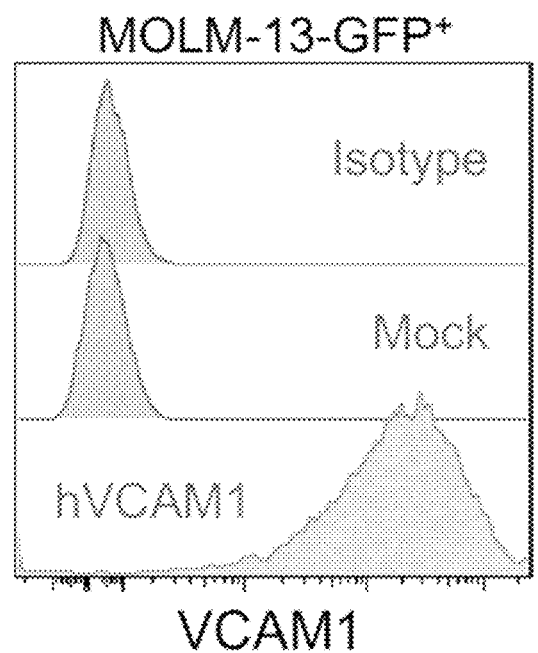
Figure 20C:
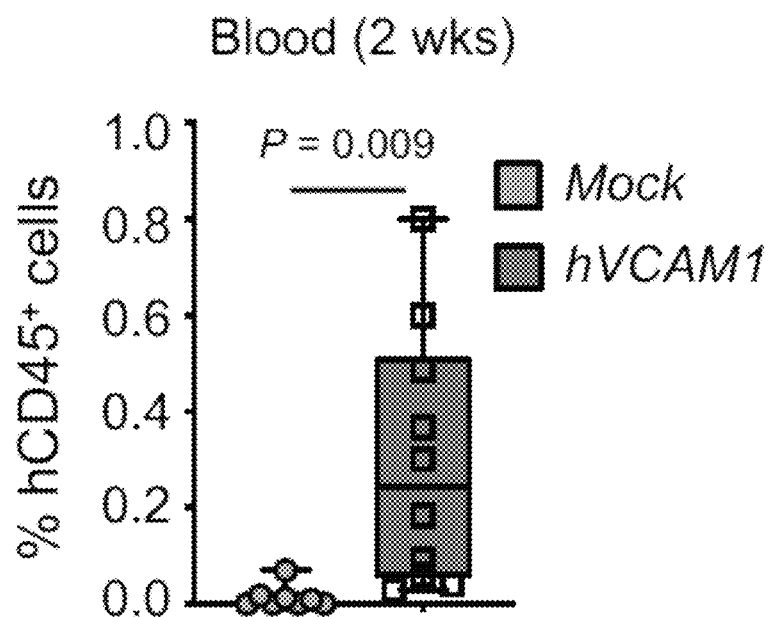
Figure 20D:
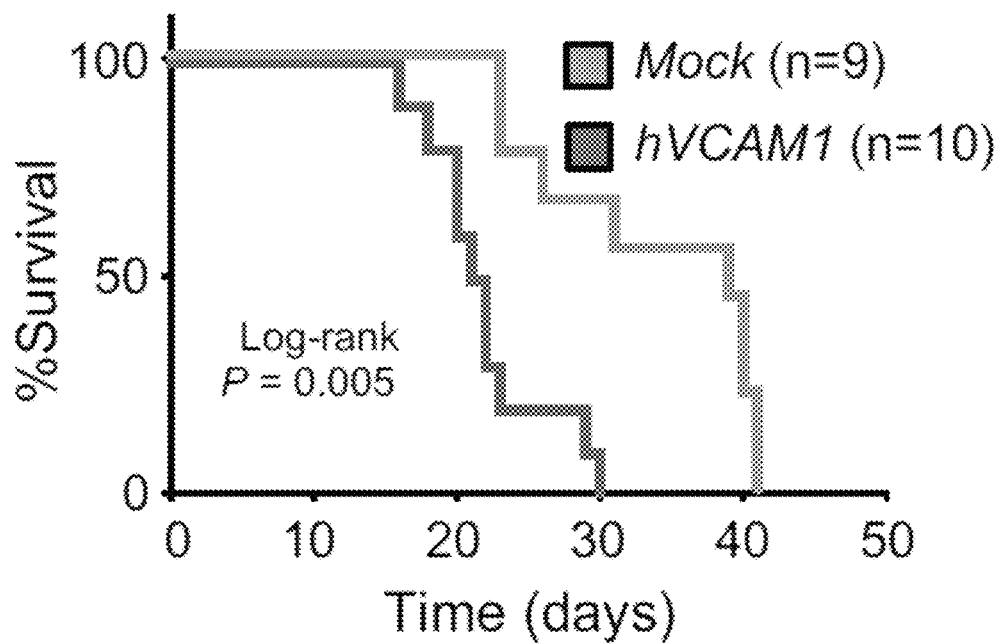
Figure 20E:
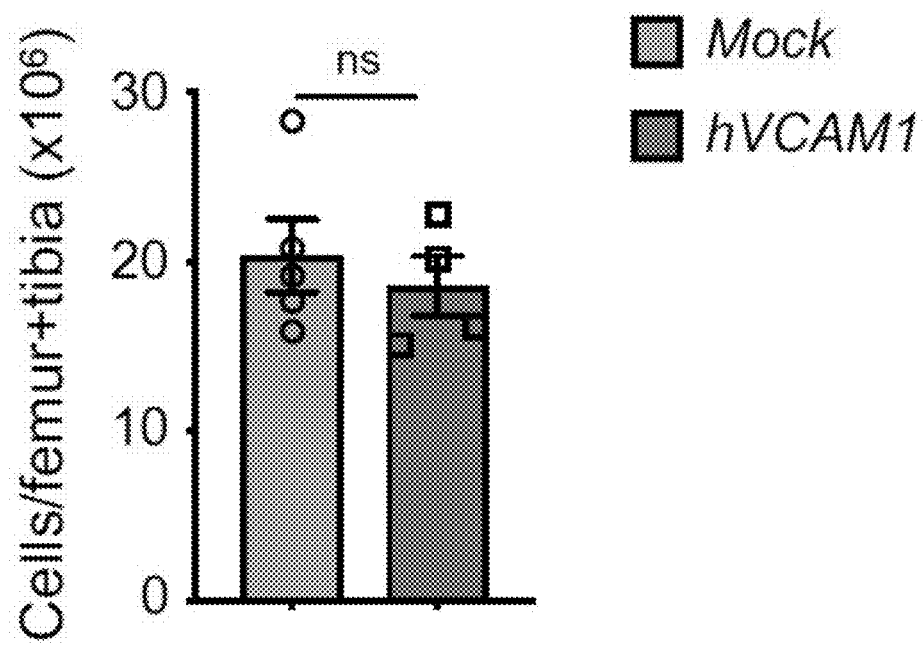
Figure 20F:
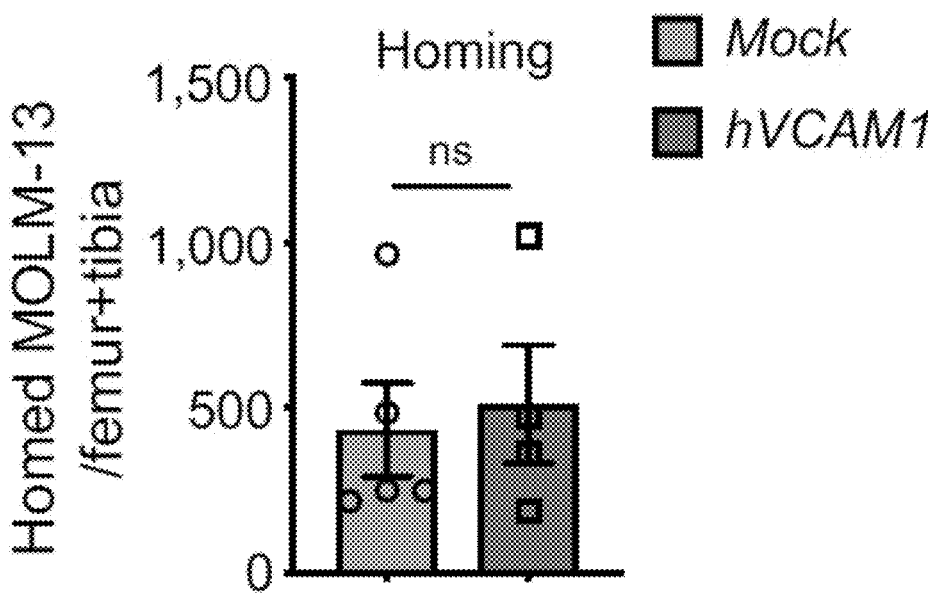
Figure 20G:
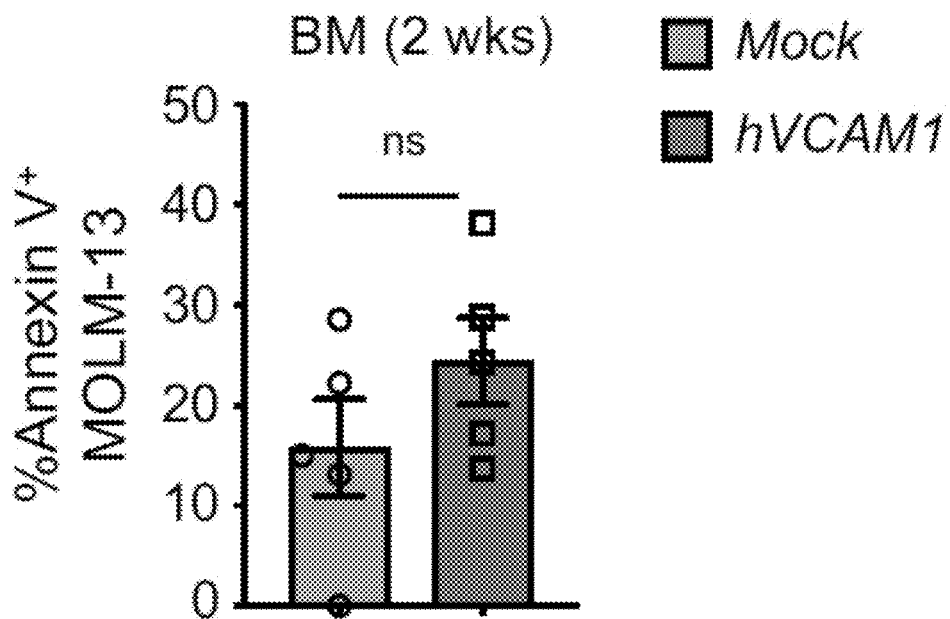
Figure 20H:
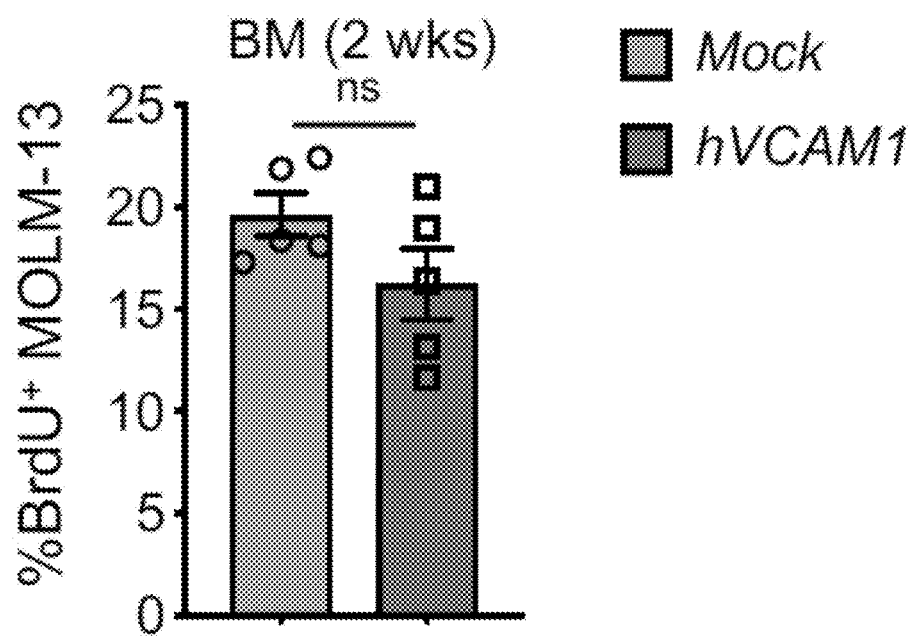
Figure 20I:
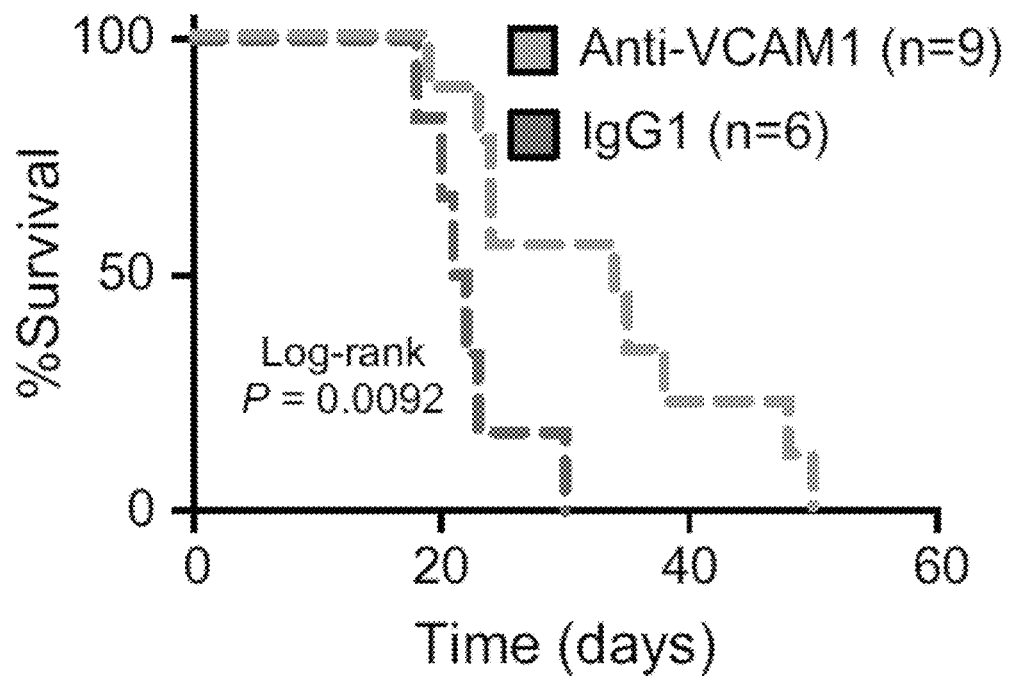
Figure 20J:
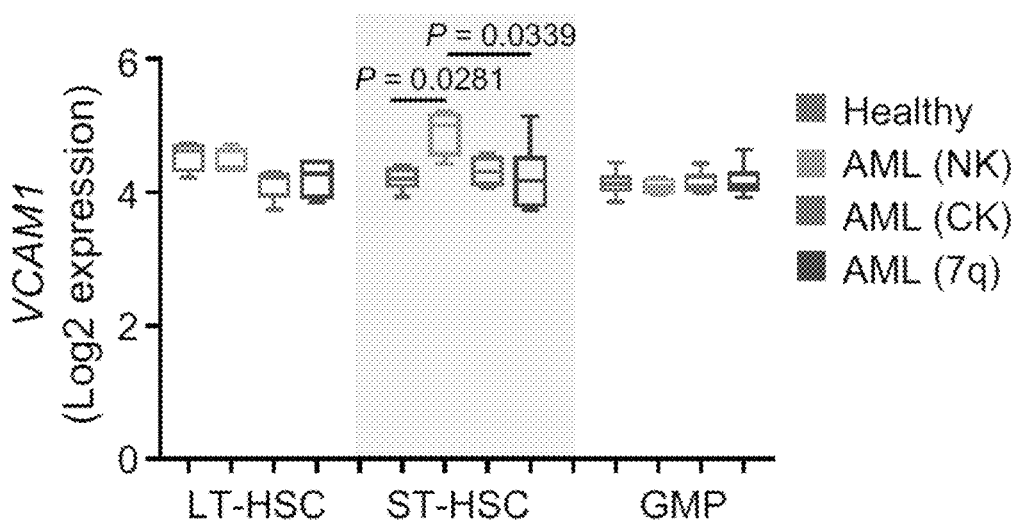

As high VCAM1 is associated with reduced survival of patients with AML in the TCGA database (FIG. 20A), the functional significance of elevated VCAM1 in human AML cells was investigated. To this end, VCAM1 was overexpressed in MOLM-13 cells, which constitutively do not express VCAM1 (FIGS. 20B, 20C), and transplanted hVCAM1-ZsGreen-transduced and ZsGreen control (Mock)-transduced MOLM-13 cells into immunocompromised NOD-scid Il2rg$^{-/-}$ (NSG) mice. Results showed that VCAM1-expressing MOLM-13 exhibited rapid disease progression and significantly higher numbers of leukemic cells in peripheral blood compared to control MOLM-13 (FIG. 20D), leading to a significant reduction in the survival of hVCAM1-MOLM-13-transplanted mice (FIG. 20E). There was no difference in homing capacity of hVCAM1-MOLM-13 cells, in vivo cell viability or cycling (FIGS. 20F-20I). Importantly, anti-human VCAM1 administration significantly extended the survival of the animals transplanted with hVCAM1-MOLM-13 cells (FIG. 20J). Thus, VCAM1 overexpression increases the tumorigenicity of human AML cells.

Figure 12A:
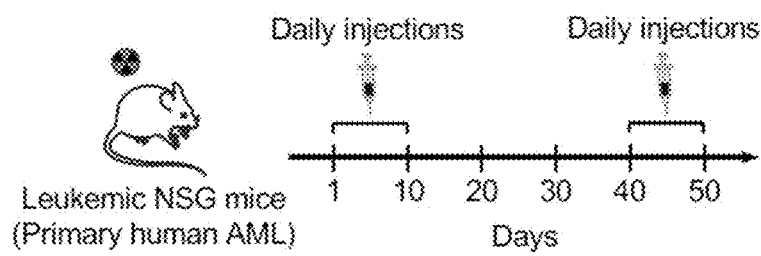
FIGS. 12A-12C.
Figure 12B:
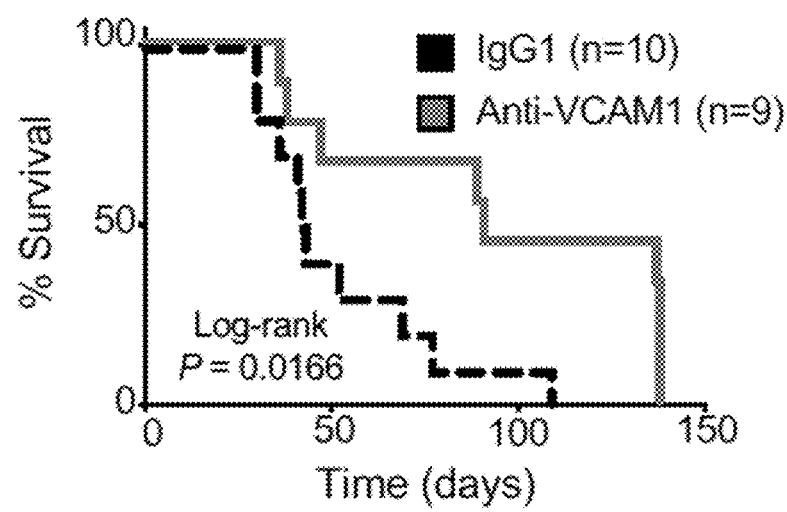
Figure 12C:
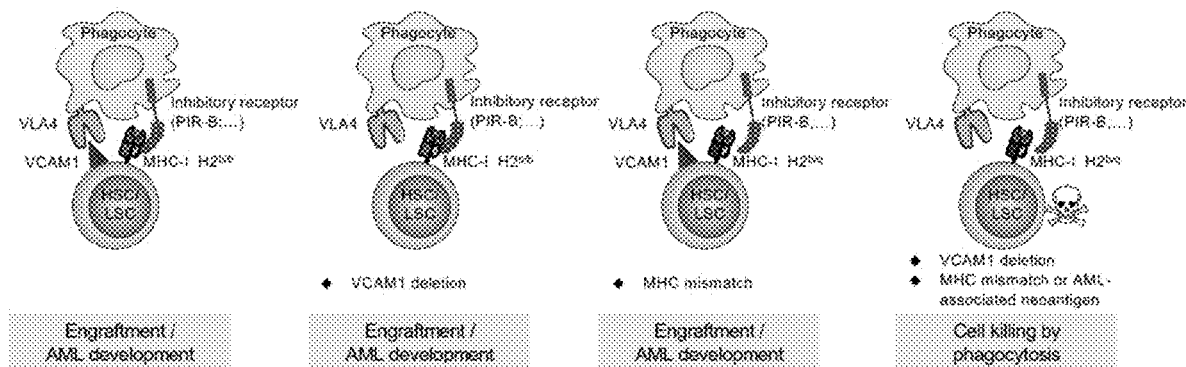

Next, VCAM1 expression was assessed in highly purified primary human AML stem and progenitor cells relative to healthy age-matched control samples from published data of AML patients with normal karyotype, complex karyotype, and deletion of chromosome 7.[90,91] Results from these experiments demonstrated that VCAM1 was significantly overexpressed in short-term repopulating HSCs (ST-HSCs), the compartment most enriched in functional human LSCs, particularly in the group with normal AML karyotype (FIG. 20K). To assess the relevance of VCAM1 signal inhibition in human AML, primary human AML samples were transplanted into NSG mice. Upon disease establishment (4-5 weeks post-transplant), the animals were treated with 2 courses of anti-human VCAM1 monoclonal antibody or control IgG1. Results demonstrated that VCAM1 inhibition significantly prolonged in the survival of leukemic mice (FIGS. 12A, 12B). Taken together, these results suggest that VCAM1 blockade is safe in pre-clinical models to reduce the leukemic burden in vivo and may synergize with Ara-C treatment to clear LSCs while sparing healthy HSCs.

Figure 21A:
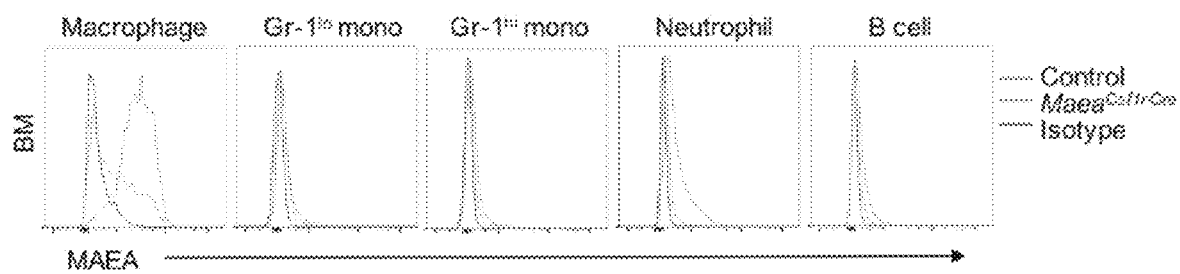
FIGS. 21A-21G.
Figure 21B:
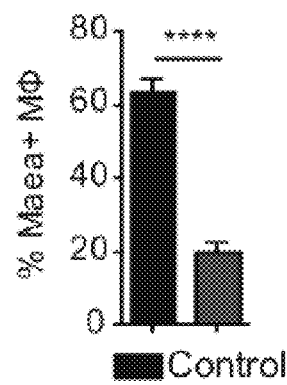
Figure 21C:
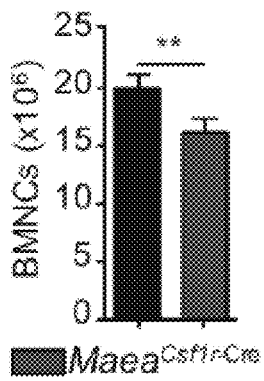
Figure 21D:
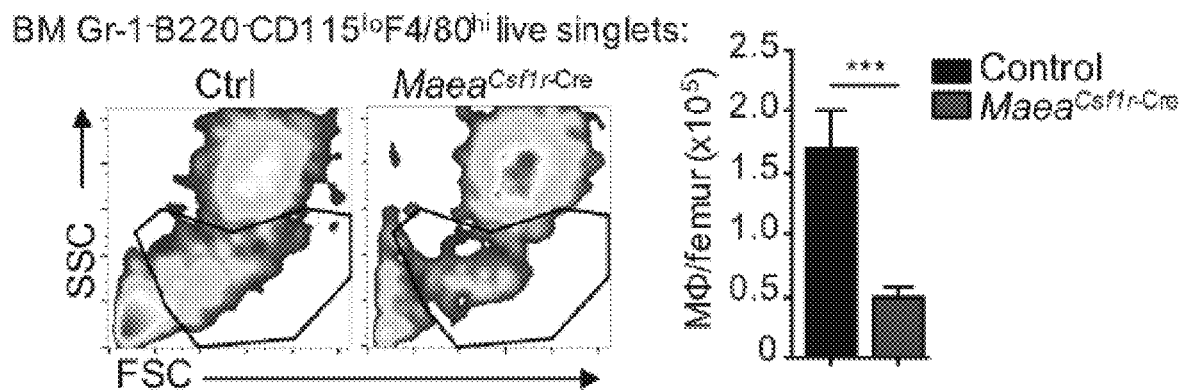
Figure 21E:
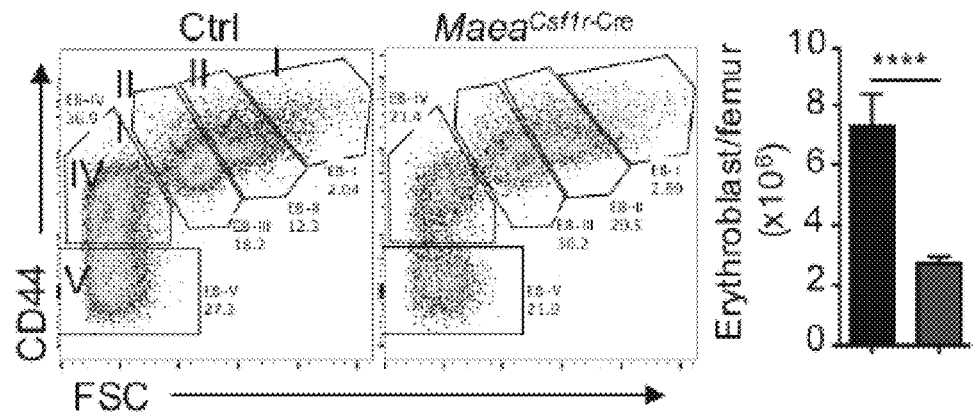
Figure 21F:
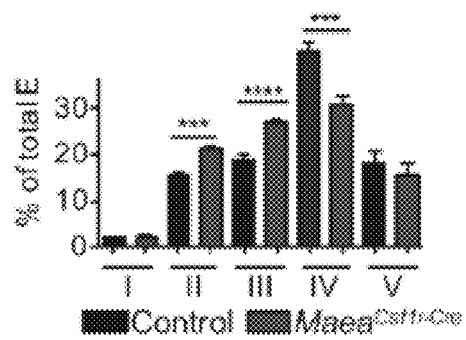
Figure 21G:
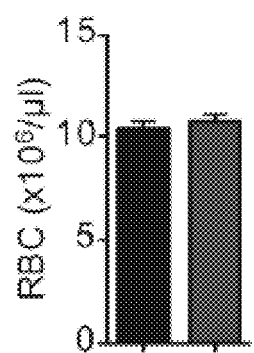
Figure 22A:
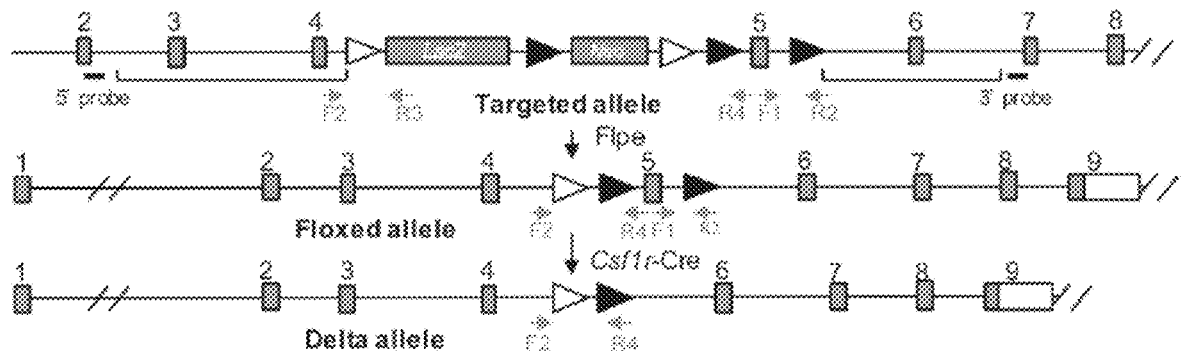
FIGS. 22A-22H.
Figure 22B:
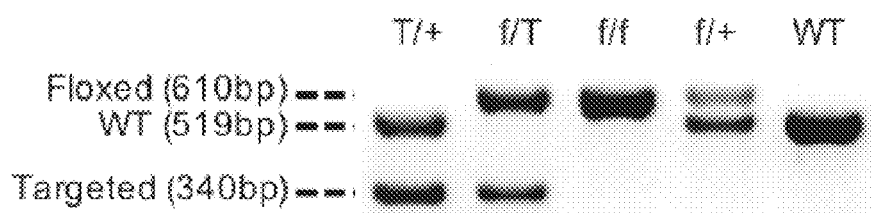
Figure 22C:
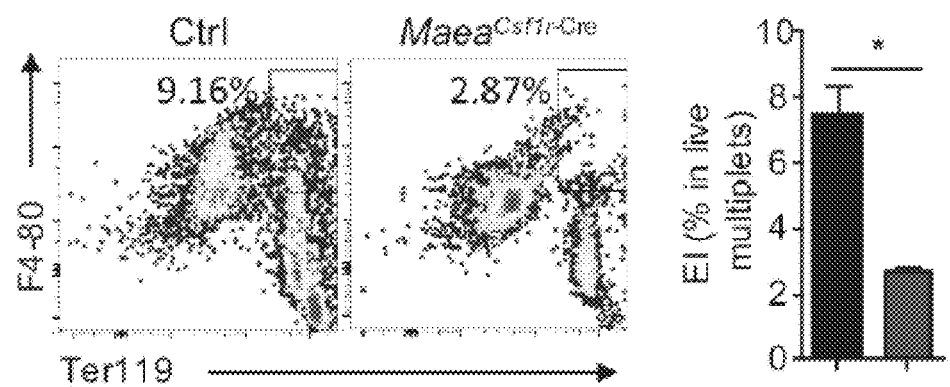
Figure 22D:
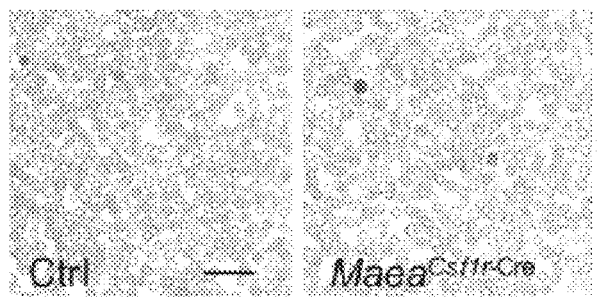
Figure 22E:
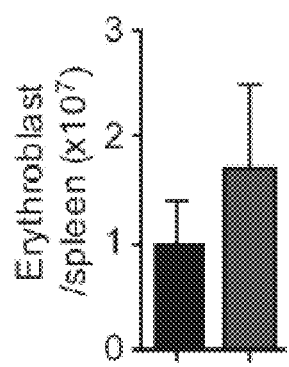
Figure 22F:
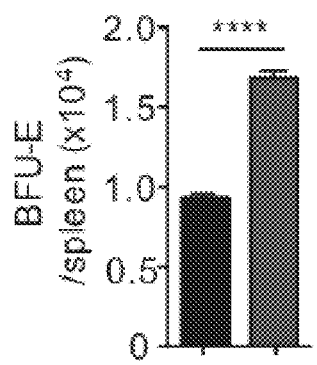
Figure 22G:
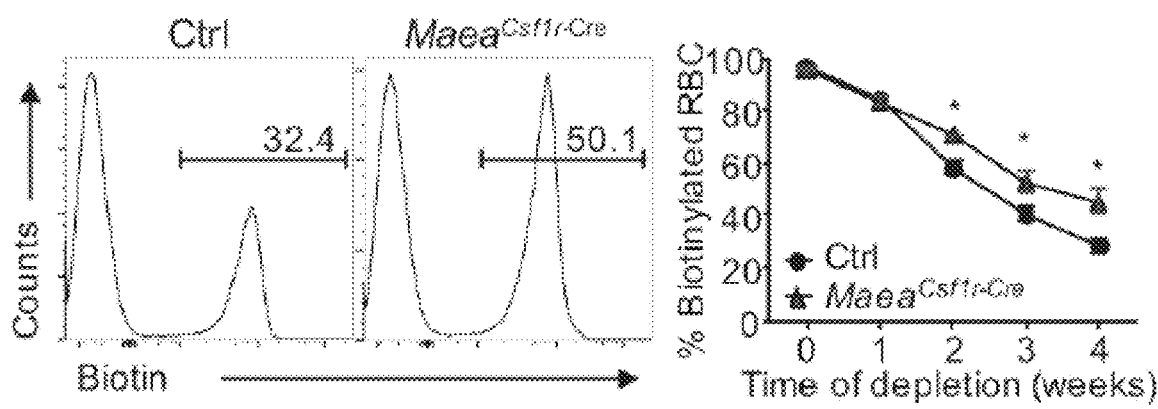
Figure 22H:
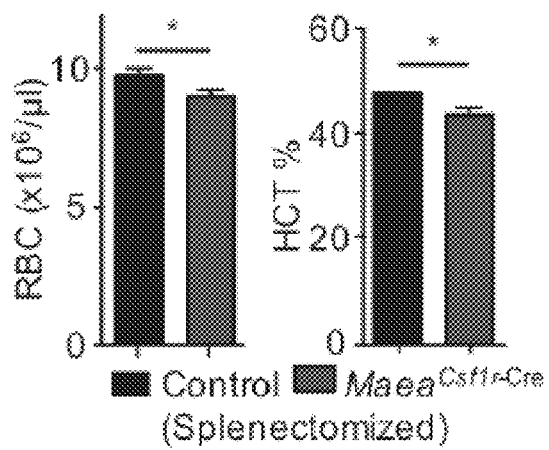

The therapeutic outcomes in AML remain poor, with relapses representing the major cause of treatment failure due to resistant disease. The immune system has emerged as a critical defense for preventing tumor initiation and controlling tumor growth.[88,89,90,92,93] Results provided herein reveal a novel function for the HSC niche molecule VCAM1 on hematopoietic and leukemic stem cells by acting cell-autonomously as a "don't-eat-me" signal in the context of MHC-I presentation. VCAM1 regulates a critical vetting process by resident phagocytes in the BM to allow the entry of healthy or malignant stem cells. This vetting requires parallel checkpoints by VCAM1 and MHC-I on the stem cells and their counter-receptors on phagocytes, where the absence or blockade of VCAM1 combined with MHC mismatch instruct phagocytes to kill (FIG. 21C). In the context of a leukemia, VCAM1 inhibition appears sufficient to give the green light to kill tumor cells, even in the setting of an immunocompetent syngeneic host, likely due to the presence of tumor neoantigens which may be perceived by host phagocytes as non-self. Interestingly, as discussed below in greater detail in Example 5, results disclosed herein identify another erythroblastic island adhesion molecule, the Macrophage-Erythroblast Attacher (MAEA), as required for AML development and progression. These studies suggest that anti-VCAM1 therapy may synergize with conventional chemotherapy and may provide effective combination treatments to enhance the innate immunity response to cancer.

Example 3: Anti-VCAM1 Therapies

The VCAM-1 protein mediates the adhesion of lymphocytes, monocytes, neutrophils, eosinophils, basophils, and sickle red blood cells (RBCs) to the vascular endothelium.[127] VCAM1 is inducible by inflammatory cytokines such as TNF-alpha and ILL. VCAM-1 also functions in leukocyte-endothelial cell signal transduction and may play a role in the development of atherosclerosis and rheumatoid arthritis (RA).[128] Given VCAM1's role in leukocyte adhesion during inflammation, we reasoned that it may be an important target to protect SCD mice from acute vaso-occlusion.

Figure 39A:
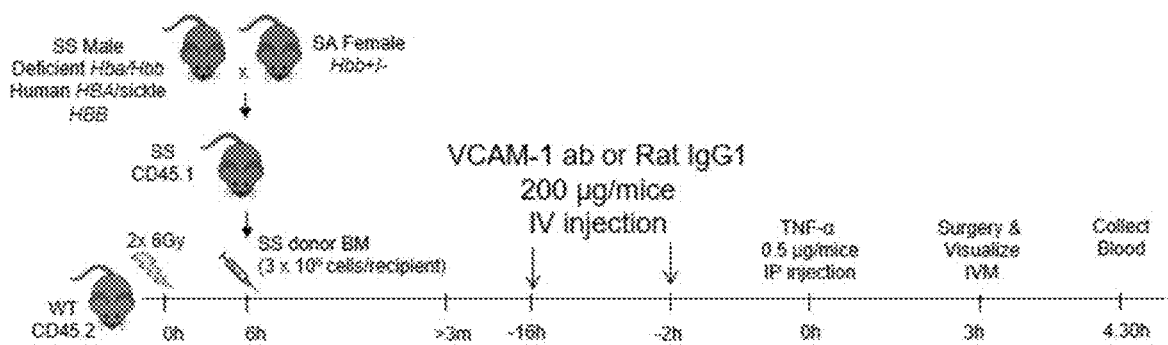
FIGS. 39A-39G.
Figure 39B:
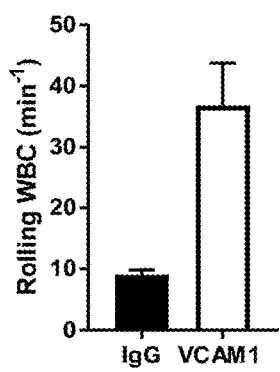
Figure 39C:
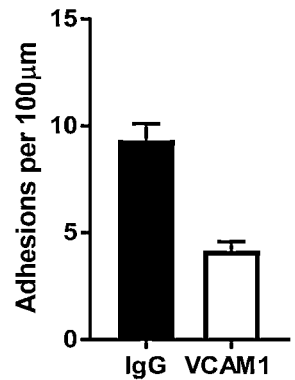
Figure 39D:
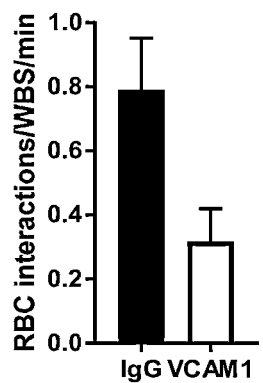
Figure 39E:
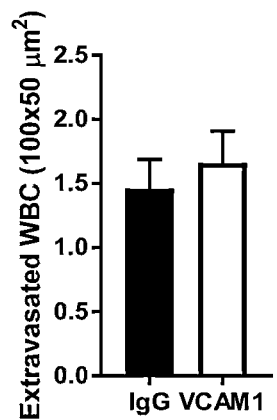
Figures 39F, 39G:
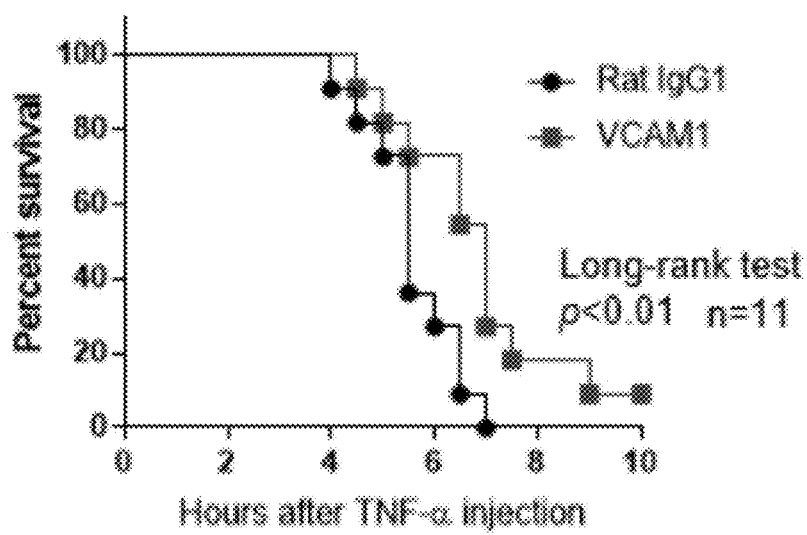

To test the effect of an anti-VCAM1 antibody on a murine model for SCD, mice were intravenously injected with 200 μg/mice rat IgG1 or anti-mouse VCAM-1 antibody (clone M/K-2.7 from BioxCell) at 16 hours and 2 hours before TNF-α challenge (n=5, rat IgG1 antibody 200 μg/mice or VCAM1 antibody 200 μg/mice). These results show that white blood cell (WBC) rolling was significantly increased (p<0.0001) in mice injected with an anti-VCAM1 antibody as compared to mice injected with rat IgG (FIG. 39B). Additionally, the number of adhesions per 100 μm (FIG. 39C; p<0.0001) and interactions between RBCs and WBCs per minute (FIG. 39D; p<0.05) were significantly decreased in mice injected with an anti-VCAM1 antibody as compared to mice injected with IgG. mice injected with rat IgG1 or VCAM1 antibody (no significant difference). FIG. 39E depicts extravasated WBCs in mice injected with rat IgG1 or VCAM1 antibody. Results further demonstrate that mice injected with an anti-VCAM1 antibody have better survival than those injected with IgG (FIG. 39F). Treatment with an anti-VCAM1 antibody additionally resulted in a significantly increased centerline velocity and lower shear rate as compared mice injected with IgG (FIG. 39G). Collectively, these results indicate that blocking VCAM1 function may help treat SCD by reducing the number of adhesions, reducing WBC activation and RBC/WBC interactions, leading to increased centerline velocity, increased shear rate, and prolonged survival during the stress of vaso-occlusion.

Figure 40A:
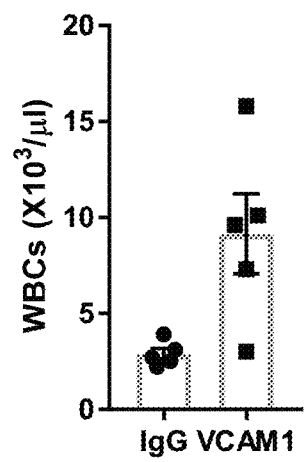
FIGS. 40A-40D.
Figure 40B:
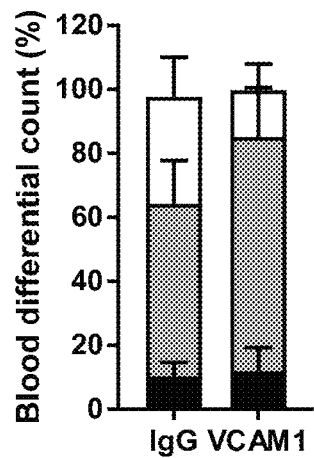
Figure 40C:
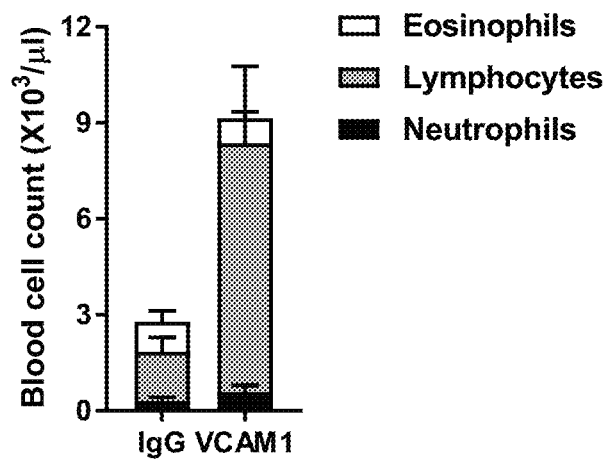
Figure 40D:
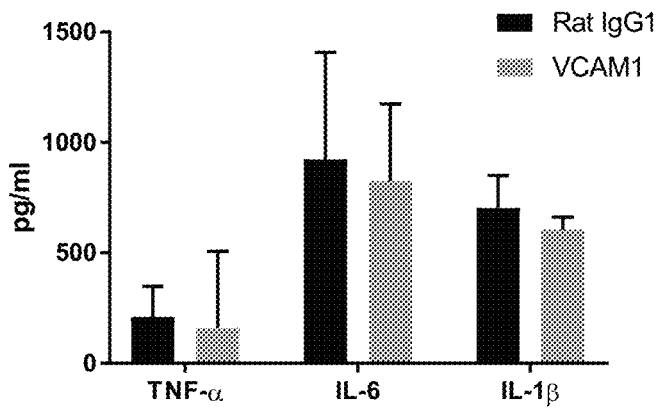

Blood was harvested and total and differential counts were obtained using an Advia cell counter. FIGS. 40A-40D. FIGS. 40A-40D depict experimental results quantifying white blood cell numbers and types in mice injected with rat IgG1 or VCAM1 antibody. FIG. 40A depicts a chart quantifying WBCs in mice injected with rat IgG1 or VCAM1 antibody ($p<0.05$ between the 2 groups). FIG. 40B depicts a chart quantifying the blood differential count (by percent) in mice injected with rat IgG1 or VCAM1 antibody (eosinophils=white; lymphocytes=grey; neutrophils=black). FIG. 40C depicts a chart quantifying the blood cell count in mice injected with rat IgG1 or VCAM1 antibody (eosinophils=white; lymphocytes=grey; neutrophils=black). FIG. 40D is a chart depicting serum inflammatory cytokine levels (pg/ml) in mice injected with rat IgG1 or VCAM1 antibody.

Figure 41:
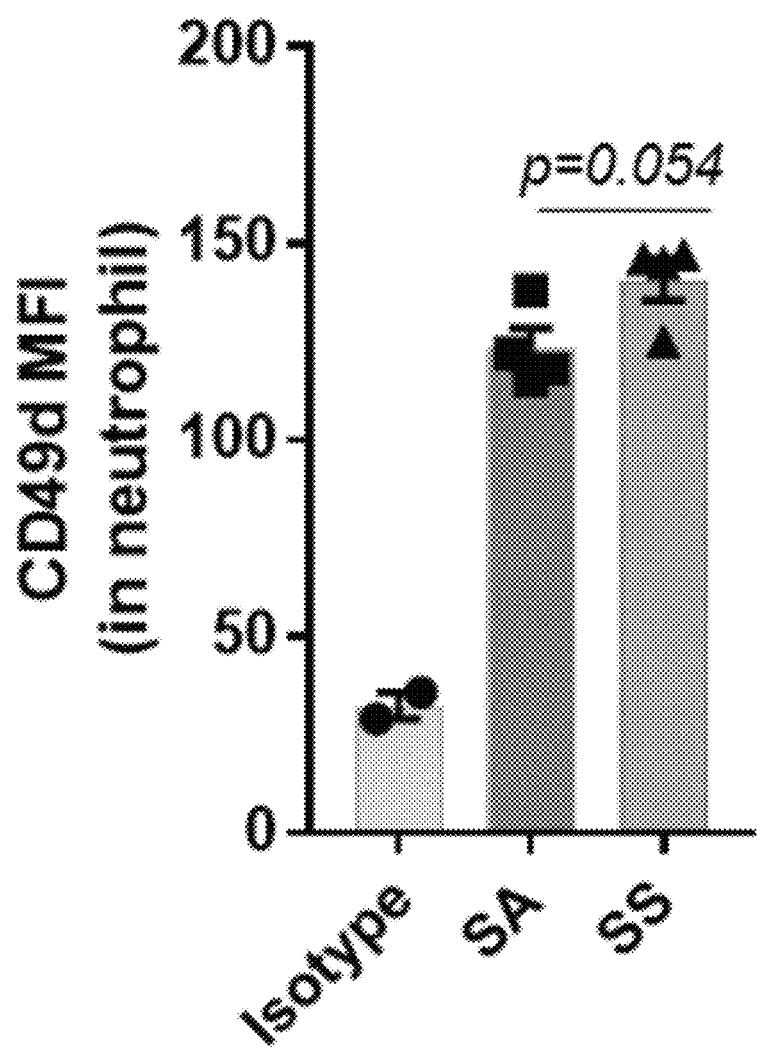
FIG. 41.

Inventors next investigated if the VCAM1 receptor, the integrin alpha4beta1 (CD49d) was expressed on the surface of neutrophils by flow cytometry. FIG. 41 depicts a chart showing data indicating that the VCAM1 receptor CD49d is expressed on mouse neutrophils from SA and SS SCD mice.

Example 4: Anti-MAEA Therapies

Conditional MAEA knockout (MAEA$^{floxed}$) mice were generated and macrophage MAEA expression deleted by Csf1r-Cre (FIGS. 21A, 21B, 22A, 22B). Macrophage MAEA expression was determined to be required for BM macrophage development and erythropoiesis at steady state (FIGS. 21D-21F, 22C-22H). Based on a previous study that depletion of macrophages could normalize polycythemia vera, Applicants investigated treatment with anti-MAEA antibody would achieve similar effects.

Figure 23A:
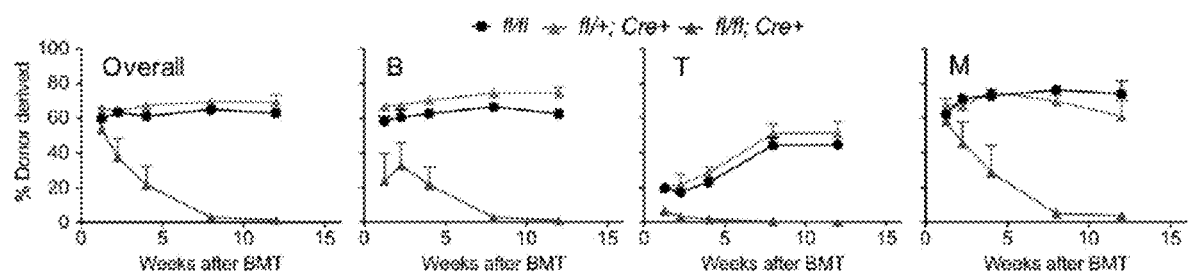
FIGS. 23A-23H.
Figure 23B:
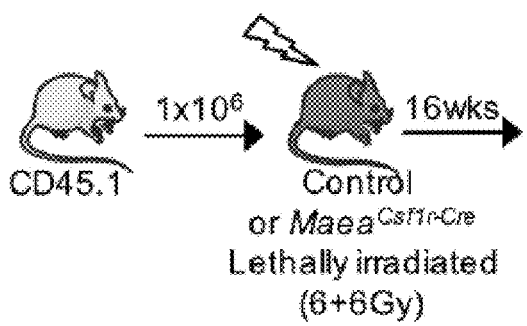
Figure 23C:
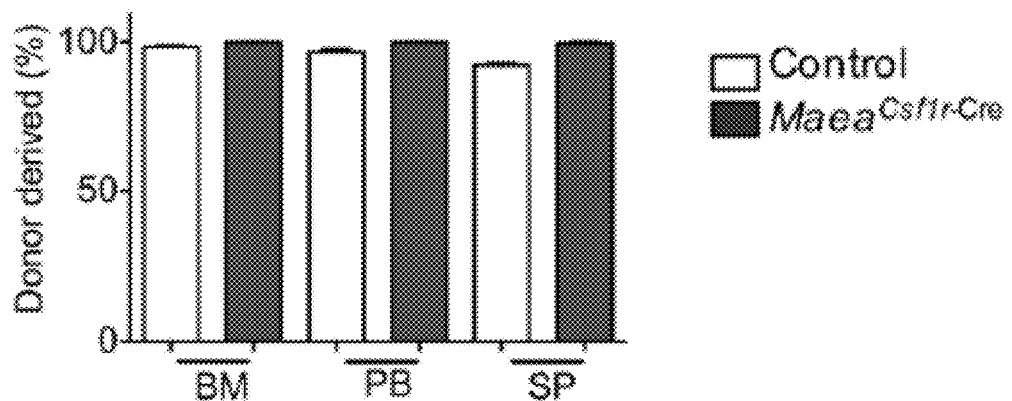
Figure 23D:
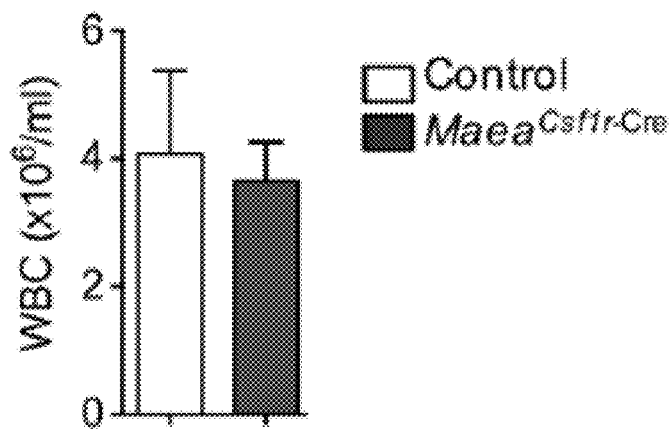
Figure 23E:
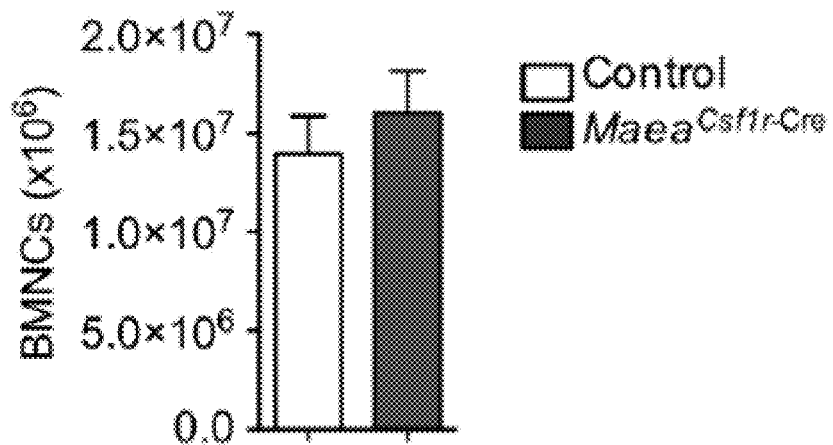
Figure 23F:
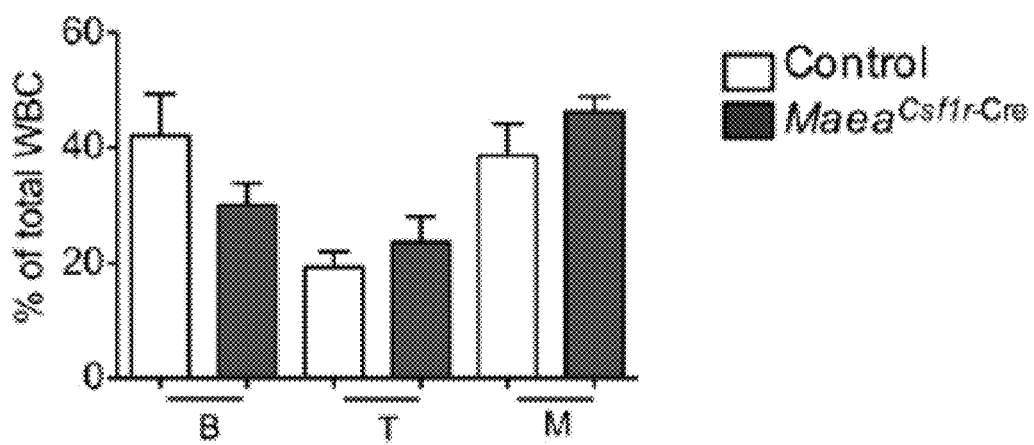
Figure 23G:
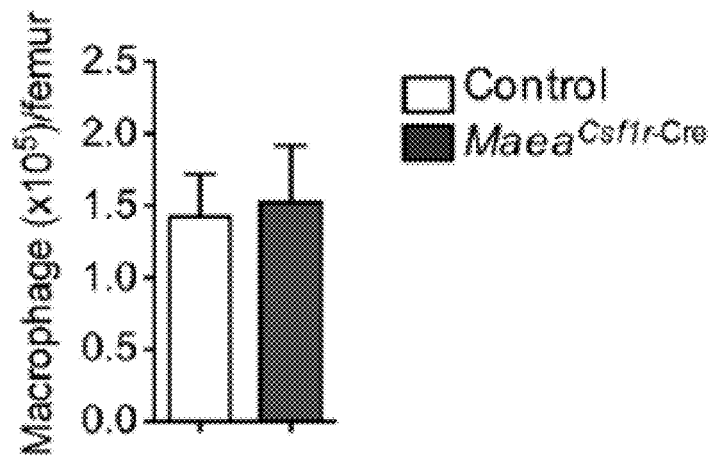
Figure 23H:
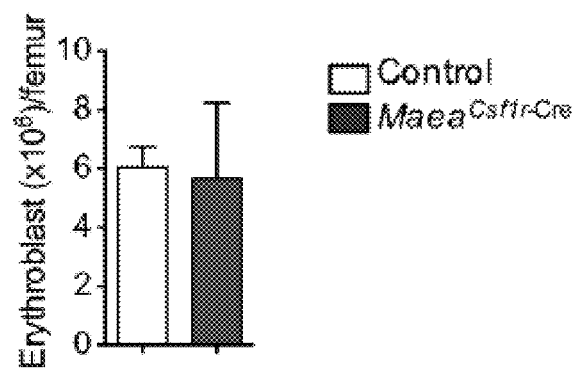
Figure 24A:
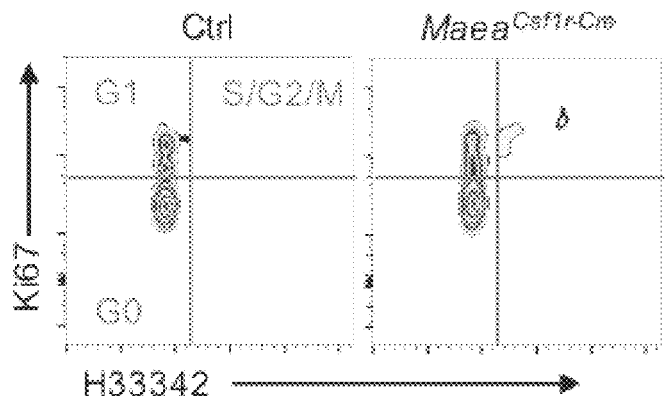
FIGS. 24A-24F.
Figure 24B:
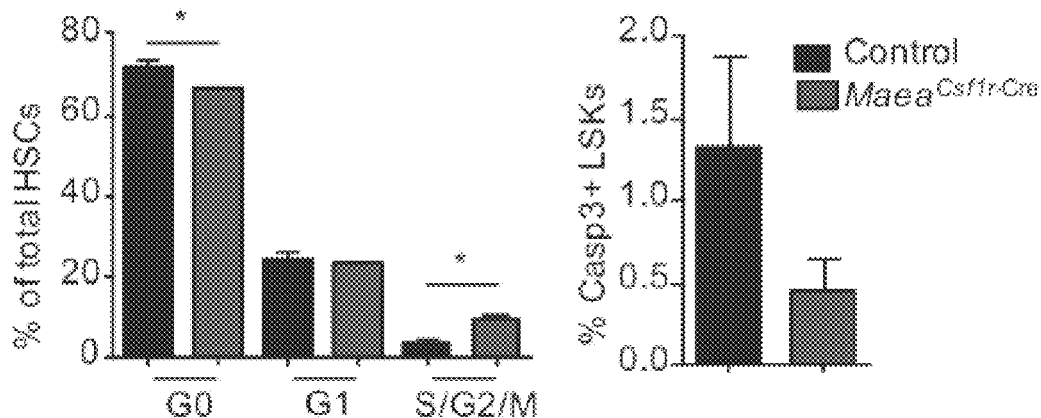
Figure 24C:
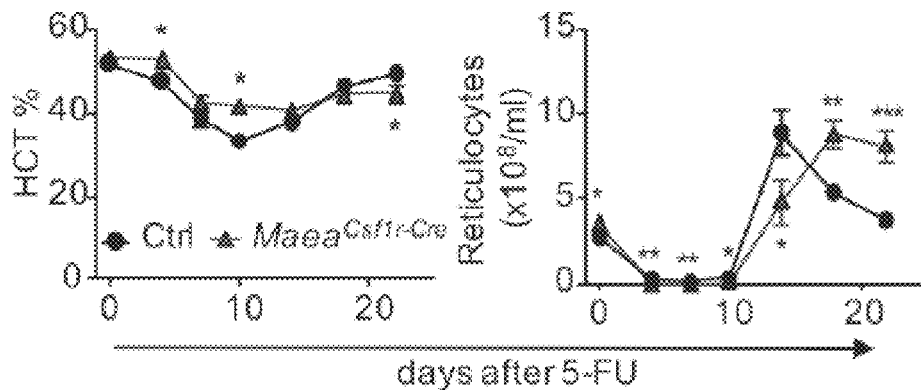
Figure 24D:
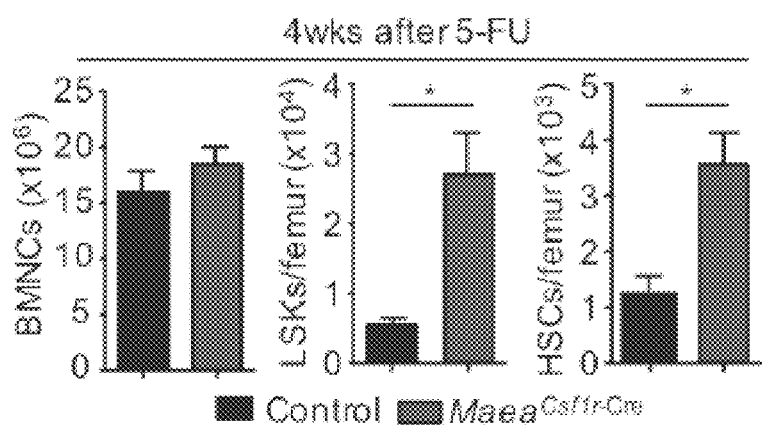
Figure 24E:
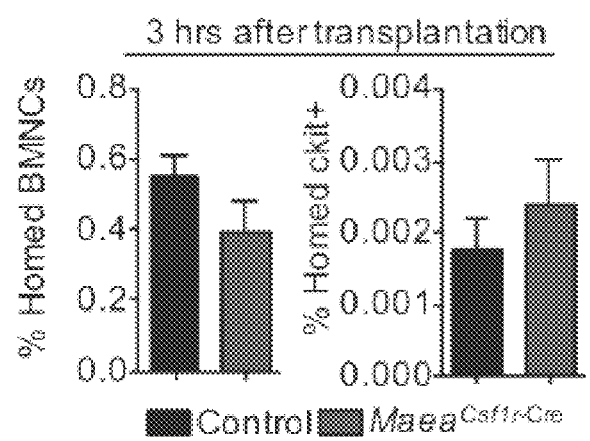
Figure 24F:
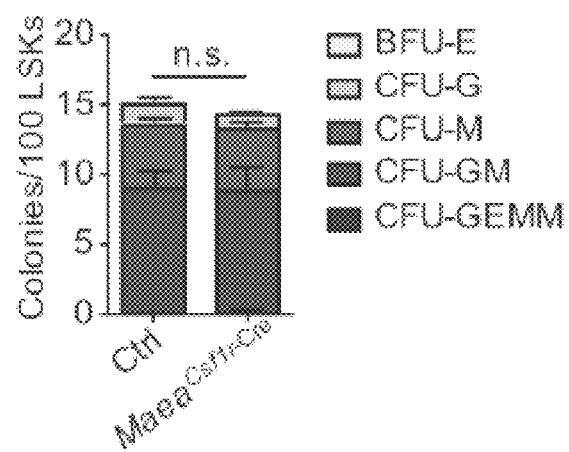
Figure 30A:
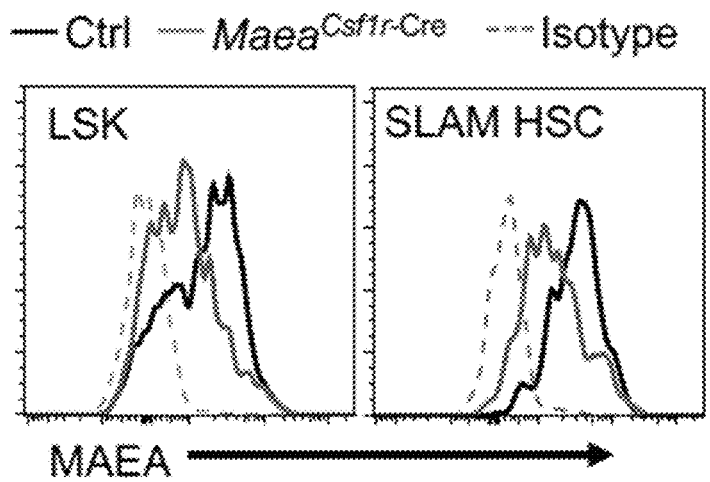
FIGS. 30A-30H.
Figure 30B:
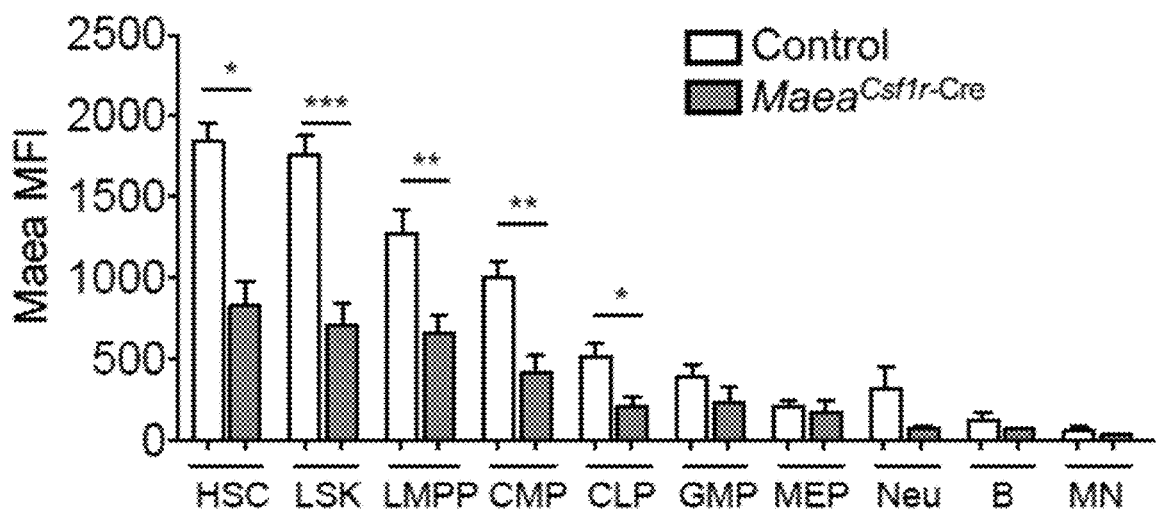
Figure 30C:
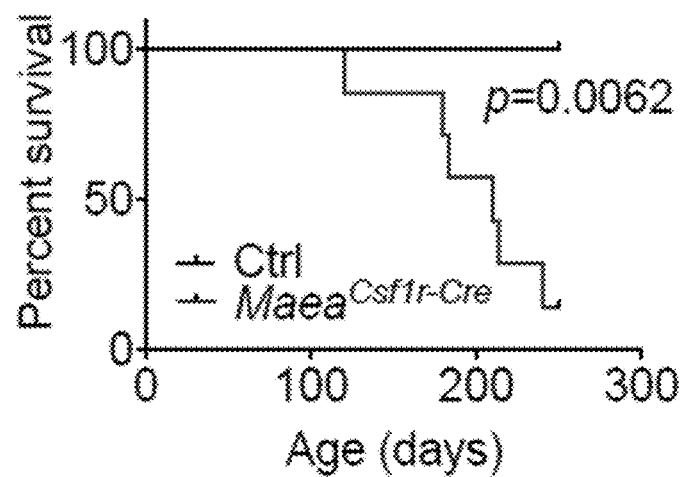
Figure 30D:
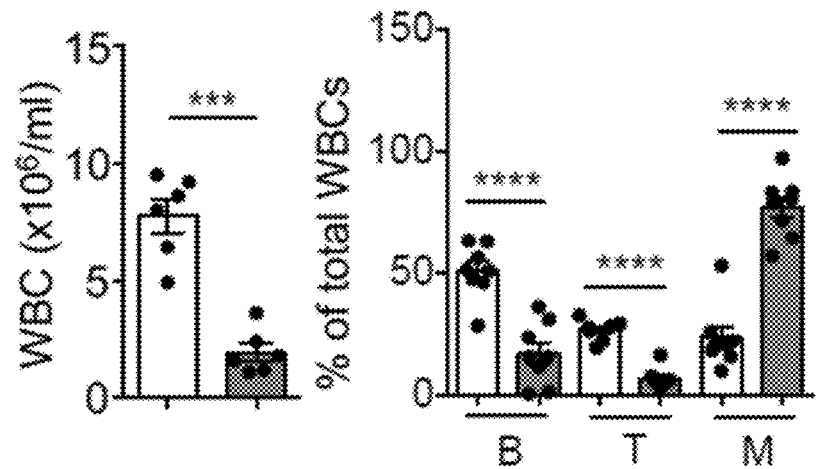
Figure 30E:
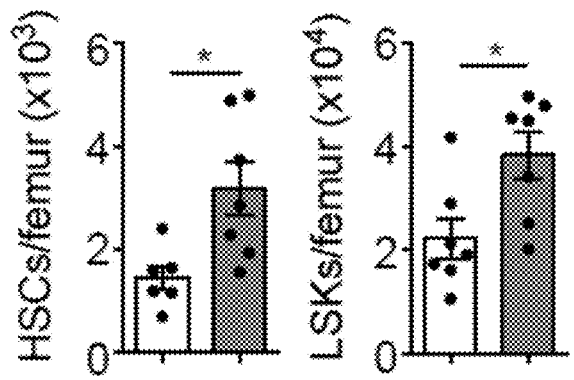
Figure 30F:
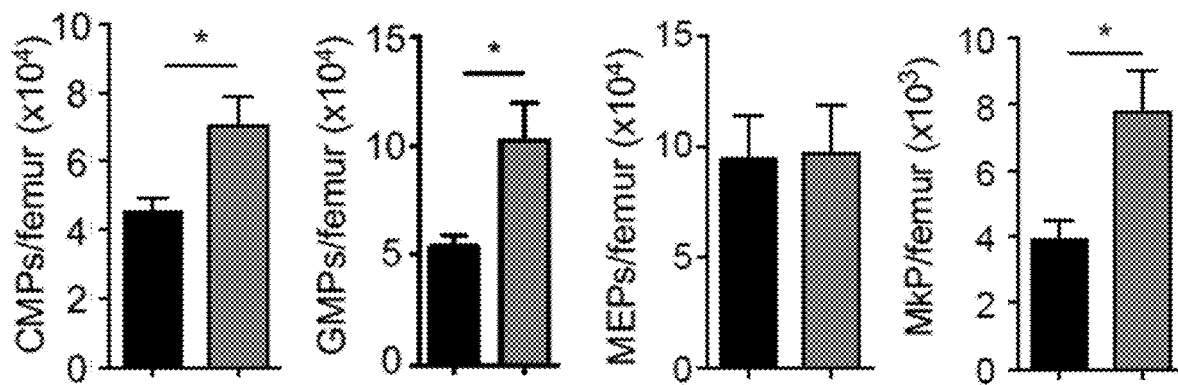
Figure 30G:
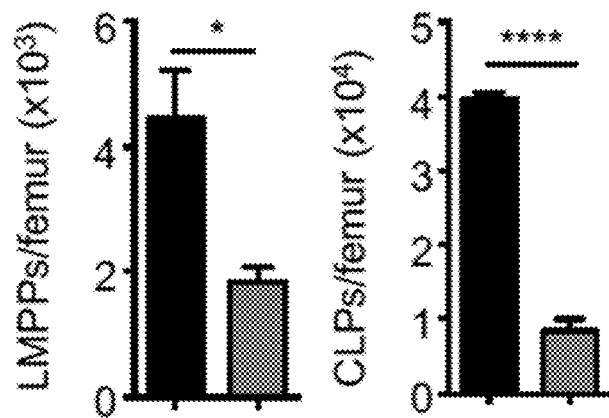

Unexpectedly, MAEA$^{Csf1r-Cre}$ mice also exhibited marked reductions in circulating leukocytes (FIG. 30D), due to a loss of B and T lymphocytes (FIG. 30D). This is likely due to MAEA expression on bone marrow hematopoietic stem and progenitor cells (HSPCs) (FIGS. 30A, 30B) and its involvement in lymphoid commitment from the HSPCs (FIGS. 30E-30G). Importantly, MEAE expression was also required for successful HSC engraftment after bone marrow transplantation (FIG. 23A), and this is not due to any microenvironmental defects (FIGS. 23B-23H). Without MAEA, HSCs are more actively cycling but do not show increased apoptosis (FIGS. 24A-24B). In addition, MAEA-deficient HSCs regenerate (FIGS. 24C, 24D), home to BM (FIG. 24E), and form colonies (FIG. 24F) comparably to control counterparts.

Figure 25A:
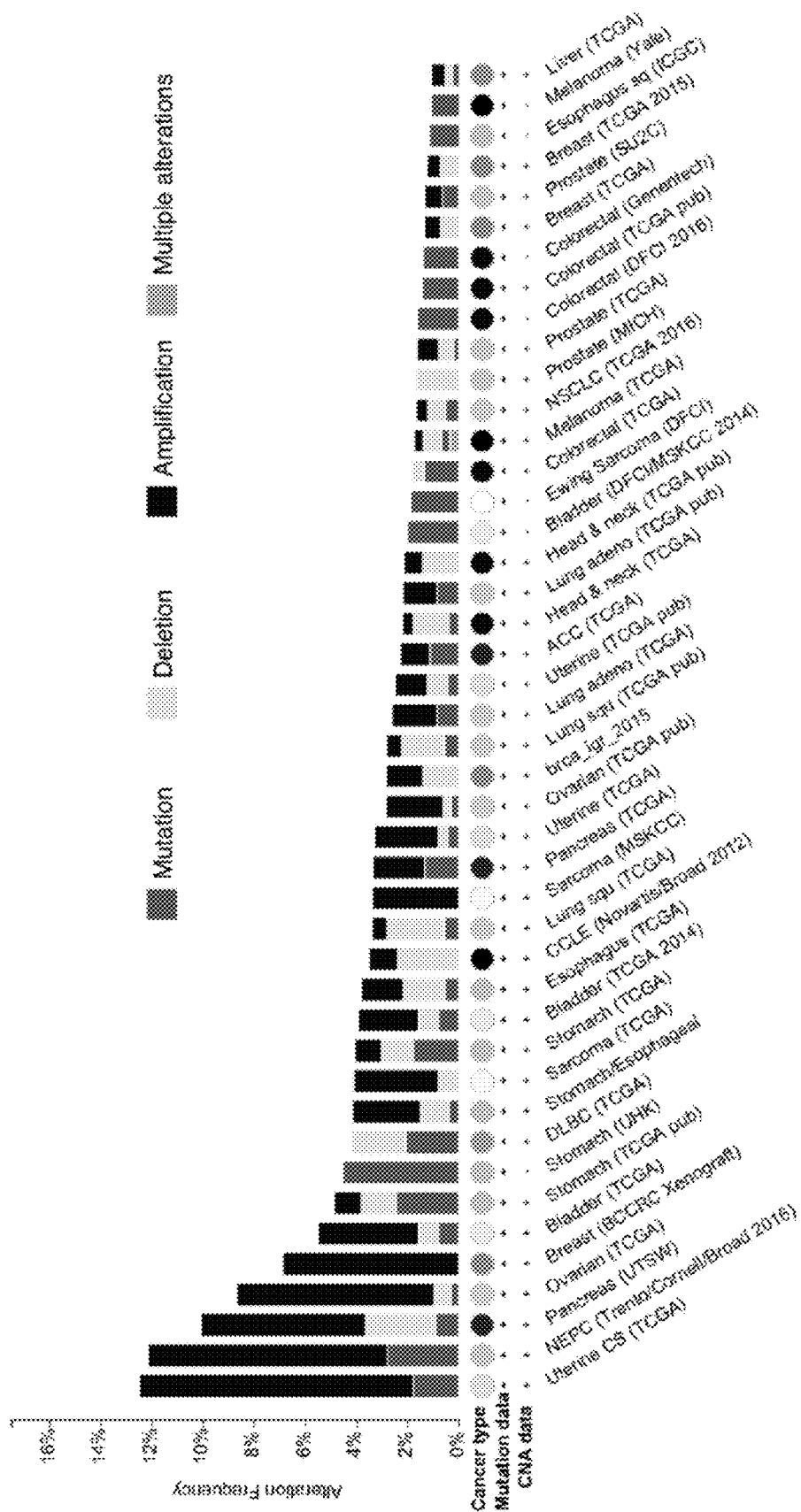
FIGS. 25A-25D.
Figure 25B:
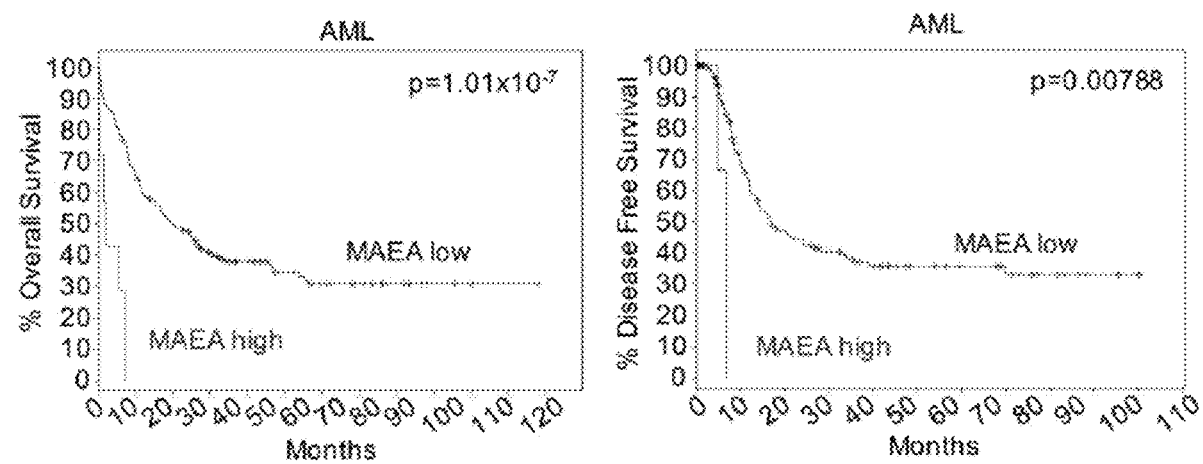
Figure 25C:
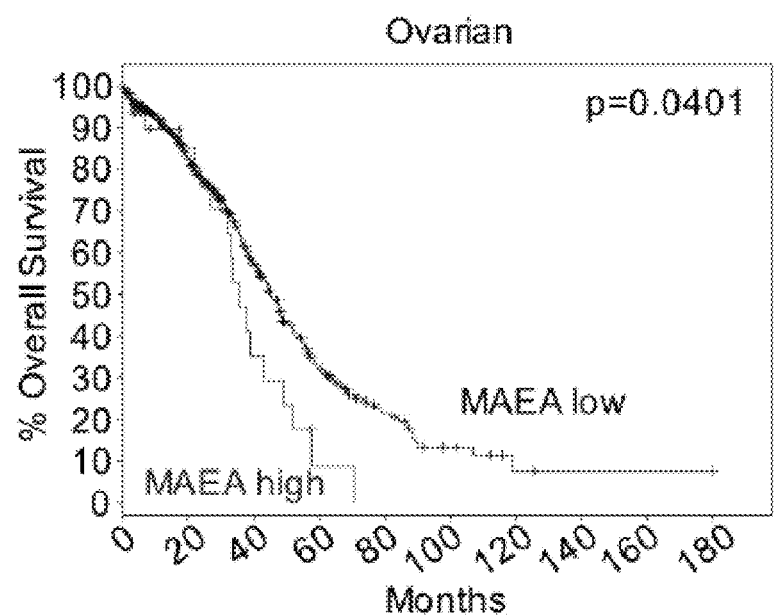
Figure 25D:
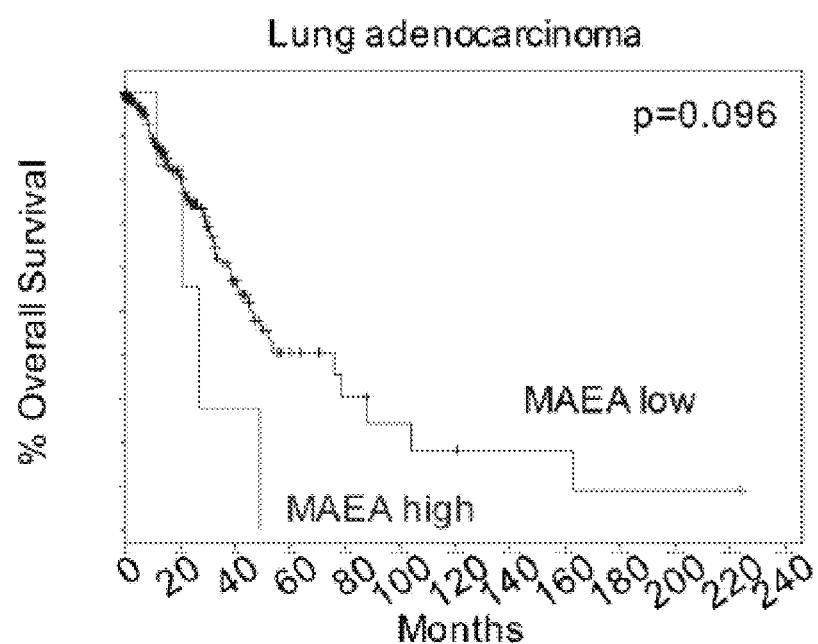
Figure 26A:
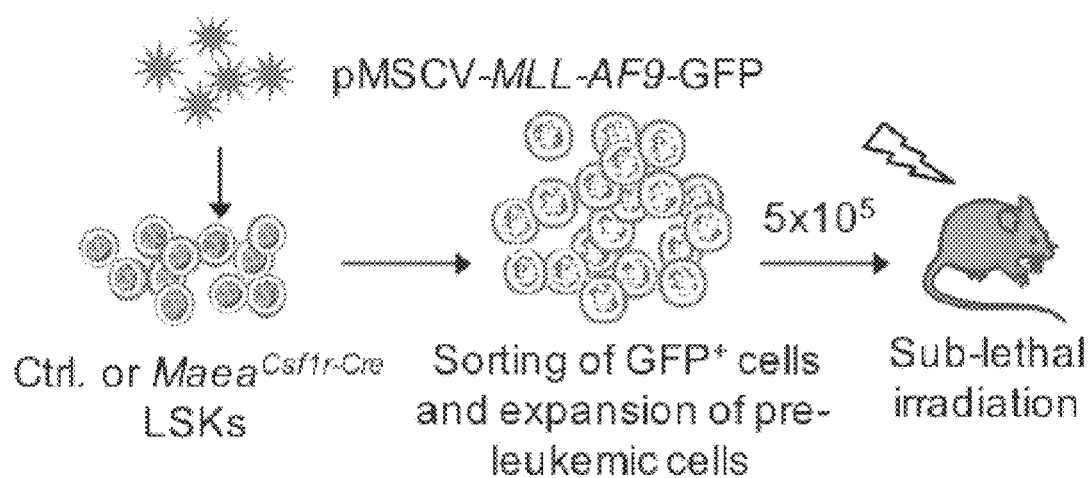
FIGS. 26A-26K.
Figure 26B:
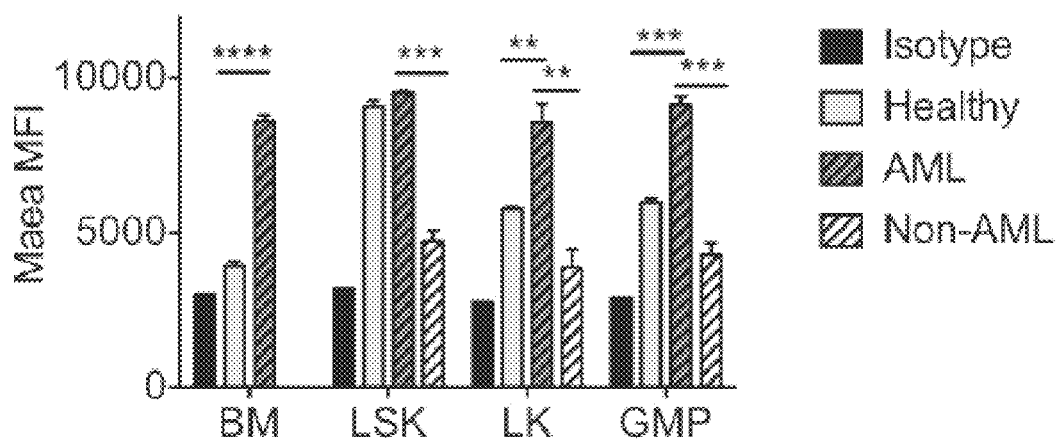

It was hypothesized that leukemia cells might hijack the same mechanism for their progression. Indeed, significant association of MAEA amplification mutations was found with many human cancer types (FIG. 25A), and MAEA up-regulation strongly correlated with poor prognosis in human AML patients (FIGS. 25B, 25D). MAEA expression is also up-regulated in a murine model of acute myeloid leukemia (FIGS. 26A, 26B). By genetically deleting MAEA expression from the AML cells using Csf1r-Cre and Mx1-Cre, MAEA expression was shown to be required for AML engraftment and progression in vivo (FIGS. 26C-26I). Importantly, treating AML-bearing mice with a polyclonal anti-MAEA antibody significantly reduced their circulating leukemia cells (FIG. 26J), but did not cause overt toxicity in healthy mice (FIG. 27). Lastly, analysis of human cancer cell lines revealed a broad expression of MAEA across cancer types (FIG. 19).

These results indicate that MAEA is a novel adverse prognosis factor and drug target expressed on malignant hematopoietic and other cancer cells, and that MAEA is a target to promote cancer cell clearance by the host immune system.

Example 5: Anti-MAEA Antibodies. MAEA Expressed by Macrophages, but not Erythroblasts, Maintains Postnatal Bone Marrow Erythroblastic Islands Red blood cell (RBC) homeostasis is tightly regulated by balanced production and clearance. Bone marrow (BM) erythroid precursors were first observed several decades ago in tight association with a central macrophage in a structure referred to as erythroblastic island (EI).[1] Macrophages regulate both normal and diseased erythropoiesis, including promotion of erythroid precursor survival and proliferation, iron homeostasis and transfer, and terminal maturation and enucleation.[2-5] These activities are promoted by direct interactions between the macrophages and erythroblasts[6,7] via several proposed adhesion mechanisms including (macrophage: erythroblast) VCAM1: VLA-4,[8,9] αV: Icam4,[10] or MAEA: MAEA,[7] CD163,[11] and Palladin[12]. However, the exact role of these adhesion molecules during in vivo adult erythropoiesis has not been determined.

Among these, MAEA was originally identified as an adhesion molecule expressed by both macrophages and erythroblasts and suggested to mediate EI formation via its homophilic interactions.[7,13] Targeted gene inactivation of MAEA caused severe defects in fetal liver erythropoiesis and macrophage development,[14] but the perinatal lethality of MAEA-null embryos has prevented detailed examination of its function in adult hematopoiesis. In this study, a conditional allele of MAEA was generated. MAEA was determined to play a critical role in adult BM macrophage development and EI function. Comparative analysis with VCAM1 deletion shows that MAEA exerts a dominant role in the EI. Selective deletion of MAEA in macrophage or erythroblast shows only disruption of BM erythropoiesis when MAEA is deleted in macrophage, suggesting that MAEA may not interact by homophilic interactions.

Methods

Animals. MAEA$^{fl/fl}$ mice were generated as described below. VCAM1$^{fl/fl}$ mice[15] were kindly provided by Dr. Thalia Papayannopoulou and backcrossed to C57BL/6 strain for at least 10 generations. Csf1r-Cre mice[16] were a gift from Dr. Jeffrey W. Pollard (University of Edinburgh) and also backcrossed onto C57BL/6 background. CD169-Cre knockin mice were previously generated and described[17]. Epor-Cre mice[18] were kindly provided by Dr. Ann Mullally (Dana-Farber/Brigham and Women's Hospital). C57BL/6 (CD45.2) and B16-Ly5.1 (CD45.1) mice were purchased from Charles River Laboratories (Frederick Cancer Research Center, Frederick, Md.)/NCI or the Jackson Laboratories (B6.SJL-Ptprc$^a$ Pepc$^b$/BoyJ). R26-tdTomato (B6.Cg-Gt(ROSA)26Sor$^{tm14(CAG-tdTomato)Hze}$/J) and Mx1-Cre (B6.Cg-Tg(Mx1-cre)1Cgn/J) mice were obtained from Jackson Laboratories. All animals were housed in specific pathogen-free barrier facility. All experimental procedures were approved by the Animal Care and Use Committee of Albert Einstein College of Medicine. All experiments were performed on mice of both genders with littermate controls from the same colony between 6-12 weeks of age.

Generation of MAEA$^{fl/fl}$ mice. The EuMMCR targeting vector PG00141_Z_1_G10 was purchased and electroporated into WW6 embryonic stem (ES) cells. After drug selection, resistant ES cell colonies were picked and screened by Southern blot analysis using 5' and 3' external probes. Correctly targeted ES cell clones were injected into C57BL/6 blastocysts and the resulting chimeric mice were bred with C57BL/6 animals to establish the MAEA$^{targeted}$ line. Once the germline transmission was confirmed, the MAEA$^{targeted}$ mice were crossed to Rosa26$^{FLP1}$ mice (Jax stock #009086) to remove the LacZ/Neo cassette and generate the floxed allele MAEA$^{fl/fl}$. Both alleles were then backcrossed onto C57BL/6 background for at least 5 generations before crossing to the various Cre strains for functional studies. Genotyping was done by ear clip genomic DNA PCR using primers F1+R1+R2 and F2+R3+R4. Primer sequences are as follows: F1: gttcagcctcaggattcagg (SEQ ID NO:1); R1: atgagcaggggacctcaac (SEQ ID NO:2); R2: aactgatggcgagctcaga (SEQ ID NO:3); F2: caccagctcaggcagttaca (SEQ ID NO:4); R3: ccacaacgggttcttctgtt (SEQ ID NO:5); R4: cgggaagaagtgggattacc (SEQ ID NO:6).

Antibodies and flow cytometry. Purified goat anti-MAEA polyclonal antibody (I-20) was purchased from Santa Cruz and used at a 1:100 concentration. Conjugated donkey anti-goat IgG secondary antibodies were from Thermo Fisher and used at a 1:800 concentration. Fluorochrome-conjugated or biotinylated antibodies against mouse Gr-1 (Ly6C/G) (clone RB6-8C5), CD115 (clone AFS98), B220 (clone RA3-6B2), F4/80 (clone BM8), VCAM1 (clone 429), CD11b (clone M1/70), CD45 (clone 30-F11), Ter119 (clone TER-119), CD71 (clone R17217) and CD44 (clone IM7), CD45.1 (clone A20), CD45.2 (clone 104), were from BioLegend or eBiosciences. DAPI-negative singlets were analyzed for all live samples unless otherwise specified. Stained sample suspensions were acquired on an LSR II (BD) and results were analyzed and visualized by FlowJo (Tree Star). For sorting, samples were processed under sterile conditions and sorted on a BD FACSAria.

Generation of MAEA monoclonal antibody (mAb). BALB/c mice were immunized with a KLH-conjugated MAEA peptide that is part of the extracellular domain (AAQKN IDRET SHVTM VVAEL EKTLS GCPA (SEQ ID NO:7)) and boosted with the same peptide and recombinant MAEA protein (Novus #NBP2-23208). Hybridomas producing mAbs to human MAEA were generated by standard techniques from splenocytes fused to Ag8.653 or NSO$^{bcl2}$ myeloma cells.[19] Clone 92 (IgG2a) was firstly selected by ELISA screen as its mAbs recognized MAEA peptide/protein, but not human IgG. Subclone 92.25 was further selected and validated by FACS staining of wild type but not MAEA$^{Csf1rCre}$ mouse BM cells due to only one amino acid difference between the human and mouse sequence in the antibody target region. mAbs were then concentrated and purified from concentrated hybridoma supernatant by Amicon Ultra-15 100K filters (Millipore) and NAb Protein A/G Spin kits (Thermo Scientific).

Complete blood count. Mice were bled ~25 µl into an Eppendorf tube containing 2 µl of 0.5 M EDTA (Life Technologies) using heparinized micro-hematocrit capillary tubes (Fisherbrand) under isoflurane anesthesia. Blood was diluted 1:20 in PBS and analyzed on an Advia counter (Siemens).

In vivo clearance of RBCs. Long-term RBC clearance was assayed as previously described.[20] Mice were given a single i.v. NHS sulfo-biotin (Thermo Scientific) injection (100 mg/kg), and the fraction of biotinylated RBCs was determined weekly from 1 of blood. Short-term clearance was assayed by i.v. injection of 2×10$^8$ CFSE-labelled wild-type RBCs and monitored at indicated time points.

Splenectomy. Mice were splenectomized under 100 mg/kg ketamine and 10 mg/kg xylazine anesthesia as previously described[21] and allowed to recover for 4 weeks before experiments.

Bone marrow transplantation. All recipient mice were lethally irradiated (600+600 cGy, at least 3 h apart) in a Shepherd Mark 1 irradiator. RBC-lysed bone marrow nucleated cells (1×10$^6$, unless otherwise indicated) were then injected retro-orbitally under isoflurane anesthesia.

Colony-forming assays. Spleen BFU-E was assayed by plating 5×10$^5$ RBC-lysed splenocytes in MethoCult™ M3436 (Stem Cell Technologies) according to the manufacturer's instructions and colonies were enumerated on day 10 of culture.

In vivo treatment. For hemolytic anemia induction, mice were injected i.p. with 40 mg/kg body weight PHZ (Sigma #114715) on day 0 and 1 of the experiment. For 5-FU challenge, a single dose (250 mg/kg body weight) of freshly made 5-FU was given i.v. to each mouse under isoflurane anesthesia. Mx1-Cre was induced by three doses of PolyI:C (Invivogen) injections every other day at 5 mg/kg i.p. For antibody treatment, purified MAEA mAb and control IgG2a (BioXcell) were diluted in PBS and injected i.p. at 100 µg daily for 3 weeks.

Cell culture. In vitro terminal differentiation and enucleation of sorted polychromatic erythroblasts (EB-III) was done as previously described.[22] Briefly, EB-III were FACS sorted and cultured at <10$^6$/ml in differentiation media composed of IMDM, 10% FBS, 1% BSA, 30 ng/ml Epo (BioLegend), 0.2 mg/ml holo-transferrin (Sigma) and 10 µg/ml insulin (ThermoFisher) for 48 hours. At the end of the culture, cells were FACS analyzed by Ter119 and H33342 staining. In vitro phagocytosis assay using bone marrow (BMDMs) or spleen (SPDMs) derived macrophages was slightly modified from previously described.[23] BMDMs or SPDMs were isolated by adherence from BM or splenic suspensions in macrophage media (RPMI1640 with 10% FBS, 10 mM HEPES and 10 ng/ml M-CSF) for 7 days.[24,25] On day 7, BMDMs, or SPDMs were harvested by gentle scraping and plated at 1×10$^5$/well in 12-well plates for 24 hours in full macrophage media. The macrophages were then serum-starved for 2 hours before adding 10×10$^6$ CFSE-labeled RBCs or 4×10$^4$ CD45.1 BM cells as target. After 2-3 hours co-incubation, non-adherent cells were washed and macrophages were scraped for FACS analysis.

Quantification and statistical analysis. In each experiment, each mouse was analyzed as a biological replicate. Data visualization (shown as mean±s.e.m.) and statistical analysis were performed using Graphpad Prism 7. Unpaired Student's t-test was used to assess statistical significance when comparing two samples unless otherwise indicated.

Results

MAEA is required for adult BM macrophage development and EI niche formation. To examine MAEA function in adult erythropoiesis, mice were generated with a floxed allele of MAEA, which leads to a frame shift and non-sense mediated decay of MAEA mRNA upon Cre-mediated recombination. Flow cytometry analysis using a MAEA-specific polyclonal antibody revealed that in adult BM mononucleated cells (BMNCs), MAEA was highly expressed in the macrophages with minimal expression by monocytes, neutrophils or B cells (gated as previously described[26]). MAEA$^{fl/fl}$ mice were intercrossed with a Csf1r-Cre transgenic line[16] to delete MAEA in the monocytic-macrophage lineage. Csf1r-Cre; MAEA$^{fl/fl}$ animals (henceforth MAEA$^{Csf1r-Cre}$) were born healthy and fertile, and survived into adulthood at expected Mendelian ratios, by contrast to the perinatal lethality reported in MAEA-null mice.[14] Efficient MAEA-depletion on BM macrophages was confirmed by FACS analysis. The BM of MAEA$^{Csf1r-Cre}$ mice exhibited a slight, but significant, reduction in cellularity. Further analysis revealed that their BM macrophage numbers represented ~30% of wild-type levels. MAEA$^{Csf1r-Cre}$ bones also appeared paler than controls, suggesting a reduced erythroid content in the marrow. Indeed, the number of BM erythroblasts was markedly reduced in MAEA$^{Csf1r-Cre}$ BM compared to littermate controls. This may be due to disruption of EI formation because there was a marked reduction in EIs (~30% of control levels) formed in vivo in the MAEA$^{Csf1r-Cre}$ BM. Profiling of the erythroblast maturation status revealed a partial block of differentiation at the polychromatic (EB-III) stage.[27] These results support a critical role of MAEA in adult BM erythroblastic island formation and functions.

MAEA is dispensable for RBC enucleation. In contrast to the prior report on MAEA-null mice,[14] peripheral blood anemia was not observed in young adult MAEA$^{Csf1r-Cre}$ mice. Although a role for MAEA in enucleation as also been suggested,[14] blood smears and FACS analyses revealed elevated CD71$^+$ Ter119$^+$ reticulocyte counts in MAEA$^{Csf1r-Cre}$ animals but no nucleated RBCs in circulating blood. To investigate further this issue, polychromatic erythroblasts (EB-III) were sorted from BM of MAEA$^{Csf1r-Cre}$ and control mice and enucleation rates were evaluated in vitro. Cultured MAEA$^{Csf1r-Cre}$-derived erythroblasts enucleated at similar rate as those of controls. These results suggest that MAEA expression is dispensable for postnatal RBC enucleation.

MAEA regulates RBC dynamics during stress erythropoiesis. Control and MAEA$^{Csf1r-Cre}$ mice were challenged with hemolytic anemia induced by the hemoglobin-oxidizing reagent phenylhydrazine (PHZ). There was a significant impairment of the reticulocytosis but not RBC or hematocrit recovery in MAEA$^{Csf1r-Cre}$ mice. Similarly, reticulocytosis in MAEA$^{Csf1r-Cre}$ mice after a single dose of cytotoxic agent 5-fluorouracil (5-FU) was significantly delayed while RBC and hematocrit showed an attenuated decline before a mild but significant delay in recovery. The attenuated early decline in hematocrit was consistent with previously described macrophage-depleted models,[20] suggesting that MAEA depletion caused macrophage defects were contributing to both the RBC production and clearance. Indeed, the RBC lifespan was significantly prolonged in MAEA$^{Csf1r-Cre}$ animals. However, no phagocytosis defects in MAEA$^{Csf1r-Cre}$ macrophages were detected, suggesting the RBC clearance defect likely reflected the overall reduction of macrophage numbers.

Differential roles of MAEA in spleen and bone marrow macrophages. Interestingly, even though Csf1r-Cre induced similarly efficient MAEA deletion in splenic red pulp macrophages (RPMs), their numbers were not significantly altered. This suggests differential requirements of MAEA in BM and spleen macrophage development or maintenance. Spleen EB numbers were not significantly altered, although profiling of their maturation revealed a similar partial block at the polychromatic stage. However, compensatory stress erythropoiesis was found in the spleen of MAEA$^{Csf1r-Cre}$ mice as evidenced by splenomegaly and elevated burst-forming unit-erythroid (BFU-E) numbers.

To further dissect the requirement of MAEA in BM and spleen erythropoiesis, splenectomy was performed on MAEA$^{Csf1r-Cre}$ and littermate control mice. Splenectomized MAEA$^{Csf1r-Cre}$ animals developed anemia over the course of 4 weeks while the control group maintained healthy peripheral blood counts, suggesting that in the context of MAEA$^{Csf1r-Cre}$ animals, the extra-medullary erythropoiesis may mask the phenotype. The splenectomized control and MAEA$^{Csf1r-Cre}$ mice were challenged with PHZ. A severely impaired recovery response was observed in MAEA$^{Csf1r-Cre}$ mice. Blood smear again did not reveal any enucleation defect in the RBCs from splenectomized MAEA$^{Csf1r-Cre}$ mice before or after PHZ treatment. These results further confirmed that MAEA is critical for adult BM erythropoiesis but not RBC enucleation.

Dominant function of MAEA over VCAM1 in EI niche formation. VCAM1 represents another adhesion molecule implicated in EI.[8,9,20] To compare the role of VCAM1 with MAEA, VCAM1 was deleted using Csf1r-Cre. Interestingly, no defects were observed in BM macrophage or erythroblast numbers in steady state VCAM1$^{Csf1r-Cre}$ mice compared to the control animals, except for a minor trend towards reduced spleen erythroblasts. EB maturation as measured by CD44 expression and cell size also indicated a normal differentiation profile. The peripheral RBC compartment during steady state and after PHZ challenge was also normal, consistent with previous studies.[28,29] These data indicate that MAEA plays a dominant role in BM EI niche function while VCAM1 is dispensable for adult erythropoiesis in vivo.

Selective MAEA deletion in macrophages, but not erythroblasts, impairs bone marrow erythropoiesis. Csf1r-Cre broadly recombines in hematopoietic stem and progenitor cells (HSPCs), and thus may not discriminate between MAEA function in macrophages or erythroblasts that descent from HSPCs. To delete selectively MAEA in macrophages, MAEA$^{fl/fl}$ was crossed with CD169-Cre,[17] which does not target the erythroid lineage. MAEA$^{CD169-Cre}$ mice phenotypically mimicked the MAEA$^{Csf1r-Cre}$ animals, with significant reduction of BM macrophage and erythroblast numbers, but no alterations in BM cellularity or circulating blood parameters. Further analyses revealed a similar defect in in vivo island formation and a partial block in BM EB maturation at the EB-III stage. Interestingly, while CD169-Cre also recombined efficiently in spleen RPMs, no significant change in RPM numbers was observed and EB numbers in the spleen of MAEA$^{CD169-Cre}$ mice were significantly increased suggesting ongoing extra-medullary erythropoiesis.

By contrast, when MAEA$^{fl/fl}$ was crossed with Epor-Cre, which recombines efficiently and selectively in erythroid progenitors,[18] MAEA$^{Epor-Cre}$ animals showed significant reductions in circulating RBC counts with increased mean corpuscular volume (MCV), but no significant change in BM macrophage and erythroblast numbers or in vivo erythroblast island formation. In addition, MAEA$^{Epor-Cre}$ EB maturation showed a distinct profile with accumulation of the mature cells in the BM. No enucleation defect was observed in blood smear or in vitro EB-II culture. Analysis of the spleen did not reveal significant difference in macrophage or EB numbers of MAEA$^{Epor-Cre}$ mice, despite efficient Epor-Cre recombination in spleen erythroid lineage. These results suggest that MAEA acts in the macrophage, but not erythroblast, to mediate EI formation in adult BM, consistent with the previous report in an in vitro EI reconstitution setting.[14] The result also further indicates that MAEA is dispensable for RBC enucleation but may play a cell autonomous function in RBC terminal maturation or egress in adult mice.

To investigate the role of macrophage or erythroblast conditional MAEA deletion in stress erythropoiesis, the two models were challenged with PHZ-induced anemia. Surprisingly, MAEA$^{CD169-Cre}$ mice showed no significant difference in hematocrit recovery or reticulocytosis. This may be due to the fact that CD169-Cre recombines at a lower frequency (~60%) in BM macrophages, and/or Csf1r-Cre model is indeed a combinatory model of MAEA-deletion in both the macrophages and erythroblasts. Indeed, BM of MAEA$^{CD169-Cre}$ mice showed constantly milder reduction of macrophage and EB numbers than MAEA$^{Csf1r-Cre}$ mice at steady state and after PHZ. In contrast, MAEA$^{Epor-Cre}$ mice showed a faster decline in RBC content during the early days and a weaker reticulocyte output during the later recovery stages. The reduction of RBCs and reticulocytes but normal BM EB numbers after PHZ in MAEA$^{Epor-Cre}$ mice also further suggests that EB MAEA expression may contribute cell autonomously to RBC terminal maturation or egress, but not in EI formation.

Postnatal MAEA deletion or inhibition uncovers important functions in adult erythropoissis. To evaluate the role of MAEA in postnatal erythropoiesis and the maintenance of the EI niche, MAEA was deleted using the Mx1-Cre line (MAEA$^{Mx1-Cre}$) in which Cre-mediated recombination is inducible by Poly I:C injections. Radiation chimeras were generated by transplantation of the BM from MAEA$^{MX1-Cre}$ or littermate controls into wild-type mice to exclude potential complications from the BM microenvironment. Two months after transplantation, Cre recombination were induced by three Poly I:C injections. Three weeks after the first Poly I:C injection, BM macrophage and erythroblast numbers were significantly reduced in MAEA$^{Mx1-Cre}$ animals, indicating that MAEA is required cell-autonomously for the maintenance of BM macrophages and the EI niche during homeostasis.

Figure 29A:
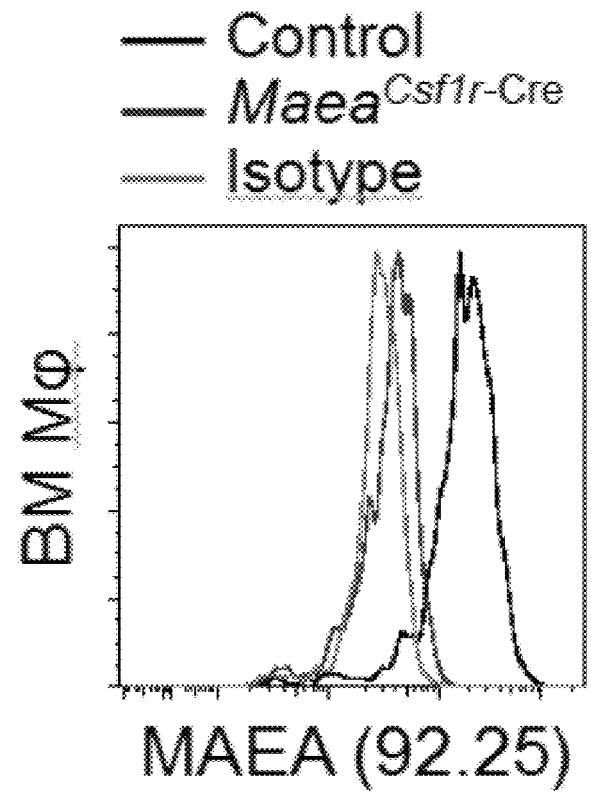
FIGS. 29A-29F.
Figure 29B:
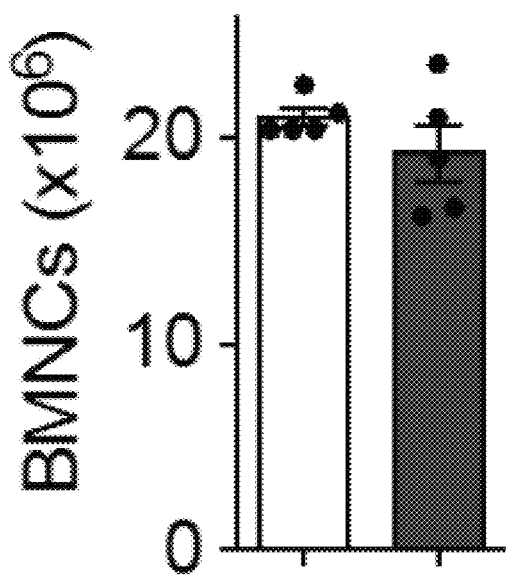
Figure 29C:
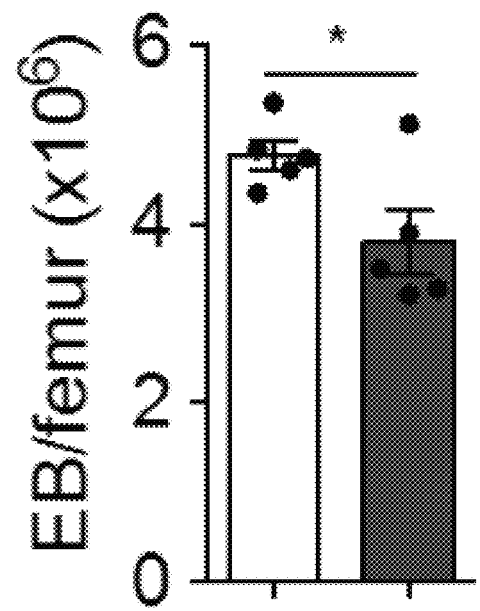
Figure 29D:
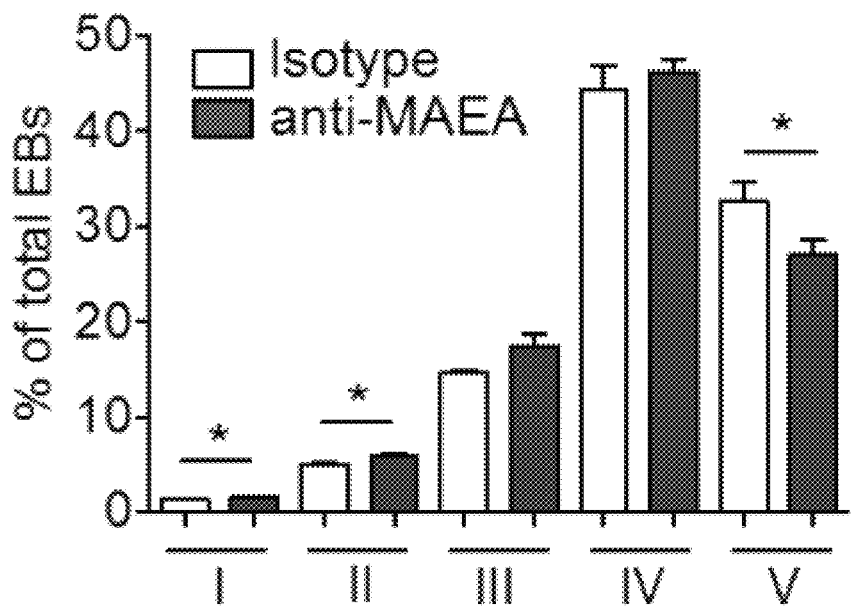
Figure 29E:
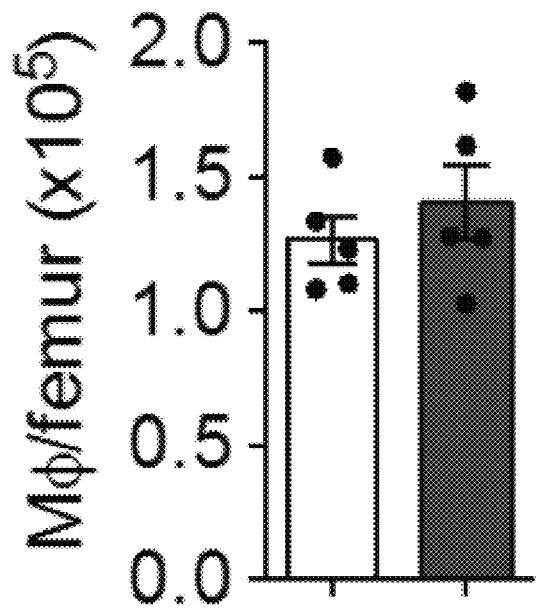
Figure 29F:
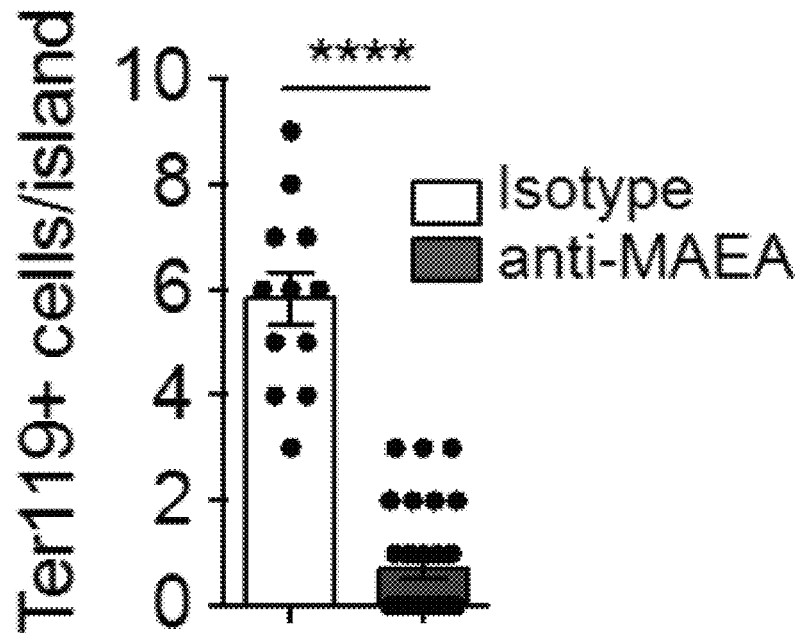

To investigate further the role of MAEA in erythropoiesis, a novel monoclonal antibody was developed by immunization of Balb/c mice with a peptide corresponding to the extracellular domain of human MAEA. Clone 92.25 (IgG2a) was isolated, which interacts specifically with both murine and human MAEA, owing to the highly conserved MAEA amino acid sequence across species (FIG. 18A). Wild-type mice were treated with 92.25 or isotype control (100 μg daily 5 days a week for 3 weeks). Anti-MAEA significantly reduced erythroblast numbers in BM without affecting the total cellularity (FIGS. 29B, 29C), but not in the spleen. The treatment also led to alterations in erythroblast differentiation similar to macrophage-selective MAEA knockouts (FIG. 30D) without reductions of macrophage numbers (FIG. 29E). Furthermore, in vitro EI reconstitution assay showed that 92.25 significantly inhibited island formation (FIG. 29F), clearly indicating that the EI phenotype from MAEA deficiency does not originate solely from a defect of macrophage maturation and direct adhesion mediated via MAEA is required for adult BM erythropoiesis.

DISCUSSION

The critical function of EI niche in erythropoiesis was initially suggested based on in vitro data[6,7] and recently confirmed in vivo.[20,30] However, in vivo studies using macrophage depletion cannot distinguish between the EI-dependent and EI-independent functions of the macrophage.[20,30] Several adhesion mechanisms have been proposed to mediate EI formation, providing an ideal model for investigations of EI-specific functions.[7,8,10-12] However, studies thus far have been largely based on in vitro EI formation assays or germline gene-deletions. Here it is shown that MAEA is critical for adult BM EI formation and homeostatic erythropoiesis via multiple mechanisms. Both constitutive and induced MAEA deletion result in severe reductions of BM macrophage numbers, indicating that MAEA is required for BM macrophage homeostasis. Interestingly, spleen macrophages are not affected by MAEA deletion, in line with recent reports indicating the independence and heterogeneity of tissue resident macrophages under steady state.[31-33] Yet, RBC clearance is delayed in MAEA$^{Csf1r-Cre}$ mice, suggesting a role of macrophages in the BM or other organs that might be affected by MAEA-deletion in RBC clearance. Additionally, antibody inhibition disrupted EI formation in vivo and in vitro confirmed that MAEA also directly mediates the adhesion of erythroblasts to macrophages to form EI.[13-14] BM EB number and maturation profile is significantly impaired even when macrophage numbers are not affected (such as after anti-MAEA antibody inhibition), suggesting EI-specific functions of the macrophage in supporting EB differentiation. The macrophage and erythroid lineage-selective MAEA deletion provides genetic evidence that MAEA-mediated adhesion is unlikely the result of a homophilic interaction.

MAEA appears dispensable for the enucleation of adult erythroblasts. The enucleation process of end-stage erythroid maturation is thought to be coordinated by the sorting and reassembly of nuclear, cytoplasmic and membrane contents among the resulting reticulocytes and pyrenocytes.[22,34,35] Previous studies have suggested that MAEA is associated with actin filaments, preferentially segregating into the extruding pyrenocytes and is required for EB enucleation.[14,35,36] However, none of the present genetic deletion models have revealed any enucleation defect in vivo or in vitro, under steady state or after stress. One possibility is that the erythroid progenitors in previously reported MAEA null embryos are so poorly differentiated due to defects upstream of the EI that they are not able to reach the enucleation stage.[14,36] Alternatively, the residual expression of MAEA in the present conditional knockout models may be masking the phenotype observed in the null embryos. It is also tempting to speculate that the enucleation process of fetal erythrocytes may be different from their adult counterpart, in parallel with their many other differences, such as the globin compositions.[37-31]

Results provided herein provide genetic evidence that the contribution of MAEA in BM EI is dominant compared to that of VCAM1, which when deleted using the same Csf1r-Cre, is dispensable for macrophage development, in vivo EI function and erythroid recovery. Although VCAM1-mediated EI formation has commonly been observed in vitro,[8,39,40] its requirement during in vivo erythropoiesis using genetic models has not been described.[28,29] Studies using antibody inhibition in whole animals have suggested a contribution of VCAM1 in erythropoiesis,[20] although VCAM1 expression and function outside of the EI, e.g., in endothelial cells[41] or the hematopoietic stem and progenitor cell niche,[42-44] cannot be excluded. Since EI mediates erythropoiesis in health and disease,[20,30] the present study indicates that MAEA is a promising therapeutic target for erythropoietic disorders.

Example 6: MAEA is an E3 Ubiquitin Ligase Promoting Autophagy and Self-Renewal of Hematopoietic Stem Cells Macrophage-Erythroblast Attacher (MAEA, also known as EMP) was originally identified as an adhesion molecule required for erythroblastic island formation.[7] Germline deletion of MAEA led to severe anemia and perinatal mortality.[97] Sequence analysis indicates that MAEA is a highly conserved RING finger domain-containing E3 ubiquitin ligase.[98,99] MAEA's functions, however, remain obscure. As shown by results provided herein, MAEA is highly expressed in hematopoietic stem cells (HSCs) where it is required for their maintenance by restricting cytokine receptor signaling and promoting autophagy. Constitutive MAEA deletion produces severe defects in HSC repopulation capacity, B- and T-lymphoid differentiation, and premature death of animals from a myeloproliferative syndrome. Postnatal MAEA deletion leads to transient HSC expansion followed by their depletion. Mechanistically, Applicants found that the surface expression of several hematopoietic cytokine receptors (e.g., MPL, FLT3) is stabilized in absence of MAEA, thereby prolonging their intracellular signaling. Additionally, the autophagy flux in HSCs, but not in mature hematopoietic cells, is markedly impaired. Administration of autophagy-inducing compounds rescued the functional defects of MAEA-deficient HSCs. Further, MAEA is upregulated in various cancers and associated with poor survival of acute myelogenous leukemia (AML), and MLL-AF9-driven AML does not develop in the absence of MAEA. These findings thus identify MAEA as an anticancer target and novel E3 ubiquitin ligase, regulating autophagy, and guarding HSC maintenance.

Figure 30H:
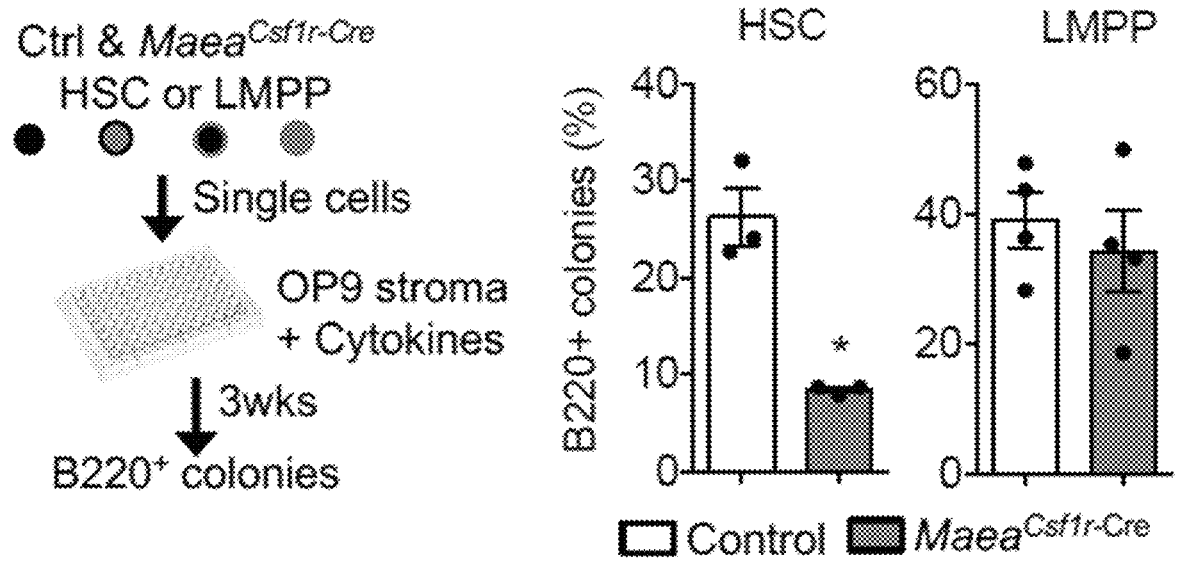
Figure 31A:
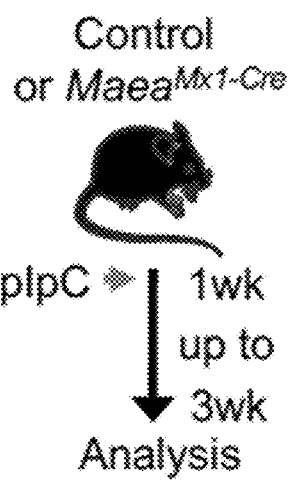
FIGS. 31A-31K.
Figure 31B:
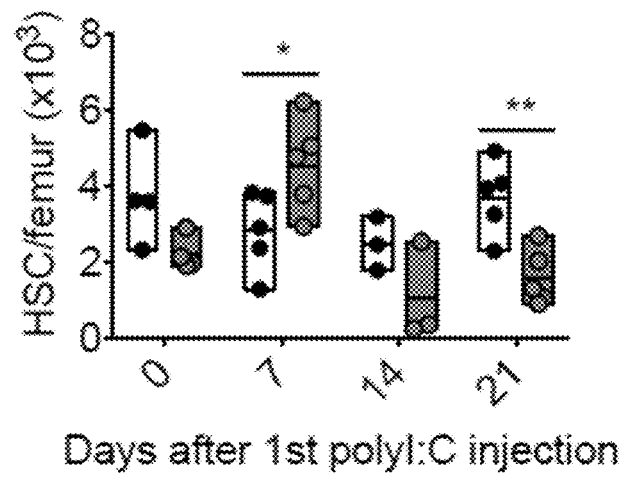
Figure 33A:
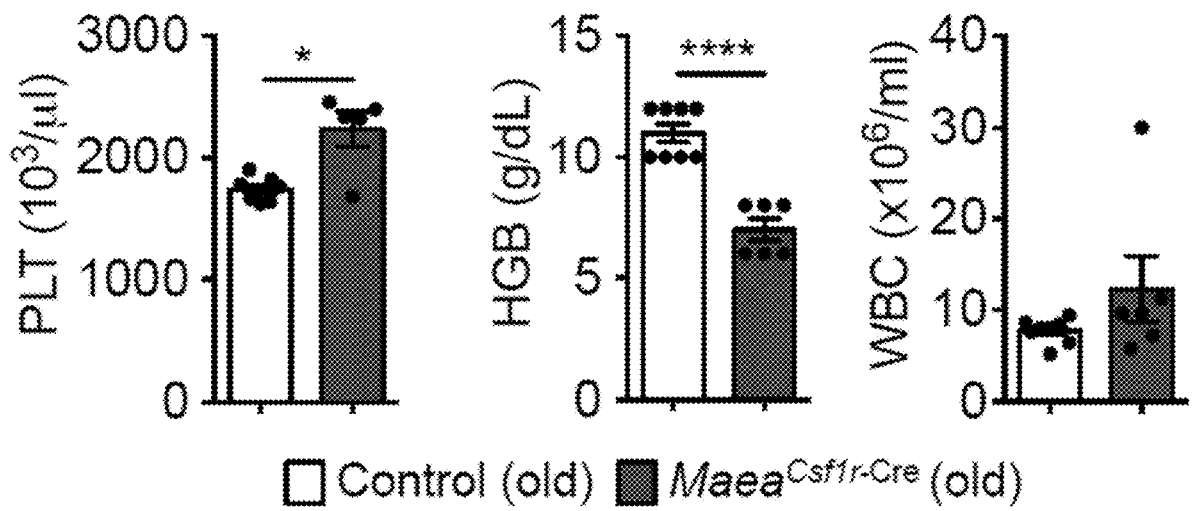
FIGS. 33A-33D.
Figure 33B:
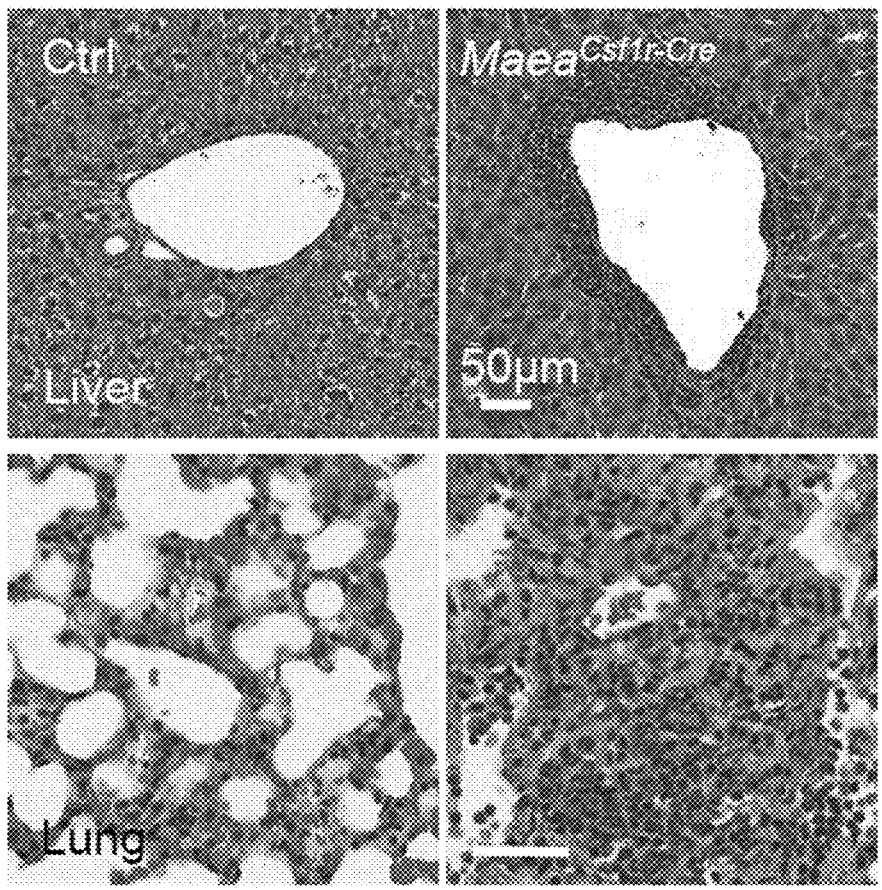
Figure 33C:
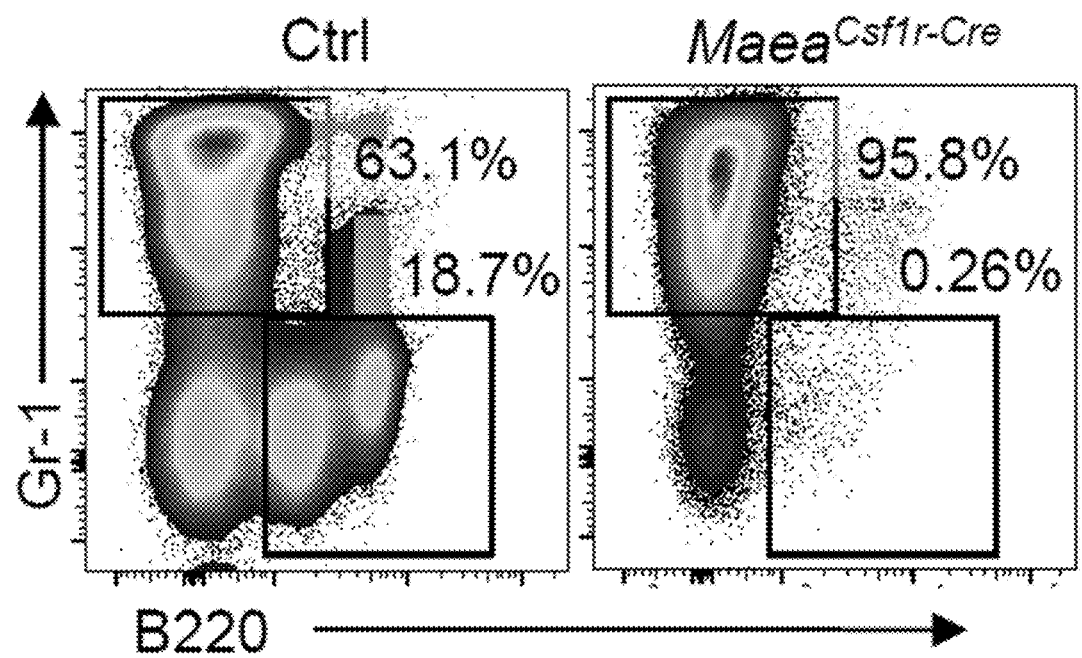
Figure 33D:
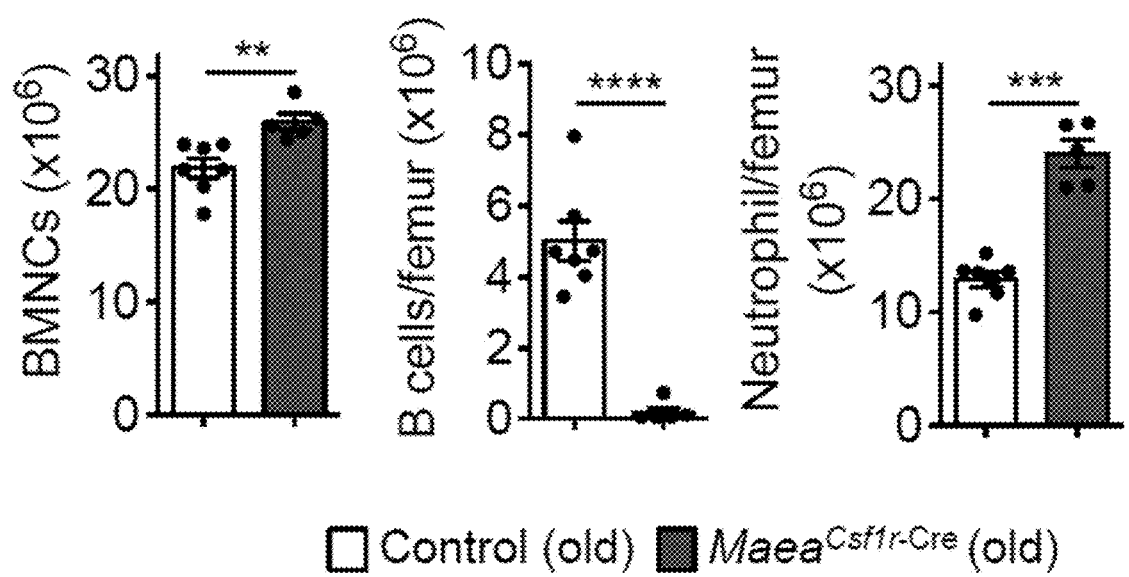

A conditional MAEA gene deletion recently revealed that MAEA expression on macrophages, but not erythroblasts, was required for postnatal EI formation.[100] Of note, MAEA was also expressed at high levels on HSCs, and efficiently deleted using Csf1r-Cre[101] (FIGS. 31A, 31B; hereafter referred to as MAEA$^{Csf1r\text{-}Cre}$). MAEA$^{Csf1r\text{-}Cre}$ mice are viable but die prematurely between 4-8 months of age from a myeloproliferative syndrome characterized by thrombocytosis, anemia and increased infiltration of myeloid cells in the lung and liver (FIGS. 30A, 33A, 33B). Examination of the bone marrow (BM) at ~7 months of age revealed a near absence of B-lymphocytes with increased BM cellularity due to Gr-1$^+$ cell expansion (FIGS. 33C, 33D). By contrast, young adult MAEA$^{Csf1r\text{-}Cre}$ mice did not exhibit anemia or a myeloproliferative syndrome but had a marked reduction (by ~75%) of circulating leukocytes due to severe lymphopenia (FIG. 30D). Analysis of their BM revealed a significant elevation of HSC numbers (CD150$^+$ CD48$^-$ LSKs) and myeloid progenitors in MAEA$^{Csf1r\text{-}Cre}$ BM compared to control animals, whereas the lymphoid progenitors were reduced (FIGS. 30E-30G, 34A-34D). To obtain insight into whether MAEA was required for lymphoid progenitor maintenance or HSC function, single lymphoid-primed multipotent progenitors (LMPPs) or HSCs were sorted from control and MAEA$^{Csf1r\text{-}Cre}$ BM onto OP9 stromal cells to examine their lymphoid differentiation potential. These results indicated that MAEA$^{Csf1r\text{-}Cre}$ HSCs, but not the LMPPs, showed reductions in lymphoid differentiation (FIG. 30H). These results suggest that HSCs in MAEA$^{Csf1r\text{-}Cre}$ mice are skewed toward the myeloid lineage at the expense of the lymphoid potential.

Figure 34A:
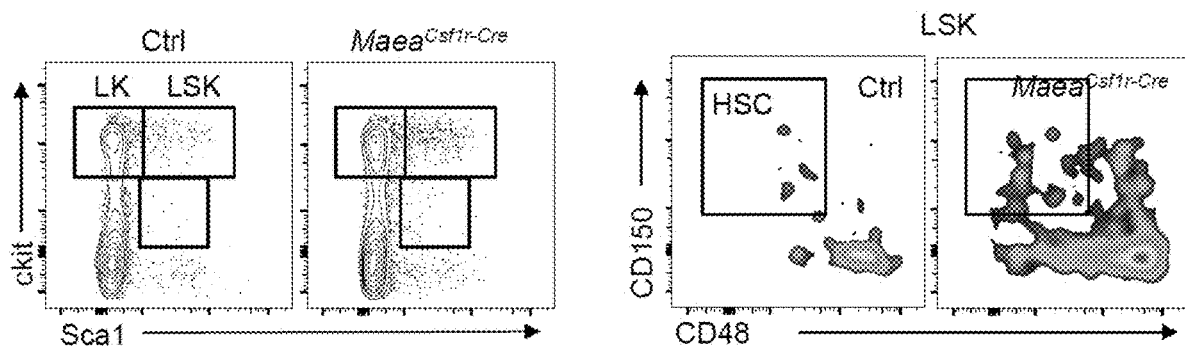
FIGS. 34A-34E.
Figure 34B:
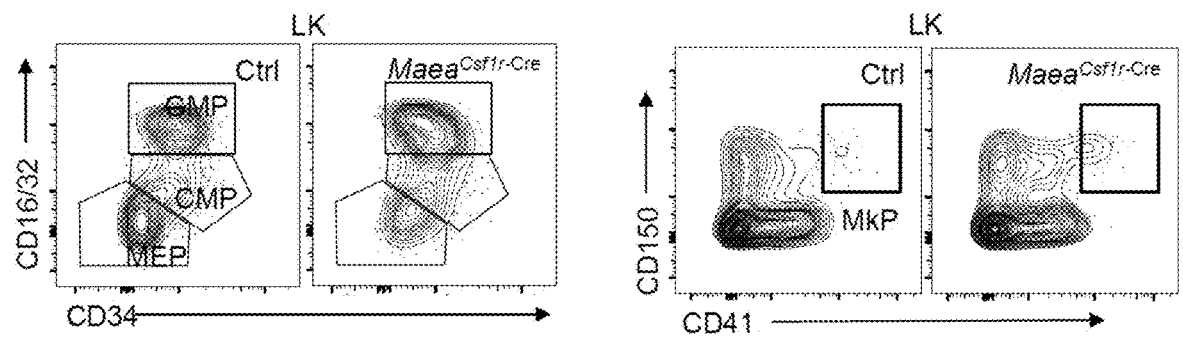
Figure 34C:
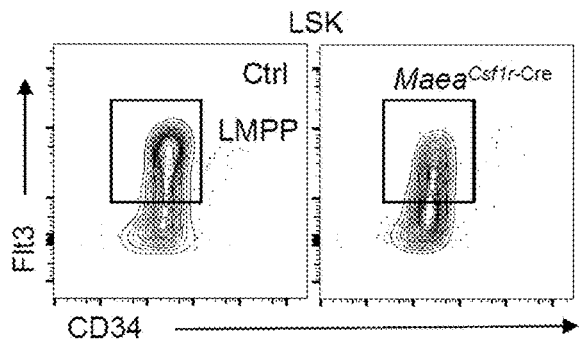
Figure 34D:
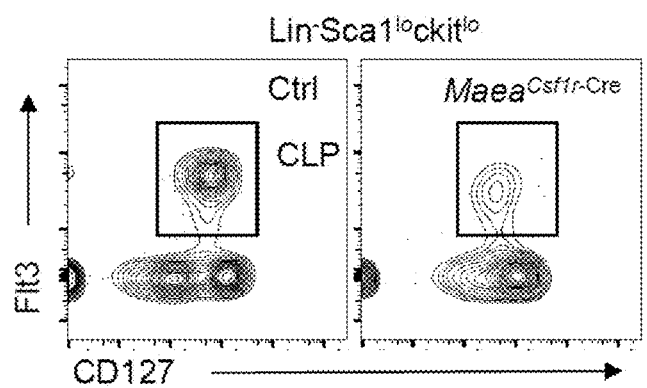
Figure 34E:
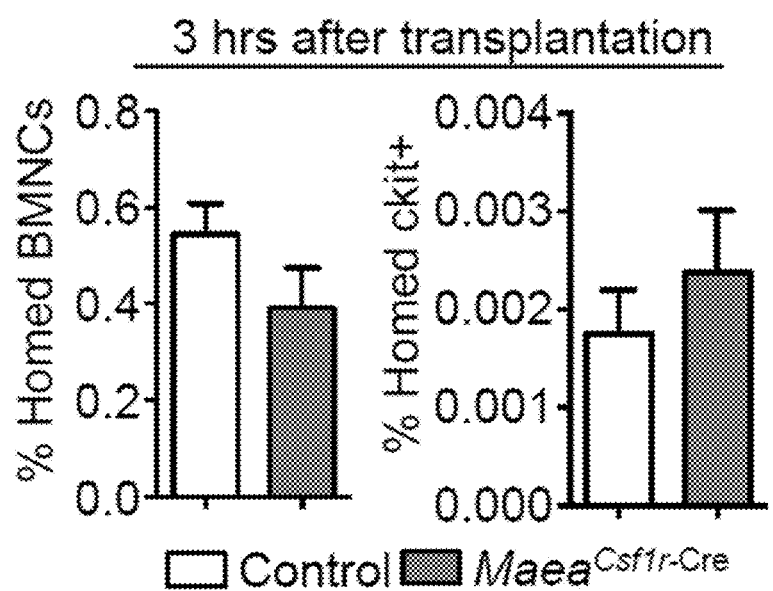

To evaluate further MAEA's function in HSCs, their ability to competitively repopulate the BM of lethally irradiated recipients was examined. Surprisingly, despite a higher frequency of phenotypic HSCs, Applicants observed a marked reduction in long-term repopulation of peripheral blood across all lineages from MAEA$^{Csf1r\text{-}Cre}$ donor cells compared to MAEA$^{fl/fl}$ and MAEA$^{fl/+}$; Csf1r-Cre$^+$ control littermates (FIGS. 30I, 34E). This was not due to the MHC haplotype mismatch of the Csf1-Cre transgenic mice as Applicants have verified that these animals were syngeneic for H-2$^{b/b}$ and MAEA$^{fl/+}$; Csf1r-Cre$^+$ engrafted as well as MAEA$^{fl/fl}$. Analysis of recipient BM at 16 weeks after transplantation confirmed the severe reduction in the HSC chimerism from MAEA$^{Csf1r\text{-}Cre}$ donors (FIG. 30J). No reduction of MAEA$^{Csf1r\text{-}Cre}$ cell homing to the bone marrow was observed (FIG. 34F), suggesting that MAEA controls HSC repopulation activity.

Figure 35A:
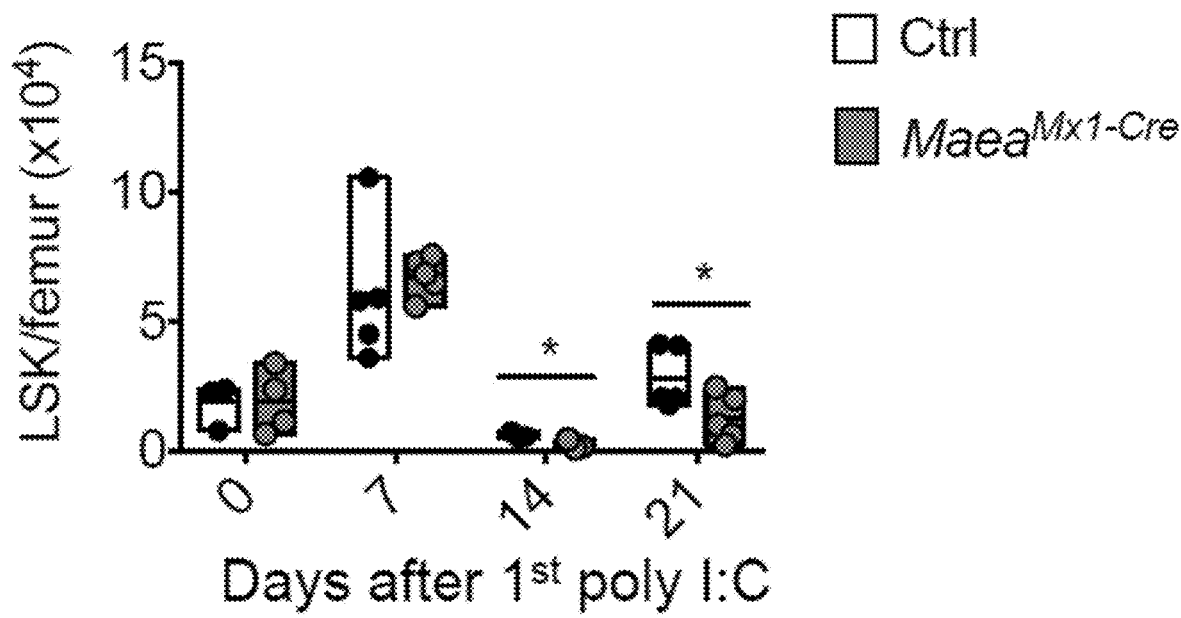
FIGS. 35A-35E.
Figure 35B:
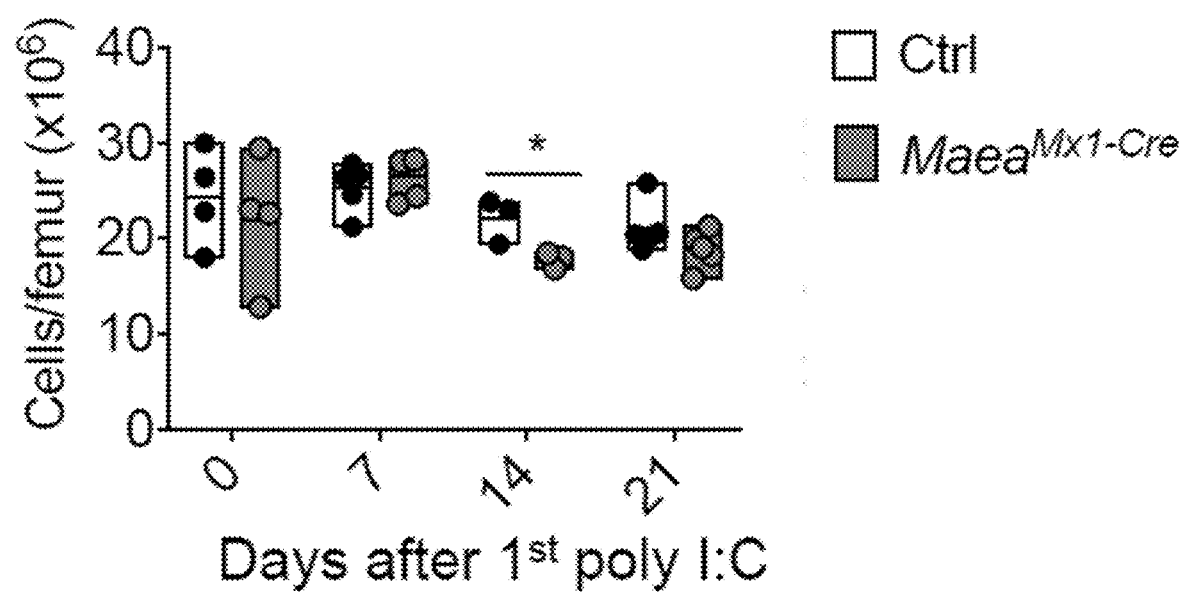
Figure 35C:
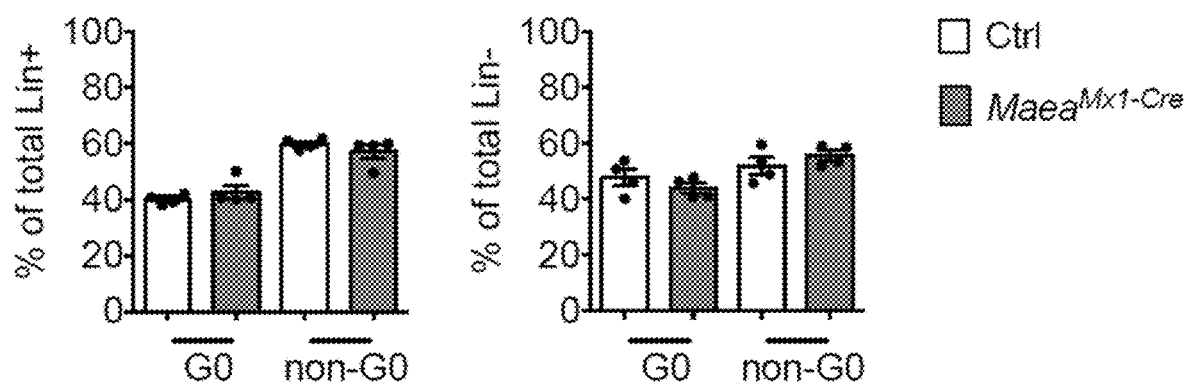
Figure 35D:
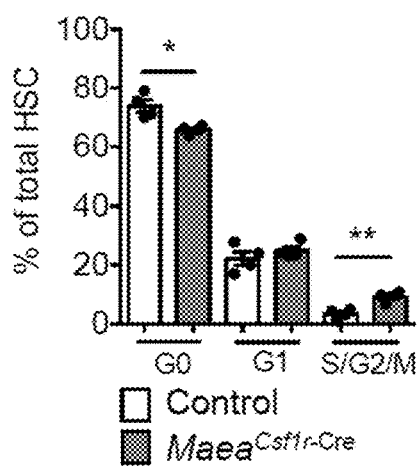
Figure 35E:
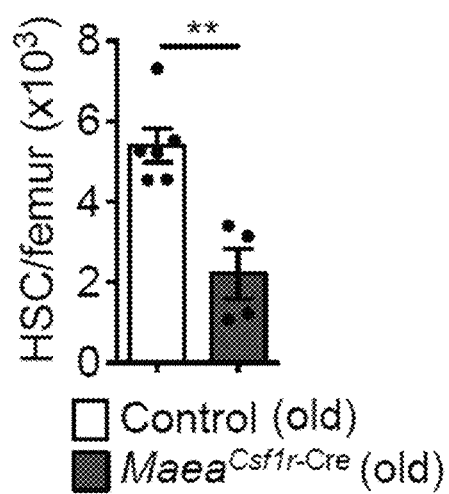

To confirm these results, HSC function was evaluated after MAEA deletion using the conditional Mx1-Cre line and poly I:C administration (FIG. 30A). During the time course of 3 weeks after the first poly I:C injection, results showed that MAEA$^{Mx1\text{-}Cre}$ HSCs initially expanded at day 7 followed by a significant reduction compared to control MAEA$^{f/f}$ mice (FIGS. 31B, 35A) while the total BM cellularity was not altered (FIG. 35B). Cell cycle analysis revealed a dramatic loss of quiescence of MAEA$^{Mx1\text{-}Cre}$ HSCs (FIG. 31C) but not of other cell populations after poly I:C induction (FIG. 35C). In addition, MAEA$^{Csf1r\text{-}Cre}$ HSCs were also actively cycling in young mice while their numbers were depleted in older mice (FIGS. 35D, 35E). These results suggest MAEA deletion depletes HSCs likely by aberrant activation, followed by their exhaustion.

Figure 31C:
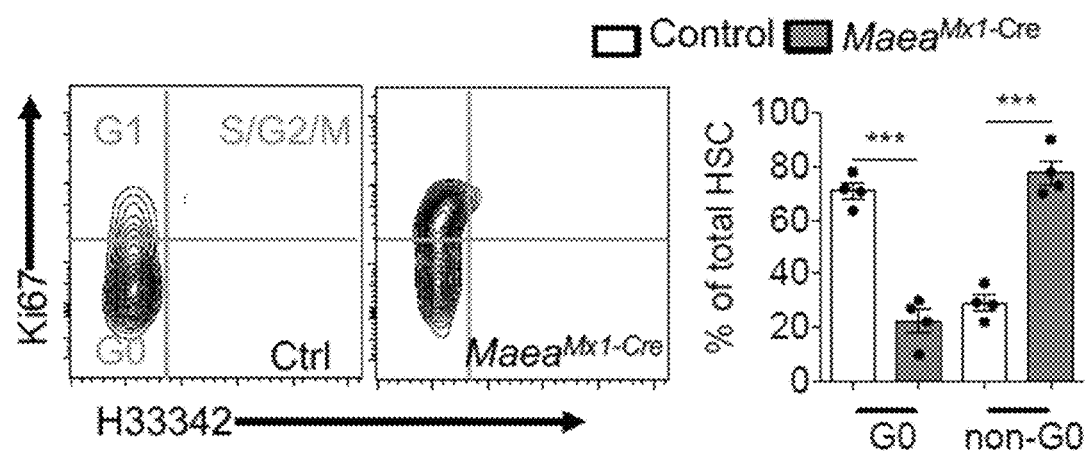
Figure 31D:
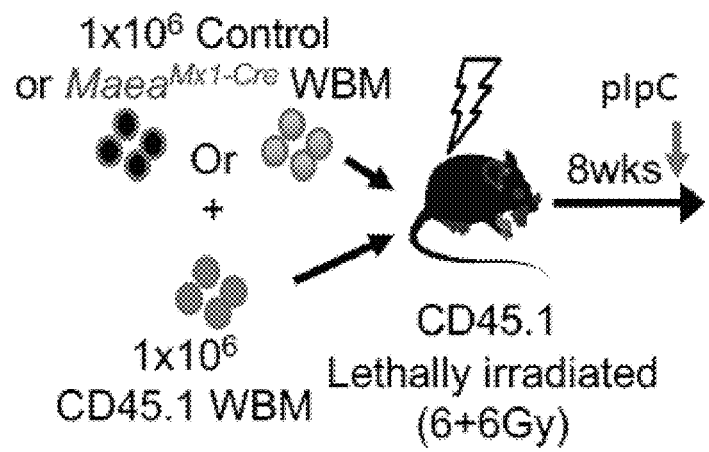
Figure 31E:
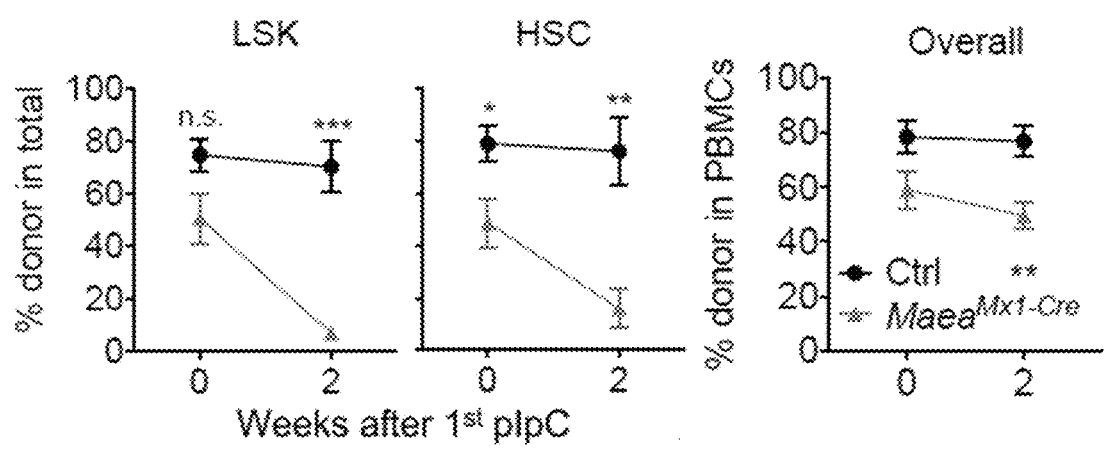

To ascertain the HSC-intrinsic requirement of MAEA, chimeric mice were generated by transplantation of an equal mixture of wild-type (CD45.1) and MAEA$^{Mx1\text{-}Cre}$ (CD45.2) BM cells into lethally irradiated wild type (CD45.1) recipients and induced MAEA-deletion after stable reconstitution (FIG. 31D). Analysis of the BM and peripheral blood donor chimerism showed a drastic reduction of BM HSCs and LSKs derived from MAEA$^{Mx1\text{-}Cre}$ cells at 2 weeks and a lower peripheral contribution over 8 weeks after poly I:C induction (FIGS. 31E, 35F). Similar results were obtained in MAEA$^{Csf1r\text{-}Cre}$ reciprocal transplantation experiments, which indicated that the phenotype was transplantable and did not depend on the BM microenvironment (FIGS. 35G-35L). Thus, these results clearly show an intrinsic role of MAEA in HSC maintenance.

Figure 31F:
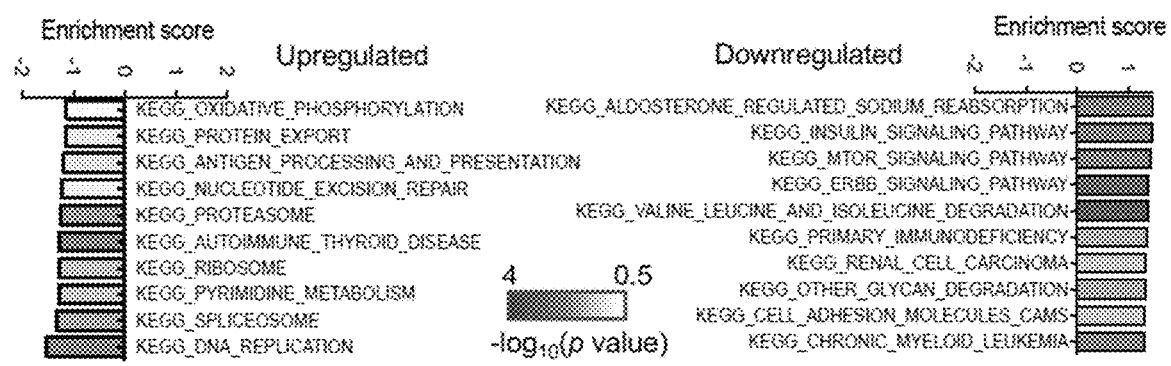
Figure 31G:
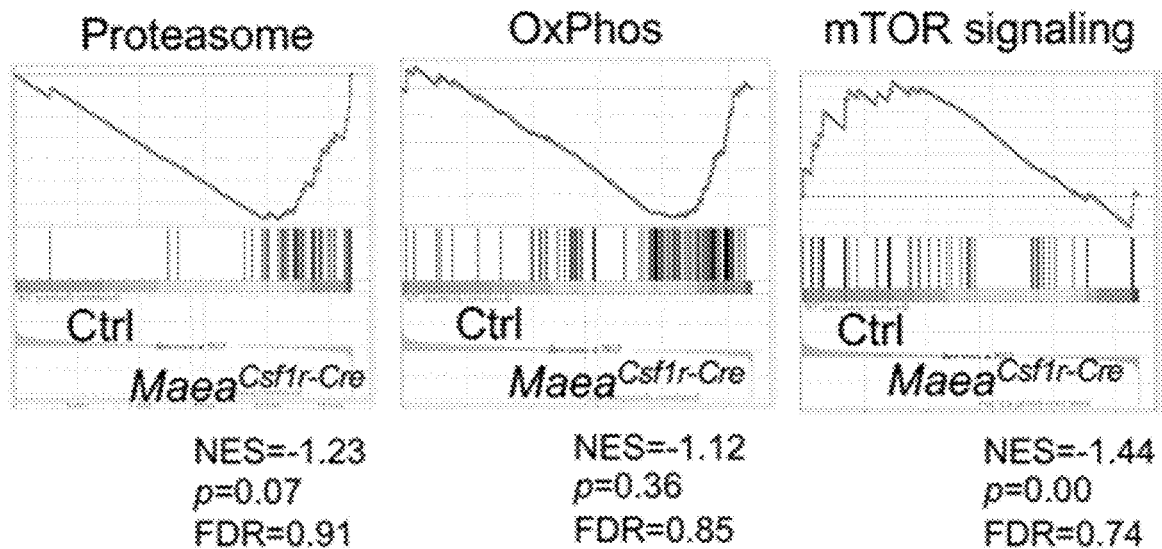
Figure 31H:
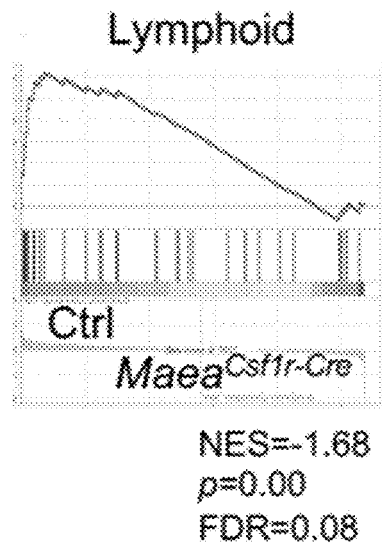
Figure 31I:
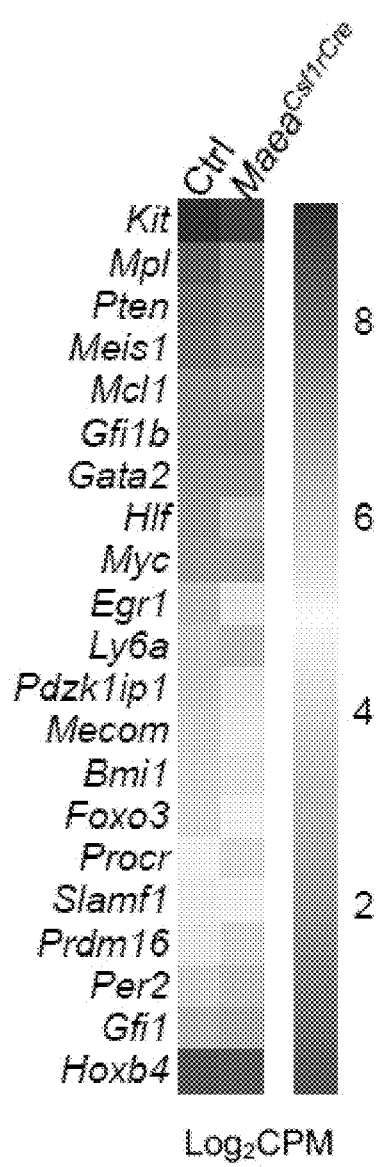
Figure 36A:
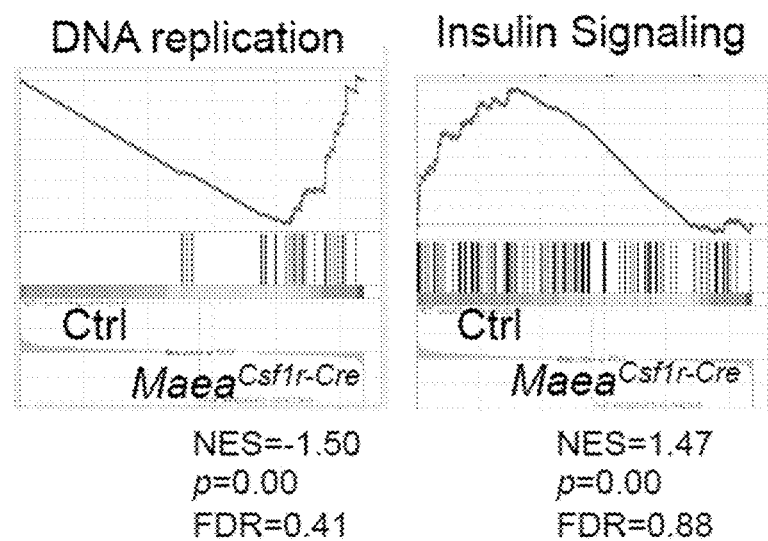
FIGS. 36A-36G.
Figure 36B:
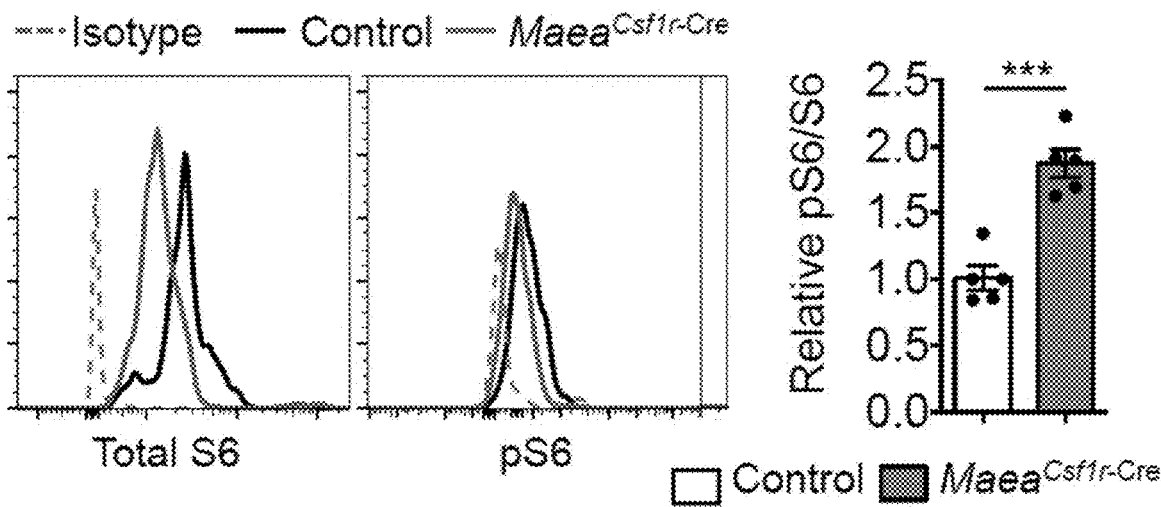
Figure 36C:
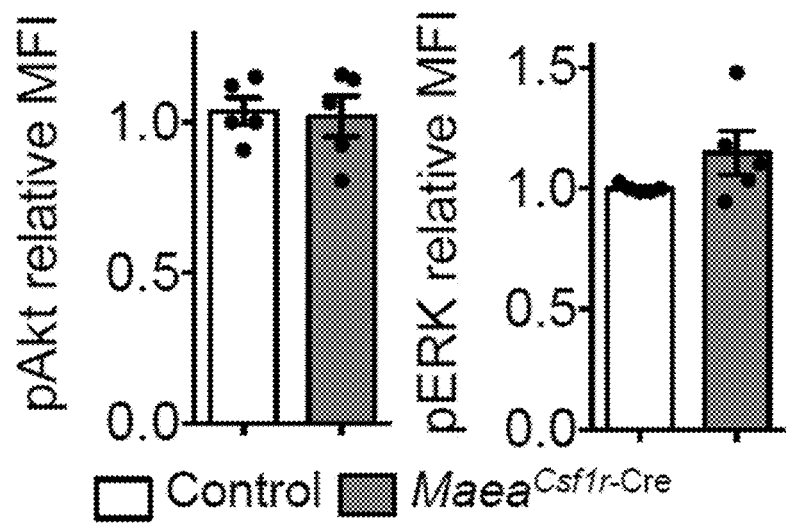

Next, the transcriptome of sorted MAEA$^{Csf1r\text{-}Cre}$ and littermate control HSCs was analyzed to gain mechanistic insight on how MAEA regulated HSC function. Gene Set Enrichment Analysis (GSEA) revealed a striking up-regulation of gene sets involved in cell activation or proliferation in MAEA$^{Csf1r\text{-}Cre}$ HSCs, such as DNA replication, protein synthesis/processing and oxidative phosphorylation, but downregulation of several major cell growth-related pathways, including insulin and mTOR signaling FIGS. 31F, 31G, 36A). Consistent with the defective lymphoid and engraftment potential, the expression of regulators of HSC lymphoid potential and maintenance was reduced (FIGS. 31H, 31I). The transcriptional downregulation of cell growth-related pathways was counterintuitive in activated HSCs. Since the activity of these pathways could be critically regulated at post-translational levels, downstream signaling molecules were assessed by intracellular phosphoflow cytometry. These results revealed a significant downregulation of total ribosomal protein S6, a downstream target of mTOR, in MAEA$^{Csf1r\text{-}Cre}$ HSCs compared to control, and a milder reduction of the phosphorylated S6 (pS6 Ser235/236). This resulted in a significant increase in the pS6/S6 ratio (FIG. 38B), suggesting hyperactivity of mTORC1 signaling. There were no significant changes in pAkt Ser473 or pErk1/2 Thr202/Tyr204 basal levels (FIG. 36C).

Figure 31J:
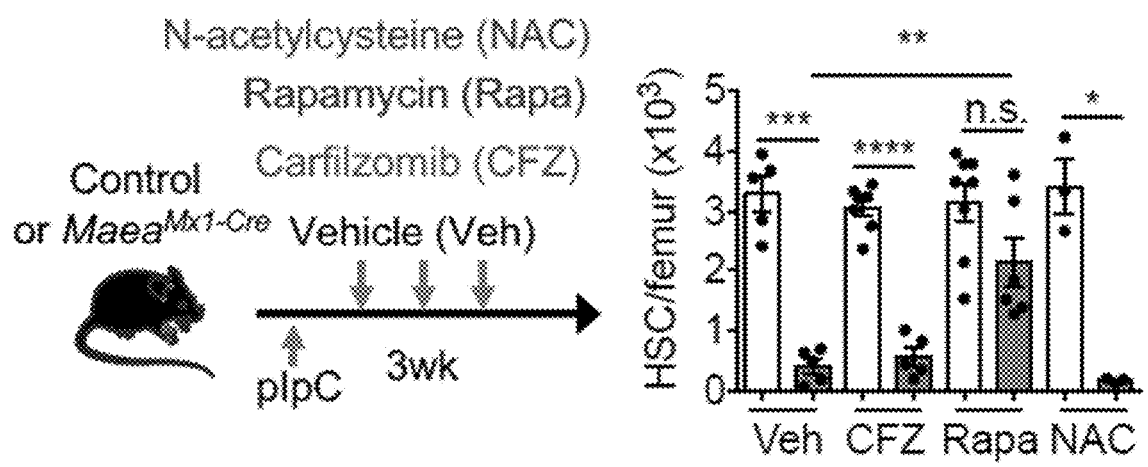
Figure 31K:
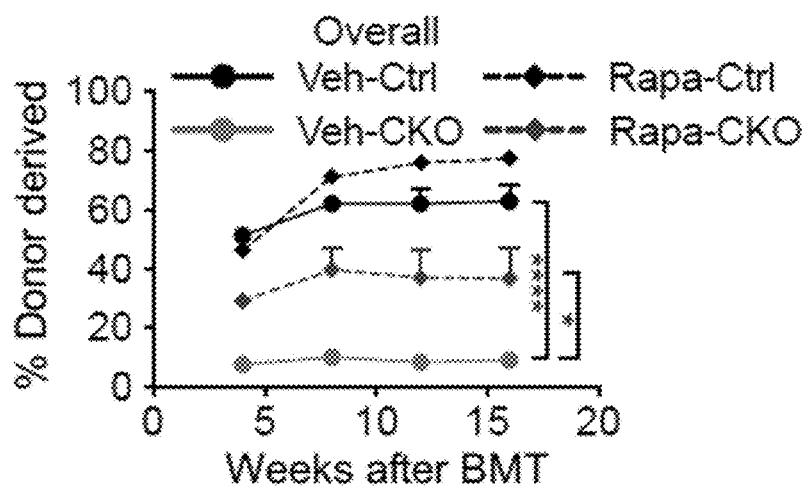
Figure 36D:
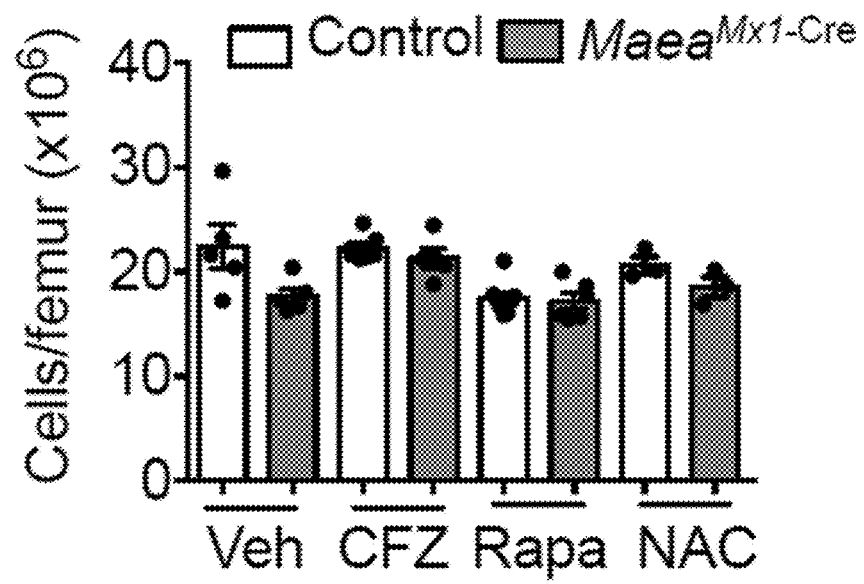
Figure 36E:
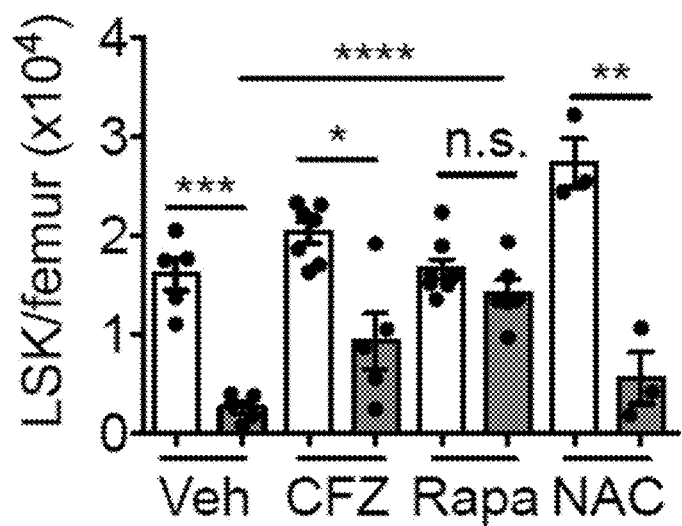
Figure 36F:
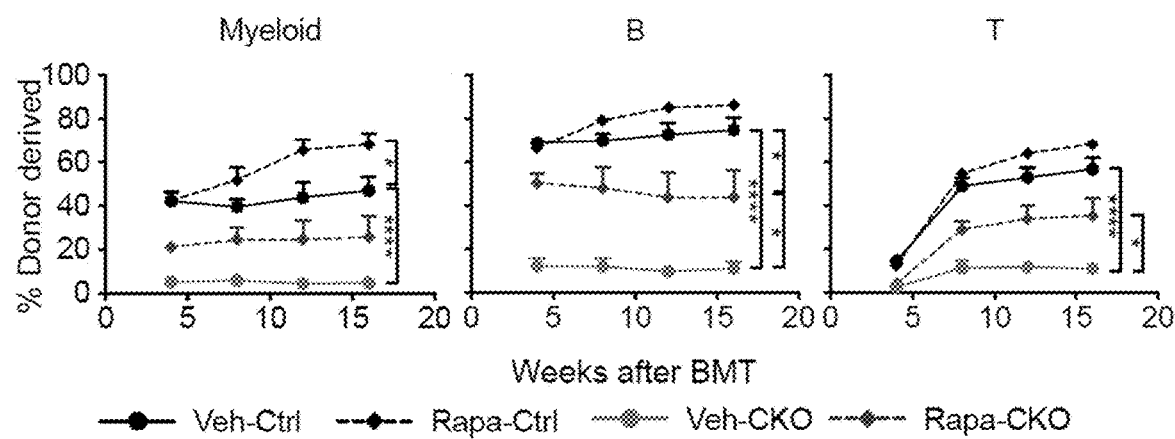
Figure 36G:
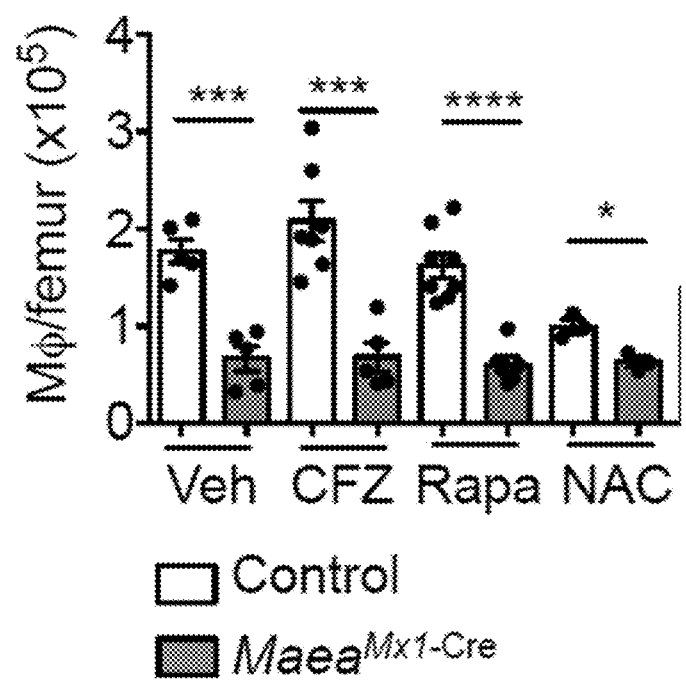

Based on these analyses, the functional significance of these enriched pathways were analyzed by treating poly I:C-induced MAEA$^{Mx1-Cre}$ mice with either a proteasome inhibitor (Carfilzomib, CFZ), an inhibitor of oxidative stress (N-acetylcysteine, NAC), or a mTOR antagonist (rapamycin). Remarkably, while none of the inhibitors significantly altered BM cellularity, rapamycin, but not CFZ or NAC, rescued the HSC numbers after MAEA-deletion (FIGS. 31J, 36D, 36E). Competitive transplantation experiments from treated and control mice also confirmed the rescue of functional HSC activity in rapamycin-treated MAEA$^{Mx1-Cre}$ mice (FIGS. 31K, 36F). Rapamycin, however, did not rescue macrophage numbers in BM due to MAEA deletion (FIG. 36G).[100] These results suggest that MAEA regulates mTOR activity in HSCs.

Figure 37A:
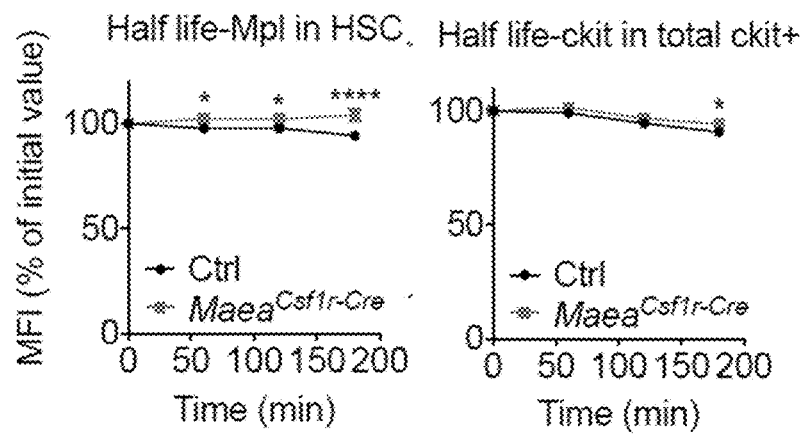
FIGS. 37A, 37B.
Figure 37B:
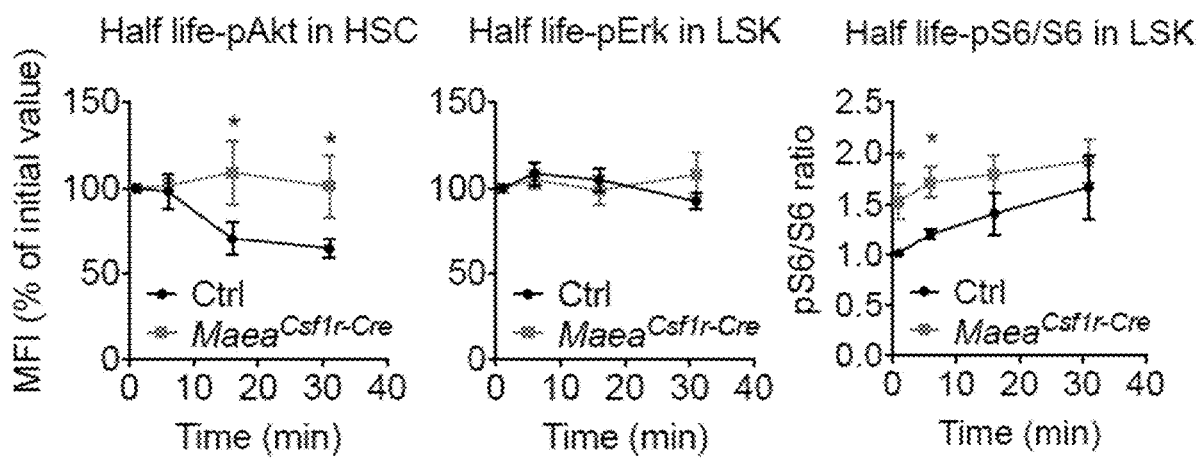

Next, experiments were performed to identify how MAEA could interfere with mTOR/intracellular signaling. Although previous studies have suggested that MAEA might be expressed in the nucleus and/or associated with the actin filaments,[97,103,104] immunofluorescence analysis of permeabilized HSCs detected MAEA expression only at the cell surface in localized foci (FIG. 31A), raising the possibility that it might be involved at surface signaling centers. Recent phylogenetic and biochemical analyses have suggested that MAEA might be a RING domain-containing subunit of a highly conserved E3 ubiquitin ligase complex.[98,99] To further investigate this possibility, the ubiquitination landscape in MAEA-deficient and sufficient HSPCs was investigated using an ubiquitin antibody array. Results provided herein demonstrate that ubiquitinated targets comprising several cell surface receptors were significantly reduced in MAEA$^{Csf1r-Cre}$ lineage-negative BM cells compared to control while three targets (Caspase-8, F-box protein 15, and p21Cdkn1a) were significantly increased (FIG. 31B). Ubiquitin modifications of protein substrates may lead to proteasome or lysosome-dependent substrate degradation or may modulate substrate interactome and subcellular localization.[105] To further investigate the functional impact of this change in receptor ubiquitination, experiments were performed to focus on the half-life and downstream signaling of Mpl, cKit, and Flt3, major receptors regulating hematopoiesis. To this end, BM cells were treated ex vivo with the translation inhibitor cycloheximide and evaluated the turnover of surface receptors in MAEA$^{Csf1r-Cre}$ and control HSPCs. According to results provided herein, the half-lives of Flt3 and Mpl, but not cKit, were significantly prolonged in MAEA$^{Csf1r-Cre}$ HSPCs (FIGS. 31C, 37A). Interestingly, a prolonged persistence of pAkt but not pErk was detected in HSCPs after cytokine stimulation, despite comparable constitutive levels (FIG. 37B). These results indicate that MAEA negatively modulates receptor tyrosine kinase signaling in HSPCs by restricting receptor half-lives.

Figure 32A:
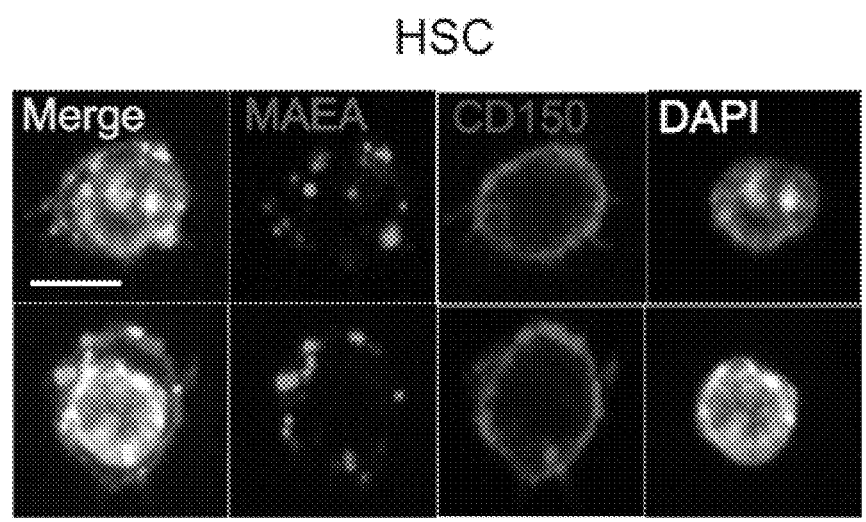
FIGS. 32A-32I.
Figure 32B:
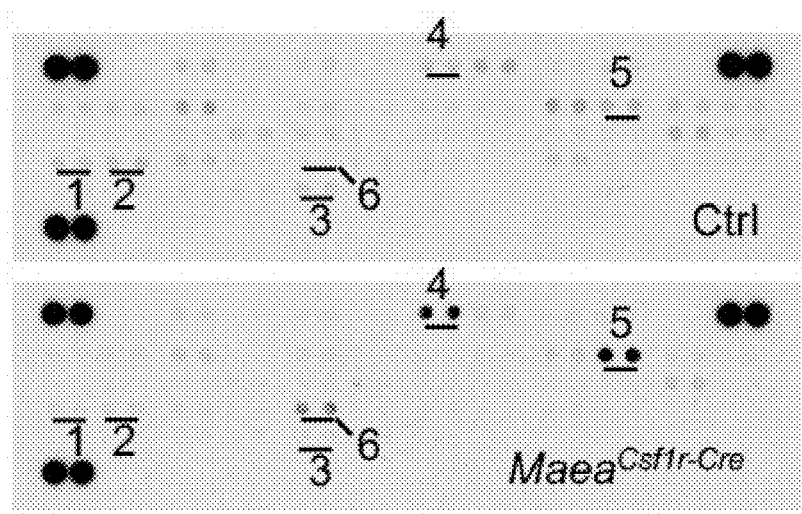
Figure 32C:
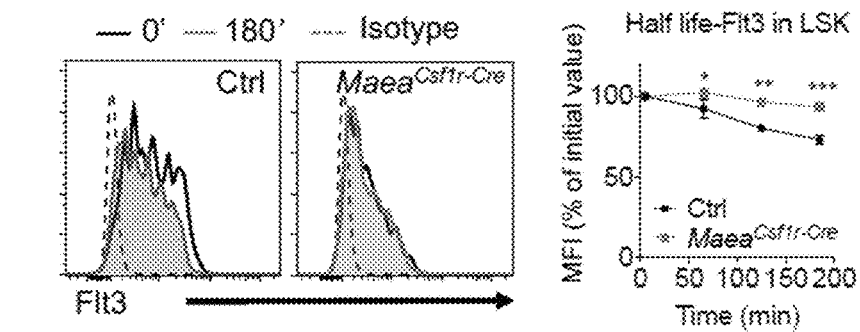
Figure 32C:
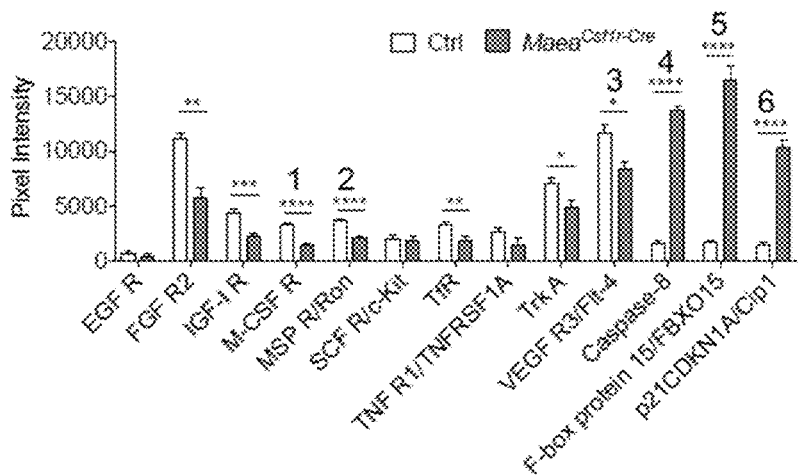
Figure 32D:
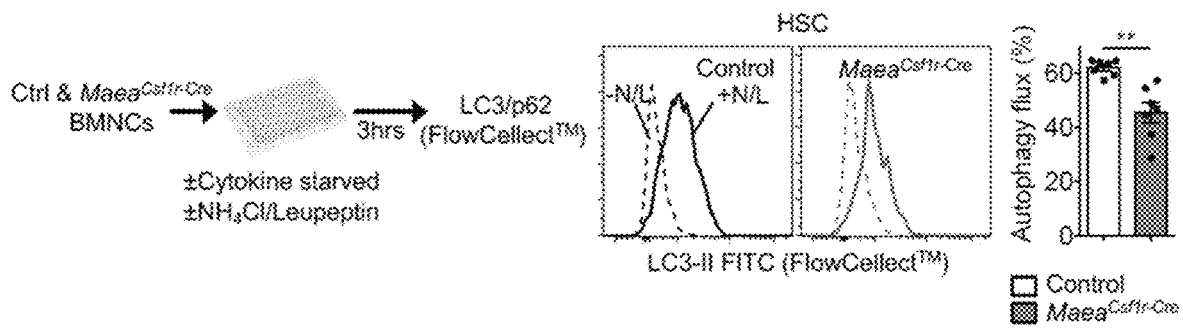
Figure 32E:
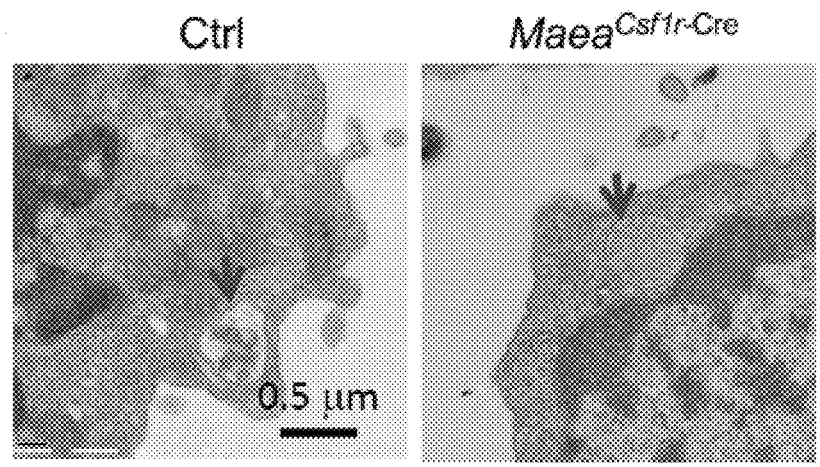
Figure 32F:
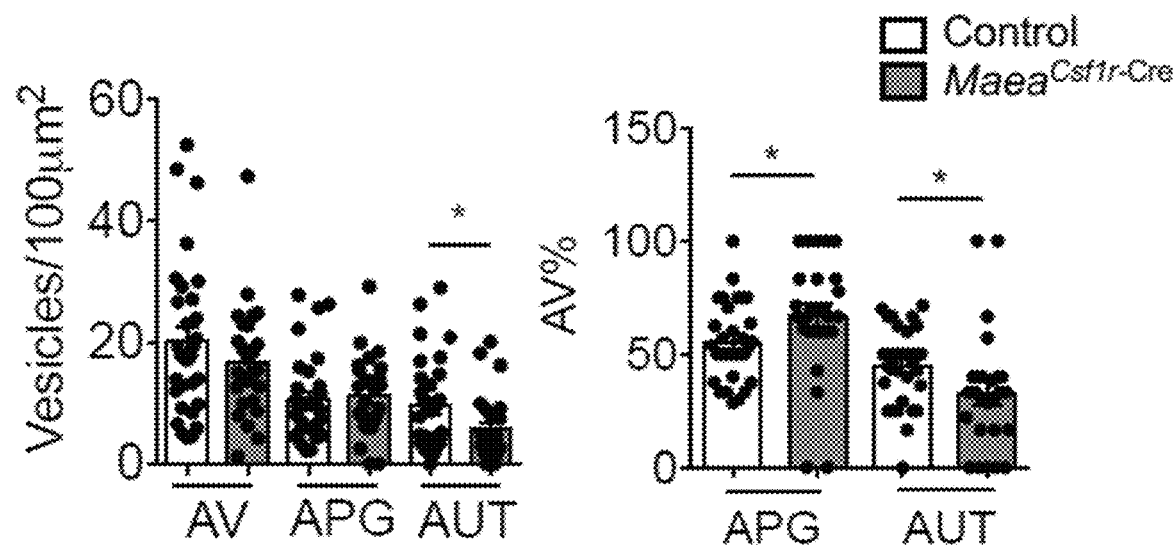
Figure 32G:
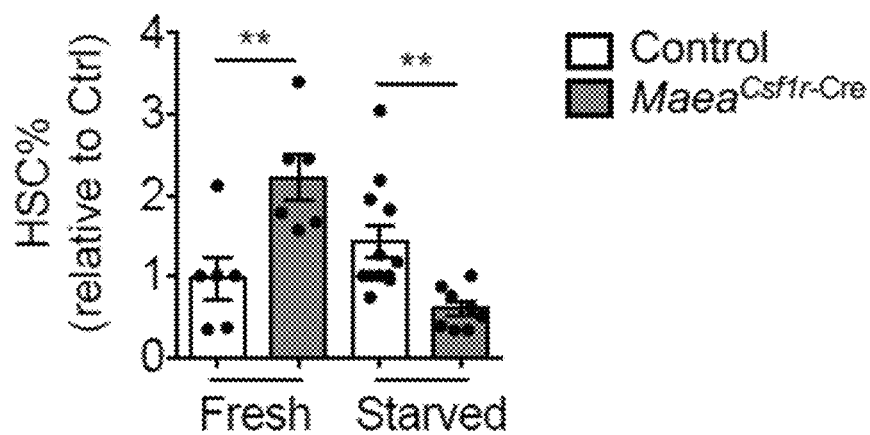
Figure 32H:
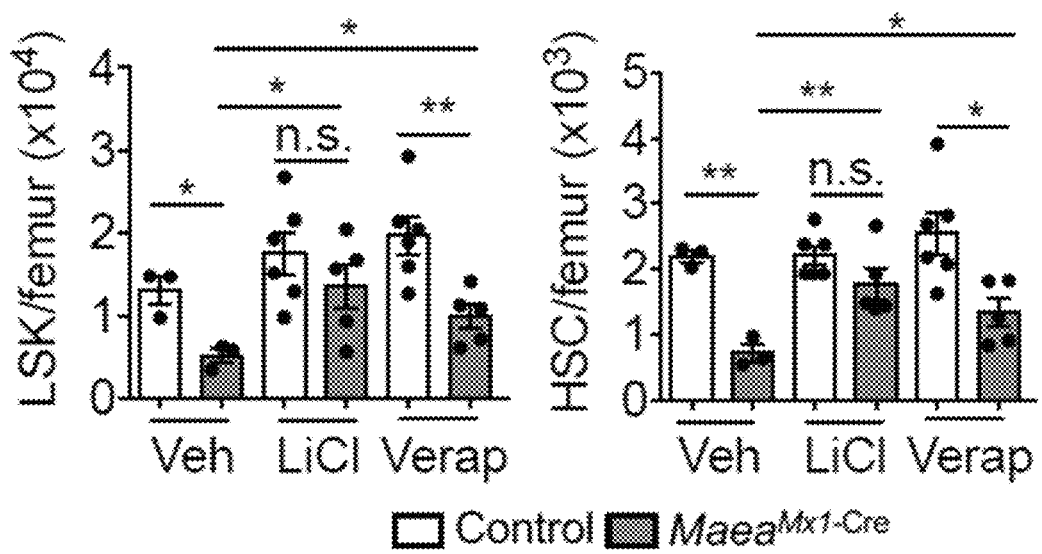
Figure 32I:
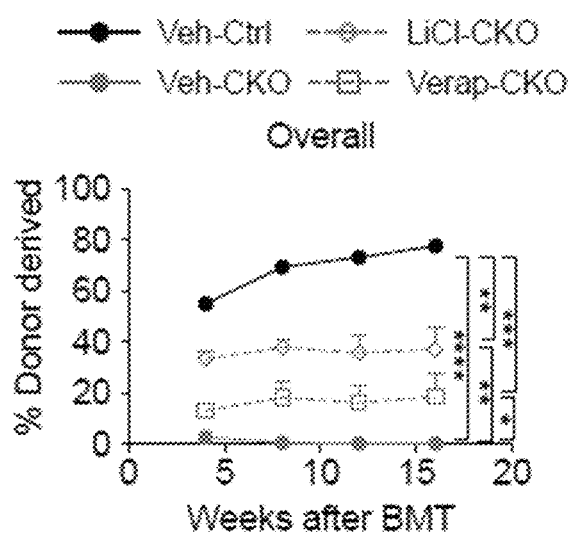
Figure 38A:
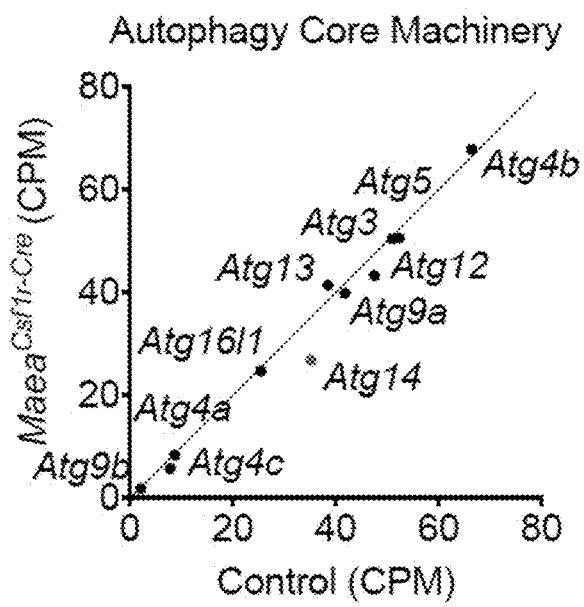
FIGS. 38A-38F.
Figure 38B:
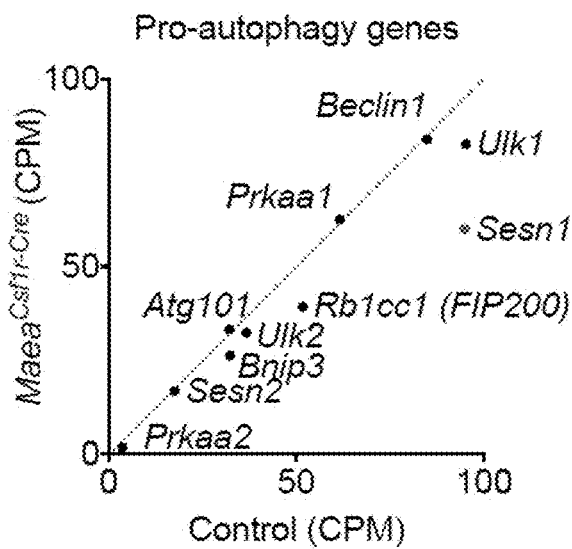
Figure 38C:
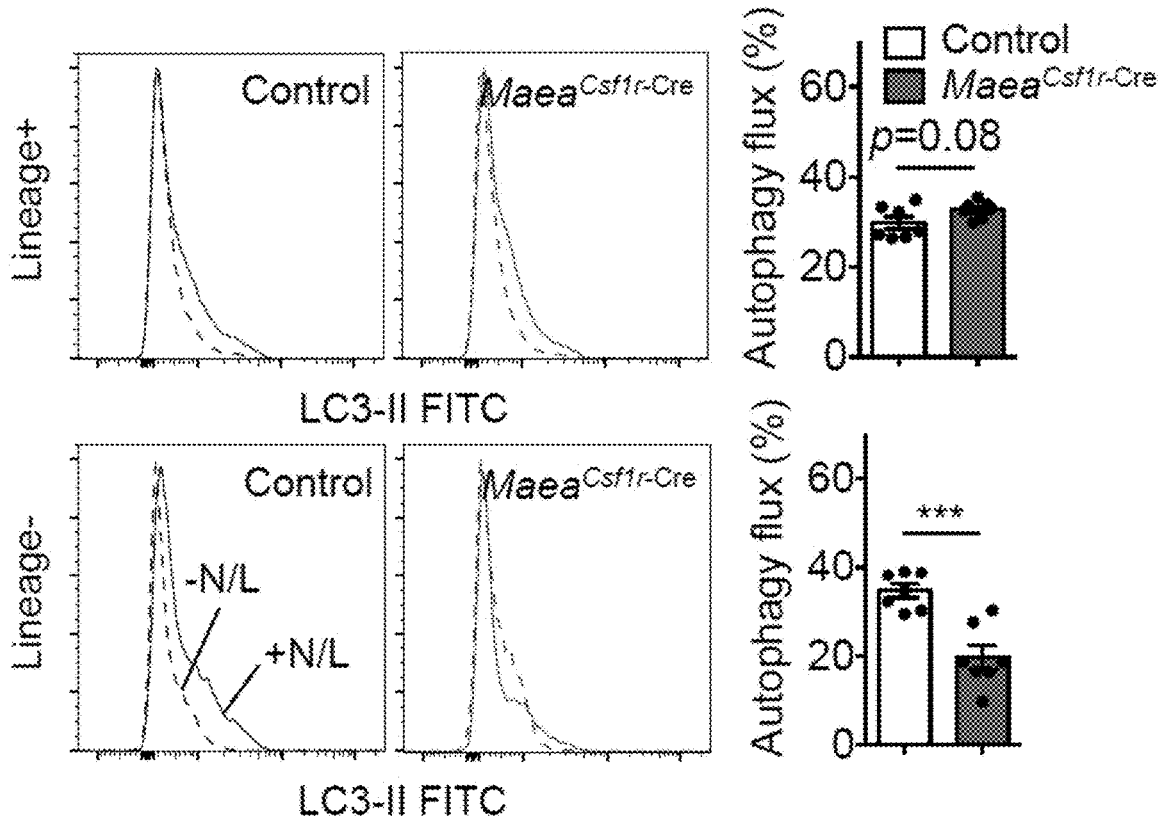
Figure 38D:
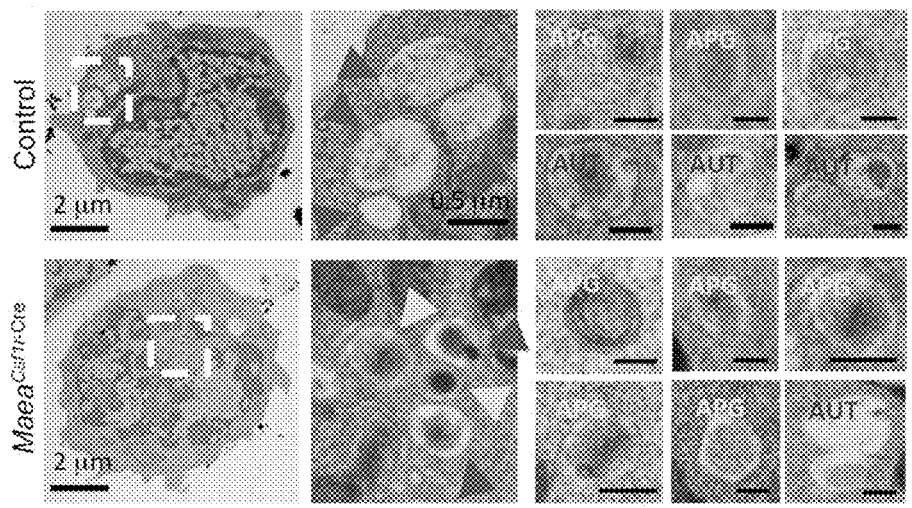
Figure 38E:
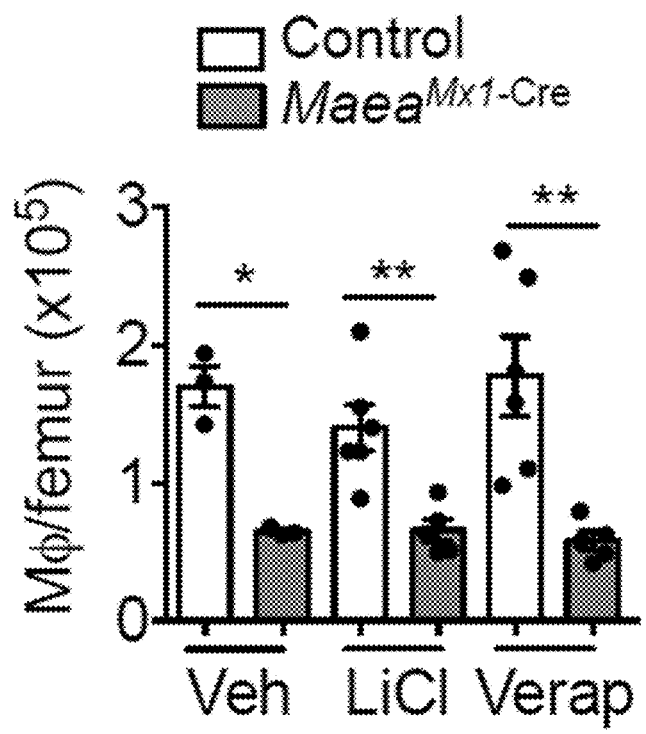
Figure 38F:
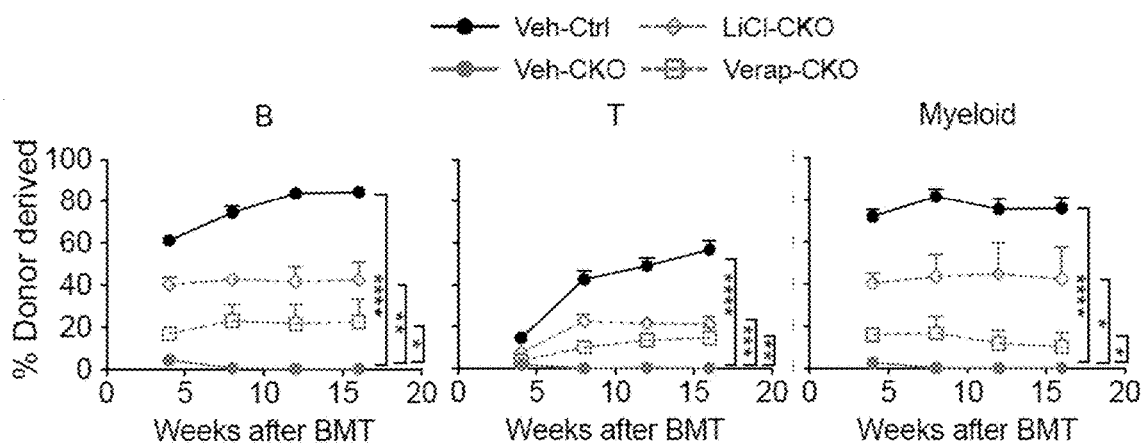

As mTOR inhibitors rescued MAEA-deficient HSCs, experiments were designed to determine if the altered protein ubiquitination may lead to dysregulation of the downstream lysosome-dependent degradation pathways (e.g., autophagy). Autophagy (macroautophagy), a highly conserved mechanism to recycle macromolecules and organelles via lysosomal degradation, was suggested to be critical for HSC quiescence and maintenance.[106-109] Indeed, mTOR signaling and activated Akt are reported to inhibit autophagy, and rapamycin is a potent inducer of autophagy.[110,111] Applicants observed no significant change in the expression of the core autophagy machinery or pro-autophagy genes in MAEA-deficient and sufficient HSCs (FIGS. 38A, 38B). However, experiments discussed herein directly measured autophagy function since its regulation mostly occurs at the posttranslational level. These experiments show that the autophagy flux in MAEA$^{Csf1r-Cre}$ HSCs was significantly reduced (FIG. 32D). When cultured under starvation conditions or in the presence of rapamycin, wild-type HSCs exhibited high levels of autophagy flux of endogenous LC3-II (distinguishable from LC3-I through a permeabilization step) compared to more differentiated cells (FIG. 38B). Interestingly, lineage-negative cells (enriched in HSPCs), but not lineage-positive cells (enriched in mature hematopoietic cells), from MAEA$^{Csf1r-Cre}$ BM presented significant reductions in LC3-II flux (FIG. 38C). In addition, morphometric analyses using electron microscopy imaging revealed that the reduced flux was, for the most part, due to a maturation defect in the autophagic compartment of MAEA$^{Csf1r-Cre}$ HSCs,[112,113] as Applicants have found a significant reduction in the percentage of autolysosomes (AUT) relative to autophagosomes (APG; FIGS. 31E, 38D) in these cells. Interestingly, albeit more discrete, MAEA$^{Csf1r-Cre}$ HSCs also had a defect in autophagy induction (APG biogenesis) that can explain why APG did not accumulate in these cells despite the observed maturation defect (FIG. 32F). Reduced autophagy flux may explain the lower survival rate of MAEA-deficient HSCs upon starvation (FIG. 32G).[114] To ascertain whether the reduced autophagy flux was responsible for the impaired HSC activity in vivo, mTOR-independent autophagy inducers (lithium[115] or verapamil[116]) were administered to poly I:C-induced MAEA$^{Mx1-Cre}$ and control mice. Results provided herein demonstrate that both autophagy inducers could rescue HSC numbers and their repopulation activity (FIGS. 32H, 32I, 38E, 38F). These results thus identify MAEA as a critical regulator of HSC maintenance by enhancing ubiquitination of cytokine receptors and promoting autophagy.

Figure 26C:
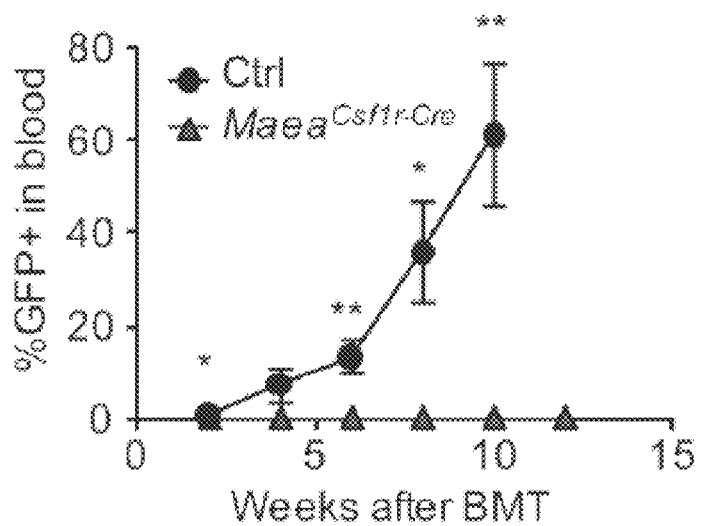
Figure 26D:
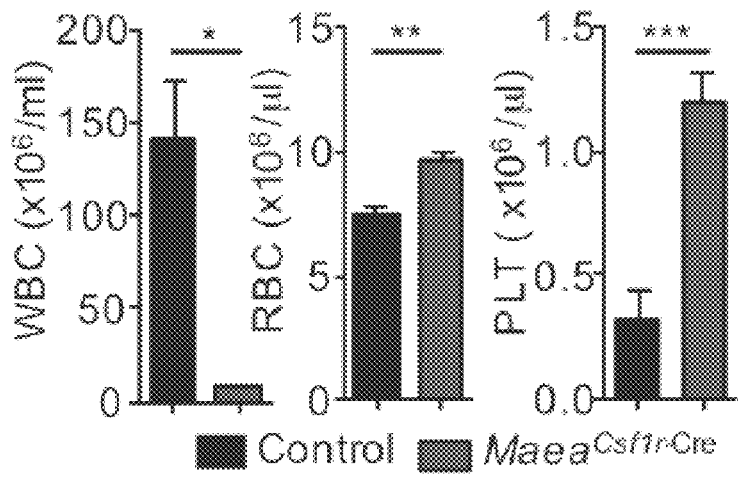
Figure 26E:
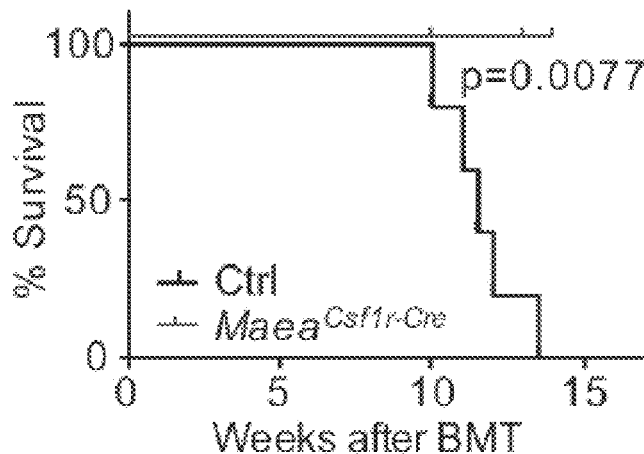
Figure 26F:
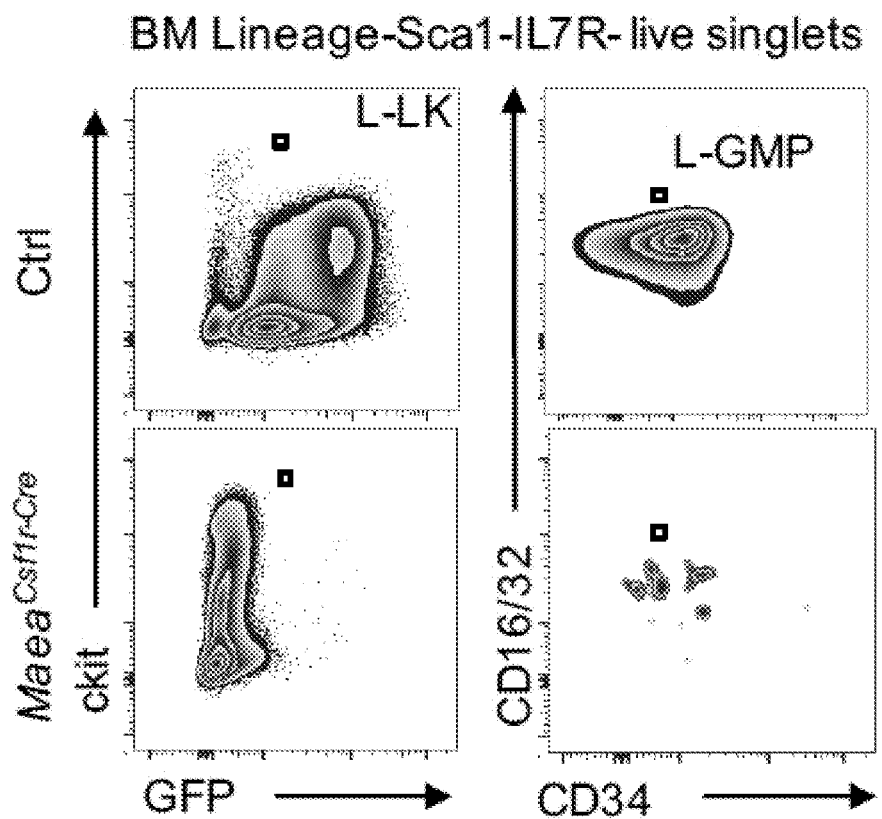
Figure 26G:
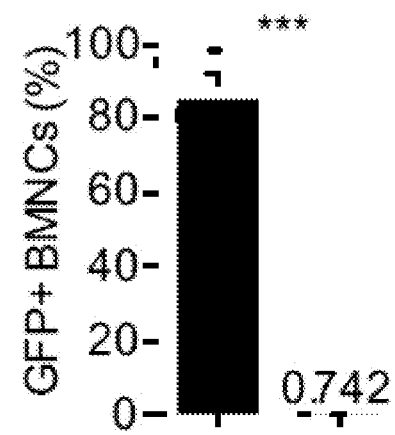
Figure 26H:
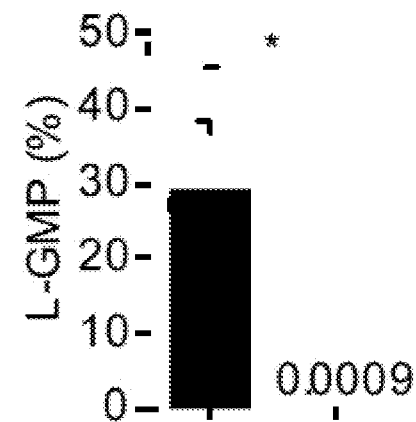
Figure 26I:
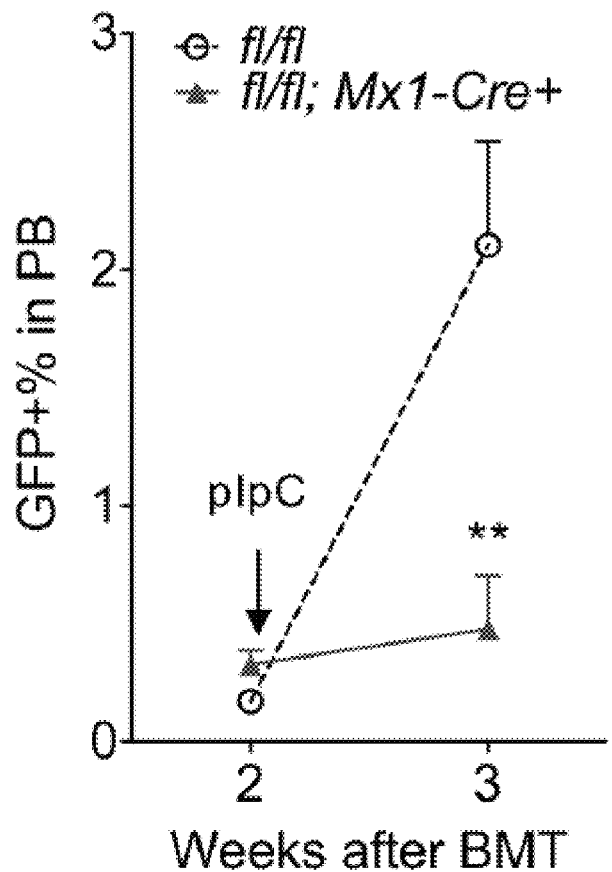
Figure 26J:
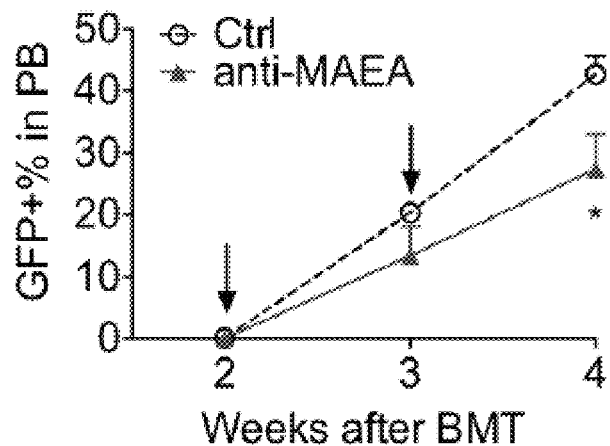
Figure 26K:
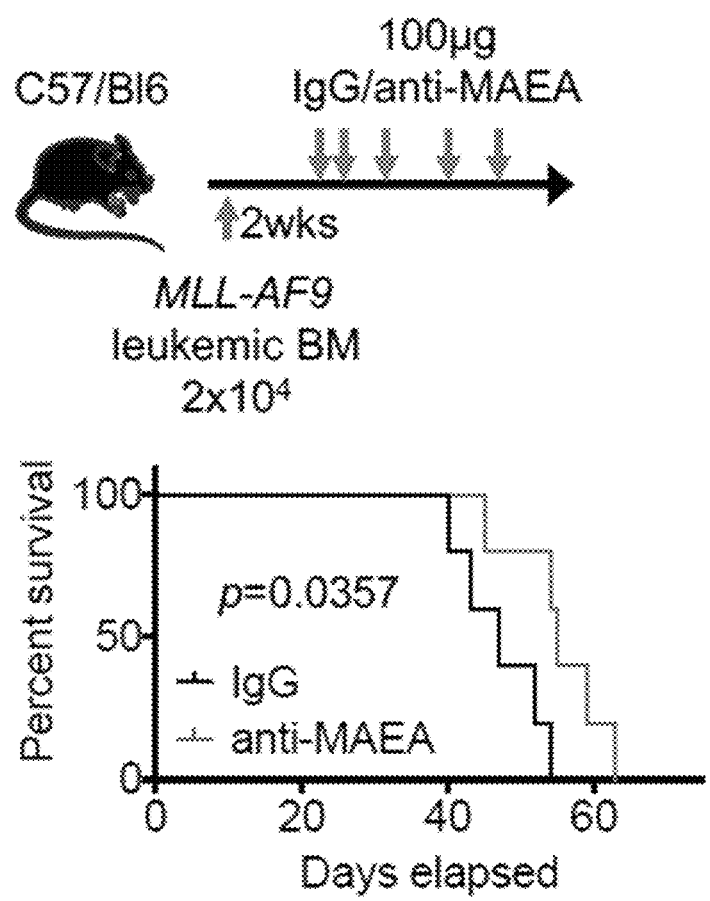
Figure 27A:
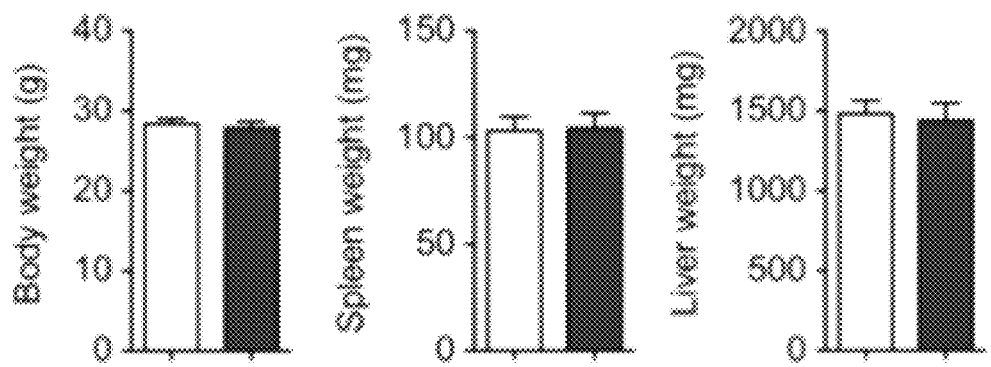
FIGS. 27A-27E.
Figure 27B:
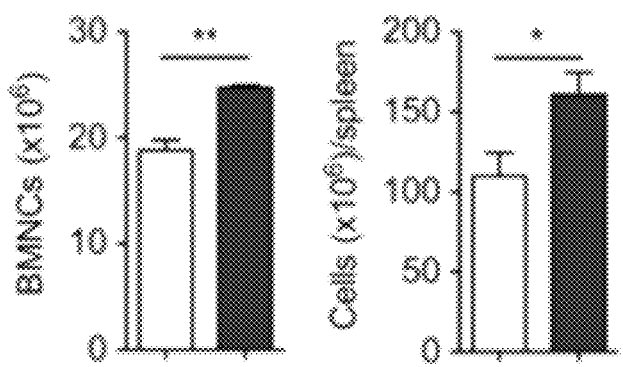
Figure 27C:
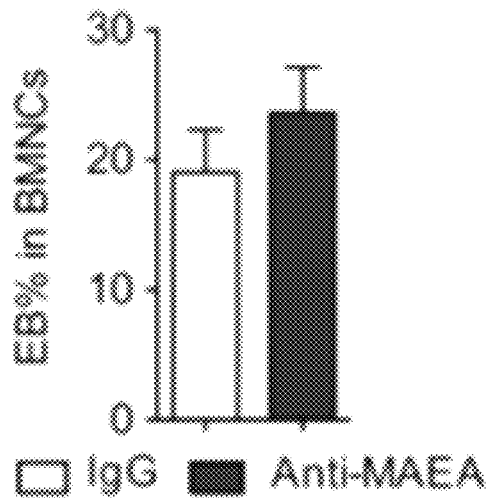
Figures 27D, 27E:
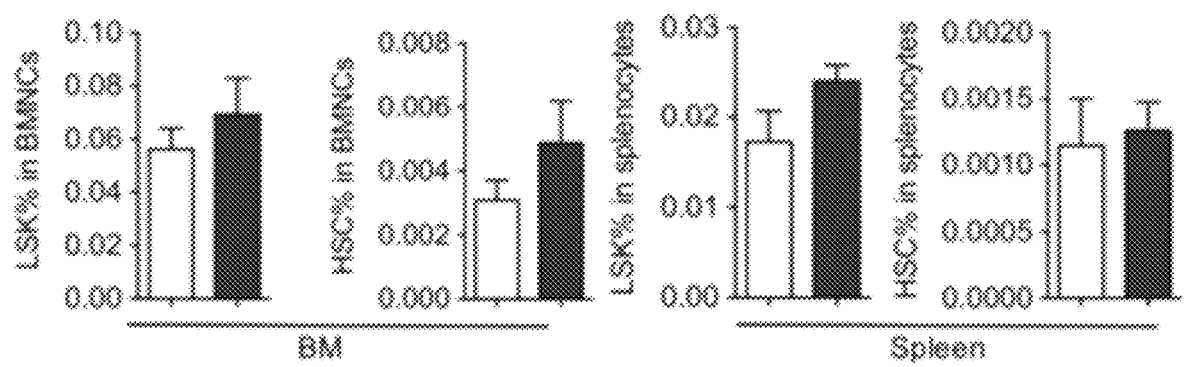
Figure 28A:
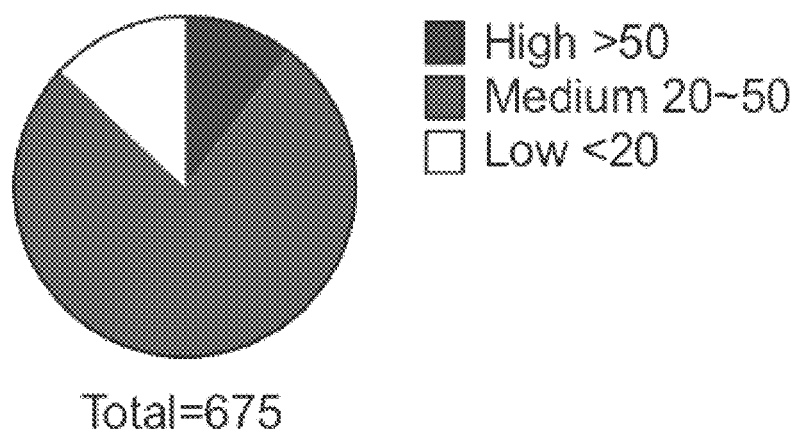
FIGS. 28A-28D.
Figure 28B:
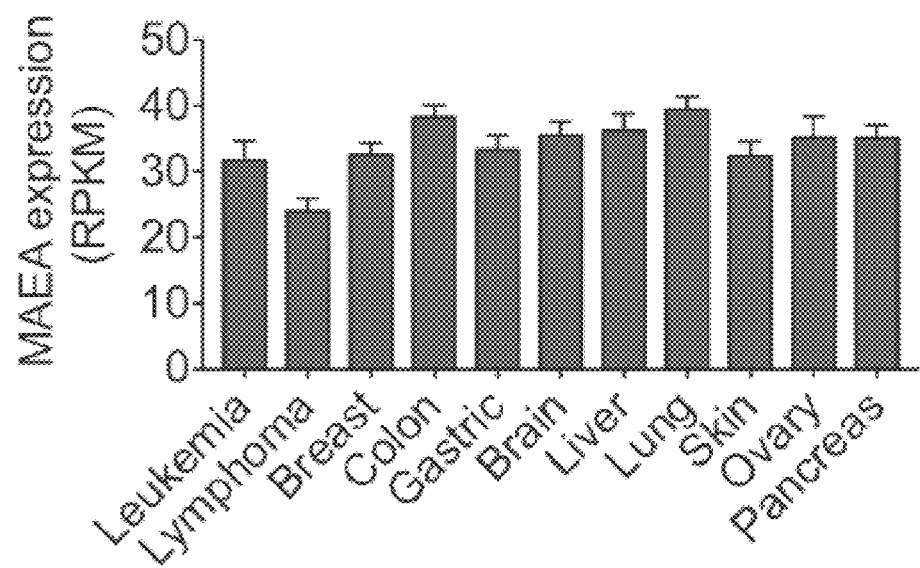
Figure 28C:
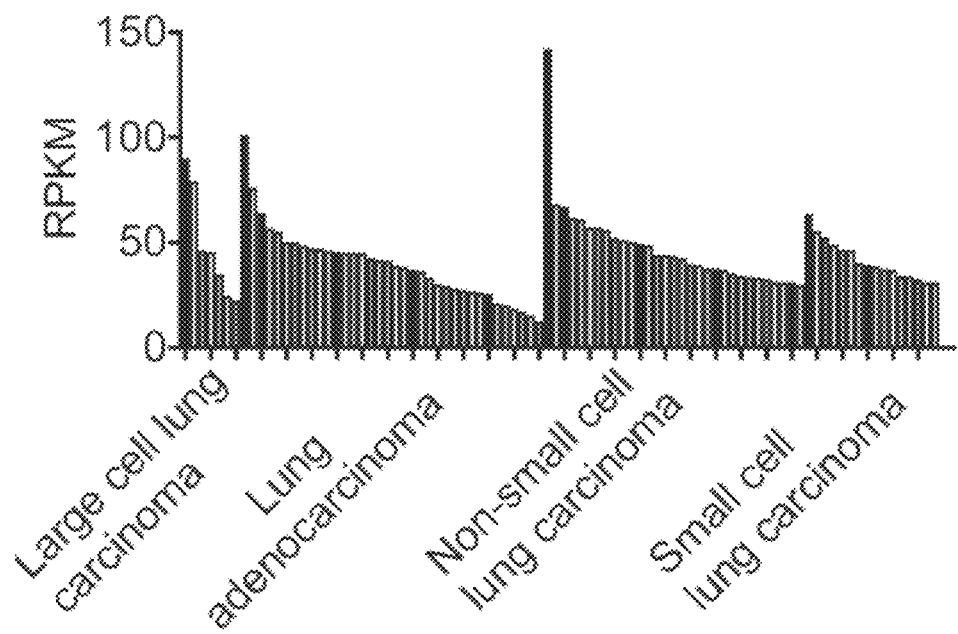
Figure 28D:
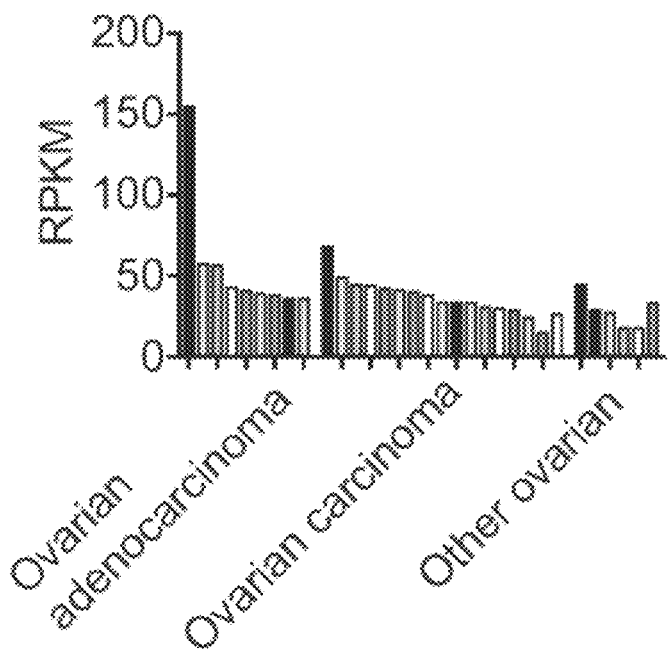

Next, the human cancer genome atlas (TCGA) database was analyzed to assess MAEA's function in cancer. These analyses revealed a significant association of MAEA amplification mutations in many human cancer types (FIG. 25A), and MAEA up-regulation was strongly correlated with poor prognosis in patients with acute myeloid leukemia (AML) and adenocarcinomas of the ovary and lung (FIGS. 25B-25D). MAEA expression was also up-regulated in the murine model of MLL-AF9 AML (FIGS. 26A, 26B). While wild-type hematopoietic cells overexpressing MLL-AF9 rapidly developed AML, MAEA-deficient cells failed to transform and progress into full-blown leukemia, indicating that MAEA expression was required for AML engraftment and progression in vivo (FIGS. 26C-26E). Importantly, treatment of AML-bearing mice with a monoclonal anti-MAEA antibody significantly prolonged their survival (FIG. 26K).

Autophagy has been increasingly recognized to be critical for HSC quiescence and maintenance by controlling mitochondria homeostasis, metabolic and oxidative stress.[109,117] However, there is little available information on the molecular mechanisms that ensure high levels of autophagy activity in HSCs relative to their downstream progeny.[106] Ubiquitination of cellular proteins fine-tunes their expression levels, cellular localization and interaction dynamics, thereby influencing many cellular processes.[118] Components of the ubiquitin proteasome system, mostly E3 ligases, have been suggested to regulate HSC fate by targeting critical signal transducers and transcription regulators.[119] Ubiquitination also plays important roles in autophagy regulation in other cell systems by influencing the stability and interaction of the autophagy core machinery and selective cargo recognition,[120,121] among others. MAEA thus acts as an E3 ubiquitin ligase that guards HSC quiescence by restricting cytokine receptor stability and signaling while ensuring high autophagy flux in HSCs.

Example 7: Anti-MAEA Antibody Therapy Benefits Jak2$^{V617F}$-Induced Polycythemia Vera (PV)

Figure 42A:
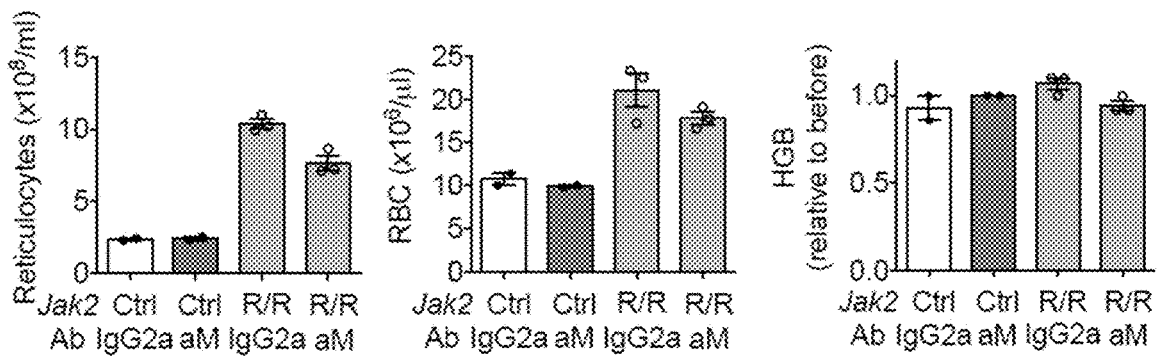
FIGS. 42A-42C.
Figure 42B:
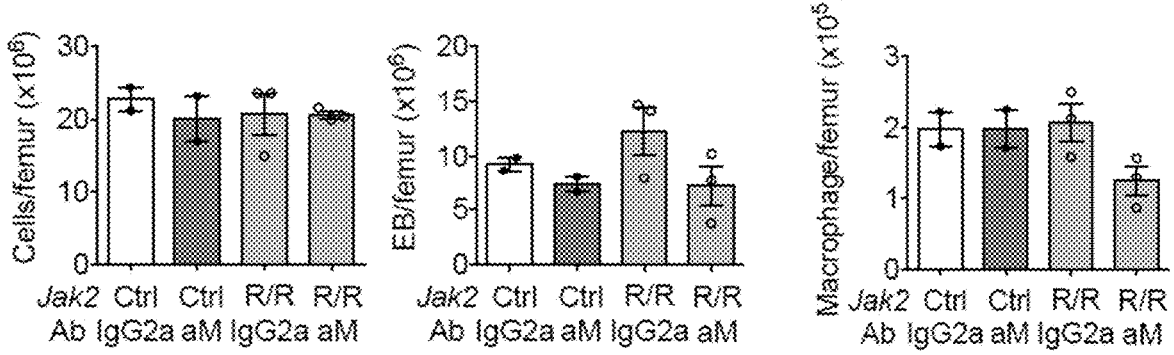
Figure 42C:
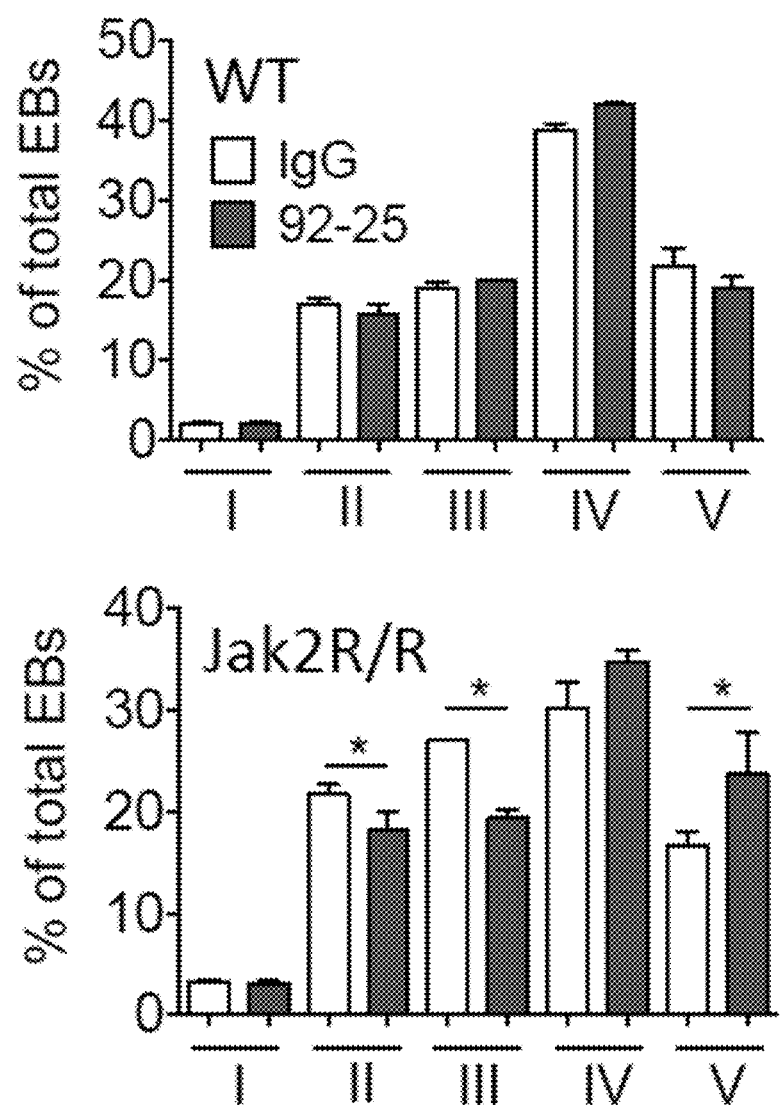

In this Example, anti-MAEA monoclonal antibody (92.25) or IgG isotype control were injected at 100 μg daily i.p. into control (Ctrl) and Jak2$^{V617F/V617F}$ (R/R) mice for one week before analysis. Critical blood count (CBC) was then analyzed and demonstrates that 92.25 injections lowered the reticulocytes, red blood cell counts (RBC), and hemoglobin levels (HGB) in the peripheral blood of Jak2$^{R/R}$ mice without affecting the control mice (FIG. 42A). In the bone marrow (BM), erythroblast (EB) numbers were reduced by 92.25 injections in both control and Jak2$^{R/R}$ mice relative to IgG control groups, while macrophage numbers were only reduced in the Jak2$^{R/R}$ mice (FIG. 42B). Moreover, 92.25 injection enhanced the maturation of EBs in the BM of Jak2$^{R/R}$ mice without altering the EB maturation profile in wild type (WT) control mice (FIG. 42C).

This is consistent with data presented in Example 5, demonstrating that MAEA is only required in BM macrophages for EB island function, but not in the spleen. As discussed in greater detail above in Example 5, VCAM1 is not required in the BM, however, it may be playing a role in the spleen. Accordingly, a combination therapy may be beneficial to subjects suffering from Jak2$^{V617F}$-induced PV.

Throughout this application various publications are referred to in superscripts. Full citations for these references may be found at the end of the specification before the claims. The disclosures of these publications are hereby incorporated by reference in their entireties into the subject application to more fully describe the art to which the subject application pertains.

From the foregoing, it will be appreciated that specific embodiments of the invention have been described herein for purposes of illustration, but that various modifications may be made without deviating from the scope of the invention. Accordingly, the invention is not limited except as by the appended claims.

REFERENCES

1 Bessis, M. [Erythroblastic island, functional unity of bone marrow]. *Rev Hematol* 13, 8-11 (1958).
2 Hom, J., Dulmovits, B. M., Mohandas, N. & Blanc, L. The erythroblastic island as an emerging paradigm in the anemia of inflammation. *Immunol Res* 63, 75-89, doi:10.1007/s12026-015-8697-2 (2015).
3 Jacobsen, R. N., Perkins, A. C. & Levesque, J. P. Macrophages and regulation of erythropoiesis. *Curr Opin Hematol* 22, 212-219, doi:10.1097/MOH.0000000000000131 (2015).
4 de Back, D. Z., Kostova, E. B., van Kraaij, M., van den Berg, T. K. & van Bruggen, R. Of macrophages and red blood cells; a complex love story. *Front Physiol* 5, 9, doi:10.3389/fphys.2014.00009 (2014).
5 Klei, T. R., Meinderts, S. M., van den Berg, T. K. & van Bruggen, R. From the Cradle to the Grave: The Role of Macrophages in Erythropoiesis and Erythrophagocytosis. *Front Immunol* 8, 73, doi:10.3389/fimmu.2017.00073 (2017).
6 Rhodes, M. M., Kopsombut, P., Bondurant, M. C., Price, J. O. & Koury, M. J. Adherence to macrophages in erythroblastic islands enhances erythroblast proliferation and increases erythrocyte production by a different mechanism than erythropoietin. *Blood* 111, 1700-1708, doi:10.1182/blood-2007-06-098178 (2008).
7 Hanspal, M. & Hanspal, J. S. The association of erythroblasts with macrophages promotes erythroid proliferation and maturation: a 30-kD heparin-binding protein is involved in this contact. *Blood* 84, 3494-3504 (1994).
8 Sadahira, Y., Yoshino, T. & Monobe, Y. Very late activation antigen 4-vascular cell adhesion molecule 1 interaction is involved in the formation of erythroblastic islands. *J Exp Med* 181, 411-415 (1995).
9 Hamamura, K. et al. A critical role of VLA-4 in erythropoiesis in vivo. *Blood* 87, 2513-2517 (1996).
10 Lee, G. et al. Targeted gene deletion demonstrates that the cell adhesion molecule ICAM-4 is critical for erythroblastic island formation. *Blood* 108, 2064-2071, doi:10.1182/blood-2006-03-006759 (2006).
11 Fabriek, B. O. et al. The macrophage CD163 surface glycoprotein is an erythroblast adhesion receptor. *Blood* 109, 5223-5229, doi:10.1182/blood-2006-08-036467 (2007).
12 Liu, X. S. et al. Disruption of palladin leads to defects in definitive erythropoiesis by interfering with erythroblastic island formation in mouse fetal liver. *Blood* 110, 870-876, doi:10.1182/blood-2007-01-068528 (2007).
13 Hanspal, M., Smockova, Y. & Uong, Q. Molecular identification and functional characterization of a novel protein that mediates the attachment of erythroblasts to macrophages. *Blood* 92, 2940-2950 (1998).
14 Soni, S. et al. Absence of erythroblast macrophage protein (Emp) leads to failure of erythroblast nuclear extrusion. *J Biol Chem* 281, 20181-20189, doi:10.1074/jbc.M603226200 (2006).
15 Koni, P. A. et al. Conditional vascular cell adhesion molecule 1 deletion in mice: impaired lymphocyte migration to bone marrow. *J Exp Med* 193, 741-754 (2001).
16 Qian, B. Z. et al. CCL2 recruits inflammatory monocytes to facilitate breast-tumour metastasis. *Nature* 475, 222-225, doi:10.1038/nature10138 (2011).
17 Karasawa, K. et al. Vascular-resident CD169-positive monocytes and macrophages control neutrophil accumulation in the kidney with ischemia-reperfusion injury. *J Am Soc Nephrol* 26, 896-906, doi:10.1681/ASN.2014020195 (2015).
18 Heinrich, A. C., Pelanda, R. & Klingmuller, U. A mouse model for visualization and conditional mutations in the erythroid lineage. *Blood* 104, 659-666, doi:10.1182/blood-2003-05-1442 (2004).
19 Sroubek, J. et al. The use of Bcl-2 over-expression to stabilize hybridomas specific to the HERG potassium channel. *J Immunol Methods* 375, 215-222, doi:10.1016/j.jim.2011.10.014 (2012).
20 Chow, A. et al. CD169(+) macrophages provide a niche promoting erythropoiesis under homeostasis and stress. *Nat Med* 19, 429-436, doi:10.1038/nm.3057 (2013).
21 Reeves, J. P., Reeves, P. A. & Chin, L. T. Survival surgery: removal of the spleen or thymus. *Curr Protoc Immunol* Chapter 1, Unit 1 10, doi:10.1002/0471142735.im0110s02 (2001).

22. Ji, P., Yeh, V., Ramirez, T., Murata-Hori, M. & Lodish, H. F. Histone deacetylase 2 is required for chromatin condensation and subsequent enucleation of cultured mouse fetal erythroblasts. *Haematologica* 95, 2013-2021, doi:10.3324/haematol.2010.029827 (2010).
23. Majeti, R. et al. CD47 is an adverse prognostic factor and therapeutic antibody target on human acute myeloid leukemia stem cells. *Cell* 138, 286-299, doi:10.1016/j.cell.2009.05.045 (2009).
24. Zhang, X., Goncalves, R. & Mosser, D. M. The isolation and characterization of murine macrophages. *Curr Protoc Immunol* Chapter 14, Unit 14 11, doi:10.1002/0471142735.im1401s83 (2008).
25. Davies, J. Q. & Gordon, S. Isolation and culture of murine macrophages. *Methods Mol Biol* 290, 91-103 (2005).
26. Chow, A. et al. Bone marrow CD169+ macrophages promote the retention of hematopoietic stem and progenitor cells in the mesenchymal stem cell niche. *J Exp Med* 208, 261-271, doi:10.1084/jem.20101688 (2011).
27. Chen, K. et al. Resolving the distinct stages in erythroid differentiation based on dynamic changes in membrane protein expression during erythropoiesis. *Proc Natl Acad Sci USA* 106, 17413-17418, doi:10.1073/pnas.0909296106 (2009).
28. Ulyanova, T., Phelps, S. R. & Papayannopoulou, T. The macrophage contribution to stress erythropoiesis: when less is enough. *Blood* 128, 1756-1765, doi:10.1182/blood-2016-05-714527 (2016).
29. Ulyanova, T., Jiang, Y., Padilla, S., Nakamoto, B. & Papayannopoulou, T. Combinatorial and distinct roles of alpha(5) and alpha(4) integrins in stress erythropoiesis in mice. *Blood* 117, 975-985, doi:10.1182/blood-2010-05-283218 (2011).
30. Ramos, P. et al. Macrophages support pathological erythropoiesis in polycythemia vera and beta-thalassemia. *Nat Med* 19, 437-445, doi:10.1038/nm.3126 (2013).
31. Hashimoto, D. et al. Tissue-resident macrophages self-maintain locally throughout adult life with minimal contribution from circulating monocytes. *Immunity* 38, 792-804, doi:10.1016/j.immuni.2013.04.004 (2013).
32. Ginhoux, F. & Guilliams, M. Tissue-Resident Macrophage Ontogeny and Homeostasis. *Immunity* 44, 439-449, doi:10.1016/j.immuni.2016.02.024 (2016).
33. Hoeffel, G. & Ginhoux, F. Fetal monocytes and the origins of tissue-resident macrophages. *Cell Immunol* 330, 5-15, doi:10.1016/j.cellimm.2018.01.001 (2018).
34. Konstantinidis, D. G. et al. Signaling and cytoskeletal requirements in erythroblast enucleation. *Blood* 119, 6118-6127, doi:10.1182/blood-2011-09-379263 (2012).
35. Lee, J. C. et al. Mechanism of protein sorting during erythroblast enucleation: role of cytoskeletal connectivity. *Blood* 103, 1912-1919, doi:10.1182/blood-2003-03-0928 (2004).
36. Soni, S., Bala, S. & Hanspal, M. Requirement for erythroblast-macrophage protein (Emp) in definitive erythropoiesis. *Blood Cells Mol Dis* 41, 141-147, doi:10.1016/j.bcmd.2008.03.008 (2008).
37. Dame, C. & Juul, S. E. The switch from fetal to adult erythropoiesis. *Clin Perinatol* 27, 507-526 (2000).
38. Dzierzak, E. & Philipsen, S. Erythropoiesis: development and differentiation. *Cold Spring Harb Perspect Med* 3, a011601, doi:10.1101/cshperspect.a011601 (2013).
39. Yanai, N., Sekine, C., Yagita, H. & Obinata, M. Roles for integrin very late activation antigen-4 in stroma-dependent erythropoiesis. *Blood* 83, 2844-2850 (1994).
40. Toda, S., Segawa, K. & Nagata, S. MerTK-mediated engulfment of pyrenocytes by central macrophages in erythroblastic islands. *Blood* 123, 3963-3971, doi:10.1182/blood-2014-01-547976 (2014).
41. Yamashita, T. et al. The microenvironment for erythropoiesis is regulated by HIF-2alpha through VCAM-1 in endothelial cells. *Blood* 112, 1482-1492, doi:10.1182/blood-2007-11-122648 (2008).
42. Sturgeon, C. M. et al. Primitive erythropoiesis is regulated by miR-126 via nonhematopoietic Vcam-1+ cells. *Dev Cell* 23, 45-57, doi:10.1016/j.devcel.2012.05.021 (2012).
43. Dutta, P. et al. Macrophages retain hematopoietic stem cells in the spleen via VCAM-1. *J Exp Med* 212, 497-512, doi:10.1084/jem.20141642 (2015).
44. Frenette, P. S., Subbarao, S., Mazo, I. B., von Andrian, U. H. & Wagner, D. D. Endothelial selectins and vascular cell adhesion molecule-1 promote hematopoietic progenitor homing to bone marrow. *Proc Natl Acad Sci USA* 95, 14423-14428 (1998).
45. Klijn C., et al. A comprehensive transcriptional portrait of human cancer cell lines. Nat Biotechnol. 2015 March; 33(3):306-12, Epub 2014 Dec. 8.
46. Piel F B, Steinberg M H, and Rees D C. Sickle Cell Disease. N Engl J Med. 2017; 376(16):1561-73.
47. Ware R E, et al. Sickle cell disease. Lancet. 2017; 390(10091):311-23.
48. Sundd P, et al. Pathophysiology of Sickle Cell Disease. Annu Rev Pathol. 2019; 14:263-92.
49. Zhang D, et al. Neutrophils, platelets, and inflammatory pathways at the nexus of sickle cell disease pathophysiology. Blood. 2016; 127(7):801-9.
50. Turhan A, et al. Primary role for adherent leukocytes in sickle cell vascular occlusion: a new paradigm. Proc Natl Acad Sci USA. 2002; 99(5):3047-51.
51. Chiang E Y, et al. Imaging receptor microdomains on leukocyte subsets in live mice. Nat Methods. 2007; 4(3):219-22.
52. Hidalgo A, et al. Heterotypic interactions enabled by polarized neutrophil microdomains mediate thromboinflammatory injury. Nat Med. 2009; 15(4):384-91.
53. Baxter E J, et al. Acquired mutation of the tyrosine kinase JAK2 in human myeloproliferative disorders. Lancet 365, 1054-1061 (2005).
54. James C, et al. A unique clonal JAK2 mutation leading to constitutive signaling causes polycythaemia vera. Nature 434, 1144-1148 (2005).
55. Kralovics R. et al. A gain-of-function mutation of JAK2 in myeloproliferative disorders. N. Engl. J. Med. 352, 1779-1790 (2005).
56. Levine R L et al. Activating mutation in the tyrosine kinase JAK2 in polycythemia vera, essential thrombocythemia, and myeloid metaplasia with myelofibrosis. Cancer Cell 7, 387-397 (2005).
57. Miyake, K. et al. A VCAM-like adhesion molecule on murine bone marrow stromal cells mediates binding of lymphocyte precursors in culture. J Cell Biol 114, 557-565 (1991).
58. Simmons, P. J. et al. Vascular cell adhesion molecule-1 expressed by bone marrow stromal cells mediates the binding of hematopoietic progenitor cells. Blood 80, 388-395 (1992).
59. Ulyanova, T. et al. VCAM-1 expression in adult hematopoietic and nonhematopoietic cells is controlled 60. Pinho, S. & Frenette, P. S. Haematopoietic stem cell activity and interactions with the niche. Nat Rev Mol Cell Biol 20, 303-320, doi:10.1038/s41580-019-0103-9 (2019).
61. Gurtner, G. C. et al. Targeted disruption of the murine VCAM1 gene: essential role of VCAM-1 in chorioallantoic fusion and placentation. Genes & development 9, 1-14 (1995).
62. Frenette, P. S., et al. Endothelial selectins and vascular cell adhesion molecule-1 promote hematopoietic progenitor homing to bone marrow. Proceedings of the National Academy of Sciences of the United States of America 95, 14423-14428 (1998).
63. Papayannopoulou, T., et al. The VLA4/VCAM-1 adhesion pathway defines contrasting mechanisms of lodgment of transplanted murine hemopoietic progenitors between bone marrow and spleen. Proceedings of the National Academy of Sciences of the United States of America 92, 9647-9651 (1995).
64. Craddock, C. F., et al. Antibodies to VLA4 integrin mobilize long-term repopulating cells and augment cytokine-induced mobilization in primates and mice. Blood 90, 4779-4788 (1997).
65. Papayannopoulou, T., Priestley, G. V. & Nakamoto, B. Anti-VLA4/VCAM-1-induced mobilization requires cooperative signaling through the kit/mkit ligand pathway. Blood 91, 2231-2239 (1998).
66. Koni, P. A. et al. Conditional vascular cell adhesion molecule 1 deletion in mice: impaired lymphocyte migration to bone marrow. The Journal of experimental medicine 193, 741-754 (2001).
67. Deng, L. et al. A novel mouse model of inflammatory bowel disease links mammalian target of rapamycin-dependent hyperproliferation of colonic epithelium to inflammation associated tumorigenesis. Am J Pathol 176, 952-967, doi:10.2353/ajpath.2010.090622 (2010).
68. Wei, Q. et al. MAEA expressed by macrophages, but not erythroblasts, maintains postnatal murine bone marrow erythroblastic islands. Blood 133, 1222-1232, doi:10.1182/blood-2018-11-888180 (2019).
69. Miyamoto, T. et al. Myeloid or lymphoid promiscuity as a critical step in hematopoietic lineage commitment. Dev Cell 3, 137-147 (2002).
70. Sarrazin, S. et al. MafB restricts M-CSF-dependent myeloid commitment divisions of hematopoietic stem cells. Cell 138, 300-313, doi:10.1016/j.cell.2009.04.057 (2009).
71. Dutta, P. et al. Macrophages retain hematopoietic stem cells in the spleen via VCAM-1. The Journal of experimental medicine 212, 497-512, doi:10.1084/jem.20141642 (2015).
72. Austin, R., et al. Harnessing the immune system in acute myeloid leukaemia. Crit Rev Oncol Hematol 103, 62-77, doi:10.1016/j.critrevonc.2016.04.020 (2016).
73. Imai, Y et al. Essential roles of VLA-4 in the hematopoietic system. Int J Hematol 91, 569-575, doi:10.1007/s12185-010-0555-3 (2010).
74. Kubagawa, H. et al. Biochemical nature and cellular distribution of the paired immunoglobulin-like receptors, PIR-A and PIR-B. The Journal of experimental medicine 189, 309-318 (1999).
75. Takai, T. Paired immunoglobulin-like receptors and their MHC class I recognition. Immunology 115, 433-440, doi:10.1111/j.1365-2567.2005.02177.x (2005).
76. Ujike, A. et al. Impaired dendritic cell maturation and increased T(H)2 responses in PIR472 B(−/−) mice. Nature immunology 3, 542-548, doi:10.1038/ni801 (2002).
77. Ding, Y. B. et al. Association of VCAM-1 overexpression with oncogenesis, tumor angiogenesis and metastasis of gastric carcinoma. World J Gastroenterol 9, 1409-1414 (2003).
78. Lin, K. Y. et al. Ectopic expression of vascular cell adhesion molecule-1 as a new mechanism for tumor immune evasion. Cancer Res 67, 1832-1841, doi:10.1158/0008-5472.CAN-06-3014 (2007).
79. Huang, J. et al. Exome sequencing of hepatitis B virus-associated hepatocellular carcinoma. Nat Genet 44, 1117-1121, doi:10.1038/ng.2391 (2012).
80. Yuan, W. et al. Commonly dysregulated genes in murine APL cells. Blood 109, 961-970, doi:10.1182/blood-2006-07-036640 (2007).
81. Chen, Q., Zhang, X. H. & Massague, J. Macrophage binding to receptor VCAM-1 transmits survival signals in breast cancer cells that invade the lungs. Cancer Cell 20, 538-549, doi:10.1016/j.ccr.2011.08.025 (2011).
82. Lu, X. et al. VCAM-1 promotes osteolytic expansion of indolent bone micrometastasis of breast cancer by engaging alpha4beta1-positive osteoclast progenitors. Cancer Cell 20, 701-714, doi:10.1016/j.ccr.2011.11.002 (2011).
83. Damiano, et al. Cell adhesion mediated drug resistance (CAM-DR): role of integrins and resistance to apoptosis in human myeloma cell lines. Blood 93, 1658-1667 (1999).
84. Jacamo, R. et al. Reciprocal leukemia-stroma VCAM-1/VLA-4-dependent activation of NF-kappaB mediates chemoresistance. Blood 123, 2691-2702, doi:10.1182/blood-2013-06-511527 (2014).
85. Matsunaga, T. et al. Interaction between leukemic-cell VLA-4 and stromal fibronectin is a decisive factor for minimal residual disease of acute myelogenous leukemia. Nature medicine 9, 1158-1165, doi:10.1038/nm909 (2003).
86. Carlson, P. et al. Targeting the perivascular niche sensitizes disseminated tumour cells to chemotherapy. Nat Cell Biol 21, 238-250, doi:10.1038/s41556-018-0267-0 (2019).
87. Krivtsov, A. V. et al. Transformation from committed progenitor to leukaemia stem cell initiated by MLL-AF9. Nature 442, 818-822, doi:10.1038/nature04980 (2006).
88. Jaiswal, S. et al. CD47 is upregulated on circulating hematopoietic stem cells and leukemia cells to avoid phagocytosis. Cell 138, 271-285, doi:10.1016/j.cell.2009.05.046 (2009).
89. Majeti, R. et al. CD47 is an adverse prognostic factor and therapeutic antibody target on human acute myeloid leukemia stem cells. Cell 138, 286-299, doi:10.1016/j.cell.2009.05.045 (2009).
90. Barkal, A. A. et al. Engagement of MHC class I by the inhibitory receptor LILRB1 suppresses macrophages and is a target of cancer immunotherapy. Nature immunology 19, 76-84, doi:10.1038/s41590-017-0004-z (2018).
91. Barreyro, L. et al. Overexpression of IL-1 receptor accessory protein in stem and progenitor cells and outcome correlation in AML and MDS. Blood 120, 1290-1298, doi:10.1182/blood-2012-01-404699 (2012).

92 Schinke, C. et al. IL8-CXCR2 pathway inhibition as a therapeutic strategy against MDS and AML stem cells. Blood 125, 3144-3152, doi:10.1182/blood-2015-01-621631 (2015).

93 Havel, J. J., Chowell, D. & Chan, T. A. The evolving landscape of biomarkers for checkpoint inhibitor immunotherapy. Nat Rev Cancer 19, 133-150, doi: 10.1038/s41568-019-0116-x (2019).

94 Woo, S. R., Corrales, L. & Gajewski, T. F. Innate immune recognition of cancer. Annual review of immunology 33, 445-474, doi:10.1146/annurev-immunol-032414-112043 (2015).

95 An, N. & Kang, Y. Using quantitative real-time PCR to determine donor cell engraftment in a competitive murine bone marrow transplantation model. J Vis Exp, e50193, doi:10.3791/50193 (2013).

96 Pinho, S. et al. Lineage-Biased Hematopoietic Stem Cells Are Regulated by Distinct Niches. Dev Cell 44, 634-641 e634, doi:10.1016/j.devcel.2018.01.016 (2018).

97 1 Hanspal, M. & Hanspal, J. S. The association of erythroblasts with macrophages promotes erythroid proliferation and maturation: a 30-kD heparin-binding protein is involved in this contact. Blood 84, 3494-3504 (1994).

98 Soni, S. et al. Absence of erythroblast macrophage protein (Emp) leads to failure of erythroblast nuclear extrusion. J Biol Chem 281, 20181-20189, doi: 10.1074/jbc.M603226200 (2006).

99 Francis, O., Han, F. & Adams, J. C. Molecular phylogeny of a RING E3 ubiquitin ligase, conserved in eukaryotic cells and dominated by homologous components, the muskelin/RanBPM/CTLH complex. PLoS One 8, e75217, doi:10.1371/journal.pone.0075217 (2013).

100 Lampert, F. et al. The multi-subunit GID/CTLH E3 ubiquitin ligase promotes cell proliferation and targets the transcription factor Hbp1 for degradation. Elife 7, doi:10.7554/eLife.35528 (2018).

101 Wei, Q. et al. MAEA expressed by macrophages, but not erythroblasts, maintains postnatal murine bone marrow erythroblastic islands. Blood 133, 1222-1232, doi:10.1182/blood-2018-11-888180 (2019).

102 Qian, B. Z. et al. CCL2 recruits inflammatory monocytes to facilitate breast-tumour metastasis. Nature 475, 222-225, doi:10.1038/nature10138 (2011).

103 Rossi, D. J. et al. Cell intrinsic alterations underlie hematopoietic stem cell aging. Proc Natl Acad Sci USA 102, 9194-9199, doi:10.1073/pnas.0503280102 (2005).

104 Lee, J. C. et al. Mechanism of protein sorting during erythroblast enucleation: role of cytoskeletal connectivity. Blood 103, 1912-1919, doi:10.1182/blood-2003-03-0928 (2004).

105 Bala, S. et al. Emp is a component of the nuclear matrix of mammalian cells and undergoes dynamic rearrangements during cell division. Biochem Biophys Res Commun 342, 1040-1048, doi:10.1016/j.bbrc.2006.02.060 (2006).

106 Kirkin, V., et al. A role for ubiquitin in selective autophagy. Mol Cell 34, 259-269, doi:10.1016/j.molcel.2009.04.026 (2009).

107 Warr, M. R. et al. FOXO3A directs a protective autophagy program in haematopoietic stem cells. Nature 494, 323-327, doi:10.1038/nature11895 (2013).

108 Mortensen, M. et al. The autophagy protein Atg7 is essential for hematopoietic stem cell maintenance. J Exp Med 208, 455-467, doi:10.1084/jem.20101145 (2011).

109 Liu, F. et al. FIP200 is required for the cell-autonomous maintenance of fetal hematopoietic stem cells. Blood 116, 4806-4814, doi:10.1182/blood-2010-06-288589 (2010).

110 Riffelmacher, T. & Simon, A. K. Mechanistic roles of autophagy in hematopoietic differentiation. FEBS J 284, 1008-1020, doi:10.1111/febs.13962 (2017).

111 Shimobayashi, M. & Hall, M. N. Making new contacts: the mTOR network in metabolism and signalling crosstalk. Nat Rev Mol Cell Biol 15, 155-162, doi: 10.1038/nrm3757 (2014).

112 Chang, Y. Y. et al. Nutrient-dependent regulation of autophagy through the target of rapamycin pathway. Biochem Soc Trans 37, 232-236, doi:10.1042/BST0370232 (2009).

113 Reggiori, F. & Ungermann, C. Autophagosome Maturation and Fusion. J Mol Biol 429, 486-496, doi: 10.1016/j.jmb.2017.01.002 (2017).

114 Eskelinen, E. L. Maturation of autophagic vacuoles in Mammalian cells. Autophagy 1, 1-10 (2005).

115 Levine, B. & Kroemer, G. Autophagy in the pathogenesis of disease. Cell 132, 27-42, doi:10.1016/j.cell.2007.12.018 (2008).

116 Sarkar, S. et al. Lithium induces autophagy by inhibiting inositol monophosphatase. J Cell Biol 170, 1101-1111, doi:10.1083/jcb.200504035 (2005).

117 Park, H. W. et al. Pharmacological correction of obesity-induced autophagy arrest using calcium channel blockers. Nat Commun 5, 4834, doi:10.1038/ncomms5834 (2014).

118 Ianniciello, A., et al. The Ins and Outs of Autophagy and Metabolism in Hematopoietic and Leukemic Stem Cells: Food for Thought. Front Cell Dev Biol 6, 120, doi:10.3389/fcell.2018.00120 (2018).

119 Lee, M. J. & Yaffe, M. B. Protein Regulation in Signal Transduction. Cold Spring Harb Perspect Biol 8, doi: 10.1101/cshperspect.a005918 (2016).

120 Moran-Crusio, K. et al. Regulation of hematopoietic stem cell fate by the ubiquitin proteasome system. Trends Immunol 33, 357-363, doi:10.1016/j.it.2012.01.009 (2012).

121 Shaid, S. et al. Ubiquitination and selective autophagy. Cell Death Differ 20, 21-30, doi:10.1038/cdd.2012.72 (2013).

122 Xie, Y. et al. Posttranslational modification of autophagy-related proteins in macroautophagy. Autophagy 11, 28-45, doi:10.4161/15548627.2014.984267 (2015).

123 Eaton et al. Sickle cell hemoglobin polymerization. Adv Protein Chem, 40: 63-279 (1990).

124 Steinberg, M H. Management of sickle cell disease. N Engl J Med 340(13): 1021-1030 (1999).

125 Ballas, S K & Smith, E D. Red blood cell changes during the evolution of the sickle cell painful crisis. Blood, 79(8) 2154-63 (1992).

126 Kassim, A A & DeBaun, M R. Sickle cell disease, vasculopathy, and therapeutics. Annu Rev Med, 64: 451-466 (2013).

127 Telen et al. Developing new pharmacotherapeutic approaches to treating sickle-cell disease. Blood 12(1) 239-247 (2006).

128 Wang et al., Experimental and Therapeutic Medicine (2015).

What is claimed is:

1. An antibody or immunogenic fragment thereof comprising a heavy chain comprising
SYTMS (CDR1); (SEQ ID NO: 54)

EISSGGSYTHYAATVTG (CDR2); (SEQ ID NO: 56)
and

GELY (CDR3) (SEQ ID NO: 58)
and a light chain comprising
KASQSLLDRGGKTFFN (CDR1); (SEQ ID NO: 68)

LVSKLDS (CDR2); (SEQ ID NO: 70)
and

WQGTHFPWT (CDR3); (SEQ ID NO: 72)

wherein said antibody or immunogenic fragment thereof specifically binds vascular cell adhesion molecule 1 (VCAM1).

2. The antibody or immunogenic fragment thereof of claim 1, comprising a VH region comprising the amino acid sequence of SEQ ID NO: 13 and a VL region comprising the amino acid sequence of SEQ ID NO:15.

3. The antibody or immunogenic fragment thereof of claim 1, wherein the antibody is selected from the group consisting of a monoclonal antibody, a chimeric antibody, a human antibody, and a humanized antibody.

4. A fusion protein comprising the antibody or immunogenic fragment thereof of claim 1.

5. A nucleic acid comprising a nucleotide sequence encoding the antibody or immunogenic fragment thereof of claim 1.

6. An antibody or immunogenic fragment thereof comprising a heavy chain comprising SYAMS (SEQ ID NO:82) (CDR1); EISSTGSYTHYPDTVTG (SEQ ID NO:84) (CDR2); and GEAL (SEQ ID NO:86) and a light chain comprising KSSHSLLDSYGKTYLN (SEQ ID NO:96) (CDR1); LVSKLDS (SEQ ID NO:98) (CDR2); and WQGTHFPWT (SEQ ID NO: 100) (CDR3); wherein said antibody or immunogenic fragment thereof specifically binds vascular cell adhesion molecule 1 (VCAM1).

7. The antibody or immunogenic fragment thereof of claim 6, comprising a VH region comprising the amino acid sequence of SEQ ID NO:17 and a VL region comprising the amino acid sequence of SEQ ID NO:19.

8. The antibody or immunogenic fragment thereof of claim 6, wherein the antibody is selected from the group consisting of a monoclonal antibody, a chimeric antibody, a human antibody, and a humanized antibody.

9. A fusion protein comprising the antibody or immunogenic fragment thereof of claim 6.

10. A nucleic acid comprising a nucleotide sequence encoding the antibody or immunogenic fragment thereof of claim 6.

* * * * *

SEQUENCE LISTING

```
Sequence total quantity: 103
SEQ ID NO: 1                    moltype = DNA   length = 20
FEATURE                         Location/Qualifiers
misc_feature                    1..20
                                note = F1 primer
source                          1..20
                                mol_type = other DNA
                                organism = synthetic construct
SEQUENCE: 1
gttcagcctc aggattcagg                                                         20

SEQ ID NO: 2                    moltype = DNA   length = 19
FEATURE                         Location/Qualifiers
misc_feature                    1..19
                                note = R1 primer
source                          1..19
                                mol_type = other DNA
                                organism = synthetic construct
SEQUENCE: 2
atgagcaggg gacctcaac                                                          19

SEQ ID NO: 3                    moltype = DNA   length = 19
FEATURE                         Location/Qualifiers
misc_feature                    1..19
                                note = R2 primer
source                          1..19
                                mol_type = other DNA
                                organism = synthetic construct
SEQUENCE: 3
aactgatggc gagctcaga                                                          19

SEQ ID NO: 4                    moltype = DNA   length = 20
FEATURE                         Location/Qualifiers
misc_feature                    1..20
                                note = F2 primer
source                          1..20
                                mol_type = other DNA
                                organism = synthetic construct
SEQUENCE: 4
caccagctca ggcagttaca                                                         20

SEQ ID NO: 5                    moltype = DNA   length = 20
FEATURE                         Location/Qualifiers
misc_feature                    1..20
                                note = R3 primer
source                          1..20
                                mol_type = other DNA
                                organism = synthetic construct
SEQUENCE: 5
ccacaacggg ttcttctgtt                                                         20

SEQ ID NO: 6                    moltype = DNA   length = 20
FEATURE                         Location/Qualifiers
misc_feature                    1..20
                                note = R4 primer
source                          1..20
                                mol_type = other DNA
                                organism = synthetic construct
SEQUENCE: 6
cgggaagaag tgggattacc                                                         20

SEQ ID NO: 7                    moltype = AA   length = 29
FEATURE                         Location/Qualifiers
REGION                          1..29
                                note = KLH-conjugated MAEA
source                          1..29
                                mol_type = protein
                                organism = synthetic construct
SEQUENCE: 7
AAQKNIDRET SHVTMVVAEL EKTLSGCPA                                               29

SEQ ID NO: 8                    moltype = DNA   length = 417
FEATURE                         Location/Qualifiers
misc_feature                    1..417
                                note = 92.25 heavy chain
source                          1..417
                                mol_type = other DNA
                                organism = synthetic construct
```

-continued

```
SEQUENCE: 8
atggaatgga gctggatctt tctctttctc ctgtcaggaa ctgcaggtgt cctctctgag    60
gtccagctgc aacagtttgg agctgagctg gtgaggcctg ggcttcagt gaagatatcc    120
tgcaaggctt ctggctacac attcactgac tacaacatgg actgggtgaa gcagagccat   180
gcaaagagac ttgagtggat tggagatatt aatcctaact atgatagtcc tacctacagc   240
cagaagttca agggaagggc cacattgact gtagacaact cctccagcac cgcctacatg   300
gagctccgca gcctgacatc tgaggacact gcagtctatt actgtgcaag ggacattac    360
tacggctacg gatacttcga tgtctggggc gcggggacca cggtcaccgt ctcctca      417

SEQ ID NO: 9          moltype = AA   length = 139
FEATURE               Location/Qualifiers
REGION                1..139
                      note = 92.25 heavy chain
source                1..139
                      mol_type = protein
                      organism = synthetic construct
SEQUENCE: 9
MEWSWIFLFL LSGTAGVLSE VQLQQFGAEL VRPGASVKIS CKASGYTFTD YNMDWVKQSH     60
AKRLEWIGDI NPNYDSPTYS QKFKGRATLT VDNSSSTAYM ELRSLTSEDT AVYYCARGHY   120
YGYGYFDVWG AGTTVTVSS                                                139

SEQ ID NO: 10         moltype = DNA   length = 381
FEATURE               Location/Qualifiers
misc_feature          1..381
                      note = 92.25 light chain
source                1..381
                      mol_type = other DNA
                      organism = synthetic construct
SEQUENCE: 10
atggagtcac agactcaggt ctttgtatac atgttgctgt ggttgtctgg tgttgatgga    60
gacattgaga tgacccagtc tcaaaaattc atgtccacag cagtaggaga cagggtcagc   120
gtcacctgca aggccagtca gaatgtgggt actaatgtag cctggtatca acagaaacca   180
gggaaatctc ctaaagtact gatttactcg gcatcctacc gctacagtgg agtccctgat   240
cgcttcagag gcagtagatc tgggacagat ttcactctca ccatcagcaa tgtgcagtct   300
gaagacttgg cagagtattt ctgtcagcaa tataacacct atccgtggac gttcggtgga   360
ggcaccaagc tggaaatcaa a                                             381

SEQ ID NO: 11         moltype = AA   length = 127
FEATURE               Location/Qualifiers
REGION                1..127
                      note = 92.25 light chain
source                1..127
                      mol_type = protein
                      organism = synthetic construct
SEQUENCE: 11
MESQTQVFVY MLLWLSGVDG DIEMTQSQKF MSTAVGDRVS VTCKASQNVG TNVAWYQQKP    60
GKSPKVLIYS ASYRYSGVPD RFRGSRSGTD FTLTISNVQS EDLAEYFCQQ YNTYPWTFGG  120
GTKLEIK                                                             127

SEQ ID NO: 12         moltype = DNA   length = 396
FEATURE               Location/Qualifiers
misc_feature          1..396
                      note = V64-8 heavy chain
source                1..396
                      mol_type = other DNA
                      organism = synthetic construct
SEQUENCE: 12
atgaacttcg ggctcagctt gattttcctt gtccctattt taaaaggtgt ccagtgtgaa    60
gtacagctgg tggagtctgg gggaggctta gtgaagcctg gagggtccct gaaactctcc   120
tgtgcagcct ctggattcac tttcagtagt tataccatgt cttgggttcg ccagtctcca   180
gagaagaggc tggagtgggt cgcagagatt agtagtggtg gtagttacac ccactatgca   240
gccactgtga cggccgatt caccatctcc agagacaatg tcaagaacac cctgtacctg    300
gaaatgagca gtctgaggtc tgaggacacg gccatgtatt actgtgcaag ggagaacttt   360
tactggggcc aagggactct ggtcactgtc tctgca                             396

SEQ ID NO: 13         moltype = AA   length = 132
FEATURE               Location/Qualifiers
REGION                1..132
                      note = V64-8 heavy chain
source                1..132
                      mol_type = protein
                      organism = synthetic construct
SEQUENCE: 13
MNFGLSLIFL VPILKGVQCE VQLVESGGGL VKPGGSLKLS CAASGFTFSS YTMSWVRQSP    60
EKRLEWVAEI SSGGSYTHYA ATVTGRFTIS RDNVKNTLYL EMSSLRSEDT AMYYCARGEL   120
YWGQGTLVTV SA                                                       132

SEQ ID NO: 14         moltype = DNA   length = 393
FEATURE               Location/Qualifiers
```

```
misc_feature            1..393
                        note = V64-8 light chain
source                  1..393
                        mol_type = other DNA
                        organism = synthetic construct
SEQUENCE: 14
atgagtcctg cccagttcct gtttctgtta gtgctctgga ttcgggaaac caacggtgat    60
gttgtgttga cccagattcc atccactttg tcggttacct tggacaacc agcctccatc   120
tcttgcaagg caagtcagag cctcttagat agaggtggaa agacattttt caattggttg   180
ttacagaggc caggccagtc tccaaaagcg ctaatctatc tggtgtctaa actggactct   240
ggagtccctg acaggttcac tggcagtgga tcaggacag atttcacact gaaaatcagc    300
agagtggagg ctgaggattt gggagtctat tattgctggc aaggtacaca ttttccgtgg   360
acgttcggtg gaggcaccag actggaaatc aaa                                393

SEQ ID NO: 15           moltype = AA  length = 131
FEATURE                 Location/Qualifiers
REGION                  1..131
                        note = V64-8 light chain
source                  1..131
                        mol_type = protein
                        organism = synthetic construct
SEQUENCE: 15
MSPAQFLFLL VLWIRETNGD VVLTQIPSTL SVTFGQPASI SCKASQSLLD RGGKTFFNWL    60
LQRPGQSPKR LIYLVSKLDS GVPDRFTGSG SGTDFTLKIS RVEAEDLGVY YCWQGTHFPW   120
TFGGGTRLEI K                                                       131

SEQ ID NO: 16           moltype = DNA  length = 396
FEATURE                 Location/Qualifiers
misc_feature            1..396
                        note = V196-4 heavy chain
source                  1..396
                        mol_type = other DNA
                        organism = synthetic construct
SEQUENCE: 16
atgaacttcg ggctcagctt gattttcctt gtccttattt taaaaggtgt ccattgtgaa    60
gtgcagctgg tggagtctgg gggagcctta gtgaagcctg gagggtccct gaaactctcc   120
tgtgtagcct ctggattcac tttcagtagc atgccatgt cttgggttcg ccagtctcca    180
gagaagaagc tggagtgggt cgcagaaatt agtagtactg gtagtacac ccactatccc    240
gacactgtga cgggccgatt caccatctcc agagacaatg ccaagaacac cctgtacctg   300
gaaatgagca gtctgaggtc tgaggacacg gccatgtatt actgtgcaag aggggaggcg   360
ctctgggtc aaggaacctc agtcaccgtc tcctca                             396

SEQ ID NO: 17           moltype = AA  length = 132
FEATURE                 Location/Qualifiers
REGION                  1..132
                        note = V196-4 heavy chain
source                  1..132
                        mol_type = protein
                        organism = synthetic construct
SEQUENCE: 17
MNFGLSLIFL VLILKGVHCE VQLVESGGAL VKPGGSLKLS CVASGFTFSS YAMSWVRQSP    60
EKKLEWVAEI SSTGSYTHYP DTVTGRFTIS RDNAKNTLYL EMSSLRSEDT AMYYCARGEA   120
LWGQGTSVTV SS                                                      132

SEQ ID NO: 18           moltype = DNA  length = 393
FEATURE                 Location/Qualifiers
misc_feature            1..393
                        note = V196-4 light chain
source                  1..393
                        mol_type = other DNA
                        organism = synthetic construct
SEQUENCE: 18
atgagtcctg cccagttcct gtttctgtta gtgctctgga ttcgggaaac caacggtgat    60
gttgtgatga cccagactcc actcactttg tcggttaccg ttggacaacc agcctccatc   120
tcttgcaagt caagtcatag cctcttagat agttatggaa agacatattt gaattggttt   180
ttacagaggc caggccagtc tccaaaagcg ctaatctatc tggtgtctaa actggactct   240
ggagtccctg acaggttcac tggcagtgga tcaggacag atttcacact gaaaatcagc    300
agagtggagg ctgaggattt ggactttat tattgctggc agggtacaca ttttccgtgg   360
acgttcggtg gaggcaccaa gctggaaatc aaa                                393

SEQ ID NO: 19           moltype = AA  length = 131
FEATURE                 Location/Qualifiers
REGION                  1..131
                        note = V196-4 light chain
source                  1..131
                        mol_type = protein
                        organism = synthetic construct
SEQUENCE: 19
MSPAQFLFLL VLWIRETNGD VVMTQTPLTL SVTVGQPASI SCKSSHSLLD SYGKTYLNWF    60
```

```
LQRPGQSPKR LIYLVSKLDS GVPDRFTGSG SGTDFTLKIS RVEAEDLGLY YCWQGTHFPW    120
TFGGGTKLEI K                                                        131

SEQ ID NO: 20           moltype = DNA   length = 90
FEATURE                 Location/Qualifiers
misc_feature            1..90
                        note = 92.25 FR1 (heavy)
source                  1..90
                        mol_type = other DNA
                        organism = synthetic construct
SEQUENCE: 20
gaggtccagc tgcaacagtt tggagctgag ctggtgaggc ctggggcttc agtgaagata    60
tcctgcaagg cttctggcta cacattcact                                    90

SEQ ID NO: 21           moltype = DNA   length = 15
FEATURE                 Location/Qualifiers
misc_feature            1..15
                        note = 92.25 CDR1 (heavy)
source                  1..15
                        mol_type = other DNA
                        organism = synthetic construct
SEQUENCE: 21
gactacaaca tggac                                                    15

SEQ ID NO: 22           moltype = DNA   length = 42
FEATURE                 Location/Qualifiers
misc_feature            1..42
                        note = 92.25 FR2 (heavy)
source                  1..42
                        mol_type = other DNA
                        organism = synthetic construct
SEQUENCE: 22
tgggtgaagc agagccatgc aaagagactt gagtggattg ga                      42

SEQ ID NO: 23           moltype = DNA   length = 51
FEATURE                 Location/Qualifiers
misc_feature            1..51
                        note = 92.25 CDR2 (heavy)
source                  1..51
                        mol_type = other DNA
                        organism = synthetic construct
SEQUENCE: 23
gatattaatc ctaactatga tagtcctacc tacagccaga agttcaaggg a             51

SEQ ID NO: 24           moltype = DNA   length = 96
FEATURE                 Location/Qualifiers
misc_feature            1..96
                        note = 92.25 FR3 (heavy)
source                  1..96
                        mol_type = other DNA
                        organism = synthetic construct
SEQUENCE: 24
agggccacat tgactgtaga caactcctcc agcaccgcct acatggagct ccgcagcctg    60
acatctgagg acactgcagt ctattactgt gcaagg                             96

SEQ ID NO: 25           moltype = DNA   length = 33
FEATURE                 Location/Qualifiers
misc_feature            1..33
                        note = 92.25 CDR3 (heavy)
source                  1..33
                        mol_type = other DNA
                        organism = synthetic construct
SEQUENCE: 25
ggacattact acggctacgg atacttcgat gtc                                33

SEQ ID NO: 26           moltype = DNA   length = 33
FEATURE                 Location/Qualifiers
misc_feature            1..33
                        note = 92.25 FR4 (heavy)
source                  1..33
                        mol_type = other DNA
                        organism = synthetic construct
SEQUENCE: 26
tggggcgcgg ggaccacggt caccgtctcc tca                                33

SEQ ID NO: 27           moltype = AA   length = 30
FEATURE                 Location/Qualifiers
REGION                  1..30
                        note = 92.25 FR1 (heavy)
```

```
source                      1..30
                            mol_type = protein
                            organism = synthetic construct
SEQUENCE: 27
EVQLQQFGAE LVRPGASVKI SCKASGYTFT                                        30

SEQ ID NO: 28               moltype = AA  length = 5
FEATURE                     Location/Qualifiers
REGION                      1..5
                            note = 92.25 CDR1 (heavy)
source                      1..5
                            mol_type = protein
                            organism = synthetic construct
SEQUENCE: 28
DYNMD                                                                    5

SEQ ID NO: 29               moltype = AA  length = 14
FEATURE                     Location/Qualifiers
REGION                      1..14
                            note = 92.25 FR2 (heavy)
source                      1..14
                            mol_type = protein
                            organism = synthetic construct
SEQUENCE: 29
WVKQSHAKRL EWIG                                                         14

SEQ ID NO: 30               moltype = AA  length = 17
FEATURE                     Location/Qualifiers
REGION                      1..17
                            note = 92.25 CDR2 (heavy)
source                      1..17
                            mol_type = protein
                            organism = synthetic construct
SEQUENCE: 30
DINPNYDSPT YSQKFKG                                                      17

SEQ ID NO: 31               moltype = AA  length = 32
FEATURE                     Location/Qualifiers
REGION                      1..32
                            note = 92.25 FR3 (heavy)
source                      1..32
                            mol_type = protein
                            organism = synthetic construct
SEQUENCE: 31
RATLTVDNSS STAYMELRSL TSEDTAVYYC AR                                     32

SEQ ID NO: 32               moltype = AA  length = 11
FEATURE                     Location/Qualifiers
REGION                      1..11
                            note = 92.25 CDR3 (heavy)
source                      1..11
                            mol_type = protein
                            organism = synthetic construct
SEQUENCE: 32
GHYYGYGYFD V                                                            11

SEQ ID NO: 33               moltype = AA  length = 11
FEATURE                     Location/Qualifiers
REGION                      1..11
                            note = 92.25 FR4 (heavy)
source                      1..11
                            mol_type = protein
                            organism = synthetic construct
SEQUENCE: 33
WGAGTTVTVS S                                                            11

SEQ ID NO: 34               moltype = DNA  length = 69
FEATURE                     Location/Qualifiers
misc_feature                1..69
                            note = 92.25 FR1 (light)
source                      1..69
                            mol_type = other DNA
                            organism = synthetic construct
SEQUENCE: 34
gacattgaga tgacccagtc tcaaaaattc atgtccacag cagtaggaga cagggtcagc        60
gtcacctgc                                                               69

SEQ ID NO: 35               moltype = AA  length = 33
FEATURE                     Location/Qualifiers
```

```
REGION                    1..33
                          note = 92.25 CDR1 (light)
source                    1..33
                          mol_type = protein
                          organism = synthetic construct
SEQUENCE: 35
AAGGCCAGTC AGAATGTGGG TACTAATGTA GCC                              33

SEQ ID NO: 36             moltype = DNA  length = 45
FEATURE                   Location/Qualifiers
misc_feature              1..45
                          note = 92.25 FR2 (light)
source                    1..45
                          mol_type = other DNA
                          organism = synthetic construct
SEQUENCE: 36
tggtatcaac agaaaccagg gaaatctcct aaagtactga tttac                 45

SEQ ID NO: 37             moltype = DNA  length = 21
FEATURE                   Location/Qualifiers
misc_feature              1..21
                          note = 92.25 CDR2 (light)
source                    1..21
                          mol_type = other DNA
                          organism = synthetic construct
SEQUENCE: 37
tcggcatcct accgctacag t                                           21

SEQ ID NO: 38             moltype = DNA  length = 96
FEATURE                   Location/Qualifiers
misc_feature              1..96
                          note = 92.25 FR3 (light)
source                    1..96
                          mol_type = other DNA
                          organism = synthetic construct
SEQUENCE: 38
ggagtccctg atcgcttcag aggcagtaga tctgggacag atttcactct caccatcagc 60
aatgtgcagt ctgaagactt ggcagagtat ttctgt                          96

SEQ ID NO: 39             moltype = DNA  length = 27
FEATURE                   Location/Qualifiers
misc_feature              1..27
                          note = 92.25 CDR3 (light)
source                    1..27
                          mol_type = other DNA
                          organism = synthetic construct
SEQUENCE: 39
cagcaatata cacctatcc gtggacg                                      27

SEQ ID NO: 40             moltype = DNA  length = 30
FEATURE                   Location/Qualifiers
misc_feature              1..30
                          note = 92.25 FR4 (light)
source                    1..30
                          mol_type = other DNA
                          organism = synthetic construct
SEQUENCE: 40
ttcggtggag gcaccaagct ggaaatcaaa                                  30

SEQ ID NO: 41             moltype = AA  length = 23
FEATURE                   Location/Qualifiers
REGION                    1..23
                          note = 92.25 FR1 (light)
source                    1..23
                          mol_type = protein
                          organism = synthetic construct
SEQUENCE: 41
DIEMTQSQKF MSTAVGDRVS VTC                                         23

SEQ ID NO: 42             moltype = AA  length = 11
FEATURE                   Location/Qualifiers
REGION                    1..11
                          note = 92.25 CDR1 (light)
source                    1..11
                          mol_type = protein
                          organism = synthetic construct
SEQUENCE: 42
KASQNVGTNV A                                                      11
```

-continued

```
SEQ ID NO: 43              moltype = AA  length = 15
FEATURE                    Location/Qualifiers
REGION                     1..15
                           note = 92.25 FR2 (light)
source                     1..15
                           mol_type = protein
                           organism = synthetic construct
SEQUENCE: 43
WYQQKPGKSP KVLIY                                                          15

SEQ ID NO: 44              moltype = AA  length = 9
FEATURE                    Location/Qualifiers
REGION                     1..9
                           note = 92.25 CDR3 (light)
source                     1..9
                           mol_type = protein
                           organism = synthetic construct
SEQUENCE: 44
QQYNTYPWT                                                                 9

SEQ ID NO: 45              moltype = AA  length = 10
FEATURE                    Location/Qualifiers
REGION                     1..10
                           note = 92.25 FR4 (light)
source                     1..10
                           mol_type = protein
                           organism = synthetic construct
SEQUENCE: 45
FGGGTKLEIK                                                                10

SEQ ID NO: 46              moltype = DNA  length = 90
FEATURE                    Location/Qualifiers
misc_feature               1..90
                           note = V64-8 FR1 (heavy)
source                     1..90
                           mol_type = other DNA
                           organism = synthetic construct
SEQUENCE: 46
gaagtacagc tggtggagtc tgggggaggc ttagtgaagc ctggagggtc cctgaaactc          60
tcctgtgcag cctctggatt cactttcagt                                          90

SEQ ID NO: 47              moltype = DNA  length = 15
FEATURE                    Location/Qualifiers
misc_feature               1..15
                           note = V64-8 CDR1 (heavy)
source                     1..15
                           mol_type = other DNA
                           organism = synthetic construct
SEQUENCE: 47
agttatacca tgtct                                                          15

SEQ ID NO: 48              moltype = DNA  length = 42
FEATURE                    Location/Qualifiers
misc_feature               1..42
                           note = V64-8 FR2 (heavy)
source                     1..42
                           mol_type = other DNA
                           organism = synthetic construct
SEQUENCE: 48
tgggttcgcc agtctccaga gaagaggctg gagtgggtcg ca                            42

SEQ ID NO: 49              moltype = DNA  length = 51
FEATURE                    Location/Qualifiers
misc_feature               1..51
                           note = V64-8 CDR2 (heavy)
source                     1..51
                           mol_type = other DNA
                           organism = synthetic construct
SEQUENCE: 49
gagattagta gtggtggtag ttacacccac tatgcagcca ctgtgacggg c                  51

SEQ ID NO: 50              moltype = DNA  length = 96
FEATURE                    Location/Qualifiers
misc_feature               1..96
                           note = V64-8 FR3 (heavy)
source                     1..96
                           mol_type = other DNA
                           organism = synthetic construct
SEQUENCE: 50
```

```
cgattcacca tctccagaga caatgtcaag aacaccctgt acctggaaat gagcagtctg    60
aggtctgagg acacggccat gtattactgt gcaagg                              96

SEQ ID NO: 51           moltype = DNA   length = 12
FEATURE                 Location/Qualifiers
misc_feature            1..12
                        note = V64-8 CDR3 (heavy)
source                  1..12
                        mol_type = other DNA
                        organism = synthetic construct
SEQUENCE: 51
ggagaacttt ac                                                        12

SEQ ID NO: 52           moltype = DNA   length = 33
FEATURE                 Location/Qualifiers
misc_feature            1..33
                        note = V64-8 FR4 (heavy)
source                  1..33
                        mol_type = other DNA
                        organism = synthetic construct
SEQUENCE: 52
tggggccaag ggactctggt cactgtctct gca                                 33

SEQ ID NO: 53           moltype = AA    length = 30
FEATURE                 Location/Qualifiers
REGION                  1..30
                        note = V64-8 FR1 (heavy)
source                  1..30
                        mol_type = protein
                        organism = synthetic construct
SEQUENCE: 53
EVQLVESGGG LVKPGGSLKL SCAASGFTFS                                     30

SEQ ID NO: 54           moltype = AA    length = 5
FEATURE                 Location/Qualifiers
REGION                  1..5
                        note = V64-8 CDR1 (heavy)
source                  1..5
                        mol_type = protein
                        organism = synthetic construct
SEQUENCE: 54
SYTMS                                                                 5

SEQ ID NO: 55           moltype = AA    length = 14
FEATURE                 Location/Qualifiers
REGION                  1..14
                        note = V64-8 FR2 (heavy)
source                  1..14
                        mol_type = protein
                        organism = synthetic construct
SEQUENCE: 55
WVRQSPEKRL EWVA                                                      14

SEQ ID NO: 56           moltype = AA    length = 17
FEATURE                 Location/Qualifiers
REGION                  1..17
                        note = V64-8 CDR2 (heavy)
source                  1..17
                        mol_type = protein
                        organism = synthetic construct
SEQUENCE: 56
EISSGGSYTH YAATVTG                                                   17

SEQ ID NO: 57           moltype = AA    length = 32
FEATURE                 Location/Qualifiers
REGION                  1..32
                        note = V64-8 FR3 (heavy)
source                  1..32
                        mol_type = protein
                        organism = synthetic construct
SEQUENCE: 57
RFTISRDNVK NTLYLEMSSL RSEDTAMYYC AR                                  32

SEQ ID NO: 58           moltype = AA    length = 4
FEATURE                 Location/Qualifiers
REGION                  1..4
                        note = V64-8 CDR3 (heavy)
source                  1..4
                        mol_type = protein
```

```
                        organism = synthetic construct
SEQUENCE: 58
GELY                                                                        4

SEQ ID NO: 59           moltype = AA  length = 11
FEATURE                 Location/Qualifiers
REGION                  1..11
                        note = V64-8 FR4 (heavy)
source                  1..11
                        mol_type = protein
                        organism = synthetic construct
SEQUENCE: 59
WGQGTLVTVS A                                                               11

SEQ ID NO: 60           moltype = DNA  length = 69
FEATURE                 Location/Qualifiers
misc_feature            1..69
                        note = V64-8 FR1 (light)
source                  1..69
                        mol_type = other DNA
                        organism = synthetic construct
SEQUENCE: 60
gatgttgtgt tgacccagat tccatccact tgtcggtta cctttggaca accagcctcc           60
atctcttgc                                                                  69

SEQ ID NO: 61           moltype = AA  length = 48
FEATURE                 Location/Qualifiers
REGION                  1..48
                        note = V64-8 CDR1 (light)
source                  1..48
                        mol_type = protein
                        organism = synthetic construct
SEQUENCE: 61
AAGGCAAGTC AGAGCCTCTT AGATAGAGGT GGAAAGACAT TTTTCAAT                       48

SEQ ID NO: 62           moltype = DNA  length = 45
FEATURE                 Location/Qualifiers
misc_feature            1..45
                        note = V64-8 FR2 (light)
source                  1..45
                        mol_type = other DNA
                        organism = synthetic construct
SEQUENCE: 62
tggttgttac agaggccagg ccagtctcca aagcgcctaa tctat                          45

SEQ ID NO: 63           moltype = DNA  length = 21
FEATURE                 Location/Qualifiers
misc_feature            1..21
                        note = V64-8 CDR2 (light)
source                  1..21
                        mol_type = other DNA
                        organism = synthetic construct
SEQUENCE: 63
ctggtgtcta aactggactc t                                                    21

SEQ ID NO: 64           moltype = DNA  length = 96
FEATURE                 Location/Qualifiers
misc_feature            1..96
                        note = V64-8 FR3 (light)
source                  1..96
                        mol_type = other DNA
                        organism = synthetic construct
SEQUENCE: 64
ggagtccctg acaggttcac tggcagtgga tcaggacag atttcacact gaaaatcagc           60
agagtggagg ctgaggattt gggagtctat tattgc                                    96

SEQ ID NO: 65           moltype = DNA  length = 27
FEATURE                 Location/Qualifiers
misc_feature            1..27
                        note = V64-8 CDR3 (light)
source                  1..27
                        mol_type = other DNA
                        organism = synthetic construct
SEQUENCE: 65
tggcaaggta cacattttcc gtggacg                                              27

SEQ ID NO: 66           moltype = DNA  length = 30
FEATURE                 Location/Qualifiers
misc_feature            1..30
```

```
                         note = V64-8 FR4 (light)
source                   1..30
                         mol_type = other DNA
                         organism = synthetic construct
SEQUENCE: 66
ttcggtggag gcaccagact ggaaatcaaa                                      30

SEQ ID NO: 67            moltype = AA  length = 23
FEATURE                  Location/Qualifiers
REGION                   1..23
                         note = V64-8 FR1 (light)
source                   1..23
                         mol_type = protein
                         organism = synthetic construct
SEQUENCE: 67
DVVLTQIPST LSVTFGQPAS ISC                                             23

SEQ ID NO: 68            moltype = AA  length = 16
FEATURE                  Location/Qualifiers
REGION                   1..16
                         note = V64-8 CDR1 (light)
source                   1..16
                         mol_type = protein
                         organism = synthetic construct
SEQUENCE: 68
KASQSLLDRG GKTFFN                                                     16

SEQ ID NO: 69            moltype = AA  length = 15
FEATURE                  Location/Qualifiers
REGION                   1..15
                         note = V64-8 FR2 (light)
source                   1..15
                         mol_type = protein
                         organism = synthetic construct
SEQUENCE: 69
WLLQRPGQSP KRLIY                                                      15

SEQ ID NO: 70            moltype = AA  length = 7
FEATURE                  Location/Qualifiers
REGION                   1..7
                         note = V64-8 CDR2 (light)
source                   1..7
                         mol_type = protein
                         organism = synthetic construct
SEQUENCE: 70
LVSKLDS                                                                7

SEQ ID NO: 71            moltype = AA  length = 32
FEATURE                  Location/Qualifiers
REGION                   1..32
                         note = V64-8 FR3 (light)
source                   1..32
                         mol_type = protein
                         organism = synthetic construct
SEQUENCE: 71
GVPDRFTGSG SGTDFTLKIS RVEAEDLGVY YC                                   32

SEQ ID NO: 72            moltype = AA  length = 9
FEATURE                  Location/Qualifiers
REGION                   1..9
                         note = V64-8 CDR3 (light)
source                   1..9
                         mol_type = protein
                         organism = synthetic construct
SEQUENCE: 72
WQGTHFPWT                                                              9

SEQ ID NO: 73            moltype = AA  length = 10
FEATURE                  Location/Qualifiers
REGION                   1..10
                         note = V64-8 FR4 (light)
source                   1..10
                         mol_type = protein
                         organism = synthetic construct
SEQUENCE: 73
FGGGTRLEIK                                                            10

SEQ ID NO: 74            moltype = DNA  length = 90
FEATURE                  Location/Qualifiers
```

```
misc_feature            1..90
                        note = V196-4 FR1 (heavy)
source                  1..90
                        mol_type = other DNA
                        organism = synthetic construct
SEQUENCE: 74
gaagtgcagc tggtggagtc tgggggagcc ttagtgaagc tggagggtc cctgaaactc      60
tcctgtgtag cctctggatt cactttcagt                                       90

SEQ ID NO: 75           moltype = DNA  length = 15
FEATURE                 Location/Qualifiers
misc_feature            1..15
                        note = V196-4 CDR1 (heavy)
source                  1..15
                        mol_type = other DNA
                        organism = synthetic construct
SEQUENCE: 75
agctatgcca tgtct                                                       15

SEQ ID NO: 76           moltype = DNA  length = 42
FEATURE                 Location/Qualifiers
misc_feature            1..42
                        note = V196-4 FR2 (heavy)
source                  1..42
                        mol_type = other DNA
                        organism = synthetic construct
SEQUENCE: 76
tggggttcgcc agtctccaga gaagaagctg gagtgggtcg ca                        42

SEQ ID NO: 77           moltype = DNA  length = 51
FEATURE                 Location/Qualifiers
misc_feature            1..51
                        note = V196-4 CDR2 (heavy)
source                  1..51
                        mol_type = other DNA
                        organism = synthetic construct
SEQUENCE: 77
gaaattagta gtactggtag ttacacccac tatcccgaca ctgtgacggg c               51

SEQ ID NO: 78           moltype = DNA  length = 96
FEATURE                 Location/Qualifiers
misc_feature            1..96
                        note = V196-4 FR3 (heavy)
source                  1..96
                        mol_type = other DNA
                        organism = synthetic construct
SEQUENCE: 78
cgattcacca tctccagaga caatgccaag aacaccctgt acctggaaat gagcagtctg      60
aggtctgagg acacggccat gtattactgt gcaaga                                96

SEQ ID NO: 79           moltype = DNA  length = 12
FEATURE                 Location/Qualifiers
misc_feature            1..12
                        note = V196-4 CDR3 (heavy)
source                  1..12
                        mol_type = other DNA
                        organism = synthetic construct
SEQUENCE: 79
ggggaggcgc tc                                                          12

SEQ ID NO: 80           moltype = DNA  length = 33
FEATURE                 Location/Qualifiers
misc_feature            1..33
                        note = V196-4 FR4 (heavy)
source                  1..33
                        mol_type = other DNA
                        organism = synthetic construct
SEQUENCE: 80
tggggtcaag gaacctcagt caccgtctcc tca                                   33

SEQ ID NO: 81           moltype = AA  length = 30
FEATURE                 Location/Qualifiers
REGION                  1..30
                        note = V196-4 FR1 (heavy)
source                  1..30
                        mol_type = protein
                        organism = synthetic construct
SEQUENCE: 81
EVQLVESGGA LVKPGGSLKL SCVASGFTFS                                       30
```

```
SEQ ID NO: 82           moltype = AA  length = 5
FEATURE                 Location/Qualifiers
REGION                  1..5
                        note = V196-4 CDR1 (heavy)
source                  1..5
                        mol_type = protein
                        organism = synthetic construct
SEQUENCE: 82
SYAMS                                                                    5

SEQ ID NO: 83           moltype = AA  length = 14
FEATURE                 Location/Qualifiers
REGION                  1..14
                        note = V196-4 FR2 (heavy)
source                  1..14
                        mol_type = protein
                        organism = synthetic construct
SEQUENCE: 83
WVRQSPEKKL EWVA                                                         14

SEQ ID NO: 84           moltype = AA  length = 17
FEATURE                 Location/Qualifiers
REGION                  1..17
                        note = 196-4 CDR2 (heavy)
source                  1..17
                        mol_type = protein
                        organism = synthetic construct
SEQUENCE: 84
EISSTGSYTH YPDTVTG                                                      17

SEQ ID NO: 85           moltype = AA  length = 32
FEATURE                 Location/Qualifiers
REGION                  1..32
                        note = V196-4 FR3 (heavy)
source                  1..32
                        mol_type = protein
                        organism = synthetic construct
SEQUENCE: 85
RFTISRDNAK NTLYLEMSSL RSEDTAMYYC AR                                     32

SEQ ID NO: 86           moltype = AA  length = 4
FEATURE                 Location/Qualifiers
REGION                  1..4
                        note = V196-4 CDR3 (heavy)
source                  1..4
                        mol_type = protein
                        organism = synthetic construct
SEQUENCE: 86
GEAL                                                                     4

SEQ ID NO: 87           moltype = AA  length = 11
FEATURE                 Location/Qualifiers
REGION                  1..11
                        note = V196-4 FR4 (heavy)
source                  1..11
                        mol_type = protein
                        organism = synthetic construct
SEQUENCE: 87
WGQGTSVTVS S                                                            11

SEQ ID NO: 88           moltype = DNA  length = 69
FEATURE                 Location/Qualifiers
misc_feature            1..69
                        note = V196-4 FR1 (light)
source                  1..69
                        mol_type = other DNA
                        organism = synthetic construct
SEQUENCE: 88
gatgttgtga tgacccagac tccactcact ttgtcggtta ccgttggaca accagcctcc       60
atctcttgc                                                               69

SEQ ID NO: 89           moltype = DNA  length = 48
FEATURE                 Location/Qualifiers
misc_feature            1..48
                        note = V196-4 CDR1 (light)
source                  1..48
                        mol_type = other DNA
                        organism = synthetic construct
```

```
SEQUENCE: 89
aagtcaagtc atagcctctt agatagttat ggaaagacat atttgaat          48

SEQ ID NO: 90           moltype = DNA   length = 45
FEATURE                 Location/Qualifiers
misc_feature            1..45
                        note = V196-4 FR2 (light)
source                  1..45
                        mol_type = other DNA
                        organism = synthetic construct
SEQUENCE: 90
tggtttttac agaggccagg ccagtctcca aagcgcctaa tctat              45

SEQ ID NO: 91           moltype = DNA   length = 20
FEATURE                 Location/Qualifiers
misc_feature            1..20
                        note = V196-4 CDR2 (light)
source                  1..20
                        mol_type = other DNA
                        organism = synthetic construct
SEQUENCE: 91
ctggtgtcta aactggactc                                          20

SEQ ID NO: 92           moltype = DNA   length = 97
FEATURE                 Location/Qualifiers
misc_feature            1..97
                        note = V196-4 FR3 (light)
source                  1..97
                        mol_type = other DNA
                        organism = synthetic construct
SEQUENCE: 92
tggagtccct gacaggttca ctggcagtgg atcagggaca gatttcacac tgaaaatcag 60
cagagtggag gctgaggatt tgggacttta ttattgc                       97

SEQ ID NO: 93           moltype = DNA   length = 27
FEATURE                 Location/Qualifiers
misc_feature            1..27
                        note = V196-4 CDR3 (light)
source                  1..27
                        mol_type = other DNA
                        organism = synthetic construct
SEQUENCE: 93
tggcagggta cacattttcc gtggacg                                  27

SEQ ID NO: 94           moltype = DNA   length = 30
FEATURE                 Location/Qualifiers
misc_feature            1..30
                        note = V196-4 FR4 (light)
source                  1..30
                        mol_type = other DNA
                        organism = synthetic construct
SEQUENCE: 94
ttcggtggag gcaccaagct ggaaatcaaa                               30

SEQ ID NO: 95           moltype = AA    length = 23
FEATURE                 Location/Qualifiers
REGION                  1..23
                        note = V196-4 FR1 (light)
source                  1..23
                        mol_type = protein
                        organism = synthetic construct
SEQUENCE: 95
DVVMTQTPLT LSVTVGQPAS ISC                                      23

SEQ ID NO: 96           moltype = AA    length = 16
FEATURE                 Location/Qualifiers
REGION                  1..16
                        note = V196-4 CDR1 (light)
source                  1..16
                        mol_type = protein
                        organism = synthetic construct
SEQUENCE: 96
KSSHSLLDSY GKTYLN                                              16

SEQ ID NO: 97           moltype = AA    length = 15
FEATURE                 Location/Qualifiers
REGION                  1..15
                        note = V196-4 FR2 (light)
source                  1..15
```

```
SEQ ID NO: 97 (continued)
                        mol_type = protein
                        organism = synthetic construct
SEQUENCE: 97
WFLQRPGQSP KRLIY                                                   15

SEQ ID NO: 98           moltype = AA  length = 7
FEATURE                 Location/Qualifiers
REGION                  1..7
                        note = V196-4 CDR2 (light)
source                  1..7
                        mol_type = protein
                        organism = synthetic construct
SEQUENCE: 98
LVSKLDS                                                            7

SEQ ID NO: 99           moltype = AA  length = 32
FEATURE                 Location/Qualifiers
REGION                  1..32
                        note = V196-4 FR3 (light)
source                  1..32
                        mol_type = protein
                        organism = synthetic construct
SEQUENCE: 99
GVPDRFTGSG SGTDFTLKIS RVEAEDLGLY YC                                 32

SEQ ID NO: 100          moltype = AA  length = 9
FEATURE                 Location/Qualifiers
REGION                  1..9
                        note = V196-4 CDR3 (light)
source                  1..9
                        mol_type = protein
                        organism = synthetic construct
SEQUENCE: 100
WQGTHFPWT                                                          9

SEQ ID NO: 101          moltype = AA  length = 10
FEATURE                 Location/Qualifiers
REGION                  1..10
                        note = V196-4 FR4 (light)
source                  1..10
                        mol_type = protein
                        organism = synthetic construct
SEQUENCE: 101
FGGGTKLEIK                                                         10

SEQ ID NO: 102          moltype = AA  length = 7
FEATURE                 Location/Qualifiers
REGION                  1..7
                        note = 92.25 CDR2 (light)
source                  1..7
                        mol_type = protein
                        organism = synthetic construct
SEQUENCE: 102
SASYRYS                                                            7

SEQ ID NO: 103          moltype = AA  length = 32
FEATURE                 Location/Qualifiers
REGION                  1..32
                        note = 92.25 FR3 (light)
source                  1..32
                        mol_type = protein
                        organism = synthetic construct
SEQUENCE: 103
GVPDRFRGSR SGTDFTLTIS NVQSEDLAEY FC                                 32
```